US011926843B2

(12) United States Patent
Crawley et al.

(10) Patent No.: US 11,926,843 B2
(45) **Date of Patent: *Mar. 12, 2024**

(54) RNA-GUIDED NUCLEASES AND ACTIVE FRAGMENTS AND VARIANTS THEREOF AND METHODS OF USE

(71) Applicant: LifeEDIT Therapeutics, Inc., Morrisville, NC (US)

(72) Inventors: Alexandra Briner Crawley, Cary, NC (US); Rodolphe Barrangou, Raleigh, NC (US); Tyson D. Bowen, Morrisville, NC (US); Michael Coyle, Chapel Hill, NC (US); Tedd D. Elich, Durham, NC (US)

(73) Assignee: LifeEDIT Therapeutics, Inc., Durham, NC (US)

( * ) Notice: Subject to any disclaimer, the term of this patent is extended or adjusted under 35 U.S.C. 154(b) by 93 days.

This patent is subject to a terminal disclaimer.

(21) Appl. No.: 17/478,374

(22) Filed: Sep. 17, 2021

(65) Prior Publication Data

US 2022/0002756 A1 Jan. 6, 2022

Related U.S. Application Data

(63) Continuation of application No. 16/432,321, filed on Jun. 5, 2019, now Pat. No. 11,162,114.

(60) Provisional application No. 62/805,041, filed on Feb. 13, 2019, provisional application No. 62/805,045, filed on Feb. 13, 2019, provisional application No. 62/686,901, filed on Jun. 19, 2018, provisional application No. 62/680,859, filed on Jun. 5, 2018, provisional application No. 62/680,846, filed on Jun. 5, 2018, provisional application No. 62/680,845, filed on Jun. 5, 2018, provisional application No. 62/680,862, filed on Jun. 5, 2018, provisional application No. 62/680,863, filed on Jun. 5, 2018, provisional application No. 62/680,853, filed on Jun. 5, 2018.

(51) Int. Cl.

| | |
|---|---|
| ***C12N 15/90*** | (2006.01) |
| ***C12N 9/22*** | (2006.01) |
| ***C12N 15/10*** | (2006.01) |
| ***C12N 15/11*** | (2006.01) |
| ***C12N 15/113*** | (2010.01) |
| ***C12N 15/52*** | (2006.01) |
| ***C12N 15/63*** | (2006.01) |

(52) U.S. Cl.

CPC ............ *C12N 15/907* (2013.01); *C12N 9/22* (2013.01); *C12N 15/11* (2013.01); *C12N 15/902* (2013.01); *C12N 2310/20* (2017.05); *C12N 2800/80* (2013.01)

(58) Field of Classification Search

None

See application file for complete search history.

(56) References Cited

U.S. PATENT DOCUMENTS

2019/0100762 A1* 4/2019 Cigan ...................... C12N 9/22

FOREIGN PATENT DOCUMENTS

| | | |
|---|---|---|
| WO | WO 2013/176772 A1 | 11/2013 |
| WO | WO 2015/071474 A2 | 5/2015 |
| WO | WO 2016/186946 A1 | 11/2016 |
| WO | WO 2017/155714 A1 | 9/2017 |
| WO | WO 2017/155717 A1 | 9/2017 |
| WO | WO 2017/222773 A1 | 12/2017 |

OTHER PUBLICATIONS

Jiang. F., et anon., "CRISPR-Cas9 Structures and Mechanisms," *Annu. Rev. Biophys.*, 2017, vol. 46(1), pp. 505-529.

Van Erp, P., et al., "The history and market impact of CRISPR RNA-guided nucleases," *Current Opinion in Virology*, 2015, vol. 12, pp. 85-90.

* cited by examiner

*Primary Examiner* — Suzanne M Noakes
*Assistant Examiner* — Jae W Lee
(74) *Attorney, Agent, or Firm* — Womble Bond Dickinson (US) LLP

(57) ABSTRACT

Compositions and methods for binding to a target sequence of interest are provided. The compositions find use in cleaving or modifying a target sequence of interest, visualization of a target sequence of interest, and modifying the expression of a sequence of interest. Compositions comprise RNA-guided nuclease polypeptides, CRISPR RNAs, trans-activating CRISPR RNAs, guide RNAs, and nucleic acid molecules encoding the same. Vectors and host cells comprising the nucleic acid molecules are also provided. Further provided are CRISPR systems for binding a target sequence of interest, wherein the CRISPR system comprises an RNA-guided nuclease polypeptide and one or more guide RNAs.

28 Claims, No Drawings

Specification includes a Sequence Listing.

RNA-GUIDED NUCLEASES AND ACTIVE FRAGMENTS AND VARIANTS THEREOF AND METHODS OF USE

CROSS-REFERENCE TO RELATED APPLICATIONS

This application is a continuation of U.S. application Ser. No. 16/432,321, filed Jun. 5, 2019, which claims the benefit of U.S. Provisional Application Nos. 62/805,041, filed Feb. 13, 2019, 62/805,045, filed Feb. 13, 2019, 62/686,901, filed Jun. 19, 2018, 62/680,845, filed Jun. 5, 2018, 62/680,846, filed Jun. 5, 2018, 62/680,853, filed Jun. 5, 2018, 62/680,859, filed Jun. 5, 2018, 62/680,862, filed Jun. 5, 2018, and 62/680,863, filed Jun. 5, 2018, each of which is incorporated by reference herein in its entirety.

REFERENCE TO A SEQUENCE LISTING SUBMITTED ELECTRONICALLY AS A TEXT FILE

The instant application contains a Sequence Listing which has been submitted in ASCII format via EFS-Web and is hereby incorporated by reference in its entirety. Said ASCII copy, created on Sep. 16, 2021, is named L103438_0111_1_Sequence_List.txt, and is 451334 bytes in size.

FIELD OF THE INVENTION

The present invention relates to the field of molecular biology and gene editing.

BACKGROUND OF THE INVENTION

Targeted genome editing or modification is rapidly becoming an important tool for basic and applied research. Initial methods involved engineering nucleases such as meganucleases, zinc finger fusion proteins or TALENs, requiring the generation of chimeric nucleases with engineered, programmable, sequence-specific DNA-binding domains specific for each particular target sequence. RNA-guided nucleases, such as the Clustered Regularly Interspaced Short Palindromic Repeats (CRISPR)-associated (cas) proteins of the CRISPR-cas bacterial system, allow for the targeting of specific sequences by complexing the nucleases with guide RNA that specifically hybridizes with a particular target sequence. Producing target-specific guide RNAs is less costly and more efficient than generating chimeric nucleases for each target sequence. Such RNA-guided nucleases can be used to edit genomes through the introduction of a sequence-specific, double-stranded break that is repaired via error-prone non-homologous end-joining (NHEJ) to introduce a mutation at a specific genomic location. Alternatively, heterologous DNA may be introduced into the genomic site via homology-directed repair.

BRIEF SUMMARY OF THE INVENTION

Compositions and methods for binding a target sequence of interest are provided. The compositions find use in cleaving or modifying a target sequence of interest, detection of a target sequence of interest, and modifying the expression of a sequence of interest. Compositions comprise RNA-guided nuclease (RGN) polypeptides, CRISPR RNAs (crRNAs), trans-activating CRISPR RNAs (tracrRNAs), guide RNAs (gRNAs), nucleic acid molecules encoding the same, and vectors and host cells comprising the nucleic acid molecules. Also provided are CRISPR systems for binding a target sequence of interest, wherein the CRISPR system comprises an RNA-guided nuclease polypeptide and one or more guide RNAs. Thus, methods disclosed herein are drawn to binding a target sequence of interest, and in some embodiments, cleaving or modifying the target sequence of interest. The target sequence of interest can be modified, for example, as a result of non-homologous end joining or homology-directed repair with an introduced donor sequence.

DETAILED DESCRIPTION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended embodiments. Although specific terms are employed herein, they are used in a generic and descriptive sense only and not for purposes of limitation.

I. Overview

RNA-guided nucleases (RGNs) allow for the targeted manipulation of a single site within a genome and are useful in the context of gene targeting for therapeutic and research applications. In a variety of organisms, including mammals, RNA-guided nucleases have been used for genome engineering by stimulating non-homologous end joining and homologous recombination, for example. The compositions and methods described herein are useful for creating single- or double-stranded breaks in polynucleotides, modifying polynucleotides, detecting a particular site within a polynucleotide, or modifying the expression of a particular gene.

The RNA-guided nucleases disclosed herein can alter gene expression by modifying a target sequence. In specific embodiments, the RNA-guided nucleases are directed to the target sequence by a guide RNA (gRNA) as part of a Clustered Regularly Interspaced Short Palindromic Repeats (CRISPR) RNA-guided nuclease system. Guide RNAs form a complex with the RNA-guided nucleases to direct the RNA-guided nuclease to bind to a target sequence and in some embodiments, introduce a single-stranded or double-stranded break at the target sequence. After the target sequence has been cleaved, the break can be repaired such that the DNA sequence of the target sequence is modified during the repair process. Thus, provided herein are methods for using the RNA-guided nucleases to modify a target sequence in the DNA of host cells. For example, RNA-guided nucleases can be used to modify a target sequence at a genomic locus of eukaryotic cells or prokaryotic cells.

II. RNA-Guided Nucleases

Provided herein are RNA-guided nucleases. The term RNA-guided nuclease (RGN) refers to a polypeptide that binds to a particular target nucleotide sequence in a sequence-specific manner and is directed to the target nucleotide sequence by a guide RNA molecule that is complexed with the polypeptide and hybridizes with the target sequence. Although an RNA-guided nuclease can be capable of cleaving the target sequence upon binding, the term RNA-guided nuclease also encompasses nuclease-dead RNA-guided nucleases that are capable of binding to, but not cleaving, a target sequence. Cleavage of a target sequence by an RNA-guided nuclease can result in a singleor double-stranded break. RNA-guided nucleases only capable of cleaving a single strand of a double-stranded nucleic acid molecule are referred to herein as nickases.

The RNA-guided nucleases disclosed herein include the APG05083.1, APG07433.1, APG07513.1, APG08290.1, APG05459.1, APG04583.1, and APG1688.1 RNA-guided nucleases, the amino acid sequences of which are set forth, respectively, as SEQ ID NOs: 1, 11, 19, 27, 36, 45, or 54, and active fragments or variants thereof that retain the ability to bind to a target nucleotide sequence in an RNA-guided sequence-specific manner. In some of these embodiments, the active fragment or variant of the APG05083.1, APG07433.1, APG07513.1, APG08290.1, APG05459.1, APG04583.1, and APG1688.1 RGN is capable of cleaving a single- or double-stranded target sequence. In some embodiments, an active variant of the APG05083.1, APG07433.1, APG07513.1, APG08290.1, APG05459.1, APG04583.1, or APG1688.1 RGN comprises an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence set forth as SEQ ID NOs: 1, 11, 19, 27, 36, 45, or 54. In certain embodiments, an active fragment of the APG05083.1, APG07433.1, APG07513.1, APG08290.1, APG05459.1, APG04583.1, or APG1688.1 RGN comprises at least 50, 100, 150, 200, 250, 300, 350, 400, 450, 500, 550, 600, 650, 700, 750, 800, 850, 900, 950, 1000, 1050 or more contiguous amino acid residues of the amino acid sequence set forth as SEQ ID NOs: 1, 11, 19, 27, 36, 45, or 54. RNA-guided nucleases provided herein can comprise at least one nuclease domain (e.g., DNase, RNase domain) and at least one RNA recognition and/or RNA binding domain to interact with guide RNAs. Further domains that can be found in RNA-guided nucleases provided herein include, but are not limited to: DNA binding domains, helicase domains, protein-protein interaction domains, and dimerization domains. In specific embodiments, the RNA-guided nucleases provided herein can comprise at least 70%, 75%, 80%, 85%, 90%, 91%, 92%, 93%, 94%, 95%, 96%, 97%, 98%, 99% to one or more of a DNA binding domains, helicase domains, protein-protein interaction domains, and dimerization domains.

A target nucleotide sequence is bound by an RNA-guided nuclease provided herein and hybridizes with the guide RNA associated with the RNA-guided nuclease. The target sequence can then be subsequently cleaved by the RNA-guided nuclease if the polypeptide possesses nuclease activity. The terms "cleave" or "cleavage" refer to the hydrolysis of at least one phosphodiester bond within the backbone of a target nucleotide sequence that can result in either single-stranded or double-stranded breaks within the target sequence. The presently disclosed RGNs can cleave nucleotides within a polynucleotide, functioning as an endonuclease or can be an exonuclease, removing successive nucleotides from the end (the 5' and/or the 3' end) of a polynucleotide. In other embodiments, the disclosed RGNs can cleave nucleotides of a target sequence within any position of a polynucleotide and thus function as both an endonuclease and exonuclease. The cleavage of a target polynucleotide by the presently disclosed RGNs can result in staggered breaks or blunt ends.

The presently disclosed RNA-guided nucleases can be wild-type sequences derived from bacterial or archaeal species. Alternatively, the RNA-guided nucleases can be variants or fragments of wild-type polypeptides. The wild-type RGN can be modified to alter nuclease activity or alter PAM specificity, for example. In some embodiments, the RNA-guided nuclease is not naturally-occurring.

In certain embodiments, the RNA-guided nuclease functions as a nickase, only cleaving a single strand of the target nucleotide sequence. Such RNA-guided nucleases have a single functioning nuclease domain. In some of these embodiments, additional nuclease domains have been mutated such that the nuclease activity is reduced or eliminated.

In other embodiments, the RNA-guided nuclease lacks nuclease activity altogether or exhibits reduced nuclease activity, and is referred to herein as nuclease-dead. Any method known in the art for introducing mutations into an amino acid sequence, such as PCR-mediated mutagenesis and site-directed mutagenesis, can be used for generating nickases or nuclease-dead RGNs. See, e.g., U.S. Publ. No. 2014/0068797 and U.S. Pat. No. 9,790,490; each of which is incorporated by reference in its entirety. RNA-guided nucleases that lack nuclease activity can be used to deliver a fused polypeptide, polynucleotide, or small molecule payload to a particular genomic location. In some of these embodiments, the RGN polypeptide or guide RNA can be fused to a detectable label to allow for detection of a particular sequence. As a non-limiting example, a nuclease-dead RGN can be fused to a detectable label (e.g., fluorescent protein) and targeted to a particular sequence associated with a disease to allow for detection of the disease-associated sequence.

Alternatively, nuclease-dead RGNs can be targeted to particular genomic locations to alter the expression of a desired sequence. In some embodiments, the binding of a nuclease-dead RNA-guided nuclease to a target sequence results in the repression of expression of the target sequence or a gene under transcriptional control by the target sequence by interfering with the binding of RNA polymerase or transcription factors within the targeted genomic region. In other embodiments, the RGN (e.g., a nuclease-dead RGN) or its complexed guide RNA further comprises an expression modulator that, upon binding to a target sequence, serves to either repress or activate the expression of the target sequence or a gene under transcriptional control by the target sequence. In some of these embodiments, the expression modulator modulates the expression of the target sequence or regulated gene through epigenetic mechanisms.

In other embodiments, the nuclease-dead RGNs or a RGN with only nickase activity can be targeted to particular genomic locations to modify the sequence of a target polynucleotide through fusion to a base-editing polypeptide, for example a deaminase polypeptide or active variant or fragment thereof that deaminates a nucleotide base, resulting in conversion from one nucleotide base to another. The base-editing polypeptide can be fused to the RGN at its N-terminal or C-terminal end. Additionally, the base-editing polypeptide may be fused to the RGN via a peptide linker. A non-limiting example of a deaminase polypeptide that is useful for such compositions and methods include cytidine deaminase or the adenosine deaminase base editor described in Gaudelli et al. (2017) Nature 551:464-471, U.S. Publ. Nos. 2017/0121693 and 2018/0073012, and International Publ. No. WO/2018/027078, each of which is herein incorporated by reference in its entirety.

RNA-guided nucleases that are fused to a polypeptide or domain can be separated or joined by a linker. The term "linker," as used herein, refers to a chemical group or a molecule linking two molecules or moieties, e.g., a binding domain and a cleavage domain of a nuclease. In some embodiments, a linker joins a gRNA binding domain of an RNA guided nuclease and a base-editing polypeptide, such as a deaminase. In some embodiments, a linker joins a nuclease-dead RGN and a deaminase. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The presently disclosed RNA-guided nucleases can comprise at least one nuclear localization signal (NLS) to enhance transport of the RGN to the nucleus of a cell. Nuclear localization signals are known in the art and generally comprise a stretch of basic amino acids (see, e.g., Lange et al., *J. Biol. Chem.* (2007) 282:5101-5105). In particular embodiments, the RGN comprises 2, 3, 4, 5, 6 or more nuclear localization signals. The nuclear localization signal(s) can be a heterologous NLS. Non-limiting examples of nuclear localization signals useful for the presently disclosed RGNs are the nuclear localization signals of SV40 Large T-antigen, nucleopasmin, and c-Myc (see, e.g., Ray et al. (2015) *Bioconjug Chem* 26(6):1004-7). In particular embodiments, the RGN comprises the NLS sequence set forth as SEQ ID NO: 67. The RGN can comprise one or more NLS sequences at its N-terminus, C-terminus, or both the N-terminus and C-terminus. For example, the RGN can comprise two NLS sequences at the N-terminal region and four NLS sequences at the C-terminal region.

Other localization signal sequences known in the art that localize polypeptides to particular subcellular location(s) can also be used to target the RGNs, including, but not limited to, plastid localization sequences, mitochondrial localization sequences, and dual-targeting signal sequences that target to both the plastid and mitochondria (see, e.g., Nassoury and Morse (2005) *Biochim Biophys Acta* 1743:5-19; Kunze and Berger (2015) *Front Physiol* dx.doi.org/10.3389/fphys.2015.00259; Hellmann and Neupert (2003) *IUBMB Life* 55:219-225; Soll (2002) *Curr Opin Plant Biol* 5:529-535; Carrie and Small (2013) *Biochim Biophys Acta* 1833:253-259; Carrie et al. (2009) *FEBS J* 276:1187-1195; Silva-Filho (2003) *Curr Opin Plant Biol* 6:589-595; Peeters and Small (2001) *Biochim Biophys Acta* 1541:54-63; Murcha et al. (2014) J Exp Bot 65:6301-6335; Mackenzie (2005) *Trends Cell Biol* 15:548-554; Glaser et al. (1998) *Plant Mol Biol* 38:311-338).

In certain embodiments, the presently disclosed RNA-guided nucleases comprise at least one cell-penetrating domain that facilitates cellular uptake of the RGN. Cell-penetrating domains are known in the art and generally comprise stretches of positively charged amino acid residues (i.e., polycationic cell-penetrating domains), alternating polar amino acid residues and non-polar amino acid residues (i.e., amphipathic cell-penetrating domains), or hydrophobic amino acid residues (i.e., hydrophobic cell-penetrating domains) (see, e.g., Milletti F. (2012) *Drug Discov Today* 17:850-860). A non-limiting example of a cell-penetrating domain is the trans-activating transcriptional activator (TAT) from the human immunodeficiency virus 1.

The nuclear localization signal, plastid localization signal, mitochondrial localization signal, dual-targeting localization signal, and/or cell-penetrating domain can be located at the amino-terminus (N-terminus), the carboxyl-terminus (C-terminus), or in an internal location of the RNA-guided nuclease.

The presently disclosed RGNs can be fused to an effector domain, such as a cleavage domain, a deaminase domain, or an expression modulator domain, either directly or indirectly via a linker peptide. Such a domain can be located at the N-terminus, the C-terminus, or an internal location of the RNA-guided nuclease. In some of these embodiments, the RGN component of the fusion protein is a nuclease-dead RGN.

In some embodiments, the RGN fusion protein comprises a cleavage domain, which is any domain that is capable of cleaving a polynucleotide (i.e., RNA, DNA, or RNA/DNA hybrid) and includes, but is not limited to, restriction endonucleases and homing endonucleases, such as Type IIS endonucleases (e.g., FokI) (see, e.g., Belfort et al. (1997) *Nucleic Acids Res.* 25:3379-3388; Linn et al. (eds.) Nucleases, Cold Spring Harbor Laboratory Press, 1993).

In other embodiments, the RGN fusion protein comprises a deaminase domain that deaminates a nucleotide base, resulting in conversion from one nucleotide base to another, and includes, but is not limited to, a cytidine deaminase or an adenosine deaminase base editor (see, e.g., Gaudelli et al. (2017) *Nature* 551:464-471, U.S. Publ. Nos. 2017/0121693 and 2018/0073012, U.S. Pat. No. 9,840,699, and International Publ. No. WO/2018/027078).

In some embodiments, the effector domain of the RGN fusion protein can be an expression modulator domain, which is a domain that either serves to upregulate or downregulate transcription. The expression modulator domain can be an epigenetic modification domain, a transcriptional repressor domain or a transcriptional activation domain.

In some of these embodiments, the expression modulator of the RGN fusion protein comprises an epigenetic modification domain that covalently modifies DNA or histone proteins to alter histone structure and/or chromosomal structure without altering the DNA sequence, leading to changes in gene expression (i.e., upregulation or downregulation). Non-limiting examples of epigenetic modifications include acetylation or methylation of lysine residues, arginine methylation, serine and threonine phosphorylation, and lysine ubiquitination and sumoylation of histone proteins, and methylation and hydroxymethylation of cytosine residues in DNA. Non-limiting examples of epigenetic modification domains include histone acetyltransferase domains, histone deacetylase domains, histone methyltransferase domains, histone demethylase domains, DNA methyltransferase domains, and DNA demethylase domains.

In other embodiments, the expression modulator of the fusion protein comprises a transcriptional repressor domain, which interacts with transcriptional control elements and/or transcriptional regulatory proteins, such as RNA polymerases and transcription factors, to reduce or terminate transcription of at least one gene. Transcriptional repressor domains are known in the art and include, but are not limited to, Sp1-like repressors, IκB, and Krüppel associated box (KRAB) domains.

In yet other embodiments, the expression modulator of the fusion protein comprises a transcriptional activation domain, which interacts with transcriptional control elements and/or transcriptional regulatory proteins, such as RNA polymerases and transcription factors, to increase or activate transcription of at least one gene. Transcriptional activation domains are known in the art and include, but are not limited to, a herpes simplex virus VP16 activation domain and an NFAT activation domain.

The presently disclosed RGN polypeptides can comprise a detectable label or a purification tag. The detectable label or purification tag can be located at the N-terminus, the C-terminus, or an internal location of the RNA-guided nuclease, either directly or indirectly via a linker peptide. In some of these embodiments, the RGN component of the fusion protein is a nuclease-dead RGN. In other embodiments, the RGN component of the fusion protein is a RGN with nickase activity.

A detectable label is a molecule that can be visualized or otherwise observed. The detectable label may be fused to the RGN as a fusion protein (e.g., fluorescent protein) or may be a small molecule conjugated to the RGN polypeptide that can be detected visually or by other means. Detectable labels that can be fused to the presently disclosed RGNs as a fusion protein include any detectable protein domain, including but not limited to, a fluorescent protein or a protein domain that can be detected with a specific antibody. Non-limiting examples of fluorescent proteins include green fluorescent proteins (e.g., GFP, EGFP, ZsGreen1) and yellow fluorescent proteins (e.g., YFP, EYFP, ZsYellow1). Non-limiting examples of small molecule detectable labels include radioactive labels, such as $^{3}H$ and $^{35}S$.

RGN polypeptides can also comprise a purification tag, which is any molecule that can be utilized to isolate a protein or fused protein from a mixture (e.g., biological sample, culture medium). Non-limiting examples of purification tags include biotin, myc, maltose binding protein (MBP), and glutathione-S-transferase (GST).

II. Guide RNA

The present disclosure provides guide RNAs and polynucleotides encoding the same. The term "guide RNA" refers to a nucleotide sequence having sufficient complementarity with a target nucleotide sequence to hybridize with the target sequence and direct sequence-specific binding of an associated RNA-guided nuclease to the target nucleotide sequence. Thus, a RGN's respective guide RNA is one or more RNA molecules (generally, one or two), that can bind to the RGN and guide the RGN to bind to a particular target nucleotide sequence, and in those instances wherein the RGN has nickase or nuclease activity, also cleave the target nucleotide sequence. In general, a guide RNA comprises a CRISPR RNA (crRNA) and a trans-activating CRISPR RNA (tracrRNA). Native guide RNAs that comprise both a crRNA and a tracrRNA generally comprise two separate RNA molecules that hybridize to each other through the repeat sequence of the crRNA and the anti-repeat sequence of the tracrRNA.

Native direct repeat sequences within a CRISPR array generally range in length from 28 to 37 base pairs, although the length can vary between about 23 bp to about 55 bp. Spacer sequences within a CRISPR array generally range from about 32 to about 38 bp in length, although the length can be between about 21 bp to about 72 bp. Each CRISPR array generally comprises less than 50 units of the CRISPR repeat-spacer sequence. The CRISPRs are transcribed as part of a long transcript termed the primary CRISPR transcript, which comprises much of the CRISPR array. The primary CRISPR transcript is cleaved by Cas proteins to produce crRNAs or in some cases, to produce pre-crRNAs that are further processed by additional Cas proteins into mature crRNAs. Mature crRNAs comprise a spacer sequence and a CRISPR repeat sequence. In some embodiments in which pre-crRNAs are processed into mature (or processed) crRNAs, maturation involves the removal of about one to about six or more 5', 3', or 5' and 3' nucleotides. For the purposes of genome editing or targeting a particular target nucleotide sequence of interest, these nucleotides that are removed during maturation of the pre-crRNA molecule are not necessary for generating or designing a guide RNA.

A CRISPR RNA (crRNA) comprises a spacer sequence and a CRISPR repeat sequence. The "spacer sequence" is the nucleotide sequence that directly hybridizes with the target nucleotide sequence of interest. The spacer sequence is engineered to be fully or partially complementary with the target sequence of interest. In various embodiments, the spacer sequence can comprise from about 8 nucleotides to about 30 nucleotides, or more. For example, the spacer sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In some embodiments, the spacer sequence is about 10 to about 26 nucleotides in length, or about 12 to about 30 nucleotides in length. In particular embodiments, the spacer sequence is about 30 nucleotides in length. In some embodiments, the degree of complementarity between a spacer sequence and its corresponding target sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the spacer sequence is free of secondary structure, which can be predicted using any suitable polynucleotide folding algorithm known in the art, including but not limited to mFold (see, e.g., Zuker and Stiegler (1981) *Nucleic Acids Res.* 9:133-148) and RNAfold (see, e.g., Gruber et al. (2008) *Cell* 106(1):23-24).

RGN proteins can have varying sensitivity to mismatches between a spacer sequence in a gRNA and its target sequence that affects the efficiency of cleavage. As discussed in Example 5, APG05459.1 RGN has an unusual sensitivity to mismatches between the spacer sequence and target sequence, extending at least 15 nucleotides 5' of the PAM site. Thus, APG05459.1 has the potential to more finely (i.e., specifically) target particular sequences with greater precision than other RGNs with less sensitivity to mismatches between the spacer sequence and target sequence.

The CRISPR RNA repeat sequence comprises a nucleotide sequence that comprises a region with sufficient complementarity to hybridize to a tracrRNA. In various embodiments, the CRISPR RNA repeat sequence can comprise from about 8 nucleotides to about 30 nucleotides, or more. For example, the CRISPR repeat sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In some embodiments, the CRISPR repeat sequence is about 21 nucleotides in length. In some embodiments, the degree of complementarity between a CRISPR repeat sequence and its corresponding tracrRNA sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the CRISPR repeat sequence comprises the nucleotide sequence of SEQ ID NOs: 2, 12, 20, 28, 37, 46, or 55, or an active variant or fragment thereof that when comprised within a guide RNA, is capable of directing the sequence-specific binding of an associated RNA-guided nuclease provided herein to a target sequence of interest. In certain embodiments, an active CRISPR repeat sequence variant of a wild-type sequence comprises a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the nucleotide sequence set forth as SEQ ID NOs: 2, 12, 20, 28, 37, 46, or 55. In certain embodiments, an active CRISPR repeat sequence fragment of a wild-type sequence comprises at least 5, 6, 7, 8, 9, 10, 11, 12, 13, 14, 15, 16, 17, 18, 19, or 20 contiguous nucleotides of the nucleotide sequence set forth as SEQ ID NOs: 2, 12, 20, 28, 37, 46, or 55.

In certain embodiments, the crRNA is not naturally-occurring. In some of these embodiments, the specific CRISPR repeat sequence is not linked to the engineered spacer sequence in nature and the CRISPR repeat sequence is considered heterologous to the spacer sequence. In certain embodiments, the spacer sequence is an engineered sequence that is not naturally occurring.

A trans-activating CRISPR RNA or tracrRNA molecule comprises a nucleotide sequence comprising a region that has sufficient complementarity to hybridize to a CRISPR repeat sequence of a crRNA, which is referred to herein as the anti-repeat region. In some embodiments, the tracrRNA molecule further comprises a region with secondary structure (e.g., stem-loop) or forms secondary structure upon hybridizing with its corresponding crRNA. In particular embodiments, the region of the tracrRNA that is fully or partially complementary to a CRISPR repeat sequence is at the 5' end of the molecule and the 3' end of the tracrRNA comprises secondary structure. This region of secondary structure generally comprises several hairpin structures, including the nexus hairpin, which is found adjacent to the anti-repeat sequence. The nexus hairpin often has a conserved nucleotide sequence in the base of the hairpin stem, with the motif UNANNG, UNANNU, or UNANNA (SEQ ID NOs: 68, 557, and 558, respectively) found in many nexus hairpins in tracrRNAs. There are often terminal hairpins at the 3' end of the tracrRNA that can vary in structure and number, but often comprise a GC-rich Rho-independent transcriptional terminator hairpin followed by a string of U's at the 3' end. See, for example, Briner et al. (2014) *Molecular Cell* 56:333-339, Briner and Barrangou (2016) *Cold Spring Haab Protoc*; doi: 10.1101/pdb.top090902, and U.S. Publication No. 2017/0275648, each of which is herein incorporated by reference in its entirety.

In various embodiments, the anti-repeat region of the tracrRNA that is fully or partially complementary to the CRISPR repeat sequence comprises from about 8 nucleotides to about 30 nucleotides, or more. For example, the region of base pairing between the tracrRNA anti-repeat sequence and the CRISPR repeat sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In particular embodiments, the anti-repeat region of the tracrRNA that is fully or partially complementary to a CRISPR repeat sequence is about 20 nucleotides in length. In some embodiments, the degree of complementarity between a CRISPR repeat sequence and its corresponding tracrRNA anti-repeat sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more.

In various embodiments, the entire tracrRNA can comprise from about 60 nucleotides to more than about 140 nucleotides. For example, the tracrRNA can be about 60, about 65, about 70, about 75, about 80, about 85, about 90, about 95, about 100, about 105, about 110, about 115, about 120, about 125, about 130, about 135, about 140, or more nucleotides in length. In particular embodiments, the tracrRNA is about 80 to about 90 nucleotides in length, including about 80, about 81, about 82, about 83, about 84, about 85, about 86, about 87, about 88, about 89, and about 90 nucleotides in length. In certain embodiments, the tracrRNA is about 85 nucleotides in length.

In particular embodiments, the tracrRNA comprises the nucleotide sequence of SEQ ID NOs: 3, 13, 21, 29, 38, 47, or 56, or an active variant or fragment thereof that when comprised within a guide RNA is capable of directing the sequence-specific binding of an associated RNA-guided nuclease provided herein to a target sequence of interest. In certain embodiments, an active tracrRNA sequence variant of a wild-type sequence comprises a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the nucleotide sequence set forth as SEQ ID NOs: 3, 13, 21, 29, 38, 47, or 56. In certain embodiments, an active tracrRNA sequence fragment of a wild-type sequence comprises at least 5, 10, 15, 20, 25, 30, 35, 40, 45, 50, 55, 60, 65, 70, 75, 80, or more contiguous nucleotides of the nucleotide sequence set forth as SEQ ID NOs: 3, 13, 21, 29, 38, 47, or 56.

Two polynucleotide sequences can be considered to be substantially complementary when the two sequences hybridize to each other under stringent conditions. Likewise, an RGN is considered to bind to a particular target sequence within a sequence-specific manner if the guide RNA bound to the RGN binds to the target sequence under stringent conditions. By "stringent conditions" or "stringent hybridization conditions" is intended conditions under which the two polynucleotide sequences will hybridize to each other to a detectably greater degree than to other sequences (e.g., at least 2-fold over background). Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3, and the temperature is at least about 30° C. for short sequences (e.g., 10 to 50 nucleotides) and at least about 60° C. for long sequences (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The Tm is the temperature (under defined ionic strength and pH) at which 50% of a complementary target sequence hybridizes to a perfectly matched sequence. For DNA-DNA hybrids, the Tm can be approximated from the equation of Meinkoth and Wahl (1984) Anal. Biochem. 138:267-284: Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, New York).

The guide RNA can be a single guide RNA or a dual-guide RNA system. A single guide RNA comprises the crRNA and tracrRNA on a single molecule of RNA, whereas a dual-guide RNA system comprises a crRNA and a tracrRNA present on two distinct RNA molecules, hybridized to one another through at least a portion of the CRISPR repeat sequence of the crRNA and at least a portion of the tracrRNA, which may be fully or partially complementary to the CRISPR repeat sequence of the crRNA. In some of those embodiments wherein the guide RNA is a single guide RNA, the crRNA and tracrRNA are separated by a linker nucleotide sequence. In general, the linker nucleotide sequence is one that does not include complementary bases in order to avoid the formation of secondary structure within or comprising nucleotides of the linker nucleotide sequence. In some embodiments, the linker nucleotide sequence between the crRNA and tracrRNA is at least 3, at least 4, at least 5, at least 6, at least 7, at least 8, at least 9, at least 10, at least 11, at least 12, or more nucleotides in length. In particular embodiments, the linker nucleotide sequence of a single guide RNA is at least 4 nucleotides in length. In certain embodiments, the linker nucleotide sequence is the nucleotide sequence set forth as SEQ ID NO: 63, 64, or 65. In other embodiments, the linker nucleotide sequence is at least 6 nucleotides in length. In certain embodiments, the linker nucleotide sequence is the nucleotide sequence set forth as SEQ ID NO: 65.

The single guide RNA or dual-guide RNA can be synthesized chemically or via in vitro transcription. Assays for determining sequence-specific binding between a RGN and a guide RNA are known in the art and include, but are not limited to, in vitro binding assays between an expressed RGN and the guide RNA, which can be tagged with a detectable label (e.g., biotin) and used in a pull-down detection assay in which the guide RNA:RGN complex is captured via the detectable label (e.g., with streptavidin beads). A control guide RNA with an unrelated sequence or structure to the guide RNA can be used as a negative control for non-specific binding of the RGN to RNA. In certain embodiments, the guide RNA is SEQ ID NO: 10, 18, 26, 35, 44, 53, or 62, wherein the spacer sequence can be any sequence and is indicated as a poly-N sequence.

As described in Example 8, certain RGNs of the invention can share certain guide RNAs. APG05083.1, APG07433.1, APG07513.1, and APG08290.1 can each function using guide RNAs comprising a crRNA comprising the nucleotide sequence of SEQ ID NOs: 2, 12, 20, or 28, with the corresponding tracrRNA comprising the nucleotide sequence of SEQ ID NOs: 3, 13, 21, or 29, respectively. Further, APG04583.1 and APG01688.1 can each function using guide RNAs comprising a crRNA comprising the nucleotide sequence of SEQ ID NOs: 46 or 55, with the corresponding tracrRNA comprising the nucleotide sequence of SEQ 47 or 56, respectively.

In certain embodiments, the guide RNA can be introduced into a target cell, organelle, or embryo as an RNA molecule. The guide RNA can be transcribed in vitro or chemically synthesized. In other embodiments, a nucleotide sequence encoding the guide RNA is introduced into the cell, organelle, or embryo. In some of these embodiments, the nucleotide sequence encoding the guide RNA is operably linked to a promoter (e.g., an RNA polymerase III promoter). The promoter can be a native promoter or heterologous to the guide RNA-encoding nucleotide sequence.

In various embodiments, the guide RNA can be introduced into a target cell, organelle, or embryo as a ribonucleoprotein complex, as described herein, wherein the guide RNA is bound to an RNA-guided nuclease polypeptide.

The guide RNA directs an associated RNA-guided nuclease to a particular target nucleotide sequence of interest through hybridization of the guide RNA to the target nucleotide sequence. A target nucleotide sequence can comprise DNA, RNA, or a combination of both and can be single-stranded or double-stranded. A target nucleotide sequence can be genomic DNA (i.e., chromosomal DNA), plasmid DNA, or an RNA molecule (e.g., messenger RNA, ribosomal RNA, transfer RNA, micro RNA, small interfering RNA). The target nucleotide sequence can be bound (and in some embodiments, cleaved) by an RNA-guided nuclease in vitro or in a cell. The chromosomal sequence targeted by the RGN can be a nuclear, plastid or mitochondrial chromosomal sequence. In some embodiments, the target nucleotide sequence is unique in the target genome.

The target nucleotide sequence is adjacent to a protospacer adjacent motif (PAM). A protospacer adjacent motif is generally within about 1 to about 10 nucleotides from the target nucleotide sequence, including about 1, about 2, about 3, about 4, about 5, about 6, about 7, about 8, about 9, or about 10 nucleotides from the target nucleotide sequence. The PAM can be 5' or 3' of the target sequence. In some embodiments, the PAM is 3' of the target sequence for the presently disclosed RGNs. Generally, the PAM is a consensus sequence of about 3-4 nucleotides, but in particular embodiments, can be 2, 3, 4, 5, 6, 7, 8, 9, or more nucleotides in length. In various embodiments, the PAM sequence recognized by the presently disclosed RGNs comprises the consensus sequence set forth as SEQ ID NOs: 6, 32, 41, 50, or 59. Non-limiting exemplary PAM sequences are the nucleotide sequences set forth as SEQ ID NO: 7, 69, 70, 71, and 72.

In particular embodiments, an RNA-guided nuclease having SEQ ID NOs: 1, 11, 19, 27, 36, 45, or 54 or an active variant or fragment thereof binds respectively a target nucleotide sequence adjacent to a PAM sequence set forth as SEQ ID NOs: 6, 32, 41, 50, 59, or 7. In some of these embodiments, the RGN binds to a guide sequence comprising a CRISPR repeat sequence set forth in SEQ ID NOs: 2, 12, 20, 28, 37, 46, or 55, respectively, or an active variant or fragment thereof, and a tracrRNA sequence set forth in SEQ ID NOs: 3, 13, 21, 29, 38, 47, or 56, respectively, or an active variant or fragment thereof. The RGN systems are described further in Example 1 and Table 1 of the present specification.

It is well-known in the art that PAM sequence specificity for a given nuclease enzyme is affected by enzyme concentration (see, e.g., Karvelis et al. (2015) *Genome Biol* 16:253), which may be modified by altering the promoter used to express the RGN, or the amount of ribonucleoprotein complex delivered to the cell, organelle, or embryo.

Upon recognizing its corresponding PAM sequence, the RGN can cleave the target nucleotide sequence at a specific cleavage site. As used herein, a cleavage site is made up of the two particular nucleotides within a target nucleotide sequence between which the nucleotide sequence is cleaved by an RGN. The cleavage site can comprise the $1^{st}$ and $2^{nd}$, $2^{nd}$ and $3^{rd}$, $3^{rd}$ and $4^{th}$, $4^{th}$ and $5^{th}$, $5^{th}$ and $6^{th}$, $7^{th}$ and $8^{th}$, or $8^{th}$ and $9^{th}$ nucleotides from the PAM in either the 5' or 3' direction. In some embodiments, the cleavage site may be over 10, 11, 12, 13, 14, 15, 16, 17, 18, 19, or 20 nucleotides from the PAM in either the 5' or 3' direction. In some embodiments, the cleavage site is 4 nucleotides away from the PAM. In other embodiments, the cleavage site is at least 15 nucleotides away from the PAM. As RGNs can cleave a target nucleotide sequence resulting in staggered ends, in some embodiments, the cleavage site is defined based on the distance of the two nucleotides from the PAM on the positive (+) strand of the polynucleotide and the distance of the two nucleotides from the PAM on the negative (−) strand of the polynucleotide.

III. Nucleotides Encoding RNA-Guided Nucleases, CRISPR RNA, and/or tracrRNA

The present disclosure provides polynucleotides comprising the presently disclosed CRISPR RNAs, tracrRNAs, and/or sgRNAs and polynucleotides comprising a nucleotide sequence encoding the presently disclosed RNA-guided nucleases, CRISPR RNAs, tracrRNAs, and/or sgRNAs. Presently disclosed polynucleotides include those comprising or encoding a CRISPR repeat sequence comprising the nucleotide sequence of SEQ ID NOs: 2, 12, 20, 28, 37, 46, or 55, or an active variant or fragment thereof that when comprised within a guide RNA is capable of directing the sequence-specific binding of an associated RNA-guided nuclease to a target sequence of interest. Also disclosed are polynucleotides comprising or encoding a tracrRNA comprising the nucleotide sequence of SEQ ID NOs: 3, 13, 21, 29, 38, 47, or 56, or an active variant or fragment thereof that when comprised within a guide RNA is capable of directing the sequence-specific binding of an associated RNA-guided nuclease to a target sequence of interest. Polynucleotides are also provided that encode an RNA-guided nuclease comprising the amino acid sequence set forth as SEQ ID NOs: 1, 11, 19, 27, 36, 45, or 54, and active fragments or variants thereof that retain the ability to bind to a target nucleotide sequence in an RNA-guided sequence-specific manner.

The use of the term "polynucleotide" is not intended to limit the present disclosure to polynucleotides comprising DNA. Those of ordinary skill in the art will recognize that polynucleotides can comprise ribonucleotides (RNA) and combinations of ribonucleotides and deoxyribonucleotides. Such deoxyribonucleotides and ribonucleotides include both naturally occurring molecules and synthetic analogues. These include peptide nucleic acids (PNAs), PNA-DNA chimers, locked nucleic acids (LNAs), and phosphothiorate linked sequences. The polynucleotides disclosed herein also encompass all forms of sequences including, but not limited to, single-stranded forms, double-stranded forms, DNA-RNA hybrids, triplex structures, stem-and-loop structures, and the like.

The nucleic acid molecules encoding RGNs can be codon optimized for expression in an organism of interest. A "codon-optimized" coding sequence is a polynucleotide coding sequence having its frequency of codon usage designed to mimic the frequency of preferred codon usage or transcription conditions of a particular host cell. Expression in the particular host cell or organism is enhanced as a result of the alteration of one or more codons at the nucleic acid level such that the translated amino acid sequence is not changed. Nucleic acid molecules can be codon optimized, either wholly or in part. Codon tables and other references providing preference information for a wide range of organisms are available in the art (see, e.g., Campbell and Gowri (1990) *Plant Physiol.* 92:1-11 for a discussion of plant-preferred codon usage). Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Polynucleotides encoding the RGNs, crRNAs, tracrRNAs, and/or sgRNAs provided herein can be provided in expression cassettes for in vitro expression or expression in a cell, organelle, embryo, or organism of interest. The cassette will include 5' and 3' regulatory sequences operably linked to a polynucleotide encoding an RGN, crRNA, tracrRNAs, and/or sgRNAs provided herein that allows for expression of the polynucleotide. The cassette may additionally contain at least one additional gene or genetic element to be cotransformed into the organism. Where additional genes or elements are included, the components are operably linked. The term "operably linked" is intended to mean a functional linkage between two or more elements. For example, an operable linkage between a promoter and a coding region of interest (e.g., region coding for an RGN, crRNA, tracrRNAs, and/or sgRNAs) is a functional link that allows for expression of the coding region of interest. Operably linked elements may be contiguous or non-contiguous. When used to refer to the joining of two protein coding regions, by operably linked is intended that the coding regions are in the same reading frame. Alternatively, the additional gene(s) or element(s) can be provided on multiple expression cassettes. For example, the nucleotide sequence encoding a presently disclosed RGN can be present on one expression cassette, whereas the nucleotide sequence encoding a crRNA, tracrRNA, or complete guide RNA can be on a separate expression cassette. Such an expression cassette is provided with a plurality of restriction sites and/or recombination sites for insertion of the polynucleotides to be under the transcriptional regulation of the regulatory regions. The expression cassette may additionally contain a selectable marker gene.

The expression cassette will include in the 5'-3' direction of transcription, a transcriptional (and, in some embodiments, translational) initiation region (i.e., a promoter), an RGN-, crRNA-, tracrRNA- and/or sgRNA-encoding polynucleotide of the invention, and a transcriptional (and in some embodiments, translational) termination region (i.e., termination region) functional in the organism of interest. The promoters of the invention are capable of directing or driving expression of a coding sequence in a host cell. The regulatory regions (e.g., promoters, transcriptional regulatory regions, and translational termination regions) may be endogenous or heterologous to the host cell or to each other. As used herein, "heterologous" in reference to a sequence is a sequence that originates from a foreign species, or, if from the same species, is substantially modified from its native form in composition and/or genomic locus by deliberate human intervention. As used herein, a chimeric gene comprises a coding sequence operably linked to a transcription initiation region that is heterologous to the coding sequence.

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional regulatory signals include, but are not limited to, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (1992) Molecular Cloning: A Laboratory Manual, ed. Maniatis et al. (Cold Spring Harbor Laboratory Press, Cold Spring Harbor, N.Y.), hereinafter "Sambrook 11"; Davis et al., eds. (1980) Advanced Bacterial Genetics (Cold Spring Harbor Laboratory Press), Cold Spring Harbor, N.Y., and the references cited therein.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, inducible, growth stage-specific, cell type-specific, tissue-preferred, tissue-specific, or other promoters for expression in the organism of interest. See, for example, promoters set forth in WO 99/43838 and in U.S. Pat. Nos. 8,575,425; 7,790,846; 8,147,856; 8,586832; 7,772,369; 7,534,939; 6,072,050; 5,659,026; 5,608,149; 5,608,144; 5,604,121; 5,569,597; 5,466,785; 5,399,680; 5,268,463; 5,608,142; and 6,177,611; herein incorporated by reference.

For expression in plants, constitutive promoters also include CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); and MAS (Velten et al. (1984) *EMBO J.* 3:2723-2730).

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the Axig1 promoter which is auxin induced and tapetum specific but also active in callus (PCT US01/22169), the steroid-responsive promoters (see, for example, the ERE promoter which is estrogen induced, and the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-specific or tissue-preferred promoters can be utilized to target expression of an expression construct within a particular tissue. In certain embodiments, the tissue-specific or tissue-preferred promoters are active in plant tissue. Examples of promoters under developmental control in plants include promoters that initiate transcription preferentially in certain tissues, such as leaves, roots, fruit, seeds, or flowers. A "tissue specific" promoter is a promoter that initiates transcription only in certain tissues. Unlike constitutive expression of genes, tissue-specific expression is the result of several interacting levels of gene regulation. As such, promoters from homologous or closely related plant species can be preferable to use to achieve efficient and reliable expression of transgenes in particular tissues. In some embodiments, the expression comprises a tissue-preferred promoter. A "tissue preferred" promoter is a promoter that initiates transcription preferentially, but not necessarily entirely or solely in certain tissues.

In some embodiments, the nucleic acid molecules encoding a RGN, crRNA, and/or tracrRNA comprise a cell type-specific promoter. A "cell type specific" promoter is a promoter that primarily drives expression in certain cell types in one or more organs. Some examples of plant cells in which cell type specific promoters functional in plants may be primarily active include, for example, BETL cells, vascular cells in roots, leaves, stalk cells, and stem cells. The nucleic acid molecules can also include cell type preferred promoters. A "cell type preferred" promoter is a promoter that primarily drives expression mostly, but not necessarily entirely or solely in certain cell types in one or more organs. Some examples of plant cells in which cell type preferred promoters functional in plants may be preferentially active include, for example, BETL cells, vascular cells in roots, leaves, stalk cells, and stem cells.

The nucleic acid sequences encoding the RGNs, crRNAs, tracrRNAs, and/or sgRNAs can be operably linked to a promoter sequence that is recognized by a phage RNA polymerase for example, for in vitro mRNA synthesis. In such embodiments, the in vitro-transcribed RNA can be purified for use in the methods described herein. For example, the promoter sequence can be a T7, T3, or SP6 promoter sequence or a variation of a T7, T3, or SP6 promoter sequence. In such embodiments, the expressed protein and/or RNAs can be purified for use in the methods of genome modification described herein.

In certain embodiments, the polynucleotide encoding the RGN, crRNA, tracrRNA, and/or sgRNA also can be linked to a polyadenylation signal (e.g., SV40 polyA signal and other signals functional in plants) and/or at least one transcriptional termination sequence. Additionally, the sequence encoding the RGN also can be linked to sequence(s) encoding at least one nuclear localization signal, at least one cell-penetrating domain, and/or at least one signal peptide capable of trafficking proteins to particular subcellular locations, as described elsewhere herein.

The polynucleotide encoding the RGN, crRNA, tracrRNA, and/or sgRNA can be present in a vector or multiple vectors. A "vector" refers to a polynucleotide composition for transferring, delivering, or introducing a nucleic acid into a host cell. Suitable vectors include plasmid vectors, phagemids, cosmids, artificial/mini-chromosomes, transposons, and viral vectors (e.g., lentiviral vectors, adeno-associated viral vectors, baculoviral vector). The vector can comprise additional expression control sequences (e.g., enhancer sequences, Kozak sequences, polyadenylation sequences, transcriptional termination sequences), selectable marker sequences (e.g., antibiotic resistance genes), origins of replication, and the like. Additional information can be found in "*Current Protocols in Molecular Biology*" Ausubel et al., John Wiley & Sons, New York, 2003 or "*Molecular Cloning: A Laboratory Manual*" Sambrook & Russell, Cold Spring Harbor Press, Cold Spring Harbor, N.Y., 3rd edition, 2001.

The vector can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D).

In some embodiments, the expression cassette or vector comprising the sequence encoding the RGN polypeptide can further comprise a sequence encoding a crRNA and/or a tracrRNA, or the crRNA and tracrRNA combined to create a guide RNA. The sequence(s) encoding the crRNA and/or tracrRNA can be operably linked to at least one transcriptional control sequence for expression of the crRNA and/or tracrRNA in the organism or host cell of interest. For example, the polynucleotide encoding the crRNA and/or tracrRNA can be operably linked to a promoter sequence that is recognized by RNA polymerase III (Pol III). Examples of suitable Pol III promoters include, but are not limited to, mammalian U6, U3, H1, and 7SL RNA promoters and rice U6 and U3 promoters.

As indicated, expression constructs comprising nucleotide sequences encoding the RGNs, crRNA, tracrRNA, and/or sgRNA can be used to transform organisms of interest. Methods for transformation involve introducing a nucleotide construct into an organism of interest. By "introducing" is intended to introduce the nucleotide construct to the host cell in such a manner that the construct gains access to the interior of the host cell. The methods of the invention do not require a particular method for introducing a nucleotide construct to a host organism, only that the nucleotide construct gains access to the interior of at least one cell of the host organism. The host cell can be a eukaryotic or prokaryotic cell. In particular embodiments, the eukaryotic host cell is a plant cell, a mammalian cell, or an insect cell. Methods for introducing nucleotide constructs into plants and other host cells are known in the art including, but not limited to, stable transformation methods, transient transformation methods, and virus-mediated methods.

The methods result in a transformed organism, such as a plant, including whole plants, as well as plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic organisms" or "transformed organisms" or "stably transformed" organisms or cells or tissues refers to organisms that have incorporated or integrated a polynucleotide encoding a RGN, crRNA, and/or tracrRNA of the invention. It is recognized that other exogenous or endogenous nucleic acid sequences or DNA fragments may also be incorporated into the host cell. *Agrobacterium*-and biolistic-mediated transformation remain the two predominantly employed approaches for transformation of plant cells. However, transformation of a host cell may be performed by infection, transfection, microinjection, electroporation, microprojection, biolistics or particle bombardment, electroporation, silica/carbon fibers, ultrasound mediated, PEG mediated, calcium phosphate co-precipitation, polycation DMSO technique, DEAE dextran procedure, and viral mediated, liposome mediated and the like. Viral-mediated introduction of a polynucleotide encoding an RGN, crRNA, and/or tracrRNA includes retroviral, lentiviral, adenoviral, and adeno-associated viral mediated introduction and expression, as well as the use of Caulimoviruses, Geminiviruses, and RNA plant viruses.

Transformation protocols as well as protocols for introducing polypeptides or polynucleotide sequences into plants may vary depending on the type of host cell (e.g., monocot or dicot plant cell) targeted for transformation. Methods for transformation are known in the art and include those set forth in U.S. Pat. Nos. 8,575,425; 7,692,068; 8,802,934; 7,541,517; each of which is herein incorporated by reference. See, also, Rakoczy-Trojanowska, M. (2002) *Cell Mol Biol Lett.* 7:849-858; Jones et al. (2005) *Plant Methods* 1:5; Rivera et al. (2012) *Physics of Life Reviews* 9:308-345; Bartlett et al. (2008) *Plant Methods* 4:1-12; Bates, G. W. (1999) *Methods in Molecular Biology* 111:359-366; Binns and Thomashow (1988) *Annual Reviews in Microbiology* 42:575-606; Christou, P. (1992) *The Plant Journal* 2:275-281; Christou, P. (1995) *Euphytica* 85:13-27; Tzfira et al. (2004) *TRENDS in Genetics* 20:375-383; Yao et al. (2006) *Journal of Experimental Botany* 57:3737-3746; Zupan and Zambryski (1995) *Plant Physiology* 107:1041-1047; Jones et al. (2005) *Plant Methods* 1:5;

Transformation may result in stable or transient incorporation of the nucleic acid into the cell. "Stable transformation" is intended to mean that the nucleotide construct introduced into a host cell integrates into the genome of the host cell and is capable of being inherited by the progeny thereof. "Transient transformation" is intended to mean that a polynucleotide is introduced into the host cell and does not integrate into the genome of the host cell.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into a transgenic organism, such as a plant, in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Alternatively, cells that have been transformed may be introduced into an organism. These cells could have originated from the organism, wherein the cells are transformed in an ex vivo approach.

The sequences provided herein may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassaya, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. Further provided is a processed plant product or byproduct that retains the sequences disclosed herein, including for example, soymeal.

The polynucleotides encoding the RGNs, crRNAs, and/or tracrRNAs can also be used to transform any prokaryotic species, including but not limited to, archaea and bacteria (e.g., *Bacillus* sp., *Klebsiella* sp. *Streptomyces* sp., *Rhizobium* sp., *Escherichia* sp., *Pseudomonas* sp., *Salmonella* sp., *Shigella* sp., *Vibrio* sp., *Yersinia* sp., *Mycoplasma* sp., *Agrobacterium, Lactobacillus* sp.).

The polynucleotides encoding the RGNs, crRNAs, and/or tracrRNAs can be used to transform any eukaryotic species, including but not limited to animals (e.g., mammals, insects, fish, birds, and reptiles), fungi, amoeba, algae, and yeast.

Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256: 808-813 (1992); Nabel & Feigner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10): 1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology, Doerfler and Bohm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration). The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Viral. 66:2731-2739 (1992); Johann et al., J. Viral. 66:1635-1640 (1992); Sommnerfelt et al., Viral. 176:58-59 (1990); Wilson et al., J. Viral. 63:2374-2378 (1989); Miller et al., 1. Viral. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Katin, Human Gene Therapy 5:793-801 (1994); Muzyczka, 1. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Viral. 63:03822-3828 (1989). Packaging cells are typically used to form virus particles that are capable of infecting a host cell. Such cells include 293 cells, which package adenovirus, and ψJ2 cells or PA317 cells, which package retrovirus.

Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences.

The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLaS3, Huhl, Huh4, Huh7, HUVEC, HASMC, HEKn, HEKa, MiaPaCell, Panel, PC-3, TF1, CTLL-2, CIR, Rath, CVI, RPTE, A10, T24, 182, A375, ARH-77, Calul, SW480, SW620, SKOV3, SK-UT, CaCo2, P388D1, SEM-K2, WEHI-231, HB56, TIB55, lurkat, 145.01, LRMB, Bcl-1, BC-3, IC21, DLD2, Raw264.7, NRK, NRK-52E, MRCS, MEF, Hep G2, HeLa B, HeLa T4. COS, COS-1, COS-6, COS-M6A, BS-C-1 monkey kidney epithelial, BALB/3T3 mouse embryo fibroblast, 3T3 Swiss, 3T3-Ll, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-I cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr−/−, COR-L23, COR-L23/CPR, COR-L235010, CORL23/R23, COS-7, COV-434, CML Tl, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepalcic7, HL-60, HMEC, HT-29, lurkat, lY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCKII, MDCKII, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit.

IV. Variants and Fragments of Polypeptides and Polynucleotides

The present disclosure provides active variants and fragments of a naturally-occurring (i.e., wild-type) RNA-guided nuclease, the amino acid sequence of which is set forth as SEQ ID NOs: 1, 11, 19, 27, 36, 45, or 54, as well as active variants and fragments of naturally-occurring CRISPR repeats, such as the sequence set forth as SEQ ID NOs: 2, 12, 20, 28, 37, 46, or 55, and active variant and fragments of naturally-occurring tracrRNAs, such as the sequence set forth as SEQ ID NOs: 3, 13, 21, 29, 38, 47, or 56, and polynucleotides encoding the same.

While the activity of a variant or fragment may be altered compared to the polynucleotide or polypeptide of interest, the variant and fragment should retain the functionality of the polynucleotide or polypeptide of interest. For example, a variant or fragment may have increased activity, decreased activity, different spectrum of activity or any other alteration in activity when compared to the polynucleotide or polypeptide of interest.

Fragments and variants of naturally-occurring RGN polypeptides, such as those disclosed herein, will retain sequence-specific, RNA-guided DNA-binding activity. In particular embodiments, fragments and variants of naturally-occurring RGN polypeptides, such as those disclosed herein, will retain nuclease activity (single-stranded or double-stranded).

Fragments and variants of naturally-occurring CRISPR repeats, such as those disclosed herein, will retain the ability, when part of a guide RNA (comprising a tracrRNA), to bind to and guide an RNA-guided nuclease (complexed with the guide RNA) to a target nucleotide sequence in a sequence-specific manner.

Fragments and variants of naturally-occurring tracrRNAs, such as those disclosed herein, will retain the ability, when part of a guide RNA (comprising a CRISPR RNA), to guide an RNA-guided nuclease (complexed with the guide RNA) to a target nucleotide sequence in a sequence-specific manner.

The term “fragment” refers to a portion of a polynucleotide or polypeptide sequence of the invention. “Fragments” or “biologically active portions” include polynucleotides comprising a sufficient number of contiguous nucleotides to retain the biological activity (i.e., binding to and directing an RGN in a sequence-specific manner to a target nucleotide sequence when comprised within a guideRNA). “Fragments” or “biologically active portions” include polypeptides comprising a sufficient number of contiguous amino acid residues to retain the biological activity (i.e., binding to a target nucleotide sequence in a sequence-specific manner when complexed with a guide RNA). Fragments of the RGN proteins include those that are shorter than the full-length sequences due to the use of an alternate downstream start site. A biologically active portion of an RGN protein can be a polypeptide that comprises, for example, 10, 25, 50, 100, 150, 200, 250, 300, 350, 400, 450, 500, 550, 600, 650, 700, 750, 800, 850, 900, 950, 1000, 1050 or more contiguous amino acid residues of SEQ ID NOs: 1, 11, 19, 27, 36, 45, or 54. Such biologically active portions can be prepared by recombinant techniques and evaluated for sequence-specific, RNA-guided DNA-binding activity. A biologically active fragment of a CRISPR repeat sequence can comprise at least 8 contiguous amino acids of SEQ ID NOs: 2, 12, 20, 28, 37, 46, or 55. A biologically active portion of a CRISPR repeat sequence can be a polynucleotide that comprises, for example, 8, 9, 10, 11, 12, 13, 14, 15, 16, 17, 18, 19, or 20 contiguous nucleotides of SEQ ID NOs: 2, 12, 20, 28, 37, 46, or 55. A biologically active portion of a tracrRNA can be a polynucleotide that comprises, for example, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80 or more contiguous nucleotides of SEQ ID NOs: 3, 13, 21, 29, 38, 47, or 56.

In general, “variants” is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a “native” or “wild type” polynucleotide or polypeptide comprises a naturally occurring nucleotide sequence or amino acid sequence, respectively. For polynucleotides, conservative variants include those sequences that, because of the degeneracy of the genetic code, encode the native amino acid sequence of the gene of interest. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode the polypeptide or the polynucleotide of interest. Generally, variants of a particular polynucleotide disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide disclosed herein (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides disclosed herein is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

In particular embodiments, the presently disclosed polynucleotides encode an RNA-guided nuclease polypeptide comprising an amino acid sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to an amino acid sequence of SEQ ID NOs: 1, 11, 19, 27, 36, 45, or 54.

A biologically active variant of an RGN polypeptide of the invention may differ by as few as about 1-15 amino acid residues, as few as about 1-10, such as about 6-10, as few as 5, as few as 4, as few as 3, as few as 2, or as few as 1 amino acid residue. In specific embodiments, the polypeptides can comprise an N-terminal or a C-terminal truncation, which can comprise at least a deletion of 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050 amino acids or more from either the N or C terminus of the polypeptide.

In certain embodiments, the presently disclosed polynucleotides comprise or encode a CRISPR repeat comprising a nucleotide sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to the nucleotide sequence set forth as SEQ ID NOs: 2, 12, 20, 28, 37, 46, or 55.

The presently disclosed polynucleotides can comprise or encode a tracrRNA comprising a nucleotide sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to the nucleotide sequence set forth as SEQ ID NOs: 3, 13, 21, 29, 38, 47, or 56.

Biologically active variants of a CRISPR repeat or tracrRNA of the invention may differ by as few as about 1-15 nucleotides, as few as about 1-10, such as about 6-10, as few as 5, as few as 4, as few as 3, as few as 2, or as few as 1 nucleotides. In specific embodiments, the polynucleotides can comprise a 5' or 3' truncation, which can comprise at least a deletion of 10, 15, 20, 25, 30, 35, 40, 45, 50, 55, 60, 65, 70, 75, 80 nucleotides or more from either the 5' or 3' end of the polynucleotide.

It is recognized that modifications may be made to the RGN polypeptides, CRISPR repeats, and tracrRNAs provided herein creating variant proteins and polynucleotides. Changes designed by man may be introduced through the application of site-directed mutagenesis techniques. Alternatively, native, as yet-unknown or as yet unidentified polynucleotides and/or polypeptides structurally and/or functionally-related to the sequences disclosed herein may also be identified that fall within the scope of the present invention. Conservative amino acid substitutions may be made in nonconserved regions that do not alter the function of the RGN proteins. Alternatively, modifications may be made that improve the activity of the RGN.

Variant polynucleotides and proteins also encompass sequences and proteins derived from a mutagenic and recombinogenic procedure such as DNA shuffling. With such a procedure, one or more different RGN proteins disclosed herein (e.g., SEQ ID NOs: 1, 11, 19, 27, 36, 45, or 54) is manipulated to create a new RGN protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the RGN sequences provided herein and other known RGN genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458. A "shuffled" nucleic acid is a nucleic acid produced by a shuffling procedure such as any shuffling procedure set forth herein. Shuffled nucleic acids are produced by recombining (physically or virtually) two or more nucleic acids (or character strings), for example in an artificial, and optionally recursive, fashion. Generally, one or more screening steps are used in shuffling processes to identify nucleic acids of interest; this screening step can be performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins." In "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Natl. Acad. Sci. USA 89:10915-10919. The BLOSUM62 matrix is often used as a default scoring substitution matrix in sequence alignment protocols. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucleic Acids Res.* 25:3389-3402, and made available to the public at the National Center for Biotechnology Information Website (www.ncbi.nlm.nih.gov). Optimal alignments, including multiple alignments, can be prepared using, e.g., PSI-BLAST, available through www.ncbi.nlm.nih.gov and described by Altschul et al. (1997) *Nucleic Acids Res.* 25:3389-3402.

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

V. Antibodies

Antibodies to the RGN polypeptides or ribonucleoproteins comprising the RGN polypeptides of the present invention, including those having the amino acid sequence set forth as SEQ ID NOs: 1, 11, 19, 27, 36, 45, or 54 or active variants or fragments thereof, are also encompassed. Methods for producing antibodies are well known in the art (see, for example, Harlow and Lane (1988) Antibodies: A Laboratory Manual, Cold Spring Harbor Laboratory, Cold Spring Harbor, N.Y.; and U.S. Pat. No. 4,196,265). These antibodies can be used in kits for the detection and isolation of RGN polypeptides or ribonucleoproteins. Thus, this disclosure provides kits comprising antibodies that specifically bind to the polypeptides or ribonucleoproteins described herein, including, for example, polypeptides having the sequence of SEQ ID NOs: 1, 11, 19, 27, 36, 45, or 54.

VI. Systems and Ribonucleoprotein Complexes for Binding a Target Sequence of Interest and Methods of Making the Same The present disclosure provides a system for binding a target sequence of interest, wherein the system comprises at least one guide RNA or a nucleotide sequence encoding the same, and at least one RNA-guided nuclease or a nucleotide sequence encoding the same. The guide RNA hybridizes to the target sequence of interest and also forms a complex with the RGN polypeptide, thereby directing the RGN polypeptide to bind to the target sequence. In some of these embodiments, the RGN comprises an amino acid sequence of SEQ ID NOs: 1, 11, 19, 27, 36, 45, or 54, or an active variant or fragment thereof. In various embodiments, the guide RNA comprises a CRISPR repeat sequence comprising the nucleotide sequence of SEQ ID NOs: 2, 12, 20, 28, 37, 46, or 55, or an active variant or fragment thereof. In particular embodiments, the guide RNA comprises a tracrRNA comprising a nucleotide sequence of SEQ ID NOs: 3, 13, 21, 29, 38, 47, or 56, or an active variant or fragment thereof. The guide RNA of the system can be a single guide RNA or a dual-guide RNA. In particular embodiments, the system comprises a RNA-guided nuclease that is heterologous to the guideRNA, wherein the RGN and guideRNA are not naturally complexed in nature.

The system for binding a target sequence of interest provided herein can be a ribonucleoprotein complex, which is at least one molecule of an RNA bound to at least one protein. The ribonucleoprotein complexes provided herein comprise at least one guide RNA as the RNA component and an RNA-guided nuclease as the protein component. Such ribonucleoprotein complexes can be purified from a cell or organism that naturally expresses an RGN polypeptide and has been engineered to express a particular guide RNA that is specific for a target sequence of interest. Alternatively, the ribonucleoprotein complex can be purified from a cell or organism that has been transformed with polynucleotides that encode an RGN polypeptide and a guide RNA and cultured under conditions to allow for the expression of the RGN polypeptide and guide RNA. Thus, methods are provided for making an RGN polypeptide or an RGN ribonucleoprotein complex. Such methods comprise culturing a cell comprising a nucleotide sequence encoding an RGN polypeptide, and in some embodiments a nucleotide sequence encoding a guide RNA, under conditions in which the RGN polypeptide (and in some embodiments, the guide RNA) is expressed. The RGN polypeptide or RGN ribonucleoprotein can then be purified from a lysate of the cultured cells.

Methods for purifying an RGN polypeptide or RGN ribonucleoprotein complex from a lysate of a biological sample are known in the art (e.g., size exclusion and/or affinity chromatography, 2D-PAGE, HPLC, reversed-phase chromatography, immunoprecipitation). In particular methods, the RGN polypeptide is recombinantly produced and comprises a purification tag to aid in its purification, including but not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His, 10×His, biotin carboxyl carrier protein (BCCP), and calmodulin. Generally, the tagged RGN polypeptide or RGN ribonucleoprotein complex is purified using immobilized metal affinity chromatography. It will be appreciated that other similar methods known in the art may be used, including other forms of chromatography or for example immunoprecipitation, either alone or in combination.

An "isolated" or "purified" polypeptide, or biologically active portion thereof, is substantially or essentially free from components that normally accompany or interact with the polypeptide as found in its naturally occurring environment. Thus, an isolated or purified polypeptide is substantially free of other cellular material, or culture medium when produced by recombinant techniques, or substantially free of chemical precursors or other chemicals when chemically synthesized. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Particular methods provided herein for binding and/or cleaving a target sequence of interest involve the use of an in vitro assembled RGN ribonucleoprotein complex. In vitro assembly of an RGN ribonucleoprotein complex can be performed using any method known in the art in which an RGN polypeptide is contacted with a guide RNA under conditions to allow for binding of the RGN polypeptide to the guide RNA. As used herein, "contact", contacting", "contacted," refer to placing the components of a desired reaction together under conditions suitable for carrying out the desired reaction. The RGN polypeptide can be purified from a biological sample, cell lysate, or culture medium, produced via in vitro translation, or chemically synthesized. The guide RNA can be purified from a biological sample, cell lysate, or culture medium, transcribed in vitro, or chemically synthesized. The RGN polypeptide and guide RNA can be brought into contact in solution (e.g., buffered saline solution) to allow for in vitro assembly of the RGN ribonucleoprotein complex.

VII. Methods of Binding, Cleaving, or Modifying a Target Sequence

The present disclosure provides methods for binding, cleaving, and/or modifying a target nucleotide sequence of interest. The methods include delivering a system comprising at least one guide RNA or a polynucleotide encoding the same, and at least one RGN polypeptide or a polynucleotide encoding the same to the target sequence or a cell, organelle, or embryo comprising the target sequence. In some of these embodiments, the RGN comprises the amino acid sequence of SEQ ID NOs: 1, 11, 19, 27, 36, 45, or 54, or an active variant or fragment thereof. In various embodiments, the guide RNA comprises a CRISPR repeat sequence comprising the nucleotide sequence of SEQ ID NOs: 2, 12, 20, 28, 37, 46, or 55, or an active variant or fragment thereof. In particular embodiments, the guide RNA comprises a tracrRNA comprising the nucleotide sequence of SEQ ID NOs: 3, 13, 21, 29, 38, 47, or 56, or an active variant or fragment thereof. The guide RNA of the system can be a single guide RNA or a dual-guide RNA. The RGN of the system may be nuclease dead RGN, have nickase activity, or may be a fusion polypeptide. In some embodiments, the fusion polypeptide comprises a base-editing polypeptide, for example a cytidine deaminase or an adenosine deaminase. In particular embodiments, the RGN and/or guide RNA is heterologous to the cell, organelle, or embryo to which the RGN and/or guide RNA (or polynucleotide(s) encoding at least one of the RGN and guide RNA) are introduced.

In those embodiments wherein the method comprises delivering a polynucleotide encoding a guide RNA and/or an RGN polypeptide, the cell or embryo can then be cultured under conditions in which the guide RNA and/or RGN polypeptide are expressed. In various embodiments, the method comprises contacting a target sequence with an RGN ribonucleoprotein complex. The RGN ribonucleoprotein complex may comprise an RGN that is nuclease dead or has nickase activity. In some embodiments, the RGN of the ribonucleoprotein complex is a fusion polypeptide comprising a base-editing polypeptide. In certain embodiments, the method comprises introducing into a cell, organelle, or embryo comprising a target sequence an RGN ribonucleoprotein complex. The RGN ribonucleoprotein complex can be one that has been purified from a biological sample, recombinantly produced and subsequently purified, or in vitro-assembled as described herein. In those embodiments wherein the RGN ribonucleoprotein complex that is contacted with the target sequence or a cell organelle, or embryo has been assembled in vitro, the method can further comprise the in vitro assembly of the complex prior to contact with the target sequence, cell, organelle, or embryo.

A purified or in vitro assembled RGN ribonucleoprotein complex can be introduced into a cell, organelle, or embryo using any method known in the art, including, but not limited to electroporation. Alternatively, an RGN polypeptide and/or polynucleotide encoding or comprising the guide RNA can be introduced into a cell, organelle, or embryo using any method known in the art (e.g., electroporation).

Upon delivery to or contact with the target sequence or cell, organelle, or embryo comprising the target sequence, the guide RNA directs the RGN to bind to the target sequence in a sequence-specific manner. In those embodiments wherein the RGN has nuclease activity, the RGN polypeptide cleaves the target sequence of interest upon binding. The target sequence can subsequently be modified via endogenous repair mechanisms, such as non-homologous end joining, or homology-directed repair with a provided donor polynucleotide.

Methods to measure binding of an RGN polypeptide to a target sequence are known in the art and include chromatin immunoprecipitation assays, gel mobility shift assays, DNA pull-down assays, reporter assays, microplate capture and detection assays. Likewise, methods to measure cleavage or modification of a target sequence are known in the art and include in vitro or in vivo cleavage assays wherein cleavage is confirmed using PCR, sequencing, or gel electrophoresis, with or without the attachment of an appropriate label (e.g., radioisotope, fluorescent substance) to the target sequence to facilitate detection of degradation products. Alternatively, the nicking triggered exponential amplification reaction (NTEXPAR) assay can be used (see, e.g., Zhang et al. (2016) *Chem. Sci.* 7:4951-4957). In vivo cleavage can be evaluated using the Surveyor assay (Guschin et al. (2010) *Methods Mol Biol* 649:247-256).

In some embodiments, the methods involve the use of a single type of RGN complexed with more than one guide RNA. The more than one guide RNA can target different regions of a single gene or can target multiple genes.

In those embodiments wherein a donor polynucleotide is not provided, a double-stranded break introduced by an RGN polypeptide can be repaired by a non-homologous end-joining (NHEJ) repair process. Due to the error-prone nature of NHEJ, repair of the double-stranded break can result in a modification to the target sequence. As used herein, a "modification" in reference to a nucleic acid molecule refers to a change in the nucleotide sequence of the nucleic acid molecule, which can be a deletion, insertion, or substitution of one or more nucleotides, or a combination thereof. Modification of the target sequence can result in the expression of an altered protein product or inactivation of a coding sequence.

In those embodiments wherein a donor polynucleotide is present, the donor sequence in the donor polynucleotide can be integrated into or exchanged with the target nucleotide sequence during the course of repair of the introduced double-stranded break, resulting in the introduction of the exogenous donor sequence. A donor polynucleotide thus comprises a donor sequence that is desired to be introduced into a target sequence of interest. In some embodiments, the donor sequence alters the original target nucleotide sequence such that the newly integrated donor sequence will not be recognized and cleaved by the RGN. Integration of the donor sequence can be enhanced by the inclusion within the donor polynucleotide of flanking sequences that have substantial sequence identity with the sequences flanking the target nucleotide sequence, allowing for a homology-directed repair process. In those embodiments wherein the RGN polypeptide introduces double-stranded staggered breaks, the donor polynucleotide can comprise a donor sequence flanked by compatible overhangs, allowing for direct ligation of the donor sequence to the cleaved target nucleotide sequence comprising overhangs by a non-homologous repair process during repair of the double-stranded break.

In those embodiments wherein the method involves the use of an RGN that is a nickase (i.e., is only able to cleave a single strand of a double-stranded polynucleotide), the method can comprise introducing two RGN nickases that target identical or overlapping target sequences and cleave different strands of the polynucleotide. For example, an RGN nickase that only cleaves the positive (+) strand of a double-stranded polynucleotide can be introduced along with a second RGN nickase that only cleaves the negative (−) strand of a double-stranded polynucleotide.

In various embodiments, a method is provided for binding a target nucleotide sequence and detecting the target sequence, wherein the method comprises introducing into a cell, organelle, or embryo at least one guide RNA or a polynucleotide encoding the same, and at least one RGN polypeptide or a polynucleotide encoding the same, expressing the guide RNA and/or RGN polypeptide (if coding sequences are introduced), wherein the RGN polypeptide is a nuclease-dead RGN and further comprises a detectable label, and the method further comprises detecting the detectable label. The detectable label may be fused to the RGN as a fusion protein (e.g., fluorescent protein) or may be a small molecule conjugated to or incorporated within the RGN polypeptide that can be detected visually or by other means.

Also provided herein are methods for modulating the expression of a target sequence or a gene of interest under the regulation of a target sequence. The methods comprise introducing into a cell, organelle, or embryo at least one guide RNA or a polynucleotide encoding the same, and at least one RGN polypeptide or a polynucleotide encoding the same, expressing the guide RNA and/or RGN polypeptide (if coding sequences are introduced), wherein the RGN polypeptide is a nuclease-dead RGN. In some of these embodiments, the nuclease-dead RGN is a fusion protein comprising an expression modulator domain (i.e., epigenetic modification domain, transcriptional activation domain or a transcriptional repressor domain) as described herein.

The present disclosure also provides methods for binding and/or modifying a target nucleotide sequence of interest. The methods include delivering a system comprising at least one guide RNA or a polynucleotide encoding the same, and at least one fusion polypeptide comprises an RGN of the invention and a base-editing polypeptide, for example a cytidine deaminase or an adenosine deaminase, or a polynucleotide encoding the fusion polypeptide, to the target sequence or a cell, organelle, or embryo comprising the target sequence.

One of ordinary skill in the art will appreciate that any of the presently disclosed methods can be used to target a single target sequence or multiple target sequences. Thus, methods comprise the use of a single RGN polypeptide in combination with multiple, distinct guide RNAs, which can target multiple, distinct sequences within a single gene and/or multiple genes. Also encompassed herein are methods wherein multiple, distinct guide RNAs are introduced in combination with multiple, distinct RGN polypeptides. These guide RNAs and guide RNA/RGN polypeptide systems can target multiple, distinct sequences within a single gene and/or multiple genes.

In one aspect, the invention provides kits containing any one or more of the elements disclosed in the above methods and compositions. In some embodiments, the kit comprises a vector system and instructions for using the kit. In some embodiments, the vector system comprises (a) a first regulatory element operably linked to a tracr mate sequence and one or more insertion sites for inserting a guide sequence upstream of the tracr mate sequence, wherein when expressed, the guide sequence directs sequence-specific binding of a CRISPR complex to a target sequence in a eukaryotic cell, wherein the CRISPR complex comprises a CRIS PR enzyme complexed with (1) the guide sequence that is hybridized to the target sequence, and (2) the tracr mate sequence that is hybridized to the tracr sequence; and/or (b) a second regulatory element operably linked to an enzyme coding sequence encoding said CRISPR enzyme comprising a nuclear localization sequence. Elements may be provided individually or in combinations, and may be provided in any suitable container, such as a vial, a bottle, or a tube.

In some embodiments, the kit includes instructions in one or more languages. In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10.

In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide.

VIII. Target Polynucleotides

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including microalgae) and modifying the cell or cells. Culturing may occur at any stage ex vivo. The cell or cells may even be re-introduced into the non-human animal or plant (including micro-algae).

Using natural variability, plant breeders combine most useful genes for desirable qualities, such as yield, quality, uniformity, hardiness, and resistance against pests. These desirable qualities also include growth, day length preferences, temperature requirements, initiation date of floral or reproductive development, fatty acid content, insect resistance, disease resistance, nematode resistance, fungal resistance, herbicide resistance, tolerance to various environmental factors including drought, heat, wet, cold, wind, and adverse soil conditions including high salinity The sources of these useful genes include native or foreign varieties, heirloom varieties, wild plant relatives, and induced mutations, e.g., treating plant material with mutagenic agents. Using the present invention, plant breeders are provided with a new tool to induce mutations. Accordingly, one skilled in the art can analyze the genome for sources of useful genes, and in varieties having desired characteristics or traits employ the present invention to induce the rise of useful genes, with more precision than previous mutagenic agents and hence accelerate and improve plant breeding programs.

The target polynucleotide of an RGN system can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence).

The target polynucleotide of a CRISPR complex may include a number of disease-associated genes and polynucleotides as well as signaling biochemical pathway-associated genes and polynucleotides. Examples of target polynucleotides include a sequence associated with a signaling biochemical pathway, e.g., a signaling biochemical pathway-associated gene or polynucleotide. Examples of target polynucleotides include a disease associated gene or polynucleotide. A “disease-associated” gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease (e.g., a causal mutation). The transcribed or translated products may be known or unknown, and further may be at a normal or abnormal level. Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

Although CRISPR systems are particularly useful for their relative ease in targeting to genomic sequences of interest, there still remains an issue of what the RGN can do to address a causal mutation. One approach is to produce a fusion protein between an RGN (preferably an inactive or nickase variant of the RGN) and a base-editing enzyme or the active domain of a base editing enzyme, such as an cytidine deaminase or an adenosine deaminase base editor (U.S. Pat. No. 9,840,699, herein incorporated by reference). In some embodiments, the methods comprise contacting a DNA molecule with (a) a fusion protein comprising an RGN of the invention and a base-editing polypeptide such as a deaminase; and (b) a gRNA targeting the fusion protein of (a) to a target nucleotide sequence of the DNA strand; wherein the DNA molecule is contacted with the fusion protein and the gRNA in an amount effective and under conditions suitable for the deamination of a nucleotide base. In some embodiments, the target DNA sequence comprises a sequence associated with a disease or disorder, and wherein the deamination of the nucleotide base results in a sequence that is not associated with a disease or disorder. In some embodiments, the target DNA sequence resides in an allele of a crop plant, wherein the particular allele of the trait of interest results in a plant of lesser agronomic value. The deamination of the nucleotide base results in an allele that improves the trait and increases the agronomic value of the plant.

In some embodiments, the DNA sequence comprises a T→C or A→G point mutation associated with a disease or disorder, and wherein the deamination of the mutant C or G base results in a sequence that is not associated with a disease or disorder. In some embodiments, the deamination corrects a point mutation in the sequence associated with the disease or disorder.

In some embodiments, the sequence associated with the disease or disorder encodes a protein, and wherein the deamination introduces a stop codon into the sequence associated with the disease or disorder, resulting in a truncation of the encoded protein. In some embodiments, the contacting is performed in vivo in a subject susceptible to having, having, or diagnosed with the disease or disorder. In some embodiments, the disease or disorder is a disease associated with a point mutation, or a single-base mutation, in the genome. In some embodiments, the disease is a genetic disease, a cancer, a metabolic disease, or a lysosomal storage disease.

Further examples of loci which are causal for certain genetic diseases, particularly loci which can be readily targeted by RGNs or RGN-base editor fusion proteins of the invention, can be found in Example 9 and corresponding Table 12.

Hurler Syndrome

An example of a genetically inherited disease which could be corrected using an approach that relies on an RGN-base editor fusion protein of the invention is Hurler Syndrome. Hurler Syndrome, also known as MPS-1, is the result of a deficiency of α-L-iduronidase (IDUA) resulting in a lysosomal storage disease characterized at the molecular level by the accumulation of dermatan sulfate and heparan sulfate in lysosomes. This disease is generally an inherited genetic disorder caused by mutations in the IDUA gene encoding α-L-iduronidase. Common IDUA mutations are W402X and Q70X, both nonsense mutations resulting in premature termination of translation. Such mutations are well addressed by precise genome editing (PGE) approaches, since reversion of a single nucleotide, for example by a base-editing approach, would restore the wild-type coding sequence and result in protein expression controlled by the endogenous regulatory mechanisms of the genetic locus. Additionally, since heterozygotes are known to be asymptomatic, a PGE therapy that targets one of these mutations would be useful to a large proportion of patients with this disease, as only one of the mutated alleles needs to be corrected (Bunge et al. (1994) Hum. Mol. Genet. 3(6): 861-866, herein incorporated by reference).

Current treatments for Hurler Syndrome include enzyme replacement therapy and bone marrow transplants (Vellodi et al. (1997) Arch. Dis. Child. 76(2): 92-99; Peters et al. (1998) *Blood* 91(7): 2601-2608, herein incorporated by reference). While enzyme replacement therapy has had a dramatic effect on the survival and quality of life of Hurler Syndrome patients, this approach requires costly and time-consuming weekly infusions. Additional approaches include the delivery of the IDUA gene on an expression vector or the insertion of the gene into a highly expressed locus such as that of serum albumin (U.S. Pat. No. 9,956,247, herein incorporated by reference). However, these approaches do not restore the original IDUA locus to the correct coding sequence. A genome-editing strategy would have a number of advantages, most notably that regulation of gene expression would be controlled by the natural mechanisms present in healthy individuals. Additionally, using base editing does not necessitate causing a double stranded DNA breaks, which could lead to large chromosomal rearrangements, cell death, or oncogenecity by the disruption of tumor suppression mechanisms. An enabling description of a method to correct the causal mutation of this disease is provided in Example 10. The described methods are an example of a general strategy directed toward using RGN-base editor fusion proteins of the invention to target and correct certain disease-causing mutations in the human genome. It will be appreciated that similar approaches to target diseases such as those described in Table 12 may also be pursued. It will be further appreciated that similar approaches to target disease-causing mutations in other species, particularly common household pets or livestock, can also be deployed using the RGNs of the invention. Common household pets and livestock include dogs, cats, horses, pigs, cows, sheep, chickens, donkeys, snakes, ferrets, fish including salmon, and shrimp.

Friedreich's Ataxia

RGNs of the invention could also be useful in human therapeutic approaches where the causal mutation is more complicated. For example, some diseases such as Friedreich's Ataxia and Huntington's Disease are the result of a significant increase in repeats of a three nucleotide motif at a particular region of a gene, which affects the ability of the expressed protein to function or to be expressed. Friedreich's Ataxia (FRDA) is an autosomal recessive disease resulting in progressive degeneration of nervous tissue in the spinal cord. Reduced levels of the frataxin (FXN) protein in the mitochondria cause oxidative damages and iron deficiencies at the cellular level. The reduced FXN expression has been linked to a GAA triplet expansion within the intron 1 of the somatic and germline FXN gene. In FRDA patients, the GAA repeat frequently consists of more than 70, sometimes even more than 1000 (most commonly 600-900) triplets, whereas unaffected individuals have about 40 repeats or less (Pandolfo et al. (2012) Handbook of Clinical Neurology 103: 275-294; Campuzano et al. (1996) Science 271: 1423-1427; Pandolfo (2002) Adv. Exp. Med. Biol. 516: 99-118; all herein incorporated by reference).

The expansion of the trinucleotide repeat sequence causing Friedreich's Ataxia (FRDA) occurs in a defined genetic locus within the FXN gene, referred to as the FRDA instability region. RNA guided nucleases (RGNs) may be used for excising the instability region in FRDA patient cells. This approach requires 1) an RGN and guide RNA sequence that can be programmed to target the allele in the human genome; and 2) a delivery approach for the RGN and guide sequence. Many nucleases used for genome editing, such as the commonly used Cas9 nuclease from *S. pyogenes* (SpCas9), are too large to be packaged into adeno-associated viral (AAV) vectors, especially when considering the length of the SpCas9 gene and the guide RNA in addition to other genetic elements required for functional expression cassettes. This makes an approach using SpCas9 more difficult.

The compact RNA guided nucleases of the invention, particularly APG07433.1 and APG08290.1, are uniquely well suited for the excision of the FRDA instability region. Each RGN has a PAM requirement that is in the vicinity of the FRDA instability region. Additionally, each of these RGNs can be packaged into an AAV vector along with a guide RNA. Packing two guide RNAs would likely require a second vector, but this approach still compares favorably to what would be required of a larger nuclease such as SpCas9, which may require splitting the protein sequence between two vectors. An enabling description of a method to correct the causal mutation of this disease is provided in Example 11. The described methods encompass a strategy using RGNs of the invention in which a region of genomic instability is removed. Such a strategy is applicable to other diseases and disorders which have a similar genetic basis, such as Huntington's Disease. Similar strategies using RGNs of the invention may also be applicable to similar diseases and disorders in non-human animals of agronomic or economic importance, including dogs, cats, horses, pigs, cows, sheep, chickens, donkeys, snakes, ferrets, fish including salmon, and shrimp Hemoglobinopathies RGNs of the invention could also be to introduce disruptive mutations that may result in a beneficial effect. Genetic defects in the genes encoding hemoglobin, particularly the beta globin chain (the HBB gene), can be responsible for a number of diseases known as hemoglobinopathies, including sickle cell anemia and thalassemias.

In adult humans, hemoglobin is a heterotetramer comprising two alpha (α)-like globin chains and two beta (β)-like globin chains and 4 heme groups. In adults the $\alpha2\beta2$ tetramer is referred to as Hemoglobin A (HbA) or adult hemoglobin. Typically, the alpha and beta globin chains are synthesized in an approximate 1:1 ratio and this ratio seems to be critical in terms of hemoglobin and red blood cell (RBC) stabilization. In a developing fetus, a different form of hemoglobin, fetal hemoglobin (HbF), is produced which has a higher binding affinity for oxygen than Hemoglobin A such that oxygen can be delivered to the baby's system via the mother's blood stream. Fetal hemoglobin also contains two a globin chains, but in place of the adult β-globin chains, it has two fetal gamma (γ)-globin chains (i.e., fetal hemoglobin is $\alpha2\gamma2$). The regulation of the switch from production of gamma- to beta-globin is quite complex, and primarily involves a down-regulation of gamma globin transcription with a simultaneous up-regulation of beta globin transcription. At approximately 30 weeks of gestation, the synthesis of gamma globin in the fetus starts to drop while the production of beta globin increases. By approximately 10 months of age, the newborn's hemoglobin is nearly all $\alpha2\beta2$ although some HbF persists into adulthood (approximately 1-3% of total hemoglobin). In the majority of patients with hemoglobinopathies, the genes encoding gamma globin remain present, but expression is relatively low due to normal gene repression occurring around parturition as described above.

Sickle cell disease is caused by a V6E mutation in the β globin gene (HBB) (a GAG to GTG at the DNA level), where the resultant hemoglobin is referred to as "hemoglobinS" or "HbS." Under lower oxygen conditions, HbS molecules aggregate and form fibrous precipitates. These aggregates cause the abnormality or 'sickling' of the RBCs, resulting in a loss of flexibility of the cells. The sickling RBCs are no longer able to squeeze into the capillary beds and can result in vaso-occlusive crisis in sickle cell patients. In addition, sickled RBCs are more fragile than normal RBCs, and tend towards hemolysis, eventually leading to anemia in the patient.

Treatment and management of sickle cell patients is a life-long proposition involving antibiotic treatment, pain management and transfusions during acute episodes. One approach is the use of hydroxyurea, which exerts its effects in part by increasing the production of gamma globin. Long term side effects of chronic hydroxyurea therapy are still unknown, however, and treatment gives unwanted side effects and can have variable efficacy from patient to patient. Despite an increase in the efficacy of sickle cell treatments, the life expectancy of patients is still only in the mid to late 50's and the associated morbidities of the disease have a profound impact on a patient's quality of life.

Thalassemias (alpha thalassemias and beta thalassemia) are also diseases relating to hemoglobin and typically involve a reduced expression of globin chains. This can occur through mutations in the regulatory regions of the genes or from a mutation in a globin coding sequence that results in reduced expression or reduced levels or functional globin protein. Treatment of thalassemias usually involves blood transfusions and iron chelation therapy. Bone marrow transplants are also being used for treatment of people with severe thalassemias if an appropriate donor can be identified, but this procedure can have significant risks.

One approach that has been proposed for the treatment of both SCD and beta thalassemias is to increase the expression of gamma globin so that HbF functionally replaces the aberrant adult hemoglobin As mentioned above, treatment of SCD patients with hydroxyurea is thought to be successful in part due to its effect on increasing gamma globin expression (DeSimone (1982) Proc Nat'l Acad Sci USA 79(14): 4428-31; Ley, et al., (1982) N. Engl. J. Medicine, 307: 1469-1475; Ley, et al., (1983) Blood 62: 370-380; Constantoulakis et al., (1988) Blood 72(6):1961-1967, all herein incorporated by reference). Increasing the expression of HbF involves identification of genes whose products play a role in the regulation of gamma globin expression. One such gene is BCL11A. BCL11A encodes a zinc finger protein that expressed in adult erythroid precursor cells, and down-regulation of its expression leads to an increase in gamma globin expression (Sankaran et at (2008) Science 322: 1839, herein incorporated by reference). Use of an inhibitory RNA targeted to the BCL11A gene has been proposed (e.g., U.S. Patent Publication 2011/0182867, herein incorporated by reference) but this technology has several potential drawbacks, including that complete knock down may not be achieved, delivery of such RNAs may be problematic, and the RNAs must be present continuously, requiring multiple treatments for life.

RGNs of the invention may be used to target the BCL11A enhancer region to disrupt expression of BCL11A, thereby increasing gamma globin expression. This targeted disruption can be achieved by non-homologous end joining (NHEJ), whereby an RGN of the invention targets to a particular sequence within the BCL11A enhancer region, makes a double-stranded break, and the cell's machinery repairs the break, typically simultaneously introducing deleterious mutations. Similar to what is described for other disease targets, the RGNs of the invention have advantages over other known RGNs due to their relatively small size, which enables packaging expression cassettes for the RGN and its guide RNA into a single AAV vector for in vivo delivery. An enabling description of this method is provided in Example 12. Similar strategies using RGNs of the invention may also be applicable to similar diseases and disorders in both humans and in non-human animals of agronomic or economic importance.

IX. Cells Comprising a Polynucleotide Genetic Modification

Provided herein are cells and organisms comprising a target sequence of interest that has been modified using a process mediated by an RGN, crRNA, and/or tracrRNA as described herein. In some of these embodiments, the RGN comprises the amino acid sequence of SEQ ID NOs: 1, 11, 19, 27, 36, 45, or 54, or an active variant or fragment thereof. In various embodiments, the guide RNA comprises a CRISPR repeat sequence comprising the nucleotide sequence of SEQ ID NOs: 2, 12, 20, 28, 37, 46, or 55, or an active variant or fragment thereof. In particular embodiments, the guide RNA comprises a tracrRNA comprising the nucleotide sequence of SEQ ID NOs: 3, 13, 21, 29, 38, 47, or 56, or an active variant or fragment thereof. The guide RNA of the system can be a single guide RNA or a dual-guide RNA.

The modified cells can be eukaryotic (e.g., mammalian, plant, insect cell) or prokaryotic. Also provided are organelles and embryos comprising at least one nucleotide sequence that has been modified by a process utilizing an RGN, crRNA, and/or tracrRNA as described herein. The genetically modified cells, organisms, organelles, and embryos can be heterozygous or homozygous for the modified nucleotide sequence.

The chromosomal modification of the cell, organism, organelle, or embryo can result in altered expression (up-regulation or down-regulation), inactivation, or the expression of an altered protein product or an integrated sequence. In those instances wherein the chromosomal modification results in either the inactivation of a gene or the expression of a non-functional protein product, the genetically modified cell, organism, organelle, or embryo is referred to as a "knock out". The knock out phenotype can be the result of a deletion mutation (i.e., deletion of at least one nucleotide), an insertion mutation (i.e., insertion of at least one nucleotide), or a nonsense mutation (i.e., substitution of at least one nucleotide such that a stop codon is introduced).

Alternatively, the chromosomal modification of a cell, organism, organelle, or embryo can produce a "knock in", which results from the chromosomal integration of a nucleotide sequence that encodes a protein. In some of these embodiments, the coding sequence is integrated into the chromosome such that the chromosomal sequence encoding the wild-type protein is inactivated, but the exogenously introduced protein is expressed.

In other embodiments, the chromosomal modification results in the production of a variant protein product. The expressed variant protein product can have at least one amino acid substitution and/or the addition or deletion of at least one amino acid. The variant protein product encoded by the altered chromosomal sequence can exhibit modified characteristics or activities when compared to the wild-type protein, including but not limited to altered enzymatic activity or substrate specificity.

In yet other embodiments, the chromosomal modification can result in an altered expression pattern of a protein. As a non-limiting example, chromosomal alterations in the regulatory regions controlling the expression of a protein product can result in the overexpression or downregulation of the protein product or an altered tissue or temporal expression pattern.

The article "a" and "an" are used herein to refer to one or more than one (i.e., to at least one) of the grammatical object of the article. By way of example, "a polypeptide" means one or more polypeptides.

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

Non-limiting embodiments include:

1. A nucleic acid molecule comprising a polynucleotide encoding an RNA-guided nuclease (RGN) polypeptide, wherein said polynucleotide comprises a nucleotide sequence encoding an RGN polypeptide comprising an amino acid sequence having at least 95% sequence identity to SEQ ID NOs: 1, 11, 19, 27, 36, 45, or 54;
   wherein said RGN polypeptide binds a target DNA sequence in an RNA-guided sequence specific manner when bound to a guide RNA (gRNA) capable of hybridizing to said target DNA sequence, and
   wherein said polynucleotide encoding an RGN polypeptide is operably linked to a promoter heterologous to said polynucleotide.

2. The nucleic acid molecule of embodiment 1, wherein said RGN polypeptide is capable of cleaving said target DNA sequence upon binding.

3. The nucleic acid molecule of embodiment 2, wherein cleavage by said RGN polypeptide generates a double-stranded break.

4. The nucleic acid molecule of embodiment 2, wherein cleavage by said RGN polypeptide generates a single-stranded break.

5. The nucleic acid molecule of any one of embodiments 1-4, wherein the RGN polypeptide is operably fused to a base-editing polypeptide.

6. The nucleic acid molecule of any one of embodiments 1-5, wherein the RGN polypeptide comprises one or more nuclear localization signals.

7. The nucleic acid molecule of any one of embodiments 1-6, wherein the RGN polypeptide is codon optimized for expression in a eukaryotic cell.

8. The nucleic acid molecule of any one of embodiments 1-7, wherein said target DNA sequence is located adjacent to a protospacer adjacent motif (PAM).

9. A vector comprising the nucleic acid molecule of any one of embodiments 1-8.

10. The vector of embodiment 9, further comprising at least one nucleotide sequence encoding said gRNA capable of hybridizing to said target DNA sequence.

11. The vector of embodiment 10, where said gRNA is a single guide RNA.

12. The vector of embodiment 10, wherein said gRNA is a dual-guide RNA.

13. The vector of any one of embodiments 10-12, wherein the guide RNA comprises a CRISPR RNA comprising a CRISPR repeat sequence having at least 95% sequence identity to SEQ ID NOs: 2, 12, 20, 28, 37, 46, or 55.

14. The vector of any one of embodiments 10-13, wherein the guide RNA comprises a tracrRNA having at least 95% sequence identity to SEQ ID NOs: 3, 13, 21, 29, 38, 47, or 56.

15. A cell comprising the nucleic acid molecule of any one of embodiments 1-8 or the vector of any one of embodiments 9-14.

16. A method for making an RGN polypeptide comprising culturing the cell of embodiment 15 under conditions in which the RGN polypeptide is expressed.

17. A method for making an RGN polypeptide comprising introducing into a cell a heterologous nucleic acid molecule comprising a nucleotide sequence encoding an RNA-guided nuclease (RGN) polypeptide comprising an amino acid sequence having at least 95% sequence identity to SEQ ID NOs: 1, 11, 19, 27, 36, 45, or 54;
   wherein said RGN polypeptide binds a target DNA sequence in an RNA-guided sequence specific manner when bound to a guide RNA (gRNA) capable of hybridizing to said target DNA sequence;
   and culturing said cell under conditions in which the RGN polypeptide is expressed.

18. The method of embodiment 16 or 17, further comprising purifying said RGN polypeptide.

19. The method of embodiment 16 or 17, wherein said cell further expresses one or more guide RNAs that binds to said RGN polypeptide to form an RGN ribonucleoprotein complex.

20. The method of embodiment 19, further comprising purifying said RGN ribonucleoprotein complex.

21. A nucleic acid molecule comprising a polynucleotide encoding a CRISPR RNA (crRNA), wherein said crRNA comprises a spacer sequence and a CRISPR repeat sequence, wherein said CRISPR repeat sequence comprises a nucleotide sequence having at least 95% sequence identity to SEQ ID NOs: 2, 12, 20, 28, 37, 46, or 55;
   wherein a guide RNA comprising:
   a) said crRNA; and
   b) a trans-activating CRISPR RNA (tracrRNA) hybridized to said CRISPR repeat sequence of said crRNA;
   is capable of hybridizing to a target DNA sequence in a sequence specific manner through the spacer sequence of said crRNA when said guide RNA is bound to an RNA-guided nuclease (RGN) polypeptide, and
   wherein said polynucleotide encoding a crRNA is operably linked to a promoter heterologous to said polynucleotide.

22. A vector comprising the nucleic acid molecule of embodiment 21.

23. The vector of embodiment 22, wherein said vector further comprises a polynucleotide encoding said tracrRNA.

24. The vector of embodiment 23, wherein said tracrRNA comprises a nucleotide sequence having at least 95% sequence identity to SEQ ID NOs: 3, 13, 21, 29, 38, 47, or 56.

25. The vector of embodiment 23 or 24, wherein said polynucleotide encoding said crRNA and said polynucleotide encoding said tracrRNA are operably linked to the same promoter and are encoded as a single guide RNA.

26. The vector of embodiment 23 or 24, wherein said polynucleotide encoding said crRNA and said polynucleotide encoding said tracrRNA are operably linked to separate promoters.

27. The vector of any one of embodiments 22-26, wherein said vector further comprises a polynucleotide encoding said RGN polypeptide, wherein said RGN polypeptide comprises an amino acid sequence having at least 95% sequence identity to SEQ ID NOs: 1, 11, 19, 27, 36, 45, or 54.

28. A nucleic acid molecule comprising a polynucleotide encoding a trans-activating CRISPR RNA (tracrRNA) comprising a nucleotide sequence having at least 95% sequence identity to SEQ ID NOs: 3, 13, 21, 29, 38, 47, or 56;

wherein a guide RNA comprising:

a) said tracrRNA; and b) a crRNA comprising a spacer sequence and a CRISPR repeat sequence, wherein said tracrRNA hybridizes with said CRISPR repeat sequence of said crRNA;

is capable of hybridizing to a target DNA sequence in a sequence specific manner through the spacer sequence of said crRNA when said guide RNA is bound to an RNA-guided nuclease (RGN) polypeptide, and wherein said polynucleotide encoding a tracrRNA is operably linked to a promoter heterologous to said polynucleotide.

29. A vector comprising the nucleic acid molecule of embodiment 28.

30. The vector of embodiment 29, wherein said vector further comprises a polynucleotide encoding said crRNA.

31. The vector of embodiment 30, wherein the CRISPR repeat sequence of said crRNA comprises a nucleotide sequence having at least 95% sequence identity to SEQ ID NOs: 2, 12, 20, 28, 37, 46, or 55.

32. The vector of embodiment 30 or 31, wherein said polynucleotide encoding said crRNA and said polynucleotide encoding said tracrRNA are operably linked to the same promoter and are encoded as a single guide RNA. 33. The vector of embodiment 30 or 31, wherein said polynucleotide encoding said crRNA and said polynucleotide encoding said tracrRNA are operably linked to separate promoters.

34. The vector of any one of embodiments 29-33, wherein said vector further comprises a polynucleotide encoding said RGN polypeptide, wherein said RGN polypeptide comprises an amino acid sequence having at least 95% sequence identity to SEQ ID NOs: 1, 11, 19, 27, 36, 45, or 54.

35. A system for binding a target DNA sequence, said system comprising:

a) one or more guide RNAs capable of hybridizing to said target DNA sequence or one or more nucleotide sequences encoding the one or more guide RNAs (gRNAs); and b) an RNA-guided nuclease (RGN) polypeptide comprising an amino acid sequence having at least 95% sequence identity to SEQ ID NOs: 1, 11, 19, 27, 36, 45, or 54 or a nucleotide sequence encoding the RGN polypeptide;

wherein said nucleotide sequences encoding the one or more guide RNAs and encoding the RGN polypeptide are each operably linked to a promoter heterologous to said nucleotide sequence;

wherein the one or more guide RNAs hybridize to the target DNA sequence, and wherein the one or more guide RNAs form a complex with the RGN polypeptide, thereby directing said RGN polypeptide to bind to said target DNA sequence.

36. The system of embodiment 35, wherein said gRNA is a single guide RNA (sgRNA).

37. The system of embodiment 35, wherein said gRNA is a dual-guide RNA.

38. The system of any one of embodiments 35-37, wherein said gRNA comprises a CRISPR repeat sequence comprising a nucleotide sequence having at least 95% sequence identity to SEQ ID NOs: 2, 12, 20, 28, 37, 46, or 55.

39. The system of any one of embodiments 35-38, wherein said gRNA comprises a tracrRNA comprising a nucleotide sequence having at least 95% sequence identity to SEQ ID NOs: 3, 13, 21, 29, 38, 47, or 56.

40. The system of any one of embodiments 35-39, wherein said target DNA sequence is located adjacent to a protospacer adjacent motif (PAM).

41. The system of any one of embodiments 35-40, wherein the target DNA sequence is within a cell.

42. The system of embodiment 41, wherein the cell is a eukaryotic cell.

43. The system of embodiment 42, wherein the eukaryotic cell is a plant cell.

44. The system of embodiment 42, wherein the eukaryotic cell is a mammalian cell.

45. The system of embodiment 42, wherein the eukaryotic cell is an insect cell.

46. The system of embodiment 41, wherein the cell is a prokaryotic cell.

47. The system of any one of embodiments 35-46, wherein when transcribed the one or more guide RNAs hybridize to the target DNA sequence and the guide RNA forms a complex with the RGN polypeptide which causes cleavage of the target DNA sequence.

48. The system of embodiment 47, wherein the cleavage generates a double-stranded break.

49. The system of embodiment 47, wherein cleavage by said RGN polypeptide generates a single-stranded break.

50. The system of any one of embodiments 35-49, wherein the RGN polypeptide is operably linked to a base-editing polypeptide.

51. The system of any one of embodiments 35-50, wherein the RGN polypeptide comprises one or more nuclear localization signals.

52. The system of any one of embodiments 35-51, wherein the RGN polypeptide is codon optimized for expression in a eukaryotic cell.

53. The system of any one of embodiments 35-52, wherein nucleotide sequences encoding the one or more guide RNAs and the nucleotide sequence encoding an RGN polypeptide are located on one vector.

54. The system of any one of embodiments 35-53, wherein said system further comprises one or more donor polynucleotides or one or more nucleotide sequences encoding the one or more donor polynucleotides.

55. A method for binding a target DNA sequence comprising delivering a system according to any one of embodiments 35-54, to said target DNA sequence or a cell comprising the target DNA sequence.

56. The method of embodiment 55, wherein said RGN polypeptide or said guide RNA further comprises a detectable label, thereby allowing for detection of said target DNA sequence.

57. The method of embodiment 55, wherein said guide RNA or said RGN polypeptide further comprises an expression modulator, thereby modulating expression of said target DNA sequence or a gene under transcriptional control by said target DNA sequence.

58. A method for cleaving or modifying a target DNA sequence comprising delivering a system according to any one of embodiments 35-54, to said target DNA sequence or a cell comprising the target DNA sequence.

59. The method of embodiment 58, wherein said modified target DNA sequence comprises insertion of heterologous DNA into the target DNA sequence.

60. The method of embodiment 58, wherein said modified target DNA sequence comprises deletion of at least one nucleotide from the target DNA sequence.

61. The method of embodiment 58, wherein said modified target DNA sequence comprises mutation of at least one nucleotide in the target DNA sequence.

62. A method for binding a target DNA sequence comprising:

a) assembling a RNA-guided nuclease (RGN) ribonucleotide complex in vitro by combining:

i) one or more guide RNAs capable of hybridizing to the target DNA sequence; and ii) an RGN polypeptide comprising an amino acid sequence having at least 95% sequence identity to SEQ ID NOs: 1, 11, 19, 27, 36, 45, or 54;

under conditions suitable for formation of the RGN ribonucleotide complex; and b) contacting said target DNA sequence or a cell comprising said target DNA sequence with the in vitro-assembled RGN ribonucleotide complex;

wherein the one or more guide RNAs hybridize to the target DNA sequence, thereby directing said RGN polypeptide to bind to said target DNA sequence.

63. The method of embodiment 62, wherein said RGN polypeptide or said guide RNA further comprises a detectable label, thereby allowing for detection of said target DNA sequence.

64. The method of embodiment 62, wherein said guide RNA or said RGN polypeptide further comprises an expression modulator, thereby allowing for the modulation of expression of said target DNA sequence.

65. A method for cleaving and/or modifying a target DNA sequence, comprising contacting the DNA molecule with:

a) an RNA-guided nuclease (RGN) polypeptide, wherein said RGN comprises an amino acid sequence having at least 95% sequence identity to SEQ ID NOs: 1, 11, 19, 27, 36, 45 or 54; and b) one or more guide RNAs capable of targeting the RGN of (a) to the target DNA sequence;

wherein the one or more guide RNAs hybridize to the target DNA sequence, thereby directing said RGN polypeptide to bind to said target DNA sequence and cleavage and/or modification of said target DNA sequence occurs.

66. The method of embodiment 65, wherein said modified target DNA sequence comprises insertion of heterologous DNA into the target DNA sequence.

67. The method of embodiment 65, wherein said modified target DNA sequence comprises deletion of at least one nucleotide from the target DNA sequence.

68. The method of embodiment 65, wherein said modified target DNA sequence comprises mutation of at least one nucleotide in the target DNA sequence.

69. The method of any one of embodiments 62-68, wherein said gRNA is a single guide RNA (sgRNA).

70. The method of any one of embodiments 62-68, wherein said gRNA is a dual-guide RNA.

71. The method of any one of embodiments 62-70, wherein said gRNA comprises a CRISPR repeat sequence comprising a nucleotide sequence having at least 95% sequence identity to SEQ ID NOs: 2, 12, 20, 28, 37, 46, or 55.

72. The method of any one of embodiments 62-71, wherein said gRNA comprises a tracrRNA comprising a nucleotide sequence having at least 95% sequence identity to SEQ ID NOs: 3, 13, 21, 29, 38, 47, or 56.

73. The method of any one of embodiments 62-72, wherein said target DNA sequence is located adjacent to a protospacer adjacent motif (PAM).

74. The method of any one of embodiments 55-73, wherein the target DNA sequence is within a cell.

75. The method of embodiment 74, wherein the cell is a eukaryotic cell.

76. The method of embodiment 75, wherein the eukaryotic cell is a plant cell.

77. The method of embodiment 75, wherein the eukaryotic cell is a mammalian cell.

78. The method of embodiment 75, wherein the eukaryotic cell is an insect cell.

79. The method of embodiment 74, wherein the cell is a prokaryotic cell.

80. The method of any one of embodiments 74-79, further comprising culturing the cell under conditions in which the RGN polypeptide is expressed and cleaves the target DNA sequence to produce a modified DNA sequence; and selecting a cell comprising said modified DNA sequence.

81. A cell comprising a modified target DNA sequence according to the method of embodiment 80.

82. The cell of embodiment 81, wherein the cell is a eukaryotic cell.

83. The cell of embodiment 82, wherein the eukaryotic cell is a plant cell.

84. A plant comprising the cell of embodiment 83.

85. A seed comprising the cell of embodiment 83.

86. The cell of embodiment 82, wherein the eukaryotic cell is a mammalian cell.

87. The cell of embodiment 82, wherein the eukaryotic cell is an insect cell.

88. The cell of embodiment 81, wherein the cell is a prokaryotic cell.

89. A method for producing a genetically modified cell with a correction in a causal mutation for a genetically inherited disease, the method comprising introducing into the cell:

a) an RNA-guided nuclease (RGN) polypeptide, wherein the RGN polypeptide comprises an amino acid sequence having at least 95% sequence identity to SEQ ID NOs: 1, 11, 19, 27, 36, 45, or 54, or a polynucleotide encoding said RGN polypeptide, wherein said polynucleotide encoding the RGN polypeptide is operably linked to a promoter to enable expression of the RGN polypeptide in the cell; and b) a guide RNA (gRNA), wherein the gRNA comprises a CRISPR repeat sequence comprising a nucleotide sequence having at least 95% sequence identity to SEQ ID NOs: 2, 12, 20, 28, 37, 46, or 55, or a polynucleotide encoding said gRNA, wherein said polynucleotide encoding the gRNA is operably linked to a promoter to enable expression of the gRNA in the cell whereby the RGN and gRNA target to the genomic location of the causal mutation and modify the genomic sequence to remove the causal mutation.

90. The method of embodiment 89, wherein the RGN is fused to a polypeptide which has base-editing activity.

91. The method of embodiment 90, wherein the polypeptide with base-editing activity is a cytidine deaminase or an adenosine deaminase.

92. The method of embodiment 89, wherein the cell is an animal cell.

93. The method of embodiment 89, wherein the cell is a mammalian cell.

94. The method of embodiment 92, wherein the cell is derived from a dog, cat, mouse, rat, rabbit, horse, cow, pig, or human.

95. The method of embodiment 92, wherein the genetically inherited disease is a disease listed in Table 12.

96. The method of embodiment 92, wherein the genetically inherited disease is Hurler Syndrome.

97. The method of embodiment 96, wherein the gRNA further comprises a spacer sequence that targets SEQ ID NO: 453, 454, or 455.

98. A method for producing a genetically modified cell with a deletion in a disease-causing genomic region of instability, the method comprising introducing into the cell:

a) an RNA-guided nuclease (RGN) polypeptide, wherein the RGN polypeptide comprises an amino acid sequence having at least 95% sequence identity to SEQ ID NOs: 1, 11, 19, 27, 36, 45, or 54, or a polynucleotide encoding said RGN polypeptide, wherein said polynucleotide encoding the RGN polypeptide is operably linked to a promoter to enable expression of the RGN polypeptide in the cell; and b) a guide RNA (gRNA), wherein the gRNA comprises a CRISPR repeat sequence comprising a nucleotide sequence having at least 95% sequence identity to SEQ ID NOs: 2, 12, 20, 28, 37, 46, or 55, or a polynucleotide encoding said gRNA, wherein said polynucleotide encoding the gRNA is operably linked to a promoter to enable expression of the gRNA in the cell, and further wherein the gRNA comprises a spacer sequence that targets the 5'flank of the genomic region of instability; and c) a second guide RNA (gRNA), wherein the gRNA comprises a CRISPR repeat sequence comprising a nucleotide sequence having at least 95% sequence identity to SEQ ID NOs: 2, 12, 20, 28, 37, 46, or 55, or a polynucleotide encoding said gRNA, wherein said polynucleotide encoding the gRNA is operably linked to a promoter to enable expression of the gRNA in the cell, and further wherein said second gRNA comprises a spacer sequence that targets the 3'flank of the genomic region of instability;

whereby the RGN and the two gRNAs target to the genomic region of instability and at least a portion of the genomic region of instability is removed.

99. The method of embodiment 98, wherein the cell is an animal cell.

100. The method of embodiment 98, wherein the cell is a mammalian cell.

101. The method of embodiment 100, wherein the cell is derived from a dog, cat, mouse, rat, rabbit, horse, cow, pig, or human.

102. The method of embodiment 99, wherein the genetically inherited disease is Friedrich's Ataxia or Huntington's Disease.

103. The method of embodiment 102, wherein the first gRNA further comprises a spacer sequence that targets SEQ ID NO: 468, 469, or 470.

104. The method of embodiment 103, wherein the second gRNA further comprises a spacer sequence that targets SEQ ID NO: 471.

105. A method for producing a genetically modified mammalian hematopoietic progenitor cell having decreased BCL11A mRNA and protein expression, the method comprising introducing into an isolated human hematopoietic progenitor cell:

a) an RNA-guided nuclease (RGN) polypeptide, wherein the RGN polypeptide comprises an amino acid sequence having at least 95% sequence identity to SEQ ID NOs: 1, 11, 19, 27, 36, 45, or 54, or a polynucleotide encoding said RGN polypeptide, wherein said polynucleotide encoding the RGN polypeptide is operably linked to a promoter to enable expression of the RGN polypeptide in the cell; and b) a guide RNA (gRNA), wherein the gRNA comprises a CRISPR repeat sequence comprising a nucleotide sequence having at least 95% sequence identity to SEQ ID NOs: 2, 12, 20, 28, 37, 46, or 55, or a polynucleotide encoding said gRNA, wherein said polynucleotide encoding the gRNA is operably linked to a promoter to enable expression of the gRNA in the cell, whereby the RGN and gRNA are expressed in the cell and cleave at the BCL11A enhancer region, resulting in genetic modification of the human hematopoietic progenitor cell and reducing the mRNA and/or protein expression of BCL11A.

106. The method of embodiment 105, wherein the gRNA further comprises a spacer sequence that targets SEQ ID NO: 473, 474, 475, 476, 477, or 478.

107. A system for binding a target DNA sequence, said system comprising:

a) one or more guide RNAs capable of hybridizing to said target DNA sequence or one or more nucleotide sequences encoding the one or more guide RNAs (gRNAs); and b) an RNA-guided nuclease (RGN) polypeptide comprising an amino acid sequence having at least 95% sequence identity to SEQ ID NOs: 1, 11, 19, 27, 36, 45, or 54;

wherein the one or more guide RNAs hybridize to the target DNA sequence, and wherein the one or more guide RNAs forms a complex with the RGN polypeptide, thereby directing said RGN polypeptide to bind to said target DNA sequence.

108. The system of embodiment 107, wherein said RGN polypeptide is nuclease dead or functions as a nickase.

109. The system of embodiment 107 or 108, wherein said RGN polypeptide is operably fused to a base-editing polypeptide.

110. The system of embodiment 109, wherein the base-editing polypeptide is a deaminase.

111. The system of embodiment 110, wherein the deaminase is a cytidine deaminase or an adenosine deaminase.

The following examples are offered by way of illustration and not by way of limitation.

EXPERIMENTAL

Example 1. Identification of RNA-Guided Nuclease

Seven distinct CRISPR-associated RNA-guided nucleases (RGN's) were identified and are described in Table 1 below. Table 1 provides the name of each RGN, its amino acid sequence, the source from which it was derived, and processed crRNA and tracrRNA sequences. Table 1 further provides a generic single guide RNA (sgRNA) sequence, where the poly-N indicates the location of the spacer sequence which determines the nucleic acid target sequence of the sgRNA. RGN systems APG systems APG05083.1, APG07433.1, APG08290.1, and APG08290.1 had a conserved sequence in the base of the hairpin stem of the tracrRNA, UNANNG (SEQ ID NO: 68). For the AP05459.1 system, the sequence in the same location is UNANNU (SEQ ID NO: 557). For APG04583.1 and APG01688.1 systems, the sequence is UNANNA (SEQ ID NO: 558).

TABLE 1

| Summary of SEQ IDs and CRISPR associated systems | | | | | |
|---|---|---|---|---|---|
| RGN ID | SEQ ID NO. | Source | crRNA repeat seq (SEQ ID NO.) | tracrRNA (SEQ ID NO.) | sgRNA (SEQ ID NO) |
| APG05083.1 | 1 | *Bacillus* sp. | 2 | 3 | 10 |
| APG07433.1 | 10 | *Bacillus* sp. | 12 | 13 | 18 |
| APG07513.1 | 18 | *Bacillus* sp. | 20 | 21 | 26 |
| APG08290.1 | 26 | *Bacillus* sp. | 28 | 29 | 35 |
| APG05459.1 | 34 | *Enterococcus* sp. | 37 | 38 | 44 |
| APG04583.1 | 42 | *Enterococcus* sp. | 46 | 47 | 53 |
| APG01688.1 | 50 | *Empedobacter* sp. | 55 | 56 | 62 |

Example 2: Guide RNA Identification and sgRNA Construction

Cultures of bacteria that natively express the RNA-guided nuclease system under investigation were grown to mid-log phase (OD600 of ~0.600), pelleted, and flash frozen. RNA was isolated from the pellets using a mirVANA miRNA Isolation Kit (Life Technologies, Carlsbad, CA), and sequencing libraries were prepared from the isolated RNA using an NEBNext Small RNA Library Prep kit (NEB, Beverly, MA). The library prep was fractionated on a 6% polyacrylamide gel into 2 size fractions corresponding to 18-65 nt and 90-200 nt RNA species to detect crRNAs and tracrRNAs, respectively. Deep sequencing (40 bp paired-end for the smaller fraction and 80 bp paired-end for the larger fraction) was performed on a Next Seq 500 (High Output kit) by a service provider (MoGene, St. Louis, MO). Reads were quality trimmed using Cutadapt and mapped to reference genomes using Bowtie2. A custom RNAseq pipeline was written in python to detect the crRNA and tracrRNA transcripts. Processed crRNA boundaries were determined by sequence coverage of the native repeat spacer array. The anti-repeat portion of the tracrRNA was identified using permissive BLASTn parameters. RNA sequencing depth confirmed the boundaries of the processed tracrRNA by identifying the transcript containing the anti-repeat. Manual curation of RNAs was performed using secondary structure prediction by NUPACK, an RNA folding software. sgRNA cassettes were prepared by DNA synthesis and were generally designed as follows (5'→3'): 20-30 bp spacer sequence—processed repeat portion of the crRNA—4 bp noncomplementary linker (AAAG; SEQ ID NO: 63)—processed tracrRNA. Other 4 bp noncomplementary linkers may also be used, for example GAAA (SEQ ID NO: 64) or ACUU (SEQ ID NO: 65). In some instances, a 6 bp nucleotide linker may be used, for example CAAAGG (SEQ ID NO: 66). For in vitro assays, sgRNAs were synthesized by in vitro transcription of the sgRNA cassettes with a GeneArt™ Precision gRNA Synthesis Kit (ThermoFisher). Processed crRNA and tracrRNA sequences for each of the RGN polypeptides are identified and are set forth in Table 1. See below for the sgRNAs constructed for PAM libraries 1 and 2.

Example 3: Determination of PAM Requirements for Each RGN

PAM requirements for each RGN were determined using a PAM depletion assay essentially adapted from Kleinstiver et al. (2015) *Nature* 523:481-485 and Zetsche et al. (2015) *Cell* 163:759-771. Briefly, two plasmid libraries (L1 and L2) were generated in a pUC18 backbone (ampR), with each containing a distinct 30 bp protospacer (target) sequence flanked by 8 random nucleotides (i.e., the PAM region). The target sequence and flanking PAM region of library 1 and library 2 for each RGN are set forth in Table 2.

The libraries were separately electroporated into *E. coli* BL21(DE3) cells harboring pRSF-1b expression vectors containing an RGN of the invention (codon optimized for *E. coli*) along with a cognate sgRNA containing a spacer sequence corresponding to the protospacer in L1 or L2. Sufficient library plasmid was used in the transformation reaction to obtain >10^6 cfu. Both the RGN and sgRNA in the pRSF-1b backbone were under the control of T7 promoters. The transformation reaction was allowed to recover for 1 hr after which it was diluted into LB media containing carbenicillin and kanamycin and grown overnight. The following day the mixture was diluted into self-inducing Overnight Express™ Instant TB Medium (Millipore Sigma) to allow expression of the RGN and sgRNA, and grown for an additional 4 h or 20 h after which the cells were spun down and plasmid DNA was isolated with a Mini-prep kit (Qiagen, Germantown, MD). In the presence of the appropriate sgRNA, plasmids containing a PAM that is recognizable by the RGN will be cleaved resulting in their removal from the population. Plasmids containing PAMs that are not recognizable by the RGN, or that are transformed into bacteria not containing an appropriate sgRNA, will survive and replicate. The PAM and protospacer regions of uncleaved plasmids were PCR-amplified and prepared for sequencing following published protocols (16s-metagenomic library prep guide 15044223B, Illumina, San Diego, CA). Deep sequencing (80 bp single end reads) was performed on a MiSeq (Illumina) by a service provider (MoGene, St. Louis, MO). Typically, 1-4M reads were obtained per amplicon. PAM regions were extracted, counted, and normalized to total reads for each sample. PAMs that lead to plasmid cleavage were identified by being underrepresented when compared to controls (i.e., when the library is transformed into *E. coli* containing the RGN but lacking an appropriate sgRNA). To represent PAM requirements for a novel RGN, the depletion ratios (frequency in sample/frequency in control) for all sequences in the region in question were converted to enrichment values with a −log base 2 transformation. Sufficient PAMs were defined as those with enrichment values >2.3 (which corresponds to depletion ratios <~0.2). PAMs above this threshold in both libraries were collected and used to generate web logos, which for example can be generated using a web-based service on the internet known as "weblogo". PAM sequences were identified and reported when there was a consistent pattern in the top enriched PAMs. A PAM (having an enrichment factor (EF)>2.3) for each RGN is provided in Table 2. For some RGNs, non-limiting exemplary PAMs (having an EF>3.3) were also identified. For APG005083.1, the exemplary PAM is NNRNCC (SEQ ID NO: 69). For APG007433.1, the exemplary PAM is NNNNCCR (SEQ ID NO: 70). For APG007513.1, the exemplary PAM is NNRNCC (SEQ ID NO: 71). For APG001688.1, the exemplary PAM is NNRANC (SEQ ID NO: 72).

TABLE 2

| PAM determination | | | | | |
|---|---|---|---|---|---|
| RGN ID | sgRNA L1 (SEQ ID NO.) | sgRNA L2 (SEQ ID NO.) | PAM (SEQ ID NO.) | Target seq and PAM region of plasmid library 1 (SEQ ID NO.) | Target seq and PAM region of plasmid library 2 (SEQ ID NO.) |
| APG05083.1 | 4 | 5 | 6 | 8 | 9 |
| APG07433.1 | 13 | 14 | 6 | 16 | 17 |
| APG07513.1 | 21 | 22 | 6 | 24 | 25 |

TABLE 2-continued

| PAM determination | | | | | |
|---|---|---|---|---|---|
| RGN ID | sgRNA L1 (SEQ ID NO.) | sgRNA L2 (SEQ ID NO.) | PAM (SEQ ID NO.) | Target seq and PAM region of plasmid library 1 (SEQ ID NO.) | Target seq and PAM region of plasmid library 2 (SEQ ID NO.) |
| APG08290.1 | 29 | 30 | 32 | 33 | 34 |
| APG05459.1 | 37 | 38 | 41 | 42 | 43 |
| APG04583.1 | 45 | 46 | 50 | 51 | 52 |
| APG01688.1 | 53 | 54 | 59 | 60 | 61 |

The cleavage site for Sequence 2 (SEQ ID NO: 559, operably fused at its 3'end to a PAM sequence for RGN APG0733.1) was determined by the following approach for the nuclease APG07433.1. After digestion, the gel purified DNA products were treated with a DNA end repair kit (Thermo Scientific K0771), ligated into linearized blunt vector, and the resulting circular DNA was transformed into *E. coli* competent cells. A staggered cut with a 5' overhang would result in detection of overlapping sequences in the clones from both cleavage products. A 3' overhang would result in missing sequence, and a blunt cut would result in all of the original sequence being detected with no overlap. This experiment also verified the finding from the above described method for sequence 1—most of the clones were detected as having originated from a cut with a 5' overlap, so it is not expected that the finding of a blunt cut is an artifact of utilizing this method.

TABLE 3

| RGN cleavage sites | | | | | | |
|---|---|---|---|---|---|---|
| | Sequence 1 | | | Sequence 2 | | |
| | Distance from PAM | | | Distance from PAM | | |
| Nuclease | NTS cut site | TS cut site | Overhang | NTS cut site | TS cut site | Overhang |
| APG07433.1 | 4 | 3 | 1 nt, 5' | 3 | 3 | None |
| APG08290.1 | 4 | 3 | 1 nt, 5' | Not determined | | |
| APG05459.1 | 3 | 3 | None | Not determined | | |
| APG04583.1 | 3 | 3 | None | Not determined | | |
| APG01688.1 | 3 | 3 | None | Not determined | | |

NTS = non-target strand;
TS = target strand

Example 4: Cleavage Determination

Cleavage sites were determined from in vitro cleavage reactions using RNPs (ribonucleoproteins). Expression plasmids containing an RGN fused to a His6 or a His10 tag were constructed and transformed into BL21 (DE3) strains of *E. coli*. Expression was performed using self-inducing media or with IPTG induction. After lysis and clarification, the proteins were purified by immobilized metal affinity chromatography.

Ribonucleoprotein complexes (comprising nuclease and an sgRNA or a crRNA and tracrRNA duplex) were formed by incubation of nuclease and the RNA in a buffered solution for 20 min at room temperature. The complex was transferred to a tube containing digestion buffer and a PCR amplified target, referred to as “Sequence 1”. Sequence 1 comprised a nucleotide sequence (SEQ ID NO: 73) directly linked at its 3' end to the corresponding PAM sequence for each RGN. Each RGN as a ribonucleoprotein complex was incubated with its respective target polynucleotide at 25° C. (APG04583.1) or 37° C. (all others) for 30 min or 60 min (APG05459.1 and APG01688.1 only). The digestion reaction was heat inactivated and run on an agarose gel. The cleavage product bands were excised from the gel and sequenced using Sanger sequencing. Cleavage sites were identified by aligning the sequencing results with the expected sequence of the PCR product. Results are shown in Table 3. As shown in Table 3, RGN APG007433.1 may also produce a blunt cut with a different target sequence.

Example 5: Mismatch Sensitivity Assay

Plasmids were designed and obtained with a target sequence (SEQ ID NO: 73) immediately 5' to a suitable PAM motif for the nuclease being evaluated. Single mismatch sequences were also generated with an altered sequence at the position indicated (Table 4). RNP complexes of purified nuclease (APG08290.1 or APG05459.1) and guide RNA were formed and incubated with PCR amplified linear DNA from the designed plasmids. After incubation for a designated period of time and nuclease inactivation, the samples were analyzed by agarose gel electrophoresis to determine the fraction of the linear PCR product remaining. The percentage of the intact band cleaved is shown in Table 5 for mismatches in each position.

TABLE 4

| Sequences tested for the mismatch sensitivity assay for APG08290.1 and APG05459.1 | | |
|---|---|---|
| Protospacer sequence | SEQ ID NO. | Mismatch position |
| GAGCGGACAGCAGCTTCCTATATCTCGTAC | 73 | None |
| GAGCGGACAGCAGCTTCCTATATCTCGTA**G** | 74 | 1 |

TABLE 4-continued

Sequences tested for the mismatch sensitivity assay for APG08290.1 and APG05459.1

| Protospacer sequence | SEQ ID NO. | Mismatch position |
|---|---|---|
| GAGCGGACAGCAGCTTCCTATATCTCGT**T**C | 75 | 2 |
| GAGCGGACAGCAGCTTCCTATATCTCG**A**AC | 76 | 3 |
| GAGCGGACAGCAGCTTCCTATATCTC**C**TAC | 77 | 4 |
| GAGCGGACAGCAGCTTCCTATATCT**G**GTAC | 78 | 5 |
| GAGCGGACAGCAGCTTCCTATATC**A**CGTAC | 79 | 6 |
| GAGCGGACAGCAGCTTCCTATAT**G**TCGTAC | 80 | 7 |
| GAGCGGACAGCAGCTTCCTATA**A**CTCGTAC | 81 | 8 |
| GAGCGGACAGCAGCTTCCTAT**T**TCTCGTAC | 82 | 9 |
| GAGCGGACAGCAGCTTCCTA**A**ATCTCGTAC | 83 | 10 |
| GAGCGGACAGCAGCTTCCT**T**TATCTCGTAC | 84 | 11 |
| GAGCGGACAGCAGCTTCC**A**ATATCTCGTAC | 85 | 12 |
| GAGCGGACAGCAGCTTC**G**TATATCTCGTAC | 86 | 13 |
| GAGCGGACAGCAGCTT**G**CTATATCTCGTAC | 87 | 14 |
| GAGCGGACAGCAGCT**A**CCTATATCTCGTAC | 88 | 15 |
| GAGCGGACAGCAGC**A**TCCTATATCTCGTAC | 89 | 16 |
| GAGCGGACAGCAG**G**TTCCTATATCTCGTAC | 90 | 17 |
| GAGCGGACAGCA**C**CTTCCTATATCTCGTAC | 91 | 18 |
| GAGCGGACAGC**T**GCTTCCTATATCTCGTAC | 92 | 19 |
| GAGCGGACAG**G**AGCTTCCTATATCTCGTAC | 93 | 20 |
| GAGCGGACA**C**CAGCTTCCTATATCTCGTAC | 94 | 21 |
| GAGCGGAC**T**GCAGCTTCCTATATCTCGTAC | 95 | 22 |
| GAGCGGA**G**AGCAGCTTCCTATATCTCGTAC | 96 | 23 |
| GAGCGG**T**CAGCAGCTTCCTATATCTCGTAC | 97 | 24 |
| GAGCG**C**ACAGCAGCTTCCTATATCTCGTAC | 98 | 25 |
| GAGC**C**GACAGCAGCTTCCTATATCTCGTAC | 99 | 26 |
| GAG**G**GGACAGCAGCTTCCTATATCTCGTAC | 100 | 27 |
| GA**C**CGGACAGCAGCTTCCTATATCTCGTAC | 101 | 28 |
| G**T**GCGGACAGCAGCTTCCTATATCTCGTAC | 102 | 29 |
| **C**AGCGGACAGCAGCTTCCTATATCTCGTAC | 103 | 30 |

TABLE 5

Mismatch sensitivity for RGN APG08290.1 and RGN APG05459.1

| Mismatch position | % cleaved APG08290.1 | % cleaved APG05459.1 |
|---|---|---|
| Incompatible PAM, no mismatch | 0 | 0 |
| No mismatch | 95 | 67 |

TABLE 5-continued

Mismatch sensitivity for RGN APG08290.1 and RGN APG05459.1

| Mismatch position | % cleaved APG08290.1 | % cleaved APG05459.1 |
|---|---|---|
| 1 | 0 | 0 |
| 2 | 0 | 74 |
| 3 | 73 | 3 |
| 4 | 0 | 0 |
| 5 | 0 | 0 |
| 6 | 31 | 30 |
| 7 | 0 | 12 |
| 8 | 0 | 51 |
| 9 | 0 | 0 |
| 10 | 75 | 52 |
| 11 | 77 | 5 |
| 12 | 79 | 62 |
| 13 | 28 | 18 |
| 14 | 8 | 5 |
| 15 | 90 | 6 |
| 16 | 85 | 5 |
| 17 | 81 | 4 |
| 18 | 100 | 0 |
| 19 | 100 | 0 |
| 20 | 100 | 2 |
| 21 | 100 | 30 |
| 22 | 100 | 48 |
| 23 | 100 | 40 |
| 24 | 100 | 45 |
| 25 | 100 | 29 |
| 26 | 100 | 33 |
| 27 | 100 | 73 |
| 28 | 100 | 46 |
| 29 | 100 | 59 |
| 30 | 100 | 57 |

A similar mismatch sensitivity experiment was performed for RGN APG07433.1. This experiment was similar to the one described above, except that the alternative base was introduced into the RNA guide rather than the DNA target. DNA sequences for mismatched sgRNA synthesis are shown in Table 6. Results of the mismatch sensitivity assay are shown in Table 7.

TABLE 6

Sequences tested for the mismatch sensitivity assay for RGN APG07433.1

| DNA template for sgRNA synthesis | SEQ ID NO. | Mismatch position |
|---|---|---|
| GAGCGGACAGCAGCTTCCTATATCTCGTAC | 73 | None |
| GAGCGGACAGCAGCTTCCTATATCTCGTA**T** | 104 | 1 |
| GAGCGGACAGCAGCTTCCTATATCTCGT**G**C | 105 | 2 |
| GAGCGGACAGCAGCTTCCTATATCTCG**C**AC | 106 | 3 |
| GAGCGGACAGCAGCTTCCTATATCTC**A**TAC | 107 | 4 |
| GAGCGGACAGCAGCTTCCTATATCT**T**GTAC | 108 | 5 |
| GAGCGGACAGCAGCTTCCTATATC**C**CGTAC | 109 | 6 |
| GAGCGGACAGCAGCTTCCTATAT**T**TCGTAC | 110 | 7 |
| GAGCGGACAGCAGCTTCCTATA**C**CTCGTAC | 111 | 8 |
| GAGCGGACAGCAGCTTCCTAT**G**TCTCGTAC | 112 | 9 |
| GAGCGGACAGCAGCTTCCTA**C**ATCTCGTAC | 113 | 10 |

TABLE 6-continued

| Sequences tested for the mismatch sensitivity assay for RGN APG07433.1 | | |
|---|---|---|
| DNA template for sgRNA synthesis | SEQ ID NO. | Mismatch position |
| GAGCGGACAGCAGCTTCCT**G**TATCTCGTAC | 114 | 11 |
| GAGCGGACAGCAGCTTCC**C**ATATCTCGTAC | 115 | 12 |
| GAGCGGACAGCAGCTTC**T**TATATCTCGTAC | 116 | 13 |
| GAGCGGACAGCAGCTT**T**CTATATCTCGTAC | 117 | 14 |
| GAGCGGACAGCAGCT**C**CCTATATCTCGTAC | 118 | 15 |
| GAGCGGACAGCAGC**C**TCCTATATCTCGTAC | 119 | 16 |
| GAGCGGACAGCAG**T**TTCCTATATCTCGTAC | 120 | 17 |
| GAGCGGACAGCA**A**CTTCCTATATCTCGTAC | 121 | 18 |
| GAGCGGACAGC**G**GCTTCCTATATCTCGTAC | 122 | 19 |
| GAGCGGACAG**T**AGCTTCCTATATCTCGTAC | 123 | 20 |
| GAGCGGACA**A**CAGCTTCCTATATCTCGTAC | 124 | 21 |
| GAGCGGAC**G**GCAGCTTCCTATATCTCGTAC | 125 | 22 |
| GAGCGGA**T**AGCAGCTTCCTATATCTCGTAC | 126 | 23 |

TABLE 7

| Mismatch sensitivity for RGN APG07433.1 | |
|---|---|
| Mismatch position | % cleaved APG07433.1 |
| No mismatch | 86 |
| 1 | 6 |
| 2 | 21 |
| 3 | −2 |
| 4 | 1 |
| 5 | −1 |
| 6 | 0 |
| 7 | 7 |
| 8 | 24 |
| 9 | 14 |
| 10 | −1 |
| 11 | 72 |
| 12 | 44 |
| 13 | 54 |
| 14 | 60 |
| 16 | 65 |
| 17 | 76 |
| 18 | 84 |
| 19 | 86 |
| 20 | 83 |
| 21 | 83 |
| 22 | 93 |
| 23 | 80 |

RGNs APG07433.1 and APG08290.1 show significant sensitivity to mismatches in positions 1-10 5' from the PAM with a few exceptions (Table 5 and Table 7). RGN APG05459.1 is sensitive as well to mismatches in this region, but its ability to cleave dsDNA is also heavily abrogated by mismatches distant from the PAM site (Table 5). The total number of sites with a significant influence on whether or not cleavage occurs is at least 15 positions in the spacer sequence. This compares favorably to other genome editing tools, such as the well-studied Cas9 nuclease from *S. pyogenes*, which is generally sensitive to between 10-13 base pairs (Hsu et al., Nat Biotechnol (2013) 31(9): 827-832). Additionally, many of the critical sites abrogating RGN APG05459.1 mediated cleavage are very far from the PAM sequence, notably in the range of 13-20 bp, where many other nucleases show little if any sensitivity to mismatches. This property could be extraordinarily useful in targeting genetic loci that have close sequence similarity to other sites in the organism of interest.

Example 6: Demonstration of Gene Editing Activity in Mammalian Cells

RGN expression cassettes were produced and introduced into vectors for mammalian expression. Each RGN was codon-optimized for human expression (SEQ ID NOs 127-133), and operably fused at the 5'end to an SV40 nuclear localization sequence (NLS; SEQ ID NO 134) and to 3×FLAG tags (SEQ ID NO: 135), and operably fused at the 3'end to nucleoplasmin NLS sequences (SEQ ID NO: 136). Each expression cassette was under control of a cytomegalovirus (CMV) promoter (SEQ ID NO: 137). It is known in the art that the CMV transcription enhancer (SEQ ID NO: 138) may also be included in constructs comprising the CMV promoter. Guide RNA expression constructs encoding a single gRNA each under the control of a human RNA polymerase III U6 promoter (SEQ ID NO. 139) were produced and introduced into the pTwist High Copy Amp vector. Sequences for the target sequences for each guide are in Table 9.

The constructs described above were introduced into mammalian cells. One day prior to transfection, $1\times10^5$ HEK293T cells/well (Sigma) were plated in 24-well dishes in Dulbecco's modified Eagle medium (DMEM) plus 10% (vol/vol) fetal bovine serum (Gibco) and 1% Penicillin-Streptomycin (Gibco). The next day when the cells were at 50-60% confluency, 500 ng of a RGN expression plasmid plus 500 ng of a single gRNA expression plasmid were co-transfected using 1.5 μL of Lipofectamine 3000 (Thermo Scientific) per well, following the manufacturer's instructions. After 48 hours of growth, total genomic DNA was harvested using a genomic DNA isolation kit (Machery-Nagel) according to the manufacturer's instructions.

The total genomic DNA was then analyzed to determine the rate of editing for each RGN for each genomic target. First, oligonucleotides were produced to be used for PCR amplification and subsequent analysis of the amplified genomic target site. Oligonucleotide sequences used are listed in Tables 8.1 to 8.5.

All PCR reactions were performed using 10 μL of 2× Master Mix Phusion High-Fidelity DNA polymerase (Thermo Scientific) in a 20 μL reaction including 0.5 μM of each primer. Large genomic regions encompassing each target gene were first amplified using PCR #1 primers, using a program of: 98° C., 1 min; 30 cycles of [98° C., 10 sec; 62° C., 15 sec; 72° C., 5 min]; 72° C., 5 min; 12° C., forever. One microliter of this PCR reaction was then further amplified using primers specific for each guide (PCR #2 primers), using a program of: 98° C., 1 min; 35 cycles of [98° C., 10 sec; 67° C., 15 sec; 72° C., 30 sec]; 72° C., 5 min; 12° C., forever. Primers for PCR #2 include Nextera Read 1 and Read 2 Transposase Adapter overhang sequences for Illumina sequencing.

TABLE 8.1

Oligonucleotides for detection of gene editing activity in mammalian cells, PCR #1

| Description | Sequence | SEQ ID NO |
|---|---|---|
| RelA FWD | 5'-CTT AGT TTC ACC GCA GGT TCT A-3' | 479 |
| RelA REV | 5'-CTG TGC ACT CAA CAC TGA TCT A-3' | 480 |
| AurkB FWD | 5'-CCC AGC CCT AGG TTG TTT ATT-3' | 481 |
| AurkB REV | 5'-CTG GCT ACA TCT TCC TTG ACT AC-3' | 482 |
| HPRT1 FWD | 5'-GTG GCA GAA GCA GTG AGT AA-3' | 483 |
| HPRT1 REV | 5'-TCC CAT CTA GGC ACT AGG TAA A-3' | 484 |

TABLE 8.2

Oligonucleotides for detection of gene editing activity in mammalian cells, PCR#2 for APG05083.1, APG07433.1, APG07513.1, and APG08290.1

| Description | SEQ ID NO. |
|---|---|
| FWD_Guide 134, Guide 135, Guide 136, Guide 137 | 485 |
| REV_Guide 134, Guide 135, Guide 136, Guide 137 | 486 |
| FWD_Guide 138, Guide 139, Guide 140, Guide 141 | 487 |
| REV_Guide 138, Guide 139, Guide 140, Guide 141 | 488 |
| REV_Guide 142, Guide 143, Guide 144, Guide 145 | 489 |
| FWD_Guide 142, Guide 143, Guide 144, Guide 145 | 490 |
| REV_Guide 164, Guide 165, Guide 166, Guide 167 | 491 |
| FWD_Guide 164, Guide 165, Guide 166, Guide 167 | 492 |
| REV_Guide 168, Guide 169, Guide 170, Guide 171 | 493 |
| FWD_Guide 168, Guide 169, Guide 170, Guide 171 | 494 |
| REV_Guide 172, Guide 173, Guide 174, Guide 175 | 495 |
| FWD_Guide 172, Guide 173, Guide 174, Guide 175 | 496 |
| REV_Guide 185, Guide 186, Guide 187, Guide 188 | 497 |
| FWD_Guide 185, Guide 186, Guide 187, Guide 188 | 498 |
| REV_Guide 189, Guide 190, Guide 191, Guide 192 | 499 |
| FWD_Guide 189, Guide 190, Guide 191, Guide 192 | 500 |
| REV_Guide 193, Guide 194, Guide 195, Guide 196 | 501 |
| FWD_Guide 193, Guide 194, Guide 195, Guide 196 | 502 |

TABLE 8.3

Oligonucleotides for detection of gene editing activity in mammalian cells, PCR#2 for APG005459.1

| Description | SEQ ID NO. |
|---|---|
| FWD_Guide 146 | 503 |
| REV_Guide 146 | 504 |
| FWD_Guide 147 | 505 |
| REV_Guide 147 | 506 |
| REV_Guide 148 | 507 |
| FWD_Guide 148 | 508 |
| REV_Guide 176 | 509 |
| FWD_Guide 176 | 510 |
| REV_Guide 177 | 511 |
| FWD_Guide 177 | 512 |
| REV_Guide 209 | 513 |
| FWD_Guide 209 | 514 |
| REV_Guide 197 | 515 |
| FWD_Guide 197 | 516 |
| REV_Guide 198 | 517 |
| FWD_Guide 198 | 518 |
| REV_Guide 199 | 519 |
| FWD_Guide 199 | 520 |

TABLE 8.4

Oligonucleotides for detection of gene editing activity in mammalian cells, PCR#2 for APG004583.1

| Description | SEQ ID NO. |
|---|---|
| FWD_Guide 149 | 521 |
| REV_Guide 149 | 522 |
| FWD_Guide 150 | 523 |
| REV_Guide 150 | 524 |
| REV_Guide 151 | 525 |
| FWD_Guide 151 | 526 |
| REV_Guide 179 | 527 |
| FWD_Guide 179 | 528 |
| REV_Guide 180 | 529 |
| FWD_Guide 180 | 530 |
| REV_Guide 181 | 531 |
| FWD_Guide 181 | 532 |
| REV_Guide 200 | 533 |
| FWD_Guide 200 | 534 |
| REV_Guide 201 | 535 |
| FWD_Guide 201 | 536 |
| REV_Guide 202 | 537 |
| FWD_Guide 202 | 538 |

TABLE 8.5

Oligonucleotides for detection of gene editing activity in mammalian cells, PCR#2 for APG01988.1

| Description | SEQ ID NO. |
|---|---|
| FWD_Guide 152 | 539 |
| REV_Guide 152 | 540 |
| FWD_Guide 153 | 541 |
| REV_Guide 153 | 542 |
| FWD_Guide 154 | 543 |
| REV_Guide 154 | 544 |
| FWD_Guide 182 | 545 |
| REV_Guide 182 | 546 |
| FWD_Guide 183 | 547 |
| REV_Guide 183 | 548 |
| FWD_Guide 184 | 549 |
| REV_Guide 184 | 550 |
| FWD_Guide 203 | 551 |
| REV_Guide 203 | 552 |
| FWD_Guide 204 | 553 |
| REV_Guide 204 | 554 |
| FWD_Guide 205 | 555 |
| REV_Guide 205 | 556 |

Purified genomic DNA was subjected to PCR #1 and PCR #2 as above. Following the second PCR amplification DNA was cleaned using a PCR cleanup kit (Zymo) according to the manufacturer's instructions and eluted in water. 200-500 ng of purified PCR #2 product was combined with 2 μL of 10×NEB Buffer 2 and water in a 20 μL reaction and annealed to form heteroduplex DNA using a program of: 95° C., 5 min; 95-85° C., cooled at a rate of 2° C./sec; 85-25° C., cooled at a rate of 0.1° C./sec.; 12° C., forever. Following annealing 5 μL of DNA was removed as a no enzyme control, and 1 μL of T7 Endonuclease I (NEB) was added and the reaction incubated at 37° C. for 1 hr. After incubation 5× FlashGel loading dye (Lonza) was added and 5 μL of each reaction and controls were analyzed by a 2.2% agarose FlashGel (Lonza) using gel electrophoresis. Following visualization of the gel, the percentage of non-homologous end joining (NHEJ) was determined using the following equation: % NHEJ events=100×[1−(1−fraction cleaved)^(½)], where (fraction cleaved) is defined as: (density of digested products)/(density of digested products+undigested parental band).

For some samples, SURVEYOR® was used to analyze the results following expression in mammalian cells. Cells were incubated at 37° C. for 72 h post-transfection before genomic DNA extraction. Genomic DNA was extracted using the QuickExtract DNA Extraction Solution (Epicentre) following the manufacturer's protocol. The genomic region flanking the RGN target site was PCR amplified, and products were purified using QiaQuick Spin Column (Qiagen) following the manufacturer's protocol. 200-500 ng total of the purified PCR products were mixed with 1 μl 10× Taq DNA Polymerase PCR buffer (Enzymatics) and ultrapure water to a final volume of 10 μl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min.

After reannealing, products were treated with SURVEYOR® nuclease and SURVEYOR® enhancer S (Integrated DNA Technologies) following the manufacturer's recommended protocol and analyzed on 4-20% Novex TBE polyacrylamide gels (Life Technologies). Gels were stained with SYBR Gold DNA stain (Life Technologies) for 10 min and imaged with a Gel Doc gel imaging system (Bio-rad). Quantification was based on relative band intensities. Indel percentage was determined by the formula, 100×(1−(1−(b+c)/(a+b+c))^½), where a is the integrated intensity of the undigested PCR product, and b and c are the integrated intensities of each cleavage product.

Additionally, products from PCR #2 containing Illumina overhang sequences underwent library preparation following the Illumina 16S Metagenomic Sequencing Library protocol. Deep sequencing was performed on an Illumina Mi-Seq platform by a service provider (MOGene). Typically 200,000 of 250 bp paired-end reads (2×100,000 reads) are generated per amplicon. The reads were analyzed using CRISPResso (Pinello, et al. 2016 Nature Biotech, 34:695-697) to calculate the rates of editing. Output alignments were hand-curated to confirm insertion and deletion sites as well as identify microhomology sites at the recombination sites. The rates of editing are shown in Table 9. All experiments were performed in human cells. The "target sequence" is the targeted sequence within the gene target. For each target sequence, the guide RNA comprised the complementary RNA target sequence and the appropriate sgRNA depending on the RGN used. A selected breakdown of experiments by guide RNA is shown in Tables 10.1-10.9.

TABLE 9

Overall rates of editing

| RGN | Guide RNA ID | Target Sequence (SEQ ID NO.) | Gene Target | Overall Editing Rate in Sample | Deletion Rate in Sample | Insertion Rate in Sample |
|---|---|---|---|---|---|---|
| APG05083.1 | 189 | 140 | RelA | 6.9% | | 100% |
| APG05083.1 | 185 | 141 | RelA | 8.2% | 79.9% | 20.1% |
| APG05083.1 | 168 | 142 | HPRT1 | 11.3% | 36.3% | 72.4% |
| APG07433.1 | 135 | 143 | AurkB | 1.7% | 88.3% | 11.7% |
| APG07433.1 | 139 | 144 | AurkB | 3.32% | 84.3% | 15.6% |
| APG07433.1 | 143 | 145 | AurkB | 2.2% | 35.1% | 64.9% |
| APG07433.1 | 190 | 146 | RelA | 60.5% | 94.8% | 5.2% |
| APG07433.1 | 194 | 147 | RelA | 6.2% | | 100% |
| APG07433.1 | 165 | 148 | HPRT1 | 3.5% | 68.0% | 32.0% |
| APG07433.1 | 169 | 149 | HPRT1 | 18.1% | 30.3% | 69.7% |
| APG07433.1 | 173 | 150 | HPRT1 | 26.6% | 91.9% | 10.0% |
| APG07513.1 | 144 | 151 | AurkB | 2.4% | 59.1% | 40.9% |
| APG07513.1 | 136 | 152 | AurkB | 0.9% | 80.5% | 19.5% |
| APG08290.1 | 145 | 153 | AurkB | 14.18% | 75.85% | 24.15% |
| APG08290.1 | 188 | 154 | RelA | 21.40% | 99.05% | 50.05% |
| APG08290.1 | 192 | 155 | RelA | 28.98% | 42.05% | 57.95% |
| APG08290.1 | 196 | 156 | RelA | 13.27% | 91.80% | 8.20% |
| APG08290.1 | 167 | 157 | HPRT1 | 14.14% | 65.98% | 34.02% |
| APG08290.1 | 171 | 158 | HPRT1 | 48.23% | 58.26% | 41.74% |
| APG08290.1 | 175 | 159 | HPRT1 | 13.60% | 74.18% | 25.82% |
| APG05459.1 | 197 | 160 | RelA | 12.95% | 92.16% | 7.84% |
| APG05459.1 | 199 | 161 | RelA | 5.19% | 100% | |
| APG05459.1 | 146 | 162 | AurkB | 1.12% | 61.50% | 38.50% |
| APG05459.1 | 148 | 163 | AurkB | 0.78% | 49.47% | 50.53% |
| APG05459.1 | 176 | 164 | HPRT1 | 6.20% | 48.91% | 51.09% |
| APG05459.1 | 177 | 165 | HPRT1 | 9.00% | 9.33% | 90.67% |
| APG05459.1 | 209 | 166 | HPRT1 | 2.50% | | 100% |
| APG04583.1 | 151 | 167 | AurkB | 0.0% | | |
| APG01688.1 | 152 | 168 | AurkB | 0.0% | | |

Specific insertions and deletions for respective guides are shown in Tables 10.1-10.7. In these tables, the target sequence is identified by bold upper case letters. The 8mer PAM regions are double underlined, with the main recognized nucleotides in bold. Insertions are identified by lowercase letters. Deletions are indicated with dashes (---). The INDEL location is calculated from the PAM proximal edge of the target sequence, with the edge being location 0. The location is positive (+) if the location is on the target side of the edge; the location is negative (−) if the location is on the PAM side of the edge.

TABLE 10.1

Specific insertions and deletions for Guide 139 using RGN APG07433.1

| Guide 139 (SEQ ID NO: 144) | # Reads | % Reads | % of INDELs | Type | INDEL Location | Size |
|---|---|---|---|---|---|---|
| CCTGGGTGTGAGGCTGGGCCATTAAAACCTCTCC | 82540 | 95.562 | | | | |
| CCTG------------------AAAACCTCTCC | 170 | 0.199 | 23.16 | Deletion | -6 | 19 |
| CCTGGGTGTGA-GCTGGGCCATTAAAACCTCTCC | 132 | 0.155 | 17.98 | Deletion | +1 | 1 |
| C------------CTGGGCCATTAAAACCTCTCC | 107 | 0.125 | 14.57 | Deletion | -9 | 12 |
| CCTGG----------------------CTCTCC | 101 | 0.118 | 13.76 | Deletion | -5 | 23 |
| C--------------GGGCCATTAAAACCTCTCC | 61 | 0.071 | 8.31 | Deletion | -9 | 14 |
| CCTGGGTGTGAGGccagacCTGGGCCATTAAAACCTCTCC | 49 | 0.057 | 6.67 | Insertion | +3 | 6 |
| CCTGGGTGTGAGgggaagctgacgtcctttccatggctgctcgcctgtgttgccaccGCTGGGCCATTAAAACCTCTCC | 44 | 0.051 | 5.99 | Insertion | +2 | 45 |
| CCTGGGTGTGA-cCTGGGCCATTAAAACCTCTCC | 39 | 0.045 | 5.31 | Deletion & Mutation | +1 | 1 |
| CCTGGGTGTGAGGaCTGGGCCATTAAAACCTCTCC | 31 | 0.036 | 4.22 | Insertion | +3 | 1 |

TABLE 10.2

Specific insertions and deletions for Guide 143 using RGN APG07433.1

| Guide 143 (SEQ ID NO: 145) | # Reads | % Reads | % of INDELs | Type | INDEL Location | Size |
|---|---|---|---|---|---|---|
| AGTTGGCAGATGCTCTAATGTACTGCCATGGGAA | 84043 | 99.646 | | | | |
| AGTTGGCAGATGC---AATGTACTGCCATGGGAA | 126 | 0.149 | 42.281 | Deletion | +3 | 3 |
| AGTTGGCAGATGC----ATGTACTGCCATGGGAA | 81 | 0.096 | 27.181 | Deletion | +3 | 4 |
| AGTTGGCAGATGCT---ATGTACTGCCATGGGAA | 42 | 0.049 | 14.093 | Deletion | +4 | 3 |
| AGTTGGCAGATGC--TAATGTACTGCCATGGGAA | 34 | 0.040 | 11.409 | Deletion | +3 | 2 |
| AGTTGGCAGATGCT---ATGTAaTGCCATGGGAA | 8 | 0.009 | 2.684 | Deletion & Mutation | +4 | 3 |
| AGTTGGCAGATGCTCT-ATGTACTGCCATGGGAA | 7 | 0.008 | 2.348 | Deletion | +6 | 1 |

TABLE 10.3

Specific insertions and deletions for Guide 190 using RGN APG07433.1

| Guide 190 (SEQ ID NO: 146) | # Reads | % Reads | % of INDELs | Type | INDEL Location | Size |
|---|---|---|---|---|---|---|
| CGA**CCTGAATGCTGTGC------------------** ----------------------------------- ----------------------------------- ----------------------------------- ------------GGCGCTCTGGCTTCATTCAATC | 64040 | 55.46 | 91.70 | Deletion | −164 | 170 |
| CGA**CCTGAATGCTGTGCGGCTCT**GCTTCCAG**GTGA** | 45619 | 39.51 | | WT | | |
| CGA**CCTGAATGCTGTGCGGC**a**TCT**GCTTCCAG**GTG** A | 3620 | 3.13 | 5.18 | Insertion | +3 | 1 |
| CGA**CCTGAATG----------CT**GCTTCCAG**GTGA** | 1110 | 0.96 | 1.58 | Deletion | +2 | 10 |
| cGA**CCTGAATGCT-------TCT**GCTTCCAG**GTGA** | 858 | 0.74 | 1.22 | Deletion | +3 | 7 |
| CGA**CCTGAA-------------T**GCTTCCAG**GTGA** | 206 | 0.17 | 0.29 | Deletion | +1 | 13 |

TABLE 10.4

Specific insertions and deletions for Guide 194 using RGN APG07433.1

| Guide 194 (SEQ ID NO: 147) | # Reads | % Reads | % of INDELs | Type | INDEL Location | Size |
|---|---|---|---|---|---|---|
| GCGTGGGGACTA**CGACCTGAATGCTGTGCGGC**TCT | 96635 | 97.318 | | | | |
| GCG-----------**ACCTGAATGCTGTGCGGC**TCT | 1194 | 1.202 | 44.836 | Deletion | −9 | 11 |
| GCGTGGGGACTA**CGA-------GCTGTGCGGC**TCT | 547 | 0.550 | 20.540 | Deletion | +3 | 7 |
| GCGTGGGGA-------**CTGAATGCTGTGCGGC**TCT | 473 | 0.476 | 17.761 | Deletion | −3 | 7 |
| GCGTGGGGACT----**CCTGAATGCTGTGCGGC**TCT | 270 | 0.271 | 10.138 | Deletion | −1 | 4 |
| GCGTGGGGACTA**CGA**a**CCTGA**a**TGCTGTGCGGC**T CT | 88 | 0.088 | 3.304 | Insertion | +3 | 1 |
| GCGTGGGGACTA**CGA-----ATGCTGTGCGGC**TCT | 41 | 0.041 | 1.539 | Deletion | +3 | 5 |
| GCGTGGGGACTA**C---CTGAATGCTGTGCGGC**TCT | 31 | 0.031 | 1.164 | Deletion | +2 | 3 |
| GCG--------------**TGAATGCTGTGCGGC**TCT | 9 | 0.009 | 0.337 | Deletion | −9 | 14 |
| GCG-----------**ACCTGA**c**TGCTGTGCGGC**TCT | 5 | 0.005 | 0.187 | Deletion & Mutation | −9 | 11 |
| GCGTGGGGACTA**CG-CCTGAATGCTGTGCGGC**TCT | 5 | 0.005 | 0.187 | Deletion | +2 | 1 |

TABLE 10.5

Specific insertions and deletions for Guide 145 using RGN APG08290.1

| Guide 145 (SESQ ID NO: 153) | # Reads | % Reads | % of INDELs | Type | INDEL Location | Size |
|---|---|---|---|---|---|---|
| ATGGAGGAGTTGGCAGA**TGCTCTAATGTACTGC** **CATG**GGAAG | 62618 | 95.889 | | | | |
| ATGGAGGAGTTGGCAGA**TGC-TAATGTACTGCC** **ATG**GGAAG | 976 | 1.494 | 36.363 | Deletion | +3 | 2 |
| ATGGAGGAGTTGGCAGA**TG--------TACTGC** **CATG**GGAAG | 319 | 0.488 | 11.885 | Deletion | +2 | 8 |
| ATG------------------------**TACTGC** **CATG**GGAAG | 168 | 0.257 | 6.259 | Deletion | −14 | 24 |
| ATGGAGGAGTTGG------------**TGTACTGC** **CATG**GGAAG | 157 | 0.240 | 5.849 | Deletion | −4 | 12 |

TABLE 10.5-continued

| Specific insertions and deletions for Guide 145 using RGN APG08290.1 | | | | | | |
|---|---|---|---|---|---|---|
| Guide 145 (SESQ ID NO: 153) | # Reads | % Reads | % of INDELs | Type | INDEL Location | Size |
| ATGGAGGAGTTGGCAGATGCTCTaAATGTACTGCCATGGGAAG | 147 | 0.225 | 5.476 | Insertion | +6 | 1 |
| ATGGAGGAGTTGGCAGATGCtctTCTAATGTACTGCCATGGGAAG | 123 | 0.188 | 4.582 | Insertion | +2 | 3 |
| ATGGAGGAGTTGGCAGATGccCTCTAATGTACTGCCATGGGAAG | 110 | 0.168 | 4.098 | Insertion | +2 | 2 |
| ATGGAGGAGTTGGCAGAT-----AATGTACTGCCATGGGAAGAAG | 103 | 0.157 | 3.837 | Deletion | +1 | 5 |
| ATGG---------------------cGTACTGCCATGGGAAGAAG | 96 | 0.147 | 3.57 | Deletion & Mutation | −7 | 21 |
| ATGGAGGAGTTGGCAGATGCtTCTAATGTACTGCCATGGGAAGAAG | 85 | 0.130 | 3.166 | Insertion | +3 | 1 |
| ATGGAGGAGTTGGCA-------------TCTGCCATGGGAAGAAG | 84 | 0.128 | 3.129 | Deletion | −2 | 13 |
| ATGGAGGAGTTGGCAGATGC---AATGTACTGCCATGGGAAGAAG | 79 | 0.120 | 2.943 | Deletion | +3 | 3 |
| ATGGAGGAGTTGGCAGATGCcaaactgaaaaacaaatcaaagcactcttattgagtgctggcgatccccgacgccacgggccgaaacccttatcatagaaaCTCTAATGTACTGCCATGGGAAG | 58 | 0.0884 | 2.160 | Insertion | +3 | 81 |
| ATGGAGGAGTTGGCAGATGCtgcttatatagacctcccaccgtacacgcctaccgcccatttTCTAATGTACTGCCATGGGAAG | 53 | 0.081 | 1.974 | Insertion | +3 | 42 |
| ATGGAGGAGTTG--------TCTAATGTACTGCCATGGGAAG | 47 | 0.071 | 1.751 | Deletion | −5 | 8 |
| ----------------------------CTGCCATGGGAAGAAG | 26 | 0.039 | 0.968 | Deletion | | |
| ATGGAGGAGTTGGCAGATGCgcggctgttcctgtacagaaccgtgggcgagatgtggatcaaggatgcTCTAATGTACTGCCATGGGAAG | 21 | 0.032 | 0.782 | Insertion | +3 | 48 |
| ATGGAGGAGTTGGCAGATGC-CTAATGTACTGCCATGGGAAG | 14 | 0.021 | 0.521 | Deletion | +3 | 1 |
| ATGGAGGAGTTGGCAGATGCtgtcatgatcttttccgctcgtcgtgggacttgctcagttctctggccagctcgTCTAATGTACTGCCATGGGAAG | 10 | 0.015 | 0.372 | Insertion | +3 | 55 |
| ATGGAGGAGTTGGCAGATGCTCT-ATGTACTGCCATGGGAAG | 8 | 0.012 | 0.29 | Deletion | +6 | 1 |

TABLE 10.6

| Specific insertions and deletions for Guide 188 using RGN APG08290.1 | | | | | | |
|---|---|---|---|---|---|---|
| Guide 188 (SEQ ID NO: 154) | # Reads | % Reads | % of INDELs | Type | INDEL Location | Size |
| CAGGGACAGTGCGCATCTCCCTGGTCACCAAG | 59686 | 97.000 | | | | |
| CAGGGACA---------------GTCACCAAG | 1286 | 2.089 | 69.664 | Deletion | 0 | 15 |
| CAGGGACAGTGCGCATCTC-CTGGTCACCAAG | 473 | 0.768 | 25.622 | Deletion | +3 | 1 |
| CAGGGACAGTGCGCATCT--CTGGTCACCAAG | 57 | 0.092 | 3.087 | Deletion | +3 | 2 |
| CAGGGACAGTGCGCATCTCCtCTGGTCACCAAG | 11 | 0.017 | 0.595 | Insertion | +3 | 1 |
| CAGGGACAGTGCGCATC---CTGGTCACCAAG | 7 | 0.011 | 0.379 | Deletion | +3 | 3 |

TABLE 10.6-continued

| Specific insertions and deletions for Guide 188 using RGN APG08290.1 | | | | | | |
|---|---|---|---|---|---|---|
| Guide 188 (SEQ ID NO: 154) | # Reads | % Reads | % of INDELs | Type | INDEL Location | Size |
| CAGGGAC---------------GGTCACCAAG | 7 | 0.011 | 0.379 | Deletion | +2 | 15 |
| CGGGGACAGgGCGCATCTC-CTGGTCACCAAG | 5 | 0.008 | 0.270 | Deletion & Mutation | +3 | 1 |

TABLE 10.7

| Specific insertions and deletions for Guide 192 using RGN APG08290.1 | | | | | | |
|---|---|---|---|---|---|---|
| Guide 192 (SEQ ID NO: 155) | # Reads | % Reads | % of INDELs | Type | Location | INDEL Size |
| CGACCTGAATGCTGTGCGGCTCTGCTTCCAGG | 62352 | 95.658 | | | | |
| CGACCTGAATGCTGTGCGGCaTCTGCTTCCAGG | 1262 | 1.936 | 44.593 | Insertion | +3 | 1 |
| CGACCTGAATGCTGTGCGGCtTCTGCTTCCAGG | 842 | 1.291 | 29.752 | Insertion | +3 | 1 |
| CGACCTGAATGCTGTG----TCTGCTTCCAGG | 686 | 1.052 | 24.240 | Deletion | +3 | 4 |
| CGACCTGcATGCTGTGCGGCaTCTGCTTCCAGG | 18 | 0.027 | 0.636 | Insertion & Mutation | +3 | 1 |
| CGACCTGcATGCTGTGCGGCtTCTGCTTCCAGG | 11 | 0.016 | 0.388 | Insertion & Mutation | +3 | 1 |
| CGACCTGcATGCTGTG----TCTGCTTCCAGG | 6 | 0.009 | 0.212 | Deletion & Mutation | +3 | 4 |
| CGACCTGAATGCTGTGCGaCaTCTGCTTCCAGG | 5 | 0.007 | 0.176 | Insertion & Mutation | +3 | 2 |

TABLE 10.8

| Specific insertions and deletions for Guide 196 using RGN APG08290.1 | | | | | | |
|---|---|---|---|---|---|---|
| Guide 196 (SEQ ID NO: 156) | # Reads | % Reads | % of INDELs | Type | INDEL Location | Size |
| TGGGGACTACGACCTGAATGCTGTGCGGCTCT | 37206 | 93.073 | | | | |
| TGGGGACTACGA-----ATGCTGTGCGGCTCT | 1288 | 3.222 | 46.514 | Deletion | +3 | 5 |
| TGGGGACTACGAgcaggcagaagtatgcaaagcatgcatctcaattCCTGAATGCTGTGCGGCTCT | 881 | 2.203 | 31.816 | Insertion | +3 | 34 |
| TGGGGACTACGAagaaggcgatagaaggccatgcgctgcgaatcgggagcggCCTGAATGCTGTGCGGCTCT | 302 | 0.755 | 10.906 | Insertion | +3 | 40 |
| TGGGGACTACGAtgactcgctgcgctcggtcgttcggctgcggcgagcggtatcagctcactcaaaggcggtaatacggCCTGAATGCTGTGCGGCTCT | 272 | 0.680 | 9.823 | Insertion | +3 | 67 |
| TGGG------------------GTGCGGCTCT | 13 | 0.032 | 0.4694 | Deletion | −5 | 18 |
| TGGGGACTACGAC-----TGCTGTGCGGCTCT | 13 | 0.032 | 0.469 | Deletion | +4 | 5 |

TABLE 10.9

Specific insertions and deletions for Guide 190 using RGN APG07433.1

| Guide 190 (SEQ ID NO: 146) | # Reads | % Reads | % of INDELs | Type | INDEL Location | Size |
|---|---|---|---|---|---|---|
| CGACCTGAATGCTGTGC------------------------------------------------------------------------------------------------------------------GGCGCTCTGGCTTCATTCAATC | 64040 | 55.46 | 91.70 | Deletion | -164 | 170 |
| CGACCTGAATGCTGTGCGGCTCTGCTTCCAGGTGA | 45619 | 39.51 | | WT | | |
| CGACCTGAATGCTGTGCGGCaTCTGCTTCCAGGTGA | 3620 | 3.13 | 5.18 | Insertion | +3 | 1 |
| CGACCTGAATG----------CTGCTTCCAGGTGA | 1110 | 0.96 | 1.58 | Deletion | +2 | 10 |
| cGACCTGAATGCT-------TCTGCTTCCAGGTGA | 858 | 0.74 | 1.22 | Deletion | +3 | 7 |
| CGACCTGAA-------------TGCTTCCAGGTGA | 206 | 0.17 | 0.29 | Deletion | +1 | 13 |

Example 7: Demonstration of Gene Editing Activity in Plant Cells

RNA-guided nuclease activity of the RGNs of the invention is demonstrated in plant cells using protocols adapted from Li, et al. (2013) *Nat. Biotech.* 31:688-691. Briefly, plant codon optimized versions of each RGN (SEQ ID NOs: 169-182) containing an N-terminal SV40 nuclear localization signal are cloned behind the strong constitutive 35S promoter in a transient transformation vector. sgRNAs targeting one or more sites in the plant PDS gene that flank an appropriate PAM sequence are cloned behind a plant U6 promoter in a second transient expression vector. The expression vectors are introduced into *Nicotiana benthamiana* mesophyll protoplasts using PEG-mediated transformation. The transformed protoplasts are incubated in the dark for up to 36 hr. Genomic DNA is isolated from the protoplasts using a DNeasy Plant Mini Kit (Qiagen). The genomic region flanking the RGN target site is PCR amplified, and products are purified using QiaQuick Spin Column (Qiagen) following the manufacturer's protocol. 200-500 ng total of the purified PCR products are mixed with 1 μl 10×Taq DNA Polymerase PCR buffer (Enzymatics) and ultrapure water to a final volume of 10 μl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min. After reannealing, products are treated with SURVEYOR nuclease and SURVEYOR enhancer S (Integrated DNA Technologies) following the manufacturer's recommended protocol and analyzed on 4-20% Novex TBE polyacrylamide gels (Life Technologies). Gels are stained with SYBR Gold DNA stain (Life Technologies) for 10 min and imaged with a Gel Doc gel imaging system (Bio-rad). Quantification is based on relative band intensities. Indel percentage is determined by the formula, $100\times(1-(1-(b+c)/(a+b+c))^{1/2})$, where a is the integrated intensity of the undigested PCR product, and b and c are the integrated intensities of each cleavage product.

Alternatively, PCR products derived from the targeted genomic sequence can be subjected to PCR similar to that described in Example 6, so that PCR products contain Illumina overhang sequences and can undergo library preparation and deep sequencing. This method allows determination of the rates of editing as shown in Table 9.

Example 8: Guide Cross-Compatibility

To determine the cross-compatibility of guide RNAs between RGNs, a two-plasmid interference experiment was performed (Esvelt et al (2013), Nat. Methods 10(11): 1116-21). The first plasmid contained the RGN with several targets containing defined PAMs on a kanamycin resistant backbone. These plasmids were transformed into *E. coli* BL21, and the transformed strains were made to be chemically competent. A second plasmid containing a guide RNA on an ampicillin resistance backbone was then introduced. Cells were plated on media containing both antibiotics. If an RGN is able to use the guide on the second plasmid, the kanamycin-resistance plasmid is cleaved and linearized, resulting in little or no colony formation. If an RGN is not able to use the guide on the second plasmid, the kanamycin-resistance plasmid is not be cleaved, resulting in high levels of colony formation. Guide RNAs for *Streptococcus pyogenes* Cas9 (SpyCas9) and *Staphylococcus aureus* Cas9 (SauCas9) were also included to determine cross-compatibility with those guide RNAs.

To calculate the depletion percentage, the number of colonies for each guide transformation is compared to the transformation efficiency using a positive control. Based on this comparison, if an RGN can use a guide, the depletion percentage should be 0, as no colonies are able to survive. If an RGN cannot use a guide, the depletion percentage should be 1 as all plasmids remain intact. Results are shown in Table 11 below. "sg" indicates the guide RNA for the recited RGN.

TABLE 11

Cross-compatibility assay

| | APG05083.1 | APG07513.1 | APG08290.1 | APG05459.1 | APG04583.1 | APG01688.1 |
|---|---|---|---|---|---|---|
| sgAPG05083.1 | 0 | 0 | 0 | 0.21 | 1 | 0.74 |
| sgAPG07433.1 | 0 | 0 | 0 | 0.16 | 0.78 | 0.33 |
| sgAPG07513.1 | 0 | 0.01 | 0 | 0.32 | 0.97 | 0.64 |
| sgAPG05459.1 | 0.24 | 0.53 | 0.26 | 0.09 | 1 | 0.49 |

TABLE 11-continued

| Cross-compatibility assay | | | | | | |
|---|---|---|---|---|---|---|
| | APG05083.1 | APG07513.1 | APG08290.1 | APG05459.1 | APG04583.1 | APG01688.1 |
| sgAPG04583.1 | 0.74 | 0.8 | 0.36 | 0.21 | 0 | 0 |
| sgAPG01688.1 | 0.12 | 0.26 | 0.18 | 0.43 | 0 | 0 |
| sgSauCas9 | 1 | 0.23 | 0.27 | 0.53 | 0.51 | 0.92 |
| sg Spy | 0.16 | 0.27 | 0.32 | 0.06 | 1 | 1 |

As Table 11 indicates, there are four groups of orthogonal systems. RGNs can recognize guides from other systems in their groups, but cannot use guides from other groups. The first group contains APG05083.1, APG07433.1, APG07513.1, and APG08290.1. The second group contains SpyCas9 and APG05459.1. The third group contains APG04583.1 and APG01688.1. The fourth group contains SauCas9.

Example 9: Identification of Disease Targets

A database of clinical variants was obtained from NCBI ClinVar database, which is available through the world wide web at the NCBI ClinVar website. Pathogenic Single Nucleotide Polymorphisms (SNPs) were identified from this list. Using the genomic locus information, CRISPR targets in the region overlapping and surrounding each SNP were identified. A selection of SNPs that can be corrected using base editing in combination with the RGNs of the invention to target the causal mutation is listed in Table 12. In Table 12, only one alias of each disease is listed. The "RS #" corresponds to the RS accession number through the SNP database at the NCBI website. The AlleleID corresponds to a causal allele accession number, and the Chromosome Accession number also provides accession reference information found through the NCBI website. Table 12 also provides genomic target sequence information suitable for the RGN listed for each disease. The target sequence information also provides protospacer sequence for the production of the necessary sgRNA for the corresponding RGN of the invention.

TABLE 12

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Ataxia-telangiectasia syndrome | 1137887 | APG04583.1 | G > A | 18083 | NC_000011.10, NC_000011.9 | ATM | 197 |
| Very long chain acyl-CoA dehydrogenase deficiency | 2309689 | APG05459.1 | G > A | 33868 | NC_000017.10, NC_000017.11 | ACADVL | 198 |
| Abnormality of T cell physiology | 3218716 | APG01688.1 | G > A | 52071 | NC_000014.8, NC_000014.9 | MYH7 | 199 |
| Cardiovascular phenotype | 5742905 | APG05083, APG07433.1, APG07513.1, APG08290.1 | T > C | 15159 | NC_000021.8, NC_000021.9 | CBS | 200 |
| 3-Oxo-5 alpha-steroid delta 4-dehydrogenase deficiency | 9332964 | APG04583.1 | G > A | 18390 | NC_000002.11, NC_000002.12 | SRD5A2 | 201 |
| Acute myeloid leukemia | 11540652 | APG05083, APG07433.1, APG07513.1, APG08290.1 | G > A | 27395 | NC_000017.10, NC_000017.11 | TP53 | 202 |
| Acute myeloid leukemia | 11540652 | APG05459.1 | G > A | 27395 | NC_000017.10, NC_000017.11 | TP53 | 203 |
| Cutaneous malignant melanoma 3 | 11547328 | APG05459.1 | C > T | 31967 | NC_000012.11, NC_000012.12 | CDK4 | 204 |
| Alpha-1-antitrypsin deficiency | 28929474 | APG05459.1 | G > A | 33006 | NC_000014.8, NC_000014.9 | SERPINA1 | 205 |
| Charcot-Marie-Tooth disease, type 2 | 28933093 | APG05459.1 | G > A | 29543 | NC_000001.10, NC_000001.11 | LMNA | 206 |
| Hereditary cancer-predisposing syndrome | 28934578 | APG05083, APG07433.1, APG07513.1, APG08290.1 | G > A | 27413 | NC_000017.10, NC_000017.11 | TP53 | 207 |
| Hereditary cancer-predisposing syndrome | 28934578 | APG01688.1 | G > A | 27413 | NC_000017.10, NC_000017.11 | TP53 | 208 |
| Hereditary cancer-predisposing syndrome | 28934872 | APG05459.1 | G > A | 27436 | NC_000016.9, NC_000016.10 | TSC2 | 209 |
| Brugada syndrome | 28937316 | APG05083, APG07433.1, APG07513.1, APG08290.1 | G > A | 24408 | NC_000003.11, NC_000003.12 | SCN5A | 210 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Brugada syndrome | 28937318 | APG05459.1 | G > A | 24429 | NC_000003.11, NC_000003.12 | SCN5A | 211 |
| GRACILE syndrome | 28937590 | APG05459.1 | A > G | 21206 | NC_000002.11, NC_000002.12 | BCS1L | 212 |
| Enhanced s-cone syndrome | 28937873 | APG05459.1 | G > A | 20571 | NC_000015.9, NC_000015.10 | NR2E3 | 213 |
| Charcot-Marie-Tooth disease, type 2 | 28940293 | APG05083, APG07433.1, APG07513.1, APG08290.1 | T > C | 17309 | NC_000001.10, NC_000001.11 | MFN2 | 214 |
| Charcot-Marie-Tooth disease, type 2 | 28940293 | APG05459.1 | T > C | 17309 | NC_000001.10, NC_000001.11 | MFN2 | 215 |
| Arylsulfatase a, allele a | 28940893 | APG05459.1 | C > T | 18091 | NC_000022.10, NC_000022.11 | ARSA | 216 |
| Familial hypercholesterolemia | 28942078 | APG05459.1 | G > A | 18733 | NC_000019.9, NC_000019.10 | LDLR | 217 |
| Familial hypercholesterolemia | 28942079 | APG05459.1 | G > A | 18734 | NC_000019.9, NC_000019.10 | LDLR | 218 |
| HEMOGLOBIN ARLINGTON PARK | 33930165 | APG05083, APG07433.1, APG07513.1, APG08290.1 | G > A | 30165 | NC_000011.9, NC_000011.10 | HBB | 219 |
| Familial hypertrophic cardiomyopathy 1 | 36211715 | APG05459.1 | G > A | 29159 | NC_000014.8, NC_000014.9 | MYH7 | 220 |
| Cardiovascular phenotype | 36211723 | APG05459.1 | G > A | 45266 | NC_000011.9, NC_000011.10 | MYBPC3 | 221 |
| Cardiovascular phenotype | 36211723 | APG01688.1 | G > A | 45266 | NC_000011.9, NC_000011.10 | MYBPC3 | 222 |
| Brugada syndrome | 45546039 | APG05083, APG07433.1, APG07513.1, APG08290.1 | G > A | 48043 | NC_000003.11, NC_000003.12 | SCN5A | 223 |
| Brugada syndrome | 45546039 | APG01688.1 | G > A | 48043 | NC_000003.11, NC_000003.12 | SCN5A | 224 |
| Hereditary cancer-predisposing syndrome | 55863639 | APG05459.1 | G > A | 176641 | NC_000017.10, NC_000017.11 | TP53 | 225 |
| Deficiency of butyryl-CoA dehydrogenase | 57443665 | APG05459.1 | T > C | 18867 | NC_000012.11, NC_000012.12 | ACADS | 226 |
| Deficiency of butyryl-CoA dehydrogenase | 57443665 | APG01688.1 | T > C | 18867 | NC_000012.11, NC_000012.12 | ACADS | 227 |
| Benign scapuloperoneal muscular dystrophy with cardiomyopathy | 59332535 | APG05459.1 | G > A | 77828 | NC_000001.10, NC_000001.11 | LMNA | 228 |
| Benign scapuloperoneal muscular dystrophy with cardiomyopathy | 60458016 | APG05459.1 | G > A | 29564 | NC_000001.10, NC_000001.11 | LMNA | 229 |
| Cone-rod dystrophy 6 | 61750173 | APG05459.1 | G > A | 24396 | NC_000017.10, NC_000017.11 | GUCY2D | 230 |
| Cone-rod dystrophy 6 | 61750173 | APG01688.1 | G > A | 24396 | NC_000017.10, NC_000017.11 | GUCY2D | 231 |
| Stargardt disease 1 | 61750641 | APG05083, APG07433.1, APG07513.1, APG08290.1 | G > A | 105317 | NC_000001.10, NC_000001.11 | ABCA4 | 232 |
| Leber congenital amaurosis 2 | 61751276 | APG05459.1 | G > A | 104715 | NC_000001.10, NC_000001.11 | RPE65 | 233 |
| Cone-rod dystrophy 3 | 61751407 | APG05459.1 | G > A | 105292 | NC_000001.10, NC_000001.11 | ABCA4 | 234 |
| Nonsyndromic Oculocutaneous Albinism | 61754375 | APG05459.1 | G > A | 18835 | NC_000011.9, NC_000011.10 | TYR | 235 |
| Phenylketonuria | 62508646 | APG05459.1 | T > C | 15654 | NC_000012.11, NC_000012.12 | PAH | 236 |
| Phenylketonuria | 62516101 | APG05083, APG07433.1, APG07513.1, APG08290.1 | G > A | 15658 | NC_000012.11, NC_000012.12 | PAH | 237 |
| Breast-ovarian cancer, familial 1 | 62625303 | APG05459.1 | C > T | 68931 | NC_000017.10, NC_000017.11 | BRCA1 | 238 |
| Hyperphenylalaninemia, non-pku | 62644499 | APG05083, APG07433.1, APG07513.1, APG08290.1 | G > A | 15656 | NC_000012.11, NC_000012.12 | PAH | 239 |
| Hyperphenylalaninemia, non-pku | 62644499 | APG05459.1 | G > A | 15656 | NC_000012.11, NC_000012.12 | PAH | 240 |
| Hereditary cancer-predisposing syndrome | 63750217 | APG05459.1 | G > A | 32138 | NC_000003.11, NC_000003.12 | MLH1 | 241 |
| Hereditary cancer-predisposing syndrome | 63750741 | APG05083, APG07433.1, APG07513.1, APG08290.1 | T > C | 94663 | NC_000002.11, NC_000002.12 | MSH6 | 242 |
| Hereditary cancer-predisposing syndrome | 63750809 | APG05459.1 | T > C | 95480 | NC_000003.11, NC_000003.12 | MLH1 | 243 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Hereditary cancer-predisposing syndrome | 63751657 | APG05083, APG07433.1, APG07513.1, APG08290.1 | G > A | 95331 | NC_000003.11, NC_000003.12 | MLH1 | 244 |
| Hereditary cancer-predisposing syndrome | 63751711 | APG05083, APG07433.1, APG07513.1, APG08290.1 | G > A | 95792 | NC_000003.11, NC_000003.12 | MLH1 | 245 |
| Hereditary cancer-predisposing syndrome | 63751711 | APG01688.1 | G > A | 95792 | NC_000003.11, NC_000003.12 | MLH1 | 246 |
| Anterior segment dysgenesis 6 | 72549387 | APG05459.1 | G > A | 22776 | NC_000002.11, NC_000002.12 | CYP1B1 | 247 |
| Brugada syndrome | 72549410 | APG05083, APG07433.1, APG07513.1, APG08290.1 | G > A | 78547 | NC_000003.11, NC_000003.12 | SCN5A | 248 |
| Brugada syndrome | 72549410 | APG05459.1 | G > A | 78547 | NC_000003.11, NC_000003.12 | SCN5A | 249 |
| Ornithine carbamoyltransferase deficiency | 72554308 | APG01688.1 | G > A | 26053 | NC_000023.10, NC_000023.11 | OTC | 250 |
| Osteogenesis imperfecta type I | 72645321 | APG05083, APG07433.1, APG07513.1, APG08290.1 | G > A | 414022 | NC_000017.10, NC_000017.11 | COL1A1 | 251 |
| Osteogenesis imperfecta type I | 72645321 | APG05083, APG07433.1, APG07513.1, APG08290.1 | G > A | 414022 | NC_000017.10, NC_000017.11 | COL1A1 | 252 |
| Constipation | 74799832 | APG05083, APG07433.1, APG07513.1, APG08290.1 | T > C | 28958 | NC_000010.10, NC_000010.11 | RET | 253 |
| Dopamine beta hydroxylase deficiency | 74853476 | APG05083, APG07433.1, APG07513.1, APG08290.1 | T > C | 16789 | NC_000009.11, NC_000009.12 | DBH | 254 |
| Cystic fibrosis | 75096551 | APG05083, APG07433.1, APG07513.1, APG08290.1 | G > A | 33858 | NC_000007.13, NC_000007.14 | CFTR | 255 |
| Phenylketonuria | 75193786 | APG01688.1 | T > C | 15675 | NC_000012.11, NC_000012.12 | PAH | 256 |
| Deficiency of UDPglucose-hexose-1-phosphate uridylyltransferase | 75391579 | APG05459.1 | A > G | 18653 | NC_000009.11, NC_000009.12 | GALT | 257 |
| Amyloid Cardiomyopathy, Transthyretin-related | 76992529 | APG05459.1 | G > A | 28465 | NC_000018.9, NC_000018.10 | TTR | 258 |
| Carbohydrate-deficient glycoprotein syndrome type I | 80338707 | APG01688.1 | G > A | 22758 | NC_000016.9, NC_000016.10 | PMM2 | 259 |
| Metachromatic leukodystrophy | 80338815 | APG01688.1 | G > A | 18090 | NC_000022.10, NC_000022.11 | ARSA | 260 |
| Smith-Lemli-Opitz syndrome | 80338857 | APG05083, APG07433.1, APG07513.1, APG08290.1 | G > A | 34128 | NC_000011.9, NC_000011.10 | DHCR7 | 261 |
| Deafness, autosomal recessive 1A | 80338940 | APG05459.1 | G > A | 32068 | NC_000013.10, NC_000013.11 | GJB2 | 262 |
| Congenital omphalocele | 80338945 | APG05083, APG07433.1, APG07513.1, APG08290.1 | T > C | 32055 | NC_000013.10, NC_000013.11 | GJB2 | 263 |
| Congenital omphalocele | 80338945 | APG05083, APG07433.1, APG07513.1, APG08290.1 | T > C | 32055 | NC_000013.10, NC_000013.11 | GJB2 | 264 |
| Congenital omphalocele | 80338945 | APG05459.1 | T > C | 32055 | NC_000013.10, NC_000013.11 | GJB2 | 265 |
| Congenital omphalocele | 80338945 | APG05459.1 | T > C | 32055 | NC_000013.10, NC_000013.11 | GJB2 | 266 |
| Congenital myotonia, autosomal dominant form | 80356701 | APG05083, APG07433.1, APG07513.1, APG08290.1 | T > C | 33902 | NC_000007.13, NC_000007.14 | CLCN1 | 267 |
| Breast-ovarian cancer, familial 1 | 80356914 | APG05459.1 | G > A | 70276 | NC_000017.10, NC_000017.11 | BRCA1 | 268 |
| Breast and/or ovarian cancer | 80356962 | APG05459.1 | G > A | 70247 | NC_000017.10, NC_000017.11 | BRCA1 | 269 |
| Breast-ovarian cancer, familial | 80357212 | APG05459.1 | G > A | 70255 | NC_000017.10, NC_000017.11 | BRCA1 | 270 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| 1 | | | | | | | |
| Breast-ovarian cancer, familial 1 | 80357281 | APG05459.1 | T > C | 70177 | NC_000017.10, NC_000017.11 | BRCA1 | 271 |
| Breast-ovarian cancer, familial 1 | 80357307 | APG05459.1 | G > A | 70275 | NC_000017.10, NC_000017.11 | BRCA1 | 272 |
| Breast-ovarian cancer, familial 1 | 80357352 | APG05459.1 | C > T | 69958 | NC_000017.10, NC_000017.11 | BRCA1 | 273 |
| Breast-ovarian cancer, familial 1 | 80358145 | APG05459.1 | G > A | 46229 | NC_000017.10, NC_000017.11 | BRCA1 | 274 |
| Inborn genetic diseases | 80358259 | APG05083, APG07433.1, APG07513.1, APG08290.1 | T > C | 18006 | NC_000018.9, NC_000018.10 | NPC1 | 275 |
| Breast-ovarian cancer, familial 2 | 80358543 | APG05459.1 | G > A | 131539 | NC_000013.10, NC_000013.11 | BRCA2 | 276 |
| Breast-ovarian cancer, familial 2 | 80358544 | APG05459.1 | G > A | 46368 | NC_000013.10, NC_000013.11 | BRCA2 | 277 |
| Breast-ovarian cancer, familial 2 | 80358997 | APG05459.1 | G > A | 67062 | NC_000013.10, NC_000013.11 | BRCA2 | 278 |
| Breast and/or ovarian cancer | 80359003 | APG05083, APG07433.1, APG07513.1, APG08290.1 | G > A | 67069 | NC_000013.10, NC_000013.11 | BRCA2 | 279 |
| Breast-ovarian cancer, familial 2 | 80359004 | APG05083, APG07433.1, APG07513.1, APG08290.1 | G > A | 46672 | NC_000013.10, NC_000013.11 | BRCA2 | 280 |
| Breast-ovarian cancer, familial 2 | 80359071 | APG05459.1 | G > A | 67203 | NC_000013.10, NC_000013.11 | BRCA2 | 281 |
| Breast-ovarian cancer, familial 2 | 80359112 | APG05459.1 | C > T | 67292 | NC_000013.10, NC_000013.11 | BRCA2 | 282 |
| Breast-ovarian cancer, familial 2 | 80359115 | APG05459.1 | C > T | 67294 | NC_000013.10, NC_000013.11 | BRCA2 | 283 |
| Smith-Lemli-Opitz syndrome | 104886033 | APG05459.1 | A > G | 21833 | NC_000011.9, NC_000011.10 | DHCR7 | 284 |
| Alport syndrome 1, X-linked recessive | 104886142 | APG05083, APG07433.1, APG07513.1, APG08290.1 | G > A | 35796 | NC_000023.10, NC_000023.11 | COL4A5 | 285 |
| Acute neuronopathic Gaucher's disease | 104886460 | APG05459.1 | G > A | 99352 | NC_000001.10, NC_000001.11 | GBA | 286 |
| Gonadotropin deficiency | 104893836 | APG05459.1 | A > G | 31062 | NC_000004.11, NC_000004.12 | GNRHR | 287 |
| Distal arthrogryposis type 1A | 104894129 | APG05459.1 | G > A | 27501 | NC_000009.11, NC_000009.12 | TPM2 | 288 |
| Distal arthrogryposis type 1A | 104894129 | APG05459.1 | G > A | 27501 | NC_000009.11 ,NC_000009.12 | TPM2 | 289 |
| Hereditary cancer-predisposing syndrome | 104894261 | APG05459.1 | C > T | 31727 | NC_000011.9, NC_000011.10 | MEN1 | 290 |
| Inborn genetic diseases | 104894313 | APG05459.1 | C > T | 18816 | NC_000011.9, NC_000011.10 | TYR | 291 |
| Death in early adulthood | 104894368 | APG05083, APG07433.1, APG07513.1, APG08290.1 | G > A | 29104 | NC_000012.11, NC_000012.12 | MYL2 | 292 |
| Death in early adulthood | 104894368 | APG05459.1 | G > A | 29104 | NC_000012.11, NC_000012.12 | MYL2 | 293 |
| Severe autosomal recessive muscular dystrophy of childhood - North African type | 104894423 | APG05459.1 | G > A | 17048 | NC_000013.10, NC_000013.11, NC_000013.9 | SGCG | 294 |
| Cardiovascular phenotype | 104894503 | APG05459.1 | G > A | 27495 | NC_000015.9, NC_000015.10 | TPM1 | 295 |
| Carbohydrate-deficient glycoprotein syndrome type I | 104894525 | APG01688.1 | G > A | 22747 | NC_000016.9, NC_000016.10 | PMM2 | 296 |
| Charcot-Marie-Tooth disease, type I | 104894621 | APG05459.1 | C > T | 23472 | NC_000017.10, NC_000017.11 | PMP22 | 297 |
| Inborn genetic diseases | 104894635 | APG05083, APG07433.1, APG07513.1, APG08290.1 | G > A | 20146 | NC_000017.10, NC_000017.11 | SGSH | 298 |
| Inborn genetic diseases | 104894635 | APG05459.1 | G > A | 20146 | NC_000017.10, NC_000017.11 | SGSH | 299 |
| Familial Mediterranean fever | 104895097 | APG05083, APG07433.1, APG07513.1, APG08290.1 | G > A | 17588 | NC_000016.9, NC_000016.10 | MEFV | 300 |
| Deafness, autosomal recessive 2 | 111033178 | APG05083, APG07433.1, APG07513.1, APG08290.1 | G > A | 52388 | NC_000011.9, NC_000011.10 | MYO7A | 301 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Deafness, autosomal recessive 2 | 111033178 | APG01688.1 | G > A | 52388 | NC_000011.9, NC_000011.10 | MYO7A | 302 |
| Deafness, X-linked 2 | 111033299 | APG05083, APG07433.1, APG07513.1, APG08290.1 | G > A | 53902 | NC_000013.10, NC_000013.11 | GJB2 | 303 |
| Enlarged vestibular aqueduct | 111033305 | APG05083, APG07433.1, APG07513.1, APG08290.1 | G > A | 52666 | NC_000007.13, NC_000007.14 | SLC26A4 | 304 |
| Congenital sensorineural hearing impairment | 111033364 | APG05459.1, APG01688.1 | G > A | 17396 | NC_000001.10, NC_000001.11 | USH2A | 305 |
| Deficiency of UDPglucose-hexose-1-phosphate uridylyltransferase | 111033728 | APG05459.1 | T > C | 36556 | NC_000009.11, NC_000009.12 | GALT | 306 |
| Very long chain acyl-CoA dehydrogenase deficiency | 112406105 | APG05459.1 | G > A | 200333 | NC_000017.10, NC_000017.11 | ACADVL | 307 |
| Cardiovascular phenotype | 112645512 | APG05459.1 | C > T | 178700 | NC_000015.10, NC_000015.9 | FBN1 | 308 |
| Pyruvate kinase deficiency of red cells | 113403872 | APG05459.1 | G > A | 16550 | NC_000001.10, NC_000001.11 | PKLR | 309 |
| Autosomal dominant progressive external ophthalmoplegia with mitochondrial DNA deletions 1 | 113994095 | APG05083, APG07433.1, APG07513.1, APG08290.1 | G > A | 28535 | NC_000015.9, NC_000015.10 | POLG | 310 |
| Very long chain acyl-CoA dehydrogenase deficiency | 113994167 | APG05459.1 | T > C | 33877 | NC_000017.10, NC_000017.11 | ACADVL | 311 |
| Cystinosis, ocular nonnephropathic | 113994205 | APG05459.1 | G > A | 19482 | NC_000017.10, NC_000017.11 | CTNS | 312 |
| Pyruvate kinase deficiency of red cells | 116100695 | APG05459.1 | C > T | 16552 | NC_000001.10, NC_000001.11 | PKLR | 313 |
| Distal myopathy, Tateyama type | 116840778 | APG01688.1 | G > A | 23322 | NC_000003.11, NC_000003.12 | CAV3; SSUH2 | 314 |
| Malignant hyperthermia, susceptibility to, 1 | 118192122 | APG05083, APG07433.1, APG07513.1, APG08290.1 | G > A | 76888 | NC_000019.9, NC_000019.10 | RYR1 | 315 |
| Malignant hyperthermia, susceptibility to, 1 | 118192122 | APG05083, APG07433.1, APG07513.1, APG08290.1 | G > A | 76888 | NC_000019.9, NC_000019.10 | RYR1 | 316 |
| Myopathy, Central Core | 118192158 | APG05083, APG07433.1, APG07513.1, APG08290.1 | G > A | 76835 | NC_000019.9, NC_000019.10 | RYR1 | 317 |
| Myopathy, Central Core | 118192158 | APG05459.1 | G > A | 76835 | NC_000019.9, NC_000019.10 | RYR1 | 318 |
| Myopathy, Central Core | 118192158 | APG01688.1 | G > A | 76835 | NC_000019.9, NC_000019.10 | RYR1 | 319 |
| Malignant hyperthermia, susceptibility to, 1 | 118192170 | APG05083, APG07433.1, APG07513.1, APG08290.1 | T > C | 28014 | NC_000019.9, NC_000019.10 | RYR1 | 320 |
| Ceroid lipofuscinosis neuronal 2 | 119455954 | APG05459.1 | G > A | 17681 | NC_000011.9, NC_000011.10 | TPP1 | 321 |
| Ceroid lipofuscinosis neuronal 2 | 119455954 | APG01688.1 | G > A | 17681 | NC_000011.9, NC_000011.10 | TPP1 | 322 |
| Niemann-Pick disease type C1 | 120074135 | APG05083, APG07433.1, APG07513.1, APG08290.1 | G > A | 18010 | NC_000018.9, NC_000018.10 | NPC1 | 323 |
| Glutaric aciduria, type 1 | 121434372 | APG05083, APG07433.1, APG07513.1, APG08290.1 | G > A | 17127 | NC_000019.9, NC_000019.10 | GCDH | 324 |
| CAPN3-Related Disorders | 121434548 | APG05083, APG07433.1, APG07513.1, APG08290.1 | G > A | 32661 | NC_000015.9, NC_000015.10 | CAPN3; POMT1 | 325 |
| CAPN3-Related Disorders | 121434548 | APG05459.1 | G > A | 32661 | NC_000015.9, NC_000015.10 | CAPN3; POMT1 | 326 |
| Glycogen storage disease, type II | 121907943 | APG05459.1 | C > T | 19073 | NC_000017.10, NC_000017.11 | GAA | 327 |

TABLE 12-continued

| Disease Targets for RGNs of the invention | | | | | | | |
|---|---|---|---|---|---|---|---|
| Disease | RS# (dbSNP) | RGN | Causal Mutation | AlleleID | ChromosomeAccession | Gene Symbol | Target Seq (SEQ ID NO) |
| Nonsyndromic Oculocutaneous Albinism | 121908011 | APG05083, APG07433.1, APG07513.1, APG08290.1 | G > A | 18814 | NC_000011.9, NC_000011.10 | TYR | 328 |
| Familial hypercholesterolemia | 121908033 | APG05459.1 | G > A | 18765 | NC_000019.9, NC_000019.10 | LDLR | 329 |
| Familial hypercholesterolemia | 121908039 | APG05459.1 | G > A | 18778 | NC_000019.9, NC_000019.10 | LDLR | 330 |
| Deafness, autosomal recessive 7 | 121908073 | APG05459.1 | C > T | 19142 | NC_000009.11, NC_000009.12 | TMC1 | 331 |
| Chronic infantile neurological, cutaneous and articular syndrome | 121908153 | APG05459.1 | G > A | 19416 | NC_000001.10, NC_000001.11 | NLRP3 | 332 |
| Eichsfeld type congenital muscular dystrophy | 121908185 | APG05459.1 | G > A | 19531 | NC_000001.10, NC_000001.11 | SELENON | 333 |
| Inborn genetic diseases | 121908192 | APG05459.1 | G > A | 23730 | NC_000016.9, NC_000016.10 | GFER | 334 |
| Hyperkalemic Periodic Paralysis Type 1 | 121908557 | APG05459.1 | G > A | 20958 | NC_000017.10, NC_000017.11 | SCN4A | 335 |
| Inclusion body myopathy 2 | 121908627 | APG05459.1 | G > A | 21067 | NC_000009.11, NC_000009.12 | GNE | 336 |
| Severe APG05083.1, APG07433.1, APG07513.1, APG08290.1 immunodeficiency due to ADA deficiency | 121908716 | APG05083, APG07433.1, APG07513.1, APG08290.1 | G > A | 16996 | NC_000020.10, NC_000020.11 | ADA | 337 |
| Severe APG05083.1, APG07433.1, APG07513.1, APG08290.1 immunodeficiency due to ADA deficiency | 121908739 | APG05083, APG07433.1, APG07513.1, APG08290.1 | T > C | 17004 | NC_000020.10, NC_000020.11 | ADA | 338 |
| Cardiovascular phenotype | 121908987 | APG05459.1 | G > A | 21885 | NC_000007.13, NC_000007.14 | PRKAG2 | 339 |
| Cystic fibrosis | 121909019 | APG05459.1 | G > A | 22197 | NC_000007.13, NC_000007.14 | CFTR | 340 |
| Cystic fibrosis | 121909036 | APG05459.1 | T > C | 22247 | NC_000007.13, NC_000007.14 | CFTR | 341 |
| Adrenocortical carcinoma, pediatric | 121912664 | APG01688.1 | G > A | 27418 | NC_000017.10, NC_000017.11 | TP53 | 342 |
| Fumarase deficiency | 121913123 | APG05459.1 | G > A | 31275 | NC_000001.10, NC_000001.11 | FH | 343 |
| Adenocarcinoma of prostate | 121913272 | APG05459.1 | T > C | 40610 | NC_000003.11, NC_000003.12 | PIK3CA | 344 |
| Familial hypertrophic cardiomyopathy 1 | 121913638 | APG05459.1 | G > A | 29144 | NC_000014.8, NC_000014.9 | MYH7 | 345 |
| Adult hypophosphatasia | 121918007 | APG05083, APG07433.1, APG07513.1, APG08290.1 | G > A | 28709 | NC_000001.10, NC_000001.11 | ALPL | 346 |
| Adult hypophosphatasia | 121918007 | APG01688.1 | G > A | 28709 | NC_000001.10, NC_000001.11 | ALPL | 347 |
| Adult hypophosphatasia | 121918007 | APG01688.1 | G > A | 28709 | NC_000001.10, NC_000001.11 | ALPL | 348 |
| Inborn genetic diseases | 121918166 | APG05083, APG07433.1, APG07513.1, APG08290.1 | G > A | 15994 | NC_000015.9, NC_000015.10 | OCA2 | 349 |
| Inborn genetic diseases | 121918243 | APG05083, APG07433.1, APG07513.1, APG08290.1 | G > A | 16464 | NC_000001.10, NC_000001.11 | MMACHC | 350 |
| Crouzon syndrome | 121918505 | APG05459.1 | T > C | 28329 | NC_000010.10, NC_000010.11 | FGFR2 | 351 |
| Propionyl-CoA carboxylase deficiency | 121964961 | APG05459.1 | A > G | 27057 | NC_000003.11, NC_000003.12 | PCCB | 352 |
| Cardiovascular phenotype | 121964962 | APG05083, APG07433.1, APG07513.1, APG08290.1 | G > A | 15156 | NC_000021.8, NC_000021.9 | CBS | 353 |
| Dysostosis multiplex | 121965019 | APG05083, APG07433.1, APG07513.1, APG08290.1 | G > A | 26947 | NC_000004.11, NC_000004.12 | IDUA | 354 |
| Multiple sulfatase deficiency | 137852850 | APG05459.1 | T > C | 17711 | NC_000003.11, NC_000003.12 | SUMF1 | 355 |
| Bifunctional peroxisomal enzyme deficiency | 137853096 | APG05459.1 | G > A | 22694 | NC_000005.9, NC_000005.10 | HSD17B4 | 356 |
| Bifunctional peroxisomal enzyme deficiency | 137853096 | APG01688.1 | G > A | 22694 | NC_000005.9, NC_000005.10 | HSD17B4 | 357 |
| Hereditary cancer-predisposing syndrome | 137853293 | APG05459.1 | C > T | 28112 | NC_000013.10, NC_000013.11 | RB1 | 358 |
| Cardiovascular phenotype | 137854478 | APG05083, APG07433.1, APG07513.1, APG08290.1 | G > A | 31496 | NC_000015.9, NC_000015.10 | FBN1 | 359 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Cardiovascular phenotype | 137854478 | APG05083, APG07433.1, APG07513.1, APG08290.1 | G > A | 31496 | NC_000015.9, NC_000015.10 | FBN1 | 360 |
| Limb-girdle muscular dystrophy, type 2L | 137854529 | APG05459.1 | C > T | 17205 | NC_000011.9, NC_000011.10 | ANO5 | 361 |
| Familial hypercholesterolemia | 137929307 | APG01688.1 | G > A | 171217 | NC_000019.9, NC_000019.10 | LDLR | 362 |
| Spastic Paraplegia, Recessive | 141659620 | APG05459.1 | G > A | 21858 | NC_000016.9, NC_000016.10 | SPG7 | 363 |
| Isovaleryl-CoA dehydrogenase deficiency | 142761835 | APG05459.1 | G > A | 177782 | NC_000015.9, NC_000015.10 | IVD | 364 |
| Familial hypercholesterolemia | 145787161 | APG05459.1 | G > A | 18783 | NC_000019.10, NC_000019.9 | LDLR | 365 |
| Biotinidase deficiency | 146015592 | APG05459.1 | G > A | 46845 | NC_000003.11, NC_000003.12 | BTD | 366 |
| Biotinidase deficiency | 146015592 | APG05459.1 | G > A | 46845 | NC_000003.11, NC_000003.12 | BTD | 367 |
| Leber congenital amaurosis | 150726175 | APG01688.1 | G > A | 45795 | NC_000001.10, NC_000001.11 | NMNAT1 | 368 |
| Familial hyperinsulinism | 151344623 | APG05083, APG07433.1, APG07513.1, APG08290.1 | G > A | 24127 | NC_000011.9, NC_000011.10 | ABCC8 | 369 |
| Familial cancer of breast | 180177122 | APG05083, APG07433.1, APG07513.1, APG08290.1 | G > A | 132185 | NC_000016.10, NC_000016.9 | PALB2 | 370 |
| Cohen syndrome | 180177366 | APG05459.1 | G > A | 71322 | NC_000008.10, NC_000008.11 | VPS13B | 371 |
| Cardiovascular phenotype | 187830361 | APG05083, APG07433.1, APG07513.1, APG08290.1 | T > C | 45267 | NC_000011.9, NC_000011.10 | MYBPC3 | 372 |
| Wilson disease | 193922103 | APG05459.1 | A > G | 44370 | NC_000013.10, NC_000013.11 | ATP7B | 373 |
| Wilson disease | 193922110 | APG05083, APG07433.1, APG07513.1, APG08290.1 | G > A | 44393 | NC_000013.10, NC_000013.11 | ATP7B | 374 |
| Wilson disease | 193922110 | APG05459.1 | G > A | 44393 | NC_000013.10, NC_000013.11 | ATP7B | 375 |
| Familial hypercholesterolemia | 193922566 | APG05459.1 | G > A | 45113 | NC_000019.9, NC_000019.10 | LDLR | 376 |
| Familial hypercholesterolemia | 193922566 | APG05459.1 | G > A | 45113 | NC_000019.9, NC_000019.10 | LDLR | 377 |
| Floating-Harbor syndrome | 199469464 | APG05459.1 | C > T | 39865 | NC_000016.9, NC_000016.10 | SRCAP | 378 |
| Congenital long QT syndrome | 199472712 | APG05083, APG07433.1, APG07513.1, APG08290.1 | G > A | 67758 | NC_000011.9, NC_000011.10 | KCNQ1 | 379 |
| Congenital long QT syndrome | 199472712 | APG05459.1 | G > A | 67758 | NC_000011.9, NC_000011.10 | KCNQ1 | 380 |
| Andersen Tawil syndrome | 199473384 | APG01688.1 | G > A | 78481 | NC_000017.10, NC_000017.11 | KCNJ2 | 381 |
| Cardiovascular phenotype | 199473460 | APG05083, APG07433.1, APG07513.1, APG08290.1 | T > C | 67776 | NC_000011.9, NC_000011.10 | KCNQ1 | 382 |
| Familial hypercholesterolemia | 200238879 | APG05459.1 | T > C | 18777 | NC_000019.9, NC_000019.10 | LDLR | 383 |
| Cardiovascular phenotype | 200411226 | APG05083, APG07433.1, APG07513.1, APG08290.1 | G > A | 174776 | NC_000011.9, NC_000011.10 | MYBPC3 | 384 |
| Gastrointestinal stroma tumor | 201286421 | APG05459.1 | C > T | 50215 | NC_000001.10, NC_000001.11 | SDHC | 385 |
| Dyskeratosis congenita | 201540674 | APG05459.1 | G > A | 51186 | NC_000020.10, NC_000020.11 | RTEL1 | 386 |
| Dyskeratosis congenita | 201540674 | APG01688.1 | G > A | 51186 | NC_000020.10, NC_000020.11 | RTEL1 | 387 |
| Glycogen storage disease IIIa | 267606640 | APG04583.1 | G > A | 16147 | NC_000001.10, NC_000001.11 | AGL | 388 |
| Dilated cardiomyopathy 1DD | 267607004 | APG05083, APG07433.1, APG07513.1, APG08290.1 | G > A | 15310 | NC_000010.10, NC_000010.11 | RBM20 | 389 |
| Renal carnitine transport defect | 267607054 | APG05459.1 | C > T | 21466 | NC_000005.9, NC_000005.10 | SLC22A5 | 390 |
| Baraitser-Winter syndrome 1 | 281875334 | APG05083, APG07433.1, APG07513.1, APG08290.1 | G > A | 38553 | NC_000007.13, NC_000007.14 | ACTB | 391 |
| Very long chain acyl-CoA dehydrogenase deficiency | 369560930 | APG05083, APG07433.1, APG07513.1, APG08290.1 | G > A | 98197 | NC_000017.10, NC_000017.11 | ACADVL | 392 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Familial hypercholesterolemia | 373822756 | APG05459.1 | A > G | 181233 | NC_000019.9, NC_000019.10 | LDLR | 393 |
| Limb-girdle muscular dystrophy, type 2A | 376107921 | APG05459.1 | G > A | 213634 | NC_000015.9, NC_000015.10 | CAPN3 | 394 |
| Familial hypercholesterolemia | 376459828 | APG05083, APG07433.1, APG07513.1, APG08290.1 | G > A | 198012 | NC_000019.10, NC_000019.9 | LDLR | 395 |
| Aortic aneurysm, familial thoracic 6 | 387906592 | APG05459.1 | G > A | 38552 | NC_000010.10, NC_000010.11 | ACTA2 | 396 |
| Acromicric dysplasia | 387906623 | APG05083, APG07433.1, APG07513.1, APG08290.1 | G > A | 38652 | NC_000015.9, NC_000015.10 | FBN1 | 397 |
| Charcot-Marie-Tooth disease type 2C | 387906905 | APG01688.1 | G > A | 39430 | NC_000012.11, NC_000012.12 | TRPV4 | 398 |
| Breast-ovarian cancer, familial 2 | 397507389 | APG01688.1 | G > A | 46666 | NC_000013.10, NC_000013.11 | BRCA2 | 399 |
| Breast-ovarian cancer, familial 1 | 397509284 | APG05459.1 | G > A | 70248 | NC_000017.10, NC_000017.11 | BRCA1 | 400 |
| Charcot-Marie-Tooth disease type 2C | 397514494 | APG05083, APG07433.1, APG07513.1, APG08290.1 | G > A | 48018 | NC_000012.11, NC_000012.12 | TRPV4 | 401 |
| Charcot-Marie-Tooth disease type 2C | 397514494 | APG01688.1 | G > A | 48018 | NC_000012.11, NC_000012.12 | TRPV4 | 402 |
| Hereditary cancer-predisposing syndrome | 397514495 | APG05459.1 | G > A | 152034 | NC_000017.10, NC_000017.11 | TP53 | 403 |
| Early infantile epileptic encephalopathy | 397514581 | APG05083, APG07433.1, APG07513.1, APG08290.1 | G > A | 48359 | NC_000020.10, NC_000020.11 | KCNQ2 | 404 |
| Early infantile epileptic encephalopathy | 397514581 | APG05459.1 | G > A | 48359 | NC_000020.10, NC_000020.11 | KCNQ2 | 405 |
| Early infantile epileptic encephalopathy | 397514581 | APG01688.1 | G > A | 48359 | NC_000020.10, NC_000020.11 | KCNQ2 | 406 |
| Acromicric dysplasia | 397515757 | APG05459.1 | G > A | 51454 | NC_000015.9, NC_000015.10 | FBN1 | 407 |
| Hypertrophic cardiomyopathy | 397515982 | APG05083, APG07433.1, APG07513.1, APG08290.1 | G > A | 51820 | NC_000011.9, NC_000011.10 | MYBPC3 | 408 |
| Cardiovascular phenotype | 397516031 | APG04583.1 | G > A | 51898 | NC_000011.9, NC_000011.10 | MYBPC3 | 409 |
| Cardiovascular phenotype | 397516074 | APG05083, APG07433.1, APG07513.1, APG08290.1 | G > A | 51962 | NC_000011.9, NC_000011.10 | MYBPC3 | 410 |
| Cardiovascular phenotype | 397516083 | APG01688.1 | G > A | 51977 | NC_000011.9, NC_000011.10 | MYBPC3 | 411 |
| Familial hypertrophic cardiomyopathy 1 | 397516269 | APG05083, APG07433.1, APG07513.1, APG08290.1 | T > C | 52276 | NC_000014.8, NC_000014.9 | MYH7 | 412 |
| Benign scapuloperoneal muscular dystrophy with cardiomyopathy | 397517889 | APG05459.1 | C > T | 57195 | NC_000001.10, NC_000001.11 | LMNA | 413 |
| Glycogen storage disease, type II | 398123172 | APG05083, APG07433.1, APG07513.1, APG08290.1 | G > A | 415590 | NC_000017.10, NC_000017.11 | GAA | 414 |
| Diffuse mesangial sclerosis | 587776576 | APG05083, APG07433.1, APG07513.1, APG08290.1 | G > A | 18532 | NC_000011.10, NC_000011.9 | WT1 | 415 |
| Colobomatous microphthalmia | 587776954 | APG05459.1 | A > G | 51108 | NC_000012.11, NC_000012.12 | C12orf57 | 416 |
| Ataxia-telangiectasia syndrome | 587779826 | APG05459.1 | T > C | 132814 | NC_000011.10, NC_000011.9 | ATM | 417 |
| Familial cancer of breast | 587780226 | APG05459.1 | C > T | 133611 | NC_000017.10, NC_000017.11 | BRIP1 | 418 |
| Limb-girdle muscular dystrophy, type 2A | 587780290 | APG01688.1 | G > A | 134019 | NC_000015.9, NC_000015.10 | CAPN3 | 419 |
| Hereditary cancer-predisposing syndrome | 587781462 | APG05459.1 | C > T | 150772 | NC_000002.11, NC_000002.12 | MSH6 | 420 |

TABLE 12-continued

Disease Targets for RGNs of the invention

| Disease | RS# (dbSNP) | RGN | Causal Mutation | AlleleID | ChromosomeAccession | Gene Symbol | Target Seq (SEQ ID NO) |
|---|---|---|---|---|---|---|---|
| Asymmetric septal hypertrophy | 587782958 | APG01688.1 | G > A | 165560 | NC_000011.10, NC_000011.9 | MYBPC3 | 421 |
| Hereditary cancer-predisposing syndrome | 587783050 | APG05459.1 | G > A | 166264 | NC_000016.10, NC_000016.9 | CDH1 | 422 |
| Familial hypertrophic cardiomyopathy 2 | 727504247 | APG05083, APG07433.1, APG07513.1, APG08290.1 | G > A | 172354 | NC_000001.10, NC_000001.11 | TNNT2 | 423 |
| Familial hypertrophic cardiomyopathy 2 | 727504247 | APG01688.1 | G > A | 172354 | NC_000001.10, NC_000001.11 | TNNT2 | 424 |
| Familial hypertrophic cardiomyopathy 2 | 727504247 | APG01688.1 | G > A | 172354 | NC_000001.10, NC_000001.11 | TNNT2 | 425 |
| Erythrocytosis, familial, 2 | 730882035 | APG01688.1 | G > A | 180121 | NC_000003.12, NC_000003.11 | VHL | 426 |
| Death in infancy | 730882246 | APG05083, APG07433.1, APG07513.1, APG08290.1 | G > A | 181441 | NC_000014.9, NC_000014.8 | ISCA2 | 427 |
| Muscular Diseases | 751995154 | APG05459.1 | G > A | 200340 | NC_000017.10, NC_000017.11 | ACADVL | 428 |
| Familial hypercholesterolemia | 756039188 | APG04583.1 | G > A | 243266 | NC_000019.9, NC_000019.10 | LDLR | 429 |
| Familial cancer of breast | 761494650 | APG05459.1 | C > T | 185659 | NC_000022.10, NC_000022.11 | CHEK2 | 430 |
| Hereditary cancer-predisposing syndrome | 762307622 | APG01688.1 | G > A | 232266 | NC_000001.10, NC_000001.11 | MUTYH | 431 |
| Familial hypercholesterolemia | 769370816 | APG05083, APG07433.1, APG07513.1, APG08290.1 | G > A | 228176 | NC_000019.10, NC_000019.9 | LDLR | 432 |
| Familial hypercholesterolemia | 775092314 | APG05083, APG07433.1, APG07513.1, APG08290.1 | T > C | 228197 | NC_000019.9, NC_000019.10 | LDLR | 433 |
| Familial hypercholesterolemia | 775924858 | APG05083, APG07433.1, APG07513.1, APG08290.1 | G > A | 246116 | NC_000019.9, NC_000019.10 | LDLR | 434 |
| Inclusion body myopathy 2 | 779694939 | APG04583.1 | T > C | 214934 | NC_000009.12, NC_000009.11 | GNE | 435 |
| Ataxia-telangiectasia syndrome | 780619951 | APG05459.1 | C > T | 212851 | NC_000011.10, NC_000011.9 | ATM | 436 |
| Benign familial neonatal-infantile seizures | 794727152 | APG04583.1 | G > A | 191718 | NC_000002.11, NC_000002.12 | SCN2A | 437 |
| Marfan Syndronne/Loeys-Dietz Syndrome/Familial Thoracic Aortic Aneurysms and Dissections | 794728228 | APG05459.1 | C > T | 197690 | NC_000015.10, NC_000015.9 | FBN1 | 438 |
| Dilated cardiomyopathy 1G | 869320740 | APG01688.1 | T > C | 136355 | NC_000002.11, NC_000002.12 | TTN | 439 |
| Familial hypercholesterolemia | 875989911 | APG05459.1 | G > A | 228151 | NC_000019.9, NC_000019.10 | LDLR | 440 |
| Breast-ovarian cancer, familial 2 | 876657678 | APG05459.1 | C > T | 230443 | NC_000013.10, NC_000013.11 | BRCA2 | 441 |
| Familial hypercholesterolemia | 879254600 | APG05459.1 | G > A | 245669 | NC_000019.10, NC_000019.9 | LDLR | 442 |
| Familial hypercholesterolemia | 879254803 | APG05083, APG07433.1, APG07513.1, APG08290.1 | T > C | 246008 | NC_000019.10, NC_000019.9 | LDLR | 443 |
| Familial hypercholesterolemia | 879254803 | APG01688.1 | T > C | 246008 | NC_000019.10, NC_000019.9 | LDLR | 444 |
| Familial hypercholesterolemia | 879254849 | APG01688.1 | T > C | 246074 | NC_000019.10, NC_000019.9 | LDLR | 445 |
| Familial cancer of breast | 1057517585 | APG01688.1 | G > A | 358911 | NC_000016.10, NC_000016.9 | PALB2 | 446 |
| Hereditary hemorrhagic telangiectasia type 2 | 1057517944 | APG05459.1 | C > T | 360048 | NC_000012.11, NC_000012.12 | ACVRL1 | 447 |

Example 10: Targeting Mutations Responsible for Hurler Syndrome

The following describes a potential treatment for Hurler Syndrome, also referred to as MPS-1, is described, using an RNA directed base editing system that corrects a mutation responsible for Hurler syndrome in a large proportion of patients with the disease. This approach utilizes a base editing fusion protein that is RNA guided and that can be packaged into a single AAV vector for delivery to a wide range of tissue types. Depending on the exact regulatory elements and base editor domain used, it may also be possible to engineer a single vector that encodes for both the base editing fusion protein and a single guide RNA to target the diseased locus.

Example 10.1: Identifying RGN with Ideal PAM

The genetic disease MPS-1 is a lysosomal storage disease characterized at the molecular level by the accumulation of dermatan sulfate and heparan sulfate in lysosomes. This disease is generally an inherited genetic disorder caused by mutations in the IDUA gene (NCBI Reference sequence NG_008103.1), which encodes α-L-iduronidase. The disease is a result of a deficiency of α-L-iduronidase. The most common IDUA mutations found in studies of individuals of Northern European background are W402X and Q70X, both nonsense mutations resulting in premature termination of translation (Bunge et al. (1994), Hum. Mol. Genet, 3(6): 861-866, herein incorporated by reference). Reversion of a single nucleotide would restore the wild-type coding sequence and result in protein expression controlled by the endogenous regulatory mechanisms of the genetic locus.

The W402X mutation of the human Idua gene accounts for a high proportion of MPS-1H cases. Base editors can target a narrow sequence window relative to the binding site of the protospacer component of the guide RNA and thus the presence of a PAM sequence a specific distance from the target locus is essential for the success of the strategy. Given the constraints that the target mutation must be on the exposed non-target strand (NTS) during the interaction of the base editing protein and that the footprint of the RGN domain will block access to the region near the PAM, an accessible locus is thought to be 10-30 bp from the PAM. To avoid editing and mutagenesis of other nearby adenosine bases in this window, different linkers are screened. The ideal window is 12-16 bp from the PAM.

A PAM sequence compatible with APG07433.1 and APG08290.1 is readily apparent at the genetic locus and within the ideal base editing window as defined above. These nucleases have a PAM sequence of NNNNCC (SEQ ID NO: 6) and NNRNCC (SEQ ID NO: 32), respectively, and are compact in size—potentially allowing delivery via a single AAV vector. This delivery approach bestows multiple advantages relative to others, such as access to a wide range of tissues (liver, muscle, CNS) and well-established safety profile and manufacturing techniques.

Cas9 from *S. pyogenes* (SpyCas9) requires a PAM sequence of NGG (SEQ ID NO: 448), which is present near the W402X locus, but the size of SpyCas9 prevents packaging of a gene encoding a fusion protein of a base editing domain and the SpyCas9 nuclease into a single AAV vector, and thus forgoes the aforementioned advantages of this approach. Including a guide RNA encoding sequence on this vector would is even less feasible, even if there are to be significant technological improvements that reduce the size of gene regulatory elements or increase the packaging limits of AAV vectors. While a dual delivery strategy may be employed (for example, Ryu et al, (2018), *Nat. Biotechnol.*, 36(6): 536-539, herein incorporated by reference), it would add significant manufacturing complexity and cost. Additionally, dual viral vector delivery significantly decreases the efficiency of gene correction, since a successful edit in a given cell requires infection with both vectors and assembly of the fusion protein in the cell.

A commonly used Cas9 ortholog from *S. aureus* (SauCas9) is considerably smaller in size relative to SpyCas9, but has a more complex PAM requirement—NGRRT (SEQ ID NO: 449). This sequence, however, is not within a range expected to be useful for base editing of the causative locus.

Example 10.2: RGN Fusion Constructs and sgRNA Sequences

A DNA sequence encoding a fusion protein with the following domains is produced using standard molecular biology techniques: 1) an RGN domain with mutations that inactivate the DNA cleavage activity ("dead" or "nickase"); 2) an adenosine deaminase useful for base editing. All constructs described in the table below comprise a fusion protein with the base editing active domain, in this example ADAT (SEQ ID NO: 450) operably fused to the N-terminal end of the RGN APG08290.1. It is known in the art that a fusion protein could also be made with the base-editing enzyme at the C-terminal end of the RGN. Additionally, the RGN and the base editor of the fusion protein are typically separated by a linker amino sequence. It is known in the art that lengths of standard linkers range from 15-30 amino acids. Further, it is known in the art that certain fusion proteins between an RGN and a base-editing enzyme, for example a cytidine deaminase, may also comprise at least one uracil glycosylase inhibitor (UGI) domain, which may increase base editing efficiency (U.S. Pat. No. 10,167,457, herein incorporated by reference). Therefore, a fusion protein may comprise APG08290.1, a base-modifying enzyme, and at least one UGI.

TABLE 13

Constructs for RNA-targeted base editing

| Seq ID No. | Construct | RGN | Dead (D) or Nickase (N) | Base editor | Linker |
|---|---|---|---|---|---|
| 451 | Nuc-ADAT-Linker-dAPG08290.1-Linker-SV40 | APG08290.1 | D | ADAT | XTEN1 |
| 452 | Nuc-ADAT-XTEN1-nAPG08290.1-Linker-SV40 | APG08290.1 | N | ADAT | XTEN1 |

The accessible editing sites of an RGN are determined by the PAM sequence. When combining an RGN with a base editing domain, the target residue for editing must reside on the non-target strand (NTS), since the NTS is single stranded while the RGN is associated with the locus. Evaluating a number of nucleases and corresponding guide RNAs enables the selection of the most appropriate gene editing tool for this particular locus. Several potential PAM sequences that can be targeted by the constructs described above in the human Idua gene are in the proximity of the mutant nucleotide responsible for the W402X mutation. A sequence encoding a guide RNA transcript containing 1) a "spacer" that is complementary to the non-coding DNA strand at the disease locus; and 2) RNA sequence required for association of the guide RNA with the RGN is also produced. Useful guide RNA sequences (sgRNA) are shown in Table 14 below. These guide RNA sequences can be evaluated for their efficiency in directing the base editors above to the locus of interest.

TABLE 14

Sequence of guide RNAs

| Sequence of target genomic sequence | SEQ ID NO. | Coding sequence of sgRNA (SEQ ID NO.) |
|---|---|---|
| 5'-GGAGCAGCTCTAGGCCGAAGTGTCG-3' | 453 | 456 |
| 5'-TAGGCCGAAGTGTCGCAGGCCGGGA-3' | 454 | 457 |
| 5'-GCTCTAGGCCGAAGTGTCGCAGGCC-3' | 455 | 458 |

Example 10.3: Assay for Activity in Cells from Hurler Disease Patients

To verify the genotype strategy and evaluate the constructs described above, fibroblasts from Hurler disease patients are used. A vector is designed containing appropriate promoters upstream of the fusion protein coding sequence and the sgRNA encoding sequence for expression of these in human cells, similar to those vectors described in Example 5. It is recognized that promoters and other DNA elements (for example enhancers, or terminators) which either are known for high levels of expression in human cells or may specifically express well in fibroblast cells may also be used. The vector is transfected into the fibroblasts using standard techniques, for example transfection similar to what is described in Example 6. Alternatively, electroporation may be used. The cells are cultured for 1-3 days. Genomic DNA (gDNA) is isolated using standard techniques. The editing efficiency is determined by performing a qPCR genotyping assay and/or next generation sequencing on the purified gDNA, as described further below.

Taqman™ qPCR analysis utilizes probes specific for the wild-type and mutant allele. These probes bear fluorophores which are resolved by their spectral excitation and/or emission properties using a qPCR instrument. A genotyping kit containing PCR primers and probes can be obtained commercially (i.e. Thermo Fisher Taqman™ SNP genotyping assayID C_27862753_10 for SNP ID rs121965019) or designed. An example of a designed primer and probe set is shown in Table 15.

TABLE 15

RT-PCR primers and probes

| Description | Sequence | SEQ ID NO. |
|---|---|---|
| Forward Amplification Primer | 5'-GACTCCTTCACCAAG-3' | 459 |
| Reverse Amplification Primer | 5'-GTAGATCAGCACCG-3' | 460 |
| Wild Type Probe | 5'-CTCTGGGCCGAAGT-3' | 461 |
| W402X Probe | 5'-CTCTAGGCCGAAGT-3' | 462 |

Following the editing experiment, the gDNA is subjected to qPCR analysis using standard methods and the primers and probes described above. Expected results are shown in Table 16. This in vitro system can be used to expediently evaluate constructs and choose one with high editing efficiency for further studies. The systems will be evaluated in comparison with cells with and without the W402X mutation, and preferably with some that are heterozygous for this mutation. The Ct values will be compared to either a reference gene or the total amplification of the locus using a dye such as Sybr green.

TABLE 16

Expected qPCR results

| Genotype | Transfected with base editor | Expected PCR result |
|---|---|---|
| $Idua^{WT/WT}$ | No | Homozygous WT |
| $Idua^{WT/W402X}$ | No | Heterozygous: 50% WT, 50% W402X |
| $Idua^{W402X/W402X}$ | No | Homozygous W402X |
| $Idua^{W402X/W402X}$ | Yes | Variable |

The tissues can also be analyzed by next generation sequencing. Primer binding sites such as the ones shown below (Table 17), or other suitable primer binding sites that can be identified by a person of skill in the art, can be used. Following PCR amplification, products containing Illumina Nextera XT overhang sequences undergo library preparation following the Illumina 16S Metagenomic Sequencing Library protocol. Deep sequencing is performed on an Illumina Mi-Seq platform. Typically, 200,000 of 250 bp paired-end reads (2×100,000 reads) are generated per amplicon. The reads are analyzed using CRISPResso (Pinello et al., 2016) to calculate the rates of editing. Output alignments are hand-curated to confirm insertion and deletion sites as well as identify microhomology sites at the recombination sites.

TABLE 17

NGS primer binding sites

| Direction | Sequence | SEQ ID NO. |
|---|---|---|
| Forward | 5'-ACTTCCTCCAGCC-3' | 463 |
| Reverse | 5'-GAACCCCGGCTTA-3' | 464 |

Western blotting of cell lysate of transfected cells and control cells using an anti-IDUA antibody is performed to verify expression of the full-length protein and an enzyme activity assay on the cell lysate using substrate 4-methylumbelliferyl a-L-iduronide verifies that the enzyme is catalytically active (Hopwood et al., *Clin. Chim. ACta* (1979), 92(2): 257-265, incorporated by reference herein). These experiments are performed in comparison with the original $Idua^{W402X/W402X}$ cell line (without transfection), the $Idua^{W402X/W402X}$ cell line transfected with the base editing construct and a random guide sequence, and a cell line expressing wild-type IDUA.

Example 10.4: Disease Treatment Validation in a Murine Model

To verify the efficacy of this therapeutic approach, a mouse model with a nonsense mutation in the analogous amino acid is used. The mouse strain bears a W392X mutation in its Idua gene (Gene ID: 15932) which corresponds to the homologous mutation in Hurler syndrome patients (Bunge et al., (1994), Hum. Mol. Genet. 3(6): 861-866, incorporated by reference herein). This locus comprises a distinct nucleotide sequence relative to that in humans, which lacks the PAM sequence necessary for correction with the base editors described in the previous examples, and thus necessitates design of a distinct fusion protein to perform the nucleotide correction. Amelioration of the disease in this animal can validate the therapeutic approach of correcting the mutation in tissues accessible by a gene delivery vector.

Mice homozygous for this mutation display a number of phenotypic characteristics similar to Hurler syndrome patients. A base editing-RGN fusion protein as described above (Table 13) along with an RNA guide sequence are incorporated into an expression vector that allows protein expression and RNA transcription in mice. A study design is shown below in Table 18. The study includes groups that are treated with a high dose of the expression vector comprising the base-editing fusion protein and RNA guide sequence, a low dose of same expression vector, control which is the model mouse treated with an expression vector that does not comprise the base editing fusion protein or the guide RNA, and a second control which is a wild type mouse treated with the same empty vector.

TABLE 18

Genome editing experiment in murine model

| Group | Mouse strain | N | Treatment |
|---|---|---|---|
| 1 | Idua-W392X[1] | ≥5 | Low dose of vector |
| 2 | Idua-W392X | ≥5 | High dose of vector |
| 3 | Idua-W392X | ≥5 | Vehicle |
| 4 | 129/Sv (WT) | 5 | Vehicle |

Endpoints to evaluate include body weight, urine GAG excretion, serum IDUA enzymatic activity, IDUA activity in tissues of interest, tissue pathology, genotyping of tissues of interest to verify correction of the SNP, and behavioral and neurological evaluation. Since some endpoints are terminal, additional groups may be added for evaluation of, for example, tissue pathology and tissue IDUA activities before the end of the study. Additional examples of endpoints can be found in published papers establishing Hurler syndrome animal models (Shull et al. (1994), Proc. Natl. Acad. Sci. U.S.A., 91(26): 12937-12941; Wang et al. (2010), Mol. Genet. Metab., 99(1): 62-71; Hartung et al. (2004), Mol. Ther., 9(6): 866-875; Liu et al. (2005), Mol. Ther., 11(1): 35-47; Clarke et al. (1997), Hum. Mol. Genet. 6(4): 503-511; all herein incorporated by reference).

One possible delivery vector utilizes the adeno associated virus (AAV). A vector is produced to include a base editor-dRGN fusion protein coding sequence (for example, SEQ ID NO: 452) preceded by a CMV enhancer (SEQ ID NO: 138) and promoter (SEQ ID NO: 137), or other suitable enhancer and promoter combination), optionally a Kozak sequence, and operably fused at the 3' end to a terminator sequence and a poly adenlylation sequence such as the minimal sequence described in Levitt, N.; Briggs, D.; Gil, A.; Proudfoot, N. J. Definition of an Efficient Synthetic Poly(A) Site. Genes Dev. 1989, 3 (7), 1019-1025. The vector may further comprise an expression cassette encoding for a single guide RNA operably linked at its 5' end to a human U6 promoter (SEQ ID NO: 139), or another promoter suitable for production of small non-coding RNAs, and further comprising inverted terminal repeat (ITR) sequences necessary and well-known in the art for packaging into the AAV capsid. Production and viral packaging is performed by standard methods, such as those described in U.S. Pat. No. 9,587,250, herein incorporated by reference.

Other possible viral vectors include adenovirus and lentivirus vectors, which are commonly used and would contain similar elements, with different packaging capabilities and requirements. Non-viral delivery methods also be used, such as mRNA and sgRNA encapsulated by lipid nanoparticles (Cullis, P. R. and Allen, T. M. (2013), Adv. Drug Deliv. Rev. 65(1): 36-48; Finn et al. (2018), Cell Rep. 22(9): 2227-2235, both incorporated by reference) hydrodynamic injection of plasmid DNA (Suda T and Liu D, (2007) Mol. Ther. 15(12): 2063-2069, herein incorporated by reference), or ribonucleoprotein complexes of sgRNA and associated with gold nanoparticles (Lee, K.; Conboy, M.; Park, H. M.; Jiang, F.; Kim, H. J.; Dewitt, M. A.; Mackley, V. A.; Chang, K.; Rao, A.; Skinner, C.; et al. Nanoparticle Delivery of Cas9 Ribonucleoprotein and Donor DNA in Vivo Induces Homology-Directed DNA Repair. Nat. Biomed. Eng. 2017, 1 (11), 889-90).

Example 10.5: Disease Correction in a Murine Model with a Humanized Locus

To evaluate the efficacy of an identical base editor construct as would be used for human therapy, a mouse model in which the nucleotides near W392 are altered to match the sequence in humans around W402 is needed. This can be accomplished by a variety of techniques, including use of an RGN and an HDR template to cut and replace the locus in mouse embryos.

Due to the high degree of amino acid conservation, most nucleotides in the mouse locus can be altered to those of the human sequence with silent mutations as shown in Table 19. The only base changes resulting in altered coding sequence in the resulting engineered mouse genome occur after the introduced stop codon.

TABLE 19

Nucleotide mutations to generate a humanized mouse locus

| | Human (W402X) | | Mouse (W392X) | | Humanized Mouse | |
|---|---|---|---|---|---|---|
| Feature | Nucleotide (SEQ ID NO: 465) | Encoded AA | Nucleotide (SEQ ID NO: 466) | Encoded AA | Nucleotide (SEQ ID NO: 467) | Encoded AA |
| Protospacer | G | E | A | G | G | G |
| | G | E | G | E | G | E |
| | A | | A | | A | |
| | G | | A | | G | |
| | C | Q | C | Q | C | Q |
| | A | | A | | A | |
| | G | | A | | G | |
| | C | L | C | L | C | L |
| | T | | T | | T | |
| | C | | C | | C | |
| | T | STOP | T | STOP | T | STOP |
| | A | | A | | A | |

TABLE 19-continued

Nucleotide mutations to generate a humanized mouse locus

| | Human (W402X) | | Mouse (W392X) | | Humanized Mouse | |
|---|---|---|---|---|---|---|
| Feature | Nucleotide (SEQ ID NO: 465) | Encoded AA | Nucleotide (SEQ ID NO: 466) | Encoded AA | Nucleotide (SEQ ID NO: 467) | Encoded AA |
| | G | | G | | G | |
| | G | A | G | A | G | A |
| | C | | C | | C | |
| | C | | A | | C | |
| | G | E | G | E | G | E |
| | A | | A | | A | |
| | A | | G | | A | |
| | G | V | G | V | G | V |
| | T | | T | | T | |
| | G | | C | | G | |
| | T | S | T | S | T | S |
| | C | | C | | C | |
| | G | | A | | G | |
| PAM, non- | C | Q | A | K | C | Q |
| critical | A | | A | | A | |
| | G | | G | | G | |
| | G | A | G | A | G | A |
| PAM, | C | | C | | C | |
| critical | C | | T | | C | |

Upon engineering of this mouse strain, similar experiments will be performed as described in Example 10.4.

Example 11: Targeting Mutations Responsible for Friedreich Ataxia

The expansion of the trinucleotide repeat sequence causing Friedreich's Ataxia (FRDA) occurs in a defined genetic locus within the FXN gene, referred to as the FRDA instability region. RNA guided nucleases (RGNs) may be used for excising the instability region in FRDA patient cells. This approach requires 1) an RGN and guide RNA sequence that can be programmed to target the allele in the human genome; and 2) a delivery approach for the RGN and guide sequence. Many nucleases used for genome editing, such as the commonly used Cas9 nuclease from *S. pyogenes* (SpCas9), are too large to be packaged into adeno-associated viral (AAV) vectors, especially when considering the length of the SpCas9 gene and the guide RNA in addition to other genetic elements required for functional expression cassettes. This makes a viable approach using SpCas9 unlikely.

The compact RNA guided nucleases of the invention, particularly APG07433.1 and APG08290.1, are uniquely well suited for the excision of the FRDA instability region. Each RGN has a PAM requirement that is in the vicinity of the FRDA instability region. Additionally, each of these RGNs can be packaged into an AAV vector along with a guide RNA. Packing two guide RNAs would likely require a second vector, but this approach still compares favorably to what would be required of a larger nuclease such as SpCas9, which would require splitting the protein sequence between two vectors.

Table 20 shows the location of genomic target sequences suitable for targeting APG07433.1 or APG08290.1 to the 5' and 3' flanks of the FRDA instability region. Once at the locus, the RGN would excise the FA instability region. Excision of the region can be verified with Illumina sequencing of the locus.

TABLE 20

Genomic target sequences for RGN systems

| Guide No. | Location relative to FRDA instability region | Genome target sequence | SEQ ID NO. |
|---|---|---|---|
| 1 | 5' | ATCACCTGAGGTCCGGAGTTCAAGA | 468 |
| 2 | 5' | GTCTTGAACTCCGGACCTCAGGTGA | 469 |
| 3 | 5' | TGAACTCCGGACCTCAGGTGATCCA | 470 |
| 4 | 3' | GAAAAGTTAGCCGGGCGTGGTGTCG | 471 |

Example 12: Targeting Mutations Responsible for Sickle Cell Diseases

Targeting sequences within the BCL11A enhancer region (SEQ ID NO: 472) may provide a mechanism for increasing fetal hemoglobulin (HbF) to either cure or alleviate the symptoms of sickle cell diseases. For example, genome wide association studies have identified a set of genetic variations at BCL11A that are associated with increased HbF levels. These variations are a collection of SNPs found in non-coding regions of BCL11A that function as a stage-specific, lineage-restricted enhancer region. Further investigation revealed that this BCL11A enhancer is required in erythroid cells for BCL11A expression (Bauer et al, (2013) Science 343:253-257, incorporated by reference herein). The enhancer region was found within intron 2 of the BCL11A gene, and three areas of DNAseI hypersensitivity (often indicative of a chromatin state that is associated with regulatory potential) in intron 2 were identified. These three areas were identified as "+62", "+58" and "+55" in accordance with the distance in kilobases from the transcription start site of BCL11A. These enhancer regions are roughly 350 (+55); 550 (+58); and 350 (+62) nucleotides in length (Bauer et al., 2013).

Example 12.1: Identifying Preferred RGN Systems

Here we describe a potential treatment for beta-hemoglobinopathies using an RGN system that disrupts BCL11A binding to its binding site within the HBB locus, which is the gene responsible for making beta-globin in adult hemoglobin. This approach uses NHEJ which is more efficient in mammalian cells. In addition, this approach uses a nuclease of sufficiently small size that can be packaged into a single AAV vector for in vivo delivery.

The GATA1 enhancer motif in the human BCL11A enhancer region (SEQ ID NO: 472) is an ideal target for disruption using RNA guided nucleases (RGNs) to reduce BCL11A expression with concurrent re-expression of HbF in adult human erythrocytes (Wu et al. (2019) *Nat Med* 387:2554). Several PAM sequences compatible with APG07433.1 and APG08290.1 are readily apparent at the genetic locus surrounding this GATA1 site. These nucleases have a PAM sequence of 5'-NNNNCC-3' (SEQ ID NO: 6) and are compact in size, potentially allowing their delivery along with an appropriate guide RNA in a single AAV or adenoviral vector. This delivery approach bestows multiple advantages relative to others, such as access to hematopoietic stem cells and a well-established safety profile and manufacturing techniques.

The commonly used Cas9 nuclease from *S. pyogenes* (SpyCas9) requires a PAM sequence of 5'-NGG-3', (SEQ ID NO: 448) several of which are present near the GATA1 motif. However, the size of SpyCas9 prevents packaging into a single AAV or adenoviral vector and thus forgoes the aforementioned advantages of this approach. While a dual delivery strategy may be employed, it would add significant manufacturing complexity and cost. Additionally, dual viral vector delivery significantly decreases the efficiency of gene correction, since a successful edit in a given cell requires infection with both vectors.

An expression cassette encoding a human codon optimized APG07433.1 (SEQ ID NO: 128) or APG08290.1 (SEQ ID NO: 130) is produced, similar to those described in Example 6. Expression cassettes which express guide RNAs for RGNs APG07433.1 and APG08290.1 are also produced. These guide RNAs comprise 1) a protospacer sequence that is complementary to either the non-coding or coding DNA strand within the BCL11A enhancer locus (the target sequence) and 2) an RNA sequence required for association of the guide RNA with the RGN (SEQ ID NO. 18 for APG07433.1 and SEQ ID NO: 35 for APG08290.1). Because several potential PAM sequences for targeting by APG07433.1 or APG08290.1 surround the BCL11A GATA1 enhancer motif, several potential guide RNA constructs are produced to determine the best protospacer sequence that produces robust cleavage and NHEJ mediated disruption of the BCL11A GATA1 enhancer sequence. The target genomic sequences in the table below (Table 21) are evaluated to direct the RGN to this locus.

TABLE 21

Target Sequences for BCL11A GATA1 enhancer locus

| Guide | Nuclease | Target genomic sequence | Target SEQ ID NO. |
|---|---|---|---|
| 1 | APG07433.1 | GCACTAGACTAGCTTCAAAGTTGTAG | 473 |
| 2 | APG07433.1 | CCTAATCAGAGGCCAAACCCTTCCTG | 474 |
| 3 | APG07433.1 | CAAGCTAACAGTTGCTTTTATCACAG | 475 |
| 4 | APG08290.1 | GCACTAGACTAGCTTCAAAGTTGTAG | 476 |
| 5 | APG08290.1 | CCTAATCAGAGGCCAAACCCTTCCTG | 477 |
| 6 | APG08290.1 | CAAGCTAACAGTTGCTTTTATCACAG | 478 |

To evaluate the efficiency with which APG07433.1 or APG08290.1 generates insertions or deletions that disrupt the BCL11A enhancer region, human cell lines such as human embryonic kidney cells (HEK cells) are used. A DNA vector comprising an RGN expression cassette (for example, as described in Example 6) is produced. A separate vector comprising an expression cassette comprising a coding sequence for a guide RNA sequence of Table 21 is also produced. Such an expression cassette may further comprise a human RNA polymerase III U6 promoter (SEQ ID NO: 139), as described in Example 6. Alternatively, a single vector comprising expression cassettes of both the RGN and guide RNA may be used. The vector is introduced into HEK cells using standard techniques such as those described in Example 6, and the cells are cultured for 1-3 days. Following this culture period, genomic DNA is isolated and the frequency of insertions or deletions is determined by using T7 Endonuclease I digestion and/or direct DNA sequencing, as described in Example 6.

A region of DNA encompassing the target BCL11A region is amplified by PCR with primers containing Illumina Nextera XT overhang sequences. These PCR amplicons are either examined for NHEJ formation using T7 Endonuclease I digestion, or undergo library preparation following the Illumina 16S Metagenomic Sequencing Library protocol or a similar Next Generation Sequencing (NGS) library preparation. Following deep sequencing, the reads generated are analyzed by CRISPResso to calculate rates of editing. Output alignments are hand-curated to confirm insertion and deletion sites. This analysis identifies the preferred RGN and the corresponding preferred guide RNA (sgRNA). The analysis may result in both APG07433.1 and APG08290.1 being equally preferred. Additionally, the analysis may determine there is more than one preferred guide RNA, or that all target genomic sequences in Table 21 are equally preferred.

Example 12.2: Assay for Expression of Fetal Hemoglobin

In this example, APG07433.1 or APG08290.1 generated insertions or deletions disrupting the BCL11A enhancer region are assayed for expression of fetal hemoglobin. Healthy human donor $CD34^+$ hematopoietic stem cells (HSCs) are used. These HSCs are cultured and vector(s) comprising expression cassettes comprising the coding regions of the preferred RGN and the preferred sgRNA are introduced using methods similar to those described in Example 11.1. Following electroporation, these cells are differentiated in vitro into erythrocytes using established protocols (for example, Giarratana et al. (2004) Nat Biotechnology 23:69-74, herein incorporated by reference). The expression of HbF is then measured using western blotting with an anti-human HbF antibody, or quantified via High Performance Liquid Chromatography (HPLC). It is expected that successful disruption of the BCL11A enhancer locus will lead to an increase in HbF production when compared to HSCs electroporated with only the RGN but no guide.

Example 12.3: Assay for Decreased Sickle Cell Formation

In this example, APG07433.1 or APG08290.1 generated insertions or deletions disrupting the BCL11A enhancer region are assayed for decreased sickle-cell formation. Donor $CD34^+$ hematopoietic stem cells (HSCs) from patients afflicted with sickle cell disease are used. These HSCs are cultured and vector(s) comprising expression cassettes comprising the coding regions of preferred RGN and the preferred sgRNA are introduced using methods similar to those described in Example 11.1. Following electroporation, these cells are differentiated in vitro into erythrocytes using established protocols (Giarratana et al. (2004) Nat Biotechnology 23:69-74). The expression of HbF is then measured using western blotting with an anti-human HbF antibody, or quantified via High Performance Liquid Chromatography (HPLC). It is expected that successful disruption of the BCL11A enhancer locus will lead to an increase in HbF production when compared to HSCs electroporated with only the RGN but no guide.

Sickle cell formation is induced in these differentiated erythrocytes by the addition of metabisulfite. The numbers of sickled vs normal erythrocytes are counted using a microscope. It is expected that the numbers of sickled cells are less in cells treated with APG07433.1 or APG08290.1 plus sgRNAs than with cells untreated, or treated with RGNs alone.

Example 12.4: Disease Treatment Validation in a Murine Model

To evaluate the efficacy of using APG07433.1 or APG08290.1 disruption of the BCL11A locus, suitable humanized mouse models of sickle cell anemia are used. Expression cassettes encoding for the preferred RGN and for the preferred sgRNA are packaged into AAV vectors or adenovirus vectors. In particular, adenovirus type Ad5/35 is effective at targeting HSCs. A suitable mouse model containing a humanized HBB locus with sickle cell alleles is chosen such as B6; FVB-Tg(LCR-HBA2,LCR-HBB*E26K)53Hhb/J or B6.Cg-Hbatm1Paz Hbbtm1Tow Tg(HBA-HBBs)41Paz/HhbJ. These mice are treated with granulocyte colony-stimulating factor alone or in combination with plerixafor to mobilize HSCs into circulation. AAVs or adenoviruses carrying the RGN and guide plasmid are then injected intravenously, and the mice are allowed to recover for a week. Blood obtained from these mice is tested in an in vitro sickling assay using metabisulfite, and the mice are followed longitudinally to monitor mortality rates and hematopoietic function. It is expected that treatment with AAVs or adenoviruses carrying an RGN and guide RNA will reduce sickling, mortality, and improve hematopoietic function when compared to mice treated with viruses lacking both expression cassettes, or with viruses carrying the RGN expression cassette alone.

That which is claimed:

1. A nucleic acid molecule comprising a polynucleotide encoding an RNA-guided nuclease (RGN) polypeptide, wherein said polynucleotide comprises a nucleotide sequence encoding an RGN polypeptide comprising an amino acid sequence:

(i) having at least 95% sequence identity to any one of SEQ ID NOs: 11, 27, 45, or 54;

(ii) having at least 98% sequence identity to SEQ ID NOs: 1 or 19; or (iii) set forth as SEQ ID NO: 36;

wherein said polynucleotide encoding an RGN polypeptide is operably linked to a promoter heterologous to said polynucleotide.

2. The nucleic acid molecule of claim 1, wherein said RGN polypeptide of (i) or (ii) is nuclease dead or functions as a nickase.

3. The nucleic acid molecule of claim 1, wherein the RGN polypeptide is operably fused to a base-editing polypeptide.

4. A vector comprising the nucleic acid molecule of claim 1.

5. The vector of claim 4, wherein said vector further comprises at least one nucleotide sequence encoding a guide RNA, and wherein the guide RNA comprises:

(a) a CRISPR RNA comprising a CRISPR repeat sequence having at least 95% sequence identity to SEQ ID NO: 12, wherein the RGN polypeptide comprises an amino acid sequence having at least 95% sequence identity to SEQ ID NO: 11;

(b) a CRISPR RNA comprising a CRISPR repeat sequence having at least 95% sequence identity to SEQ ID NO: 28, wherein the RGN polypeptide comprises an amino acid sequence having at least 95% sequence identity to SEQ ID NO: 27;

(c) a CRISPR RNA comprising a CRISPR repeat sequence having at least 95% sequence identity to SEQ ID NO: 46, wherein the RGN polypeptide comprises an amino acid sequence having at least 95% sequence identity to SEQ ID NO: 45;

(d) a CRISPR RNA comprising a CRISPR repeat sequence having at least 95% sequence identity to SEQ ID NO: 55, wherein the RGN polypeptide comprises an amino acid sequence having at least 95% sequence identity to SEQ ID NO: 54;

(e) a CRISPR RNA comprising a CRISPR repeat sequence having at least 95% sequence identity to SEQ ID NO: 2, wherein the RGN polypeptide comprises an amino acid sequence having at least 98% sequence identity to SEQ ID NO: 1;

(f) a CRISPR RNA comprising a CRISPR repeat sequence having at least 95% sequence identity to SEQ ID NO: 20, wherein the RGN polypeptide comprises an amino acid sequence having at least 98% sequence identity to SEQ ID NO: 19; or (g) a CRISPR RNA comprising a CRISPR repeat sequence having at least 95% sequence identity to SEQ ID NO: 37, wherein the RGN polypeptide comprises an amino acid sequence set forth as SEQ ID NO: 36.

6. The vector of claim 4, wherein the guide RNA comprises:

(a) a tracrRNA comprising a nucleotide sequence having at least 95% sequence identity to SEQ ID NO: 13, wherein the RGN polypeptide comprises an amino acid sequence having at least 95% sequence identity to SEQ ID NO: 11;

(b) a tracrRNA comprising a nucleotide sequence having at least 95% sequence identity to SEQ ID NO: 29, wherein the RGN polypeptide comprises an amino acid sequence having at least 95% sequence identity to SEQ ID NO: 27;

(c) a tracrRNA comprising a nucleotide sequence having at least 95% sequence identity to SEQ ID NO: 47, wherein the RGN polypeptide comprises an amino acid sequence having at least 95% sequence identity to SEQ ID NO: 45;

(d) a tracrRNA comprising a nucleotide sequence having at least 95% sequence identity to SEQ ID NO: 56, wherein the RGN polypeptide comprises an amino acid sequence having at least 95% sequence identity to SEQ ID NO: 54;

(e) a tracrRNA comprising a nucleotide sequence having at least 95% sequence identity to SEQ ID NO: 3, wherein the RGN polypeptide comprises an amino acid sequence having at least 98% sequence identity to SEQ ID NO: 1;

(f) a tracrRNA comprising a nucleotide sequence having at least 95% sequence identity to SEQ ID NO: 21, wherein the RGN polypeptide comprises an amino acid sequence having at least 98% sequence identity to SEQ ID NO: 19; or (g) a tracrRNA comprising a nucleotide sequence having at least 95% sequence identity to SEQ ID NO: 38, wherein the RGN polypeptide comprises an amino acid sequence set forth as SEQ ID NO: 36.

7. A cell comprising the nucleic acid molecule of claim 1.

8. A system, said system comprising:

a) one or more guide RNAs (gRNAs), or one or more nucleotide sequences encoding the one or more gRNAs; and b) an RNA-guided nuclease (RGN) polypeptide comprising an amino acid sequence:
(i) having at least 95% sequence identity to any one of SEQ ID NOs: 11, 27, 45, or 54;
(ii) having at least 98% sequence identity to SEQ ID NOs: 1 or 19; or
(iii) set forth as SEQ ID NO: 36, or a nucleotide sequence encoding the RGN polypeptide; wherein said nucleotide sequences encoding the one or more gRNAs and encoding the RGN polypeptide are each operably linked to a promoter heterologous to each said nucleotide sequence.

9. The system of claim 8, wherein the one or more gRNAs hybridize to a target DNA sequence within a eukaryotic cell.

10. The system of claim 8, wherein said RGN polypeptide of (i) or (ii) is nuclease dead or functions as a nickase, and wherein the RGN polypeptide is operably linked to a base-editing polypeptide.

11. The system of claim 8, wherein said system further comprises one or more donor polynucleotides, or one or more nucleotide sequences encoding the one or more donor polynucleotides, wherein each of said one or more nucleotide sequences encoding the one or more donor polynucleotides is operably linked to a promoter heterologous to each of said one or more nucleotide sequences.

12. A method for binding a target DNA sequence comprising delivering a system according to claim 8, to said target DNA sequence or a cell comprising the target DNA sequence.

13. A method for cleaving and/or modifying a target DNA sequence, comprising contacting the target DNA sequence with:
a) an RNA-guided nuclease (RGN) polypeptide, wherein said RGN comprises an amino acid sequence:
(i) having at least 95% sequence identity to any one of SEQ ID NOs: 11, 27, 45 or 54;
(ii) having at least 98% sequence identity to SEQ ID NOs: 1 or 19; or
(iii) set forth as SEQ ID NO: 36;

and
b) one or more guide RNAs capable of hybridizing to the target DNA sequence thereby cleaving and/or modifying said target DNA sequence to obtain a modified target DNA sequence.

14. The method of claim 13, wherein said modified target DNA sequence comprises insertion of heterologous DNA into the target DNA sequence.

15. The method of claim 13, wherein said modified target DNA sequence comprises deletion of at least one nucleotide from the target DNA sequence.

16. The method of claim 13, wherein said modified target DNA sequence comprises mutation of at least one nucleotide in the target DNA sequence.

17. The method of claim 13, wherein the target DNA sequence is within a cell.

18. The method of claim 17, wherein the cell is a eukaryotic cell.

19. The method of claim 17, further comprising culturing the cell; and selecting cells comprising said modified DNA sequence.

20. The nucleic acid molecule of claim 1, wherein the RGN polypeptide is capable of binding a guide RNA capable of hybridizing to a target DNA sequence.

21. The nucleic acid molecule of claim 20, wherein said target DNA sequence is located adjacent to a protospacer adjacent motif (PAM) site of:
(a) NNNNCC (SEQ ID NO: 6), wherein the RGN polypeptide comprises an amino acid sequence having at least 95% sequence identity to SEQ ID NO: 11;
(b) NNRNCC (SEQ ID NO: 32), wherein the RGN polypeptide comprises an amino acid sequence having at least 95% sequence identity to SEQ ID NO: 27;
(c) NNRAATY (SEQ ID NO: 50), wherein the RGN polypeptide comprises an amino acid sequence having at least 95% sequence identity to SEQ ID NO: 45;
(d) NNRNNC (SEQ ID NO: 59), wherein the RGN polypeptide comprises an amino acid sequence having at least 95% sequence identity to SEQ ID NO: 54;
(e) NNNNCC (SEQ ID NO: 6), wherein the RGN polypeptide comprises an amino acid sequence having at least 98% sequence identity to SEQ ID NO: 1;
(f) NNNNCC (SEQ ID NO: 6), wherein the RGN polypeptide comprises an amino acid sequence having at least 98% sequence identity to SEQ ID NO: 19; or
(g) NGG (SEQ ID NO: 41), wherein the RGN polypeptide comprises an amino acid sequence set forth as SEQ ID NO: 36.

22. A nucleic acid molecule comprising a polynucleotide encoding an RNA-guided nuclease (RGN) polypeptide that is nuclease dead or is a nickase, wherein said RGN polypeptide comprises an amino acid sequence set forth as SEQ ID NO: 36 modified by one or more mutations, wherein each of the one or more mutations results in said RGN polypeptide that is nuclease dead or is a nickase.

23. An RNA polynucleotide comprising at least one synthetic ribonucleotide analogue, wherein said RNA polynucleotide comprises a nucleotide sequence encoding an RNA-guided nuclease (RGN) polypeptide comprising an amino acid sequence:
(i) having at least 95% sequence identity to any one of SEQ ID NOs: 11, 27, 45, or 54;
(ii) having at least 98% sequence identify to SEQ ID NOs: 1 or 19; or
(iii) set forth as SEQ ID NO: 36.

24. The RNA polynucleotide of claim 23, wherein the RNA polynucleotide further comprises a nucleotide sequence encoding a base-editing polypeptide operably linked to the nucleotide sequence encoding the RGN polypeptide.

25. The RNA polynucleotide of claim 23, wherein the RNA polynucleotide is an mRNA.

26. A eukaryotic cell comprising a nucleic acid molecule comprising a polynucleotide encoding an RNA-guided nuclease (RGN) polypeptide, wherein said polynucleotide comprises a nucleotide sequence encoding an RGN polypeptide comprising an amino acid sequence:
(i) having at least 95% sequence identity to any one of SEQ ID NOs: 11, 27, 45, or 54;
(ii) having at least 98% sequence identity to SEQ ID NOs: 1 or 19; or
(iii) set forth as SEQ ID NO: 36.

27. The eukaryotic cell of claim 26, wherein said polynucleotide is an mRNA.

28. The eukaryotic cell of claim 26, wherein the RGN polypeptide is operably fused to a base-editing polypeptide.

* * * * *

SEQUENCE LISTING

```
<160> NUMBER OF SEQ ID NOS: 651

<210> SEQ ID NO 1
<211> LENGTH: 1070
<212> TYPE: PRT
<213> ORGANISM: Bacillus sp.
<220> FEATURE:
<221> NAME/KEY: source
<223> OTHER INFORMATION: /note="APG05083.1"

<400> SEQUENCE: 1

Met Arg Glu Leu Asp Tyr Arg Ile Gly Leu Asp Ile Gly Thr Asn Ser
1               5                   10                  15

Ile Gly Trp Gly Ile Ile Glu Leu Ser Trp Asn Lys Asp Arg Glu Gln
            20                  25                  30

Tyr Glu Lys Ala Arg Ile Val Asp Lys Gly Val Arg Met Phe Asp Lys
        35                  40                  45

Ala Glu Ile Pro Lys Thr Gly Ala Ser Leu Ala Glu Pro Arg Arg Ile
    50                  55                  60

Ala Arg Ser Ser Arg Arg Arg Leu Asn Arg Lys Ser Gln Arg Lys Lys
65                  70                  75                  80

Asp Ile Arg Asn Leu Leu Val Gln His Glu Ile Ile Ser Gln Lys Glu
                85                  90                  95

Leu Ala Ser Leu Tyr Pro Leu Thr Lys Ser Ser Met Asp Ile Trp Asp
            100                 105                 110

Ile Arg Leu Asp Gly Leu Asp Arg Leu Leu Asp Arg Phe Glu Trp Thr
        115                 120                 125
```

-continued

```
Arg Leu Leu Ile His Leu Ala Gln Arg Arg Gly Phe Lys Ser Asn Arg
    130                 135                 140

Lys Ser Glu Leu Lys Asp Val Glu Thr Gly Lys Val Leu Ser Ser Ile
145                 150                 155                 160

Gln Ala Asn Glu Lys Arg Leu Ser Leu Tyr Arg Thr Val Gly Glu Met
                165                 170                 175

Trp Met Lys Asn Glu Asp Phe Ser Lys Tyr Asp Lys Arg Arg Asn Ser
            180                 185                 190

Ser Asn Glu Tyr Val Phe Ser Val Ser Arg Ala Asp Leu Glu Lys Glu
        195                 200                 205

Ile Val Thr Leu Phe Glu Ala Gln Arg Lys Phe Gln Ser Ser Tyr Ala
    210                 215                 220

Ser Ala Asp Leu Gln Lys Thr Tyr Leu Gln Ile Trp Ala His Gln Leu
225                 230                 235                 240

Pro Phe Ala Ser Gly Asn Ala Ile Val Asn Lys Val Gly Tyr Cys Ser
                245                 250                 255

Leu Leu Lys Gly Lys Glu Lys Arg Val Pro Lys Ala Thr Tyr Thr Phe
            260                 265                 270

Gln Tyr Phe Ser Thr Leu Asp Gln Ile Asn Arg Thr Arg Leu Gly Pro
        275                 280                 285

Asn Phe Gln Pro Phe Thr Lys Glu Gln Arg Asp Val Ile Leu Asp Glu
    290                 295                 300

Met Phe Asn Arg Thr Asp Tyr Tyr Lys Lys Lys Thr Ile Pro Glu Val
305                 310                 315                 320

Thr Tyr Tyr Asp Ile Arg Lys Trp Leu Ala Leu Asp Glu Thr Ile Gln
                325                 330                 335

Phe Lys Gly Leu Thr Tyr Asp Pro Asn Glu Glu Leu Lys Lys Ile Glu
            340                 345                 350

Leu Lys Ser Phe Ile Asn Leu Lys Pro Phe Tyr Glu Ile Lys Lys Val
        355                 360                 365

Val Thr Asn Tyr Ala Lys Lys Thr Asn Glu Ala Phe Ser Thr Leu Asp
    370                 375                 380

Tyr Asp Thr Phe Ala Tyr Ala Leu Thr Val Tyr Lys Thr Asp Lys Asp
385                 390                 395                 400

Ile Arg Ser Tyr Leu Lys Lys Ser Asn Asn Leu Ser Lys Cys Cys Tyr
                405                 410                 415

Asp Asp Gln Leu Ile Glu Glu Leu Leu Thr Leu Ser Tyr Thr Lys Phe
            420                 425                 430

Gly His Leu Ser Phe Lys Ala Ile Asn His Val Leu Pro Ile Met Gln
        435                 440                 445

Glu Gly Arg Thr Tyr Gln Glu Ala Ile His Gln Leu Gly Tyr Asp Ala
    450                 455                 460

Thr Asn Leu Lys Lys Glu Asn Arg Ser Met Phe Leu Pro Leu Phe Pro
465                 470                 475                 480

Asp Glu Ile Thr Asn Pro Ile Val Lys Arg Ala Leu Thr Gln Ala Arg
                485                 490                 495

Lys Val Val Asn Ala Ile Ile Arg Arg Tyr Gly Ser Pro Asn Ser Val
            500                 505                 510

His Ile Glu Leu Ala Arg Glu Leu Ser Lys Ser His Asp Glu Arg Thr
        515                 520                 525

Lys Ile Met Lys Ala His Asp Glu Asn Tyr Lys Lys Asn Lys Gly Ala
    530                 535                 540

Ile Ser Ile Leu Ile Glu Asn Gly Ile Leu Asn Pro Thr Gly Tyr Asp
```

-continued

```
545                 550                 555                 560

Ile Val Arg Tyr Lys Leu Trp Lys Glu Gln Gly Glu Arg Cys Ala Tyr
                565                 570                 575

Ser Leu Lys Gln Ile Pro Ala Asn Thr Phe Phe Asn Glu Met Lys Lys
            580                 585                 590

Glu Arg Ser Gly Ser Pro Val Leu Glu Ile Asp His Ile Leu Pro Tyr
        595                 600                 605

Ser Gln Ser Phe Ile Asp Ser Tyr His Asn Lys Val Leu Val Tyr Gly
    610                 615                 620

Asp Glu Asn Gln Lys Lys Gly Asn Arg Ile Pro Tyr Thr Tyr Phe Leu
625                 630                 635                 640

Glu Gly Asn Lys Asp Trp Glu Ser Phe Glu Ser Tyr Val Arg Leu Asn
                645                 650                 655

Ser Phe Phe Ser Lys Lys Lys Arg Gly Tyr Leu Leu Lys Lys Ala Tyr
            660                 665                 670

Leu Pro Arg Glu Ser Asn Met Ile Lys Glu Arg His Leu Asn Asp Thr
        675                 680                 685

Arg Tyr Ala Ser Ser Tyr Leu Lys Asn Phe Ile Glu Lys Asn Leu Lys
    690                 695                 700

Phe Lys Glu Val Glu Gly Ser Thr Arg Lys Lys His Val Gln Thr Val
705                 710                 715                 720

Asn Gly Ile Ile Thr Ala His Leu Arg Lys Arg Trp Gly Leu Glu Lys
                725                 730                 735

Asp Arg Gln Glu Thr Tyr Leu His His Ala Met Asp Ala Ile Ile Val
            740                 745                 750

Ala Cys Thr Asp His His Met Val Thr Lys Val Thr Glu Tyr Tyr Gln
        755                 760                 765

Ile Lys Glu Ser Asn Lys Ser Ile Arg Lys Pro Tyr Phe Pro Leu Pro
    770                 775                 780

Trp Val Gly Phe Arg Glu Glu Ile Leu Ser His Leu Ala Arg Gln Pro
785                 790                 795                 800

Ile Ala Arg Lys Ile Ser Glu Glu Leu Lys Ile Gly Tyr Gln Ser Phe
                805                 810                 815

Asp Tyr Ile Leu Val Ser Arg Met Pro Lys Arg Ser Val Thr Gly Ala
            820                 825                 830

Ala His Glu Gln Thr Ile Met Lys Lys Gly Gly Ile Asp Lys Lys Gly
        835                 840                 845

Lys Thr Ile Ile Ile Lys Arg Val Tyr Leu Lys Asp Ile Lys Phe Asp
    850                 855                 860

Glu Asn Gly Asp Phe Lys Met Val Gly Lys Glu Gln Asp Leu Ala Thr
865                 870                 875                 880

Tyr Glu Ala Ile Lys Gln Arg Tyr Ile Glu Tyr Gly Lys Glu Ser Lys
                885                 890                 895

Lys Ala Phe Glu Thr Pro Leu Tyr Lys Pro Ser Lys Lys Gly Lys Gly
            900                 905                 910

Asn Leu Ile Lys Lys Ile Lys Val Glu Val Gln Thr Lys Ser Phe Val
        915                 920                 925

Arg Glu Val Asn Gly Gly Val Ala Gln Asn Gly Asp Leu Val Arg Val
    930                 935                 940

Asp Leu Phe Glu Lys Asp Asn Arg Tyr Tyr Met Ile Pro Ile Tyr Val
945                 950                 955                 960

Met Asp Thr Val His Ser Glu Leu Pro Asn Lys Ala Val Thr Ser Ser
                965                 970                 975
```

```
Lys Gly Tyr Glu Gln Trp Leu Thr Ile Asp Asn Ser Phe Thr Phe Lys
            980                 985                 990

Phe Ser Leu Tyr Pro Tyr Asp Leu  Val Arg Leu Val Lys  Gly Asn Glu
        995                 1000                 1005

Asp Arg  Phe Leu Tyr Phe Ser  Thr Leu Asp Ile Asn  Ser Asp Arg
    1010                 1015                 1020

Leu Asn  Phe Lys Asp Val Asn  Lys Pro Ser Lys Gln  Ala Glu Asn
    1025                 1030                 1035

Arg Tyr  Ser Leu Lys Thr Ile  Glu Asn Leu Glu Lys  Tyr Glu Val
    1040                 1045                 1050

Gly Val  Leu Gly Asp Leu Arg  Phe Val Arg Gln Glu  Ile Arg Lys
    1055                 1060                 1065

Asn Phe
    1070
```

<210> SEQ ID NO 2
<211> LENGTH: 19
<212> TYPE: RNA
<213> ORGANISM: Bacillus sp.
<220> FEATURE:
<221> NAME/KEY: source
<223> OTHER INFORMATION: /note="crRNA"

<400> SEQUENCE: 2
gucauaguuc cauuauugc 19

<210> SEQ ID NO 3
<211> LENGTH: 84
<212> TYPE: RNA
<213> ORGANISM: Bacillus sp.
<220> FEATURE:
<221> NAME/KEY: source
<223> OTHER INFORMATION: /note="tracrRNA"

<400> SEQUENCE: 3
gcuuugaugu uucuaugaua agggcuuagg cccguggcgu uggggaucgc cugcccauuu 60
uaaugggcuu cuccccaucu auuu 84

<210> SEQ ID NO 4
<211> LENGTH: 137
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="sgRNA L1"

<400> SEQUENCE: 4
gagcggacag cagcuuccua uaucucguac gucauaguuc cauuauugca aaggcuuuga 60
uguuucuaug auaagggcuu aggcccgugg cguuggggau cgccugccca uuuuaauggg 120
cuucucccca ucuauuu 137

<210> SEQ ID NO 5
<211> LENGTH: 137
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic polynucleotide"
<220> FEATURE:
<221> NAME/KEY: source
<223> OTHER INFORMATION: /note="sgRNA L2"

<400> SEQUENCE: 5
ccaugauaua gacguugugg cuguuguagu gucauaguuc cauuauugca aaggcuuuga 60
uguuucuaug auaagggcuu aggcccgugg cguuggggau cgccugccca uuuuaauggg 120
cuucucccca ucuauuu 137

<210> SEQ ID NO 6
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="PAM"
<220> FEATURE:
<221> NAME/KEY: modified_base
<222> LOCATION: (1)..(4)
<223> OTHER INFORMATION: a, c, t, g, unknown or other

<400> SEQUENCE: 6 nnnncc 6

<210> SEQ ID NO 7
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="PAM examplary"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 7 nnrncc 6

<210> SEQ ID NO 8
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Target seq and PAM region of plasmid library 1"
<220> FEATURE:
<221> NAME/KEY: modified_base
<222> LOCATION: (31)..(38)
<223> OTHER INFORMATION: a, c, t, g, unknown or other

<400> SEQUENCE: 8
gagcggacag cagcttccta tatctcgtac nnnnnnnn 38

<210> SEQ ID NO 9
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Target seq and PAM region of plasmid library 2"
<220> FEATURE:
<221> NAME/KEY: modified_base
<222> LOCATION: (31)..(38)
<223> OTHER INFORMATION: a, c, t, g, unknown or other

<400> SEQUENCE: 9
ccatgatata gacgttgtgg ctgttgtagt nnnnnnnn 38

<210> SEQ ID NO 10
<211> LENGTH: 132
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="sgRNA with N's"
<220> FEATURE:
<221> NAME/KEY: modified_base
<222> LOCATION: (1)..(25)
<223> OTHER INFORMATION: a, c, u, g, unknown or other

<400> SEQUENCE: 10
nnnnnnnnnn nnnnnnnnnn nnnnngucau aguuccauua uugcaaaggc uuugauguuu 60
cuaugauaag ggcuuaggcc cguggcguug gggaucgccu gcccauuuua augggcuucu 120
ccccaucuau uu 132

<210> SEQ ID NO 11
<211> LENGTH: 1071
<212> TYPE: PRT
<213> ORGANISM: Bacillus sp.
<220> FEATURE:
<221> NAME/KEY: source
<223> OTHER INFORMATION: /note="APG07433.1"

<400> SEQUENCE: 11

Met Arg Glu Leu Asp Tyr Arg Ile Gly Leu Asp Ile Gly Thr Asn Ser
1 5 10 15

Ile Gly Trp Gly Val Ile Glu Leu Ser Trp Asn Lys Asp Arg Glu Arg
20 25 30

Tyr Glu Lys Val Arg Ile Val Asp Gln Gly Val Arg Met Phe Asp Arg
35 40 45

Ala Glu Met Pro Lys Thr Gly Ala Ser Leu Ala Glu Pro Arg Arg Ile
50 55 60

Ala Arg Ser Ser Arg Arg Arg Leu Asn Arg Lys Ser Gln Arg Lys Lys
65 70 75 80

Asn Ile Arg Asn Leu Leu Val Gln His Gly Val Ile Thr Gln Glu Glu
85 90 95

Leu Asp Ser Leu Tyr Pro Leu Ser Lys Lys Ser Met Asp Ile Trp Gly

-continued

```
            100                 105                 110

Ile Arg Leu Asp Gly Leu Asp Arg Leu Leu Asn His Phe Glu Trp Ala
        115                 120                 125

Arg Leu Leu Ile His Leu Ala Gln Arg Arg Gly Phe Lys Ser Asn Arg
    130                 135                 140

Lys Ser Glu Leu Lys Asp Thr Glu Thr Gly Lys Val Leu Ser Ser Ile
145                 150                 155                 160

Gln Leu Asn Glu Lys Arg Leu Ser Leu Tyr Arg Thr Val Gly Glu Met
                165                 170                 175

Trp Met Lys Asp Pro Asp Phe Ser Lys Tyr Asp Arg Lys Arg Asn Ser
            180                 185                 190

Pro Asn Glu Tyr Val Phe Ser Val Ser Arg Ala Glu Leu Glu Lys Glu
        195                 200                 205

Ile Val Thr Leu Phe Ala Ala Gln Arg Arg Phe Gln Ser Pro Tyr Ala
    210                 215                 220

Ser Lys Asp Leu Gln Glu Thr Tyr Leu Gln Ile Trp Thr His Gln Leu
225                 230                 235                 240

Pro Phe Ala Ser Gly Asn Ala Ile Leu Asn Lys Val Gly Tyr Cys Ser
                245                 250                 255

Leu Leu Lys Gly Lys Glu Arg Arg Ile Pro Lys Ala Thr Tyr Thr Phe
            260                 265                 270

Gln Tyr Phe Ser Ala Leu Asp Gln Val Asn Arg Thr Arg Leu Gly Pro
        275                 280                 285

Asp Phe Gln Pro Phe Thr Lys Glu Gln Arg Glu Ile Ile Leu Asn Asn
    290                 295                 300

Met Phe Gln Arg Thr Asp Tyr Tyr Lys Lys Lys Thr Ile Pro Glu Val
305                 310                 315                 320

Thr Tyr Tyr Asp Ile Arg Lys Trp Leu Glu Leu Asp Glu Thr Ile Gln
                325                 330                 335

Phe Lys Gly Leu Asn Tyr Asp Pro Asn Glu Glu Leu Lys Lys Ile Glu
            340                 345                 350

Lys Lys Pro Phe Ile Asn Leu Lys Ala Phe Tyr Glu Ile Asn Lys Val
        355                 360                 365

Val Ala Asn Tyr Ser Glu Arg Thr Asn Glu Thr Phe Ser Thr Leu Asp
    370                 375                 380

Tyr Asp Gly Ile Gly Tyr Ala Leu Thr Val Tyr Lys Thr Asp Lys Asp
385                 390                 395                 400

Ile Arg Ser Tyr Leu Lys Ser Ser His Asn Leu Pro Lys Arg Cys Tyr
                405                 410                 415

Asp Asp Gln Leu Ile Glu Glu Leu Leu Ser Leu Ser Tyr Thr Lys Phe
            420                 425                 430

Gly His Leu Ser Leu Lys Ala Ile Asn His Val Leu Ser Ile Met Gln
        435                 440                 445

Lys Gly Asn Thr Tyr Lys Glu Ala Val Asp Gln Leu Gly Tyr Asp Thr
    450                 455                 460

Ser Gly Leu Lys Lys Glu Lys Arg Ser Lys Phe Leu Pro Pro Ile Ser
465                 470                 475                 480

Asp Glu Ile Thr Asn Pro Ile Val Lys Arg Ala Leu Thr Gln Ala Arg
                485                 490                 495

Lys Val Val Asn Ala Ile Ile Arg Arg His Gly Ser Pro His Ser Val
            500                 505                 510

His Ile Glu Leu Ala Arg Glu Leu Ser Lys Asn His Asp Glu Arg Thr
        515                 520                 525
```

```
Lys Ile Val Ser Ala Gln Asp Glu Asn Tyr Lys Lys Asn Lys Gly Ala
    530                 535                 540

Ile Ser Ile Leu Ser Glu His Gly Ile Leu Asn Pro Thr Gly Tyr Asp
545                 550                 555                 560

Ile Val Arg Tyr Lys Leu Trp Lys Glu Gln Gly Glu Arg Cys Ala Tyr
                565                 570                 575

Ser Leu Lys Glu Ile Pro Ala Asp Thr Phe Phe Asn Glu Leu Lys Lys
            580                 585                 590

Glu Arg Asn Gly Ala Pro Ile Leu Glu Val Asp His Ile Leu Pro Tyr
        595                 600                 605

Ser Gln Ser Phe Ile Asp Ser Tyr His Asn Lys Val Leu Val Tyr Ser
    610                 615                 620

Asp Glu Asn Arg Lys Lys Gly Asn Arg Ile Pro Tyr Thr Tyr Phe Leu
625                 630                 635                 640

Glu Thr Asn Lys Asp Trp Glu Ala Phe Glu Arg Tyr Val Arg Ser Asn
                645                 650                 655

Lys Phe Phe Ser Lys Lys Lys Arg Glu Tyr Leu Leu Lys Arg Ala Tyr
            660                 665                 670

Leu Pro Arg Glu Ser Glu Leu Ile Lys Glu Arg His Leu Asn Asp Thr
        675                 680                 685

Arg Tyr Ala Ser Thr Phe Leu Lys Asn Phe Ile Glu Gln Asn Leu Gln
    690                 695                 700

Phe Lys Glu Ala Glu Asp Asn Pro Arg Lys Arg Arg Val Gln Thr Val
705                 710                 715                 720

Asn Gly Val Ile Thr Ala His Phe Arg Lys Arg Trp Gly Leu Glu Lys
                725                 730                 735

Asp Arg Gln Glu Thr Tyr Leu His His Ala Met Asp Ala Ile Ile Val
            740                 745                 750

Ala Cys Thr Asp His His Met Val Thr Arg Val Thr Glu Tyr Tyr Gln
        755                 760                 765

Ile Lys Glu Ser Asn Lys Ser Val Lys Lys Pro Tyr Phe Pro Met Pro
    770                 775                 780

Trp Glu Gly Phe Arg Asp Glu Leu Leu Ser His Leu Ala Ser Gln Pro
785                 790                 795                 800

Ile Ala Lys Lys Ile Ser Glu Glu Leu Lys Ala Gly Tyr Gln Ser Leu
                805                 810                 815

Asp Tyr Ile Phe Val Ser Arg Met Pro Lys Arg Ser Ile Thr Gly Ala
            820                 825                 830

Ala His Lys Gln Thr Ile Met Arg Lys Gly Gly Ile Asp Lys Lys Gly
        835                 840                 845

Lys Thr Ile Ile Ile Glu Arg Leu His Leu Lys Asp Ile Lys Phe Asp
    850                 855                 860

Glu Asn Gly Asp Phe Lys Met Val Gly Lys Glu Gln Asp Met Ala Thr
865                 870                 875                 880

Tyr Glu Ala Ile Lys Gln Arg Tyr Leu Glu His Gly Lys Asn Ser Lys
                885                 890                 895

Lys Ala Phe Glu Thr Pro Leu Tyr Lys Pro Ser Lys Lys Gly Thr Gly
            900                 905                 910

Asn Leu Ile Lys Arg Val Lys Val Glu Gly Gln Ala Lys Ser Phe Val
        915                 920                 925

Arg Glu Val Asn Gly Gly Val Ala Gln Asn Gly Asp Leu Val Arg Val
    930                 935                 940
```

```
Asp Leu Phe Glu Lys Asp Asp Lys Tyr Tyr Met Val Pro Ile Tyr Val
945                 950                 955                 960

Pro Asp Thr Val Cys Ser Glu Leu Pro Lys Lys Val Val Ala Ser Ser
                965                 970                 975

Lys Gly Tyr Glu Gln Trp Leu Thr Leu Asp Asn Ser Phe Thr Phe Lys
            980                 985                 990

Phe Ser Leu Tyr Pro Tyr Asp Leu  Val Arg Leu Val Lys  Gly Asp Glu
        995                 1000                 1005

Asp Arg  Phe Leu Tyr Phe Gly  Thr Leu Asp Ile Asp  Ser Asp Arg
    1010                 1015                 1020

Leu Asn  Phe Lys Asp Val Asn  Lys Pro Ser Lys Lys  Asn Glu Tyr
    1025                 1030                 1035

Arg Tyr  Ser Leu Lys Thr Ile  Glu Asp Leu Glu Lys  Tyr Glu Val
    1040                 1045                 1050

Gly Val  Leu Gly Asp Leu Arg  Leu Val Arg Lys Glu  Thr Arg Arg
    1055                 1060                 1065

Asn Phe  His
    1070
```

<210> SEQ ID NO 12
<211> LENGTH: 21
<212> TYPE: RNA
<213> ORGANISM: Bacillus sp.
<220> FEATURE:
<221> NAME/KEY: source
<223> OTHER INFORMATION: /note="crRNA"

<400> SEQUENCE: 12
gucauaguuc cauuaaagcc a 21

<210> SEQ ID NO 13
<211> LENGTH: 85
<212> TYPE: RNA
<213> ORGANISM: Bacillus sp.
<220> FEATURE:
<221> NAME/KEY: source
<223> OTHER INFORMATION: /note="tracrRNA"

<400> SEQUENCE: 13
uggcuuugau guuucuauga uaaggguuuc gacccguggc gucggggauc gccugcccau 60
ugaaaugggc uucuccccau uuauu 85

<210> SEQ ID NO 14
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="sgRNA L1"

<400> SEQUENCE: 14
gagcggacag cagcuuccua uaucucguac gucauaguuc cauuaaagcc agaaauggcu 60
uugauguuuc uaugauaagg guuucgaccc guggcgucgg ggaucgccug cccauugaaa 120
ugggcuucuc cccauuuauu 140

<210> SEQ ID NO 15
<211> LENGTH: 140

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L2"

<400> SEQUENCE: 15

ccaugauaua gacguugugg cuguuguagu gucauaguuc cauuaaagcc agaaauggcu     60

uugauguuuc uaugauaagg guuucgaccc guggcgucgg ggaucgccug cccauugaaa    120

ugggcuucuc cccauuuauu                                                140


<210> SEQ ID NO 16
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 1"
<220> FEATURE:
<221> NAME/KEY: modified_base
<222> LOCATION: (31)..(38)
<223> OTHER INFORMATION: a, c, t, g, unknown or other

<400> SEQUENCE: 16

gagcggacag cagcttccta tatctcgtac nnnnnnnn                             38


<210> SEQ ID NO 17
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 2"
<220> FEATURE:
<221> NAME/KEY: modified_base
<222> LOCATION: (31)..(38)
<223> OTHER INFORMATION: a, c, t, g, unknown or other

<400> SEQUENCE: 17

ccatgatata gacgttgtgg ctgttgtagt nnnnnnnn                             38


<210> SEQ ID NO 18
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA with N's"
<220> FEATURE:
<221> NAME/KEY: modified_base
<222> LOCATION: (1)..(25)
<223> OTHER INFORMATION: a, c, u, g, unknown or other
```

<400> SEQUENCE: 18
nnnnnnnnnn nnnnnnnnnn nnnnngucau aguuccauua aagccaaaag uggcuuugau 60
guuucuauga uaaggguuuc gacccguggc gucggggauc gccugcccau ugaaaugggc 120
uucuccccau uuauu 135

<210> SEQ ID NO 19
<211> LENGTH: 1071
<212> TYPE: PRT
<213> ORGANISM: Bacillus sp.
<220> FEATURE:
<221> NAME/KEY: source
<223> OTHER INFORMATION: /note="APG07513.1"

<400> SEQUENCE: 19

```
Met Arg Glu Leu Asp Tyr Arg Ile Gly Leu Asp Ile Gly Thr Asn Ser
1               5                   10                  15

Ile Gly Trp Gly Val Ile Glu Leu Ser Trp Asn Lys Asp Arg Glu Gln
            20                  25                  30

Tyr Glu Lys Thr Arg Ile Val Asp Lys Gly Val Arg Met Phe Asp Lys
        35                  40                  45

Ala Glu Ile Pro Lys Thr Gly Ala Ser Leu Ala Glu Pro Arg Arg Ile
    50                  55                  60

Ala Arg Ser Ser Arg Arg Arg Leu Asn Arg Lys Ser Gln Arg Lys Lys
65                  70                  75                  80

Asp Ile Arg Asn Leu Leu Val Gln His Glu Ile Ile Ser Gln Lys Glu
                85                  90                  95

Leu Thr Ser Leu Tyr Pro Leu Ser Lys Ser Ser Met Asp Ile Trp Asp
            100                 105                 110

Ile Arg Leu Asp Gly Leu Asp Arg Leu Leu Asp Arg Phe Glu Trp Ala
        115                 120                 125

Arg Leu Leu Ile His Leu Ala Gln Arg Arg Gly Phe Lys Ser Asn Arg
    130                 135                 140

Lys Ser Glu Leu Lys Asp Val Glu Thr Gly Lys Val Leu Ser Ser Ile
145                 150                 155                 160

Gln Val Asn Glu Lys Arg Leu Ser Leu Tyr Arg Thr Val Gly Glu Met
                165                 170                 175

Trp Met Lys Asn Ala Asp Cys Ser Lys Tyr Gly Lys Arg Arg Asn Ser
            180                 185                 190

Pro Asn Glu Tyr Val Phe Ser Val Ser Arg Ala Asp Leu Glu Lys Glu
        195                 200                 205

Ile Val Thr Leu Phe Glu Ala Gln Arg Lys Phe His Ser Ser Tyr Ala
    210                 215                 220

Ser Val Asp Leu Gln Lys Thr Tyr Ile Gln Ile Trp Ala His Gln Leu
225                 230                 235                 240

Pro Phe Ala Ser Gly Asn Ala Ile Val Asn Lys Val Gly Tyr Cys Ser
                245                 250                 255

Leu Leu Lys Gly Lys Glu Lys Arg Val Pro Lys Ala Thr Tyr Thr Phe
            260                 265                 270

Gln Tyr Phe Asn Thr Leu Asp Gln Ile Asn Arg Thr Arg Leu Gly Pro
        275                 280                 285

Asn Phe Gln Pro Phe Thr Lys Glu Gln Arg Asp Ile Ile Leu Asp Lys
    290                 295                 300

Met Phe Gln Arg Thr Asp Tyr Tyr Lys Lys Lys Thr Ile Pro Glu Val
305                 310                 315                 320
```

```
Thr Tyr Tyr Asp Ile Arg Lys Trp Leu Ala Leu Asp Glu Thr Ile Gln
                325                 330                 335

Phe Lys Gly Leu Thr Tyr Asp Pro Asn Glu Glu Leu Lys Lys Ile Glu
            340                 345                 350

Met Lys Pro Phe Ile Asn Leu Lys Pro Phe Tyr Glu Ile Lys Lys Val
        355                 360                 365

Val Thr Asn Tyr Ala Lys Lys Thr Asn Glu Val Phe Ser Ala Leu Asp
    370                 375                 380

Tyr Asp Thr Val Ala Tyr Ala Leu Thr Val Tyr Lys Thr Asp Lys Asp
385                 390                 395                 400

Ile Arg Ser Tyr Leu Lys Arg Ser Asn Asn Leu Ser Lys Arg Cys Tyr
                405                 410                 415

Asp Asp Gln Leu Ile Glu Glu Leu Leu Thr Leu Ser Tyr Thr Lys Phe
            420                 425                 430

Gly His Leu Ser Phe Lys Ala Ile Asn His Val Leu Pro Ile Met Gln
        435                 440                 445

Glu Gly Arg Thr Tyr Gln Glu Ala Ile His Gln Leu Gly Tyr Asp Thr
    450                 455                 460

Thr Asn Leu Lys Lys Glu Asn Arg Ser Met Phe Leu Pro Ile Ile Pro
465                 470                 475                 480

Asp Glu Ile Thr Asn Pro Ile Val Lys Arg Ala Leu Thr Gln Ala Arg
                485                 490                 495

Lys Val Val Asn Ala Ile Ile Arg Arg Tyr Gly Ser Pro Asn Ser Val
            500                 505                 510

His Ile Glu Leu Ala Arg Glu Leu Ser Lys Ser His Asp Glu Arg Lys
        515                 520                 525

Lys Ile Met Thr Ala His Asp Glu Asn Tyr Lys Lys Asn Lys Gly Ala
    530                 535                 540

Val Ser Ile Leu Ile Asp Asn Gly Ile Leu Asn Pro Thr Gly Tyr Asp
545                 550                 555                 560

Ile Val Arg Tyr Lys Leu Trp Lys Glu Gln Gly Glu Arg Cys Ala Tyr
                565                 570                 575

Ser Leu Lys Lys Ile Pro Ala Asn Thr Phe Phe Asn Glu Leu Lys Lys
            580                 585                 590

Glu Arg Ser Gly Pro Pro Val Leu Glu Val Asp His Ile Leu Pro Tyr
        595                 600                 605

Ser Gln Ser Phe Ile Asp Ser Tyr His Asn Lys Val Leu Val Tyr Gly
    610                 615                 620

Asp Glu Asn Gln Lys Lys Gly Asn Arg Ile Pro Tyr Thr Phe Phe Ser
625                 630                 635                 640

Glu Glu Asp Lys Glu Trp Glu Ser Phe Glu Ser Tyr Val Arg Ser Asn
                645                 650                 655

Ser Phe Phe Ser Lys Lys Lys Arg Gly Tyr Leu Leu Lys Lys Ala Tyr
            660                 665                 670

Leu Pro Arg Glu Ser Asn Leu Ile Lys Glu Arg His Leu Asn Asp Thr
        675                 680                 685

Arg Tyr Ala Ser Ser Tyr Leu Lys Asn Phe Ile Glu Lys Asn Leu Lys
    690                 695                 700

Phe Lys Glu Ala Val Gly Ile Thr Arg Lys Lys Tyr Val Gln Thr Val
705                 710                 715                 720

Asn Gly Val Ile Thr Ala His Leu Arg Lys Arg Trp Gly Leu Glu Lys
                725                 730                 735

Asp Arg Gln Glu Thr Tyr Leu His His Ala Met Asp Ala Ile Ile Val
```

```
            740                 745                 750

Ala Cys Thr Asp His His Met Val Thr Lys Val Thr Glu Tyr Tyr Gln
        755                 760                 765

Ile Lys Glu Gly Asn Lys Ser Ile Lys Lys Pro Tyr Phe Pro Leu Pro
    770                 775                 780

Trp Met Gly Phe Arg Glu Glu Ile Leu Ser His Leu Glu Ser Gln Pro
785                 790                 795                 800

Ile Ala Arg Lys Ile Ser Glu Glu Leu Lys Ile Gly Tyr Gln Ser Pro
                805                 810                 815

Asp Tyr Ile Leu Val Ser Arg Met Pro Lys Arg Ser Val Thr Gly Ser
            820                 825                 830

Ala His Asp Gln Thr Val Met Lys Lys Gly Asp Ile Asp Lys Lys Gly
        835                 840                 845

Lys Thr Ile Ile Ile Lys Arg Val His Leu Lys Asp Ile Lys Phe Asp
    850                 855                 860

Glu Asn Gly Asp Phe Lys Met Val Gly Lys Glu Gln Asp Leu Ala Thr
865                 870                 875                 880

Tyr Glu Ala Ile Lys Gln Arg Tyr Leu Glu Tyr Arg Lys Glu Ser Lys
                885                 890                 895

Lys Ala Phe Glu Thr Pro Leu Tyr Lys Pro Ser Lys Lys Gly Lys Gly
            900                 905                 910

Asn Leu Ile Lys Lys Ile Lys Val Glu Val Gln Thr Lys Ser Phe Val
        915                 920                 925

Arg Glu Ile Asn Gly Gly Val Ala Gln Asn Gly Asp Leu Val Arg Val
    930                 935                 940

Asp Leu Phe Glu Lys Asp Asn Arg Tyr Tyr Met Val Pro Ile Tyr Val
945                 950                 955                 960

Val Asp Thr Val Arg Ser Glu Leu Pro Asn Lys Ala Val Thr Ser Ser
                965                 970                 975

Lys Gly Tyr Glu Gln Trp Leu Ser Ile Asp Asn Ser Phe Thr Phe Lys
            980                 985                 990

Phe Ser Leu Tyr Pro Tyr Asp Leu  Val Arg Leu Val Lys  Gly Asp Glu
        995                 1000                1005

Asp Arg  Phe Leu Tyr Phe Ser  Thr Leu Asp Ile Asn  Ser Asp Arg
    1010                1015                1020

Leu Asn  Phe Lys Asp Val Asn  Lys Pro Ser Lys Gln  Ala Glu Tyr
    1025                1030                1035

Arg Tyr  Ser Leu Lys Thr Ile  Glu Asn Leu Glu Lys  Tyr Glu Ile
    1040                1045                1050

Gly Val  Leu Gly Asp Leu Arg  Leu Val Arg Gln Glu  Thr Arg Lys
    1055                1060                1065

Ile Phe  Lys
    1070


<210> SEQ ID NO 20
<211> LENGTH: 27
<212> TYPE: RNA
<213> ORGANISM: Bacillus sp.
<220> FEATURE:
<221> NAME/KEY: source
<223> OTHER INFORMATION: /note="crRNA"

<400> SEQUENCE: 20

gucauaguuc cauuaaagcc auugcug                                27
```

<210> SEQ ID NO 21
<211> LENGTH: 93
<212> TYPE: RNA
<213> ORGANISM: Bacillus sp.
<220> FEATURE:
<221> NAME/KEY: source
<223> OTHER INFORMATION: /note="tracrRNA"

<400> SEQUENCE: 21
acagcaaugg cuuugauguu ucuaugauaa gggcuucggc ccguggcguu ggggaucgcc 60
ugcccauuuu aaugggcuuc uccccaucua uuu 93

<210> SEQ ID NO 22
<211> LENGTH: 154
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="sgRNA L1"

<400> SEQUENCE: 22
gagcggacag cagcuuccua uaucucguac gucauaguuc cauuaaagcc auugcugaaa 60
gacagcaaug gcuuugaugu uucuaugaua agggcuucgg cccguggcgu uggggaucgc 120
cugcccauuu uaaugggcuu cuccccaucu auuu 154

<210> SEQ ID NO 23
<211> LENGTH: 154
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="sgRNA L2"

<400> SEQUENCE: 23
ccaugauaua gacguugugg cuguuguagu gucauaguuc cauuaaagcc auugcugaaa 60
gacagcaaug gcuuugaugu uucuaugaua agggcuucgg cccguggcgu uggggaucgc 120
cugcccauuu uaaugggcuu cuccccaucu auuu 154

<210> SEQ ID NO 24
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Target seq and PAM region of plasmid library 1"
<220> FEATURE:
<221> NAME/KEY: modified_base
<222> LOCATION: (31)..(38)
<223> OTHER INFORMATION: a, c, t, g, unknown or other

<400> SEQUENCE: 24
gagcggacag cagcttccta tatctcgtac nnnnnnnn 38

-continued

```
<210> SEQ ID NO 25
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 2"
<220> FEATURE:
<221> NAME/KEY: modified_base
<222> LOCATION: (31)..(38)
<223> OTHER INFORMATION: a, c, t, g, unknown or other

<400> SEQUENCE: 25

ccatgatata gacgttgtgg ctgttgtagt nnnnnnnn                          38


<210> SEQ ID NO 26
<211> LENGTH: 149
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA with N's"
<220> FEATURE:
<221> NAME/KEY: modified_base
<222> LOCATION: (1)..(25)
<223> OTHER INFORMATION: a, c, u, g, unknown or other

<400> SEQUENCE: 26

nnnnnnnnnn nnnnnnnnnn nnnnngucau aguuccauua aagccauugc ugaaagacag     60

caauggcuuu gauguuucua ugauaagggc uucggcccgu ggcguugggg aucgccugcc    120

cauuuuaaug ggcuucuccc caucuauuu                                      149


<210> SEQ ID NO 27
<211> LENGTH: 1072
<212> TYPE: PRT
<213> ORGANISM: Bacillus sp.
<220> FEATURE:
<221> NAME/KEY: source
<223> OTHER INFORMATION: /note="APG08290.1"

<400> SEQUENCE: 27

Met Ser Glu Leu Asp Tyr Arg Ile Gly Leu Asp Ile Gly Thr Asn Ser
1               5                   10                  15

Ile Gly Trp Gly Val Ile Glu Leu Phe Trp Asn Lys Asp Arg Glu Arg
            20                  25                  30

Tyr Glu Lys Val Arg Ile Val Asp Lys Gly Val Arg Met Phe Asp Lys
        35                  40                  45

Ala Glu Ile Pro Asn Lys Gly Ala Ser Leu Ala Glu Pro Arg Arg Ile
    50                  55                  60

Ala Arg Ser Ser Arg Arg Arg Leu Asn Arg Lys Ser Gln Arg Lys Lys
65                  70                  75                  80

Glu Ile Arg Asn Leu Leu Val Gln His Gly Met Ile Thr Gln Glu Glu
                85                  90                  95

Leu Asp Leu Leu Tyr Pro Leu Ser Lys Lys Ser Ile Asp Ile Trp Asp
            100                 105                 110

Ile Arg Leu Asp Gly Leu Asp Arg Leu Leu Asn His Leu Glu Trp Ala
```

```
        115                 120                 125

Arg Leu Leu Ile His Leu Ala Gln Arg Arg Gly Phe Lys Ser Asn Arg
    130                 135                 140

Lys Ser Glu Leu Lys Asp Ala Glu Thr Gly Lys Val Leu Ser Ser Ile
145                 150                 155                 160

Gln Val Asn Glu Lys Arg Leu Phe Leu Tyr Arg Thr Val Gly Glu Met
                165                 170                 175

Trp Ile Lys Asp Ala Glu Phe Ser Lys Tyr Asp Arg Arg Arg Asn Ser
            180                 185                 190

Pro Asn Glu Tyr Val Phe Ser Val Ser Arg Ala Asp Leu Glu Lys Glu
        195                 200                 205

Ile Val Thr Leu Phe Glu Ala Gln Arg Lys Phe Gln Ser Ser Tyr Ala
    210                 215                 220

Ser Lys Asn Leu Gln Glu Thr Tyr Leu Gln Ile Trp Ala His Gln Leu
225                 230                 235                 240

Pro Phe Ala Ser Gly Asn Ala Ile Leu Asn Lys Val Gly Tyr Cys Ser
                245                 250                 255

Leu Leu Lys Gly Lys Glu Arg Arg Ile Pro Lys Ala Thr Tyr Thr Phe
            260                 265                 270

Gln Tyr Phe Ser Ala Leu Asp Gln Val Asn Arg Thr Arg Leu Gly Pro
        275                 280                 285

Asp Phe Gln Pro Phe Thr Gln Glu Gln Lys Glu Ile Ile Leu Asp Lys
    290                 295                 300

Met Phe Gln Arg Thr Asp Tyr Tyr Lys Lys Lys Thr Ile Pro Glu Val
305                 310                 315                 320

Ser Tyr Tyr Asp Ile Arg Lys Trp Leu Glu Leu Asp Glu Thr Ile Gln
                325                 330                 335

Phe Lys Gly Leu Asn Tyr Asp Pro Asn Glu Glu Leu Lys Lys Ile Glu
            340                 345                 350

Lys Lys Pro Phe Ile Asn Leu Lys Ala Phe Tyr Glu Ile Lys Lys Val
        355                 360                 365

Val Ala Asn Tyr Ala Glu Arg Thr Asn Glu Ala Phe Ser Thr Leu Asp
    370                 375                 380

Tyr Asp Ala Ile Ala Tyr Ala Leu Thr Val Tyr Lys Thr Asp Lys Asp
385                 390                 395                 400

Ile Arg Ser Tyr Leu Lys Lys Ser Asn Asn Leu Ser Lys Arg Cys Tyr
                405                 410                 415

Asp Asp Gln Leu Ile Glu Glu Leu Phe Thr Leu Ser Tyr Thr Lys Phe
            420                 425                 430

Gly His Leu Ser Phe Lys Ala Ile Asn His Val Leu Pro Ile Met Gln
        435                 440                 445

Glu Gly Arg Thr Tyr Gln Glu Ala Ile His Gln Leu Gly Tyr Asp Thr
    450                 455                 460

Thr Asn Leu Lys Lys Glu Asn Arg Ser Met Phe Leu Pro Leu Ile Pro
465                 470                 475                 480

Asp Glu Ile Thr Asn Pro Ile Val Lys Arg Ala Ile Thr Gln Ala Arg
                485                 490                 495

Lys Val Val Asn Ala Ile Ile Arg Arg Tyr Gly Ser Pro Asn Ser Val
            500                 505                 510

His Ile Glu Leu Ala Arg Glu Leu Ser Lys Ser His Asp Glu Arg Lys
        515                 520                 525

Lys Ile Met Thr Ala His Asp Glu Asn Tyr Lys Lys Asn Lys Gly Ala
    530                 535                 540
```

-continued

```
Ile Ser Ile Leu Ile Glu Asn Gly Ile Leu Asn Pro Thr Gly Tyr Asp
545                 550                 555                 560

Ile Val Arg Tyr Lys Leu Trp Lys Glu Gln Gly Glu Arg Cys Ala Tyr
                565                 570                 575

Ser Leu Lys Glu Ile Pro Pro Asp Thr Phe Phe Asn Glu Leu Lys Lys
            580                 585                 590

Glu Arg Asn Gly Ser Pro Ile Leu Glu Val Asp His Ile Leu Pro Tyr
        595                 600                 605

Ser Gln Ser Phe Ile Asp Ser Tyr His Asn Lys Val Leu Val Tyr Ser
    610                 615                 620

Asp Glu Asn Arg Asn Lys Gly Asn Arg Ile Pro Tyr Thr Tyr Phe Leu
625                 630                 635                 640

Glu Thr Asn Lys Asp Trp Glu Ala Phe Glu Arg Tyr Val Arg Ser Asn
                645                 650                 655

Lys Leu Phe Ser Lys Lys Lys Arg Glu Tyr Leu Leu Lys Lys Thr Tyr
            660                 665                 670

Leu Pro Arg Glu Ser Glu Leu Ile Lys Glu Arg His Leu Asn Asp Thr
        675                 680                 685

Arg Tyr Ala Ser Thr Phe Leu Lys Asn Phe Ile Glu Gln Asn Leu Gln
    690                 695                 700

Phe Lys Glu Val Glu Val Asn Leu Arg Lys Lys Arg Val Gln Thr Val
705                 710                 715                 720

Asn Gly Val Ile Thr Ala His Leu Arg Lys Arg Trp Gly Leu Glu Lys
                725                 730                 735

Asn Arg Gln Glu Thr Tyr Leu His His Ala Met Asp Ala Ile Ile Val
            740                 745                 750

Ala Cys Thr Asp His His Met Val Thr Arg Ile Thr Glu Tyr Tyr Gln
        755                 760                 765

Ile Lys Glu Ser Asn Lys Ser Val Lys Lys Pro Tyr Phe Pro Met Pro
    770                 775                 780

Trp Glu Gly Phe Arg Asp Glu Leu Leu Ser His Leu Ala Ser Gln Pro
785                 790                 795                 800

Ile Ala Lys Lys Ile Ser Glu Glu Leu Lys Ala Gly Tyr Gln Ser Ser
                805                 810                 815

Asp Tyr Ile Phe Val Ser Arg Met Pro Lys Arg Ser Val Thr Gly Ala
            820                 825                 830

Ala His Asp Gln Thr Ile Arg Arg Lys Gly Gly Ile Asp Lys Lys Gly
        835                 840                 845

Lys Thr Ile Ile Ile Lys Arg Val Arg Leu Lys Asp Ile Lys Phe Asp
    850                 855                 860

Glu Asn Gly Asp Phe Lys Met Val Gly Lys Glu Gln Asp Leu Ala Thr
865                 870                 875                 880

Tyr Glu Ala Ile Lys Gln Arg Tyr Leu Glu His Arg Lys Asn Ser Lys
                885                 890                 895

Lys Ala Phe Glu Thr Pro Leu Tyr Lys Pro Ser Lys Lys Gly Thr Gly
            900                 905                 910

Asn Leu Ile Lys Arg Val Lys Ile Glu Gly Gln Thr Lys Ala Phe Val
        915                 920                 925

Arg Glu Val Asn Gly Gly Val Ala Gln Asn Ser Asp Leu Val Arg Val
    930                 935                 940

Asp Leu Phe Glu Lys Asp Asp Lys Tyr Tyr Met Val Pro Ile Tyr Val
945                 950                 955                 960
```

```
Pro Asp Thr Val Cys Ser Glu Leu Pro Lys Lys Val Val Lys Ser Gly
                965                 970                 975

Lys Gly Tyr Glu Gln Trp Leu Thr Leu Asp Asn Ser Phe Thr Phe Lys
            980                 985                 990

Ser Ser Leu Tyr Pro Tyr Asp Leu  Val Arg Leu Val Lys  Gly Asn Glu
        995                 1000                 1005

Asp Arg  Phe Leu Tyr Phe Gly  Thr Leu Asp Ile Asp  Ser Asp Arg
    1010                 1015                 1020

Leu Asn  Phe Lys Asp Val Asn  Lys Pro Ser Lys Gln  Asn Glu Tyr
    1025                 1030                 1035

Arg Tyr  Ser Leu Lys Thr Ile  Glu Asn Leu Glu Lys  Tyr Glu Val
    1040                 1045                 1050

Gly Val  Leu Gly Asp Leu Arg  Leu Val Lys Gln Glu  Thr Arg Arg
    1055                 1060                 1065

Ile Phe  Asn Arg
    1070


<210> SEQ ID NO 28
<211> LENGTH: 21
<212> TYPE: RNA
<213> ORGANISM: Bacillus sp.
<220> FEATURE:
<221> NAME/KEY: source
<223> OTHER INFORMATION: /note="crRNA"

<400> SEQUENCE: 28

gucauaguuc caugaaagcc a                                               21


<210> SEQ ID NO 29
<211> LENGTH: 85
<212> TYPE: RNA
<213> ORGANISM: Bacillus sp.
<220> FEATURE:
<221> NAME/KEY: source
<223> OTHER INFORMATION: /note="tracrRNA"

<400> SEQUENCE: 29

uggcuuugau guuucuauga uaaggguuuc ggcccguggc gucggggauc gccugcccau     60

uccgaugggc uucuccccau uuauu                                           85


<210> SEQ ID NO 30
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L1"

<400> SEQUENCE: 30

gagcggacag cagcuuccua uaucucguac gucauaguuc caugaaagcc aaaaguggcu     60

uugauguuuc uaugauaagg guuucggccc guggcgucgg ggaucgccug cccauuccga    120

ugggcuucuc cccauuuauu                                                140


<210> SEQ ID NO 31
<211> LENGTH: 140
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L2"

<400> SEQUENCE: 31

ccaugauaua gacguugugg cuguuguagu gucauaguuc caugaaagcc aaaaguggcu      60

uugauguuuc uaugauaagg guuucggccc guggcgucgg ggaucgccug cccauuccga     120

ugggcuucuc cccauuuauu                                                 140


<210> SEQ ID NO 32
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="PAM"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 32

nnrncc                                                                  6


<210> SEQ ID NO 33
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 1"
<220> FEATURE:
<221> NAME/KEY: modified_base
<222> LOCATION: (31)..(38)
<223> OTHER INFORMATION: a, c, t, g, unknown or other

<400> SEQUENCE: 33

gagcggacag cagcttccta tatctcgtac nnnnnnnn                              38


<210> SEQ ID NO 34
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 2"
<220> FEATURE:
<221> NAME/KEY: modified_base
<222> LOCATION: (31)..(38)
<223> OTHER INFORMATION: a, c, t, g, unknown or other
```

<400> SEQUENCE: 34
ccatgatata gacgttgtgg ctgttgtagt nnnnnnnn 38

<210> SEQ ID NO 35
<211> LENGTH: 135
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="sgRNA with N's"
<220> FEATURE:
<221> NAME/KEY: modified_base
<222> LOCATION: (1)..(25)
<223> OTHER INFORMATION: a, c, u, g, unknown or other

<400> SEQUENCE: 35
nnnnnnnnnn nnnnnnnnnn nnnnngucau aguuccauga aagccaaaag uggcuuugau 60
guuucuauga uaaggguuuc ggcccguggc gucggggauc gccugcccau uccgaugggc 120
uucuccccau uuauu 135

<210> SEQ ID NO 36
<211> LENGTH: 1337
<212> TYPE: PRT
<213> ORGANISM: Enterococcus sp.
<220> FEATURE:
<221> NAME/KEY: source
<223> OTHER INFORMATION: /note="APG05459.1"

<400> SEQUENCE: 36

Met Lys Lys Asp Tyr Val Ile Gly Leu Asp Ile Gly Thr Asn Ser Val
1 5 10 15

Gly Trp Ala Val Met Thr Glu Asp Tyr Gln Leu Val Lys Lys Lys Met
20 25 30

Pro Ile Tyr Gly Asn Thr Glu Lys Lys Lys Ile Lys Lys Asn Phe Trp
35 40 45

Gly Val Arg Leu Phe Glu Glu Gly His Thr Ala Glu Asp Arg Arg Leu
50 55 60

Lys Arg Thr Ala Arg Arg Arg Ile Ser Arg Arg Arg Asn Arg Leu Arg
65 70 75 80

Tyr Leu Gln Ala Phe Phe Glu Glu Ala Met Thr Ala Leu Asp Glu Asn
85 90 95

Phe Phe Ala Arg Leu Gln Glu Ser Phe Leu Val Pro Glu Asp Lys Lys
100 105 110

Trp His Arg His Pro Ile Phe Ala Lys Leu Glu Asp Glu Val Ala Tyr
115 120 125

His Glu Thr Tyr Pro Thr Ile Tyr His Leu Arg Lys Lys Leu Ala Asp
130 135 140

Ser Ser Glu Gln Ala Asp Leu Arg Leu Ile Tyr Leu Ala Leu Ala His
145 150 155 160

Ile Val Lys Tyr Arg Gly His Phe Leu Ile Glu Gly Lys Leu Ser Thr
165 170 175

Glu Asn Ile Ser Val Lys Glu Gln Phe Gln Gln Phe Met Ile Ile Tyr
180 185 190

Asn Gln Thr Phe Val Asn Gly Glu Ser Arg Leu Val Ser Ala Pro Leu
195 200 205

-continued

```
Pro Glu Ser Val Leu Ile Glu Glu Glu Leu Thr Glu Lys Ala Ser Arg
    210                 215                 220

Thr Lys Lys Ser Glu Lys Val Leu Gln Gln Phe Pro Gln Glu Lys Ala
225                 230                 235                 240

Asn Gly Leu Phe Gly Gln Phe Leu Lys Leu Met Val Gly Asn Lys Ala
                245                 250                 255

Asp Phe Lys Lys Val Phe Gly Leu Glu Glu Glu Ala Lys Ile Thr Tyr
            260                 265                 270

Ala Ser Glu Ser Tyr Glu Glu Asp Leu Glu Gly Ile Leu Ala Lys Val
        275                 280                 285

Gly Asp Glu Tyr Ser Asp Val Phe Leu Ala Ala Lys Asn Val Tyr Asp
    290                 295                 300

Ala Val Glu Leu Ser Thr Ile Leu Ala Asp Ser Asp Lys Lys Ser His
305                 310                 315                 320

Ala Lys Leu Ser Ser Ser Met Ile Val Arg Phe Thr Glu His Gln Glu
                325                 330                 335

Asp Leu Lys Lys Phe Lys Arg Phe Ile Arg Glu Asn Cys Pro Asp Glu
            340                 345                 350

Tyr Asp Asn Leu Phe Lys Asn Glu Gln Lys Asp Gly Tyr Ala Gly Tyr
        355                 360                 365

Ile Ala His Ala Gly Lys Val Ser Gln Leu Lys Phe Tyr Gln Tyr Val
    370                 375                 380

Lys Lys Ile Ile Gln Asp Ile Ala Gly Ala Glu Tyr Phe Leu Glu Lys
385                 390                 395                 400

Ile Ala Gln Glu Asn Phe Leu Arg Lys Gln Arg Thr Phe Asp Asn Gly
                405                 410                 415

Val Ile Pro His Gln Ile His Leu Ala Glu Leu Gln Ala Ile Ile His
            420                 425                 430

Arg Gln Ala Ala Tyr Tyr Pro Phe Leu Lys Glu Asn Gln Glu Lys Ile
        435                 440                 445

Glu Gln Leu Val Thr Phe Arg Ile Pro Tyr Tyr Val Gly Pro Leu Ser
    450                 455                 460

Lys Gly Asp Ala Ser Thr Phe Ala Trp Leu Lys Arg Gln Ser Glu Glu
465                 470                 475                 480

Pro Ile Arg Pro Trp Asn Leu Gln Glu Thr Val Asp Leu Asp Gln Ser
                485                 490                 495

Ala Thr Ala Phe Ile Glu Arg Met Thr Asn Phe Asp Thr Tyr Leu Pro
            500                 505                 510

Ser Glu Lys Val Leu Pro Lys His Ser Leu Leu Tyr Glu Lys Phe Met
        515                 520                 525

Val Phe Asn Glu Leu Thr Lys Ile Ser Tyr Thr Asp Asp Arg Gly Ile
    530                 535                 540

Lys Ala Asn Phe Ser Gly Lys Glu Lys Glu Lys Ile Phe Asp Tyr Leu
545                 550                 555                 560

Phe Lys Thr Arg Arg Lys Val Lys Lys Lys Asp Ile Ile Gln Phe Tyr
                565                 570                 575

Arg Asn Glu Tyr Asn Thr Glu Ile Val Thr Leu Ser Gly Leu Glu Glu
            580                 585                 590

Asp Gln Phe Asn Ala Ser Phe Ser Thr Tyr Gln Asp Leu Leu Lys Cys
        595                 600                 605

Gly Leu Thr Arg Ala Glu Leu Asp His Pro Asp Asn Ala Glu Lys Leu
    610                 615                 620
```

-continued

```
Glu Asp Ile Ile Lys Ile Leu Thr Ile Phe Glu Asp Arg Gln Arg Ile
625                 630                 635                 640

Arg Thr Gln Leu Ser Thr Phe Lys Gly Gln Phe Ser Ala Glu Val Leu
                645                 650                 655

Lys Lys Leu Glu Arg Lys His Tyr Thr Gly Trp Gly Arg Leu Ser Lys
            660                 665                 670

Lys Leu Ile Asn Gly Ile Tyr Asp Lys Glu Ser Gly Lys Thr Ile Leu
        675                 680                 685

Asp Tyr Leu Ile Lys Asp Asp Gly Val Ser Lys His Tyr Asn Arg Asn
    690                 695                 700

Phe Met Gln Leu Ile Asn Asp Ser Gln Leu Ser Phe Lys Asn Ala Ile
705                 710                 715                 720

Gln Lys Ala Gln Ser Ser Glu His Glu Glu Thr Leu Ser Glu Thr Val
                725                 730                 735

Asn Glu Leu Ala Gly Ser Pro Ala Ile Lys Lys Gly Ile Tyr Gln Ser
            740                 745                 750

Leu Lys Ile Val Asp Glu Leu Val Ala Ile Met Gly Tyr Ala Pro Lys
        755                 760                 765

Arg Ile Val Val Glu Met Ala Arg Glu Asn Gln Thr Thr Ser Thr Gly
    770                 775                 780

Lys Arg Arg Ser Ile Gln Arg Leu Lys Ile Val Glu Lys Ala Met Ala
785                 790                 795                 800

Glu Ile Gly Ser Asn Leu Leu Lys Glu Gln Pro Thr Thr Asn Glu Gln
                805                 810                 815

Leu Arg Asp Thr Arg Leu Phe Leu Tyr Tyr Met Gln Asn Gly Lys Asp
            820                 825                 830

Met Tyr Thr Gly Asp Glu Leu Ser Leu His Arg Leu Ser His Tyr Asp
        835                 840                 845

Ile Asp His Ile Ile Pro Gln Ser Phe Met Lys Asp Asp Ser Leu Asp
    850                 855                 860

Asn Leu Val Leu Val Gly Ser Thr Glu Asn Arg Gly Lys Ser Asp Asp
865                 870                 875                 880

Val Pro Ser Lys Glu Val Val Lys Asp Met Lys Ala Tyr Trp Glu Lys
                885                 890                 895

Leu Tyr Ala Ala Gly Leu Ile Ser Gln Arg Lys Phe Gln Arg Leu Thr
            900                 905                 910

Lys Gly Glu Gln Gly Gly Leu Thr Leu Glu Asp Lys Ala His Phe Ile
        915                 920                 925

Gln Arg Gln Leu Val Glu Thr Arg Gln Ile Thr Lys Asn Val Ala Gly
    930                 935                 940

Ile Leu Asp Gln Arg Tyr Asn Ala Asn Ser Lys Glu Lys Lys Val Gln
945                 950                 955                 960

Ile Ile Thr Leu Lys Ala Ser Leu Thr Ser Gln Phe Arg Ser Ile Phe
                965                 970                 975

Gly Leu Tyr Lys Val Arg Glu Val Asn Asp Tyr His His Gly Gln Asp
            980                 985                 990

Ala Tyr Leu Asn Cys Val Val Ala  Thr Thr Leu Leu Lys  Val Tyr Pro
        995                 1000                1005

Asn Leu  Ala Pro Glu Phe Val  Tyr Gly Glu Tyr Pro  Lys Phe Gln
    1010                1015                1020

Ala Phe  Lys Glu Asn Lys Ala  Thr Ala Lys Thr Ile  Ile Tyr Thr
    1025                1030                1035

Asn Leu  Met Arg Phe Phe Thr  Glu Asp Glu Pro Arg  Phe Met Lys
```

```
    1040                1045                1050

Asp Gly  Glu Ile Leu Trp Ser  Asn Ser Tyr Leu Lys  Asn Ile Lys
    1055                1060                1065

Lys Glu  Leu Asn Tyr His Gln  Met Asn Ile Val Lys  Lys Val Glu
    1070                1075                1080

Val Gln  Lys Gly Gly Phe Ser  Lys Glu Ser Ile Lys  Pro Lys Gly
    1085                1090                1095

Pro Ser  Asn Lys Leu Ile Pro  Val Lys Asn Gly Leu  Asp Pro Gln
    1100                1105                1110

Lys Tyr  Gly Gly Phe Asp Ser  Pro Val Val Ala Tyr  Thr Val Leu
    1115                1120                1125

Phe Thr  His Glu Lys Gly Lys  Lys Pro Leu Ile Lys  Gln Glu Ile
    1130                1135                1140

Leu Gly  Ile Thr Ile Met Glu  Lys Thr Arg Phe Glu  Gln Asn Pro
    1145                1150                1155

Ile Leu  Phe Leu Glu Glu Lys  Gly Phe Leu Arg Pro  Arg Val Leu
    1160                1165                1170

Met Lys  Leu Pro Lys Tyr Thr  Leu Tyr Glu Phe Pro  Glu Gly Arg
    1175                1180                1185

Arg Arg  Leu Leu Ala Ser Ala  Lys Glu Ala Gln Lys  Gly Asn Gln
    1190                1195                1200

Met Val  Leu Pro Glu His Leu  Leu Thr Leu Leu Tyr  His Ala Lys
    1205                1210                1215

Gln Cys  Leu Leu Pro Asn Gln  Ser Glu Ser Leu Ala  Tyr Val Glu
    1220                1225                1230

Gln His  Gln Pro Glu Phe Gln  Glu Ile Leu Glu Arg  Val Val Asp
    1235                1240                1245

Phe Ala  Glu Val His Thr Leu  Ala Lys Ser Lys Val  Gln Gln Ile
    1250                1255                1260

Val Lys  Leu Phe Glu Ala Asn  Gln Thr Ala Asp Val  Lys Glu Ile
    1265                1270                1275

Ala Ala  Ser Phe Ile Gln Leu  Met Gln Phe Asn Ala  Met Gly Ala
    1280                1285                1290

Pro Ser  Thr Phe Lys Phe Phe  Gln Lys Asp Ile Glu  Arg Ala Arg
    1295                1300                1305

Tyr Thr  Ser Ile Lys Glu Ile  Phe Asp Ala Thr Ile  Ile Tyr Gln
    1310                1315                1320

Ser Thr  Thr Gly Leu Tyr Glu  Thr Arg Arg Lys Val  Val Asp
    1325                1330                1335
```

<210> SEQ ID NO 37
<211> LENGTH: 16
<212> TYPE: RNA
<213> ORGANISM: Enterococcus sp.
<220> FEATURE:
<221> NAME/KEY: source
<223> OTHER INFORMATION: /note="crRNA"

<400> SEQUENCE: 37
guuuuagagu cauguu 16

<210> SEQ ID NO 38
<211> LENGTH: 74
<212> TYPE: RNA
<213> ORGANISM: Enterococcus sp.
<220> FEATURE:
<221> NAME/KEY: source
<223> OTHER INFORMATION: /note="tracrRNA"

<400> SEQUENCE: 38
aacauagcaa guuaaaauaa gguuuuaacc guaaucaacu guaaaguggc gcuguuucgg 60
cgcuuuuuuu guuu 74

<210> SEQ ID NO 39
<211> LENGTH: 124
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="sgRNA L1"

<400> SEQUENCE: 39
gagcggacag cagcuuccua uaucucguac guuuuagagu cauguuaaag aacauagcaa 60
guuaaaauaa gguuuuaacc guaaucaacu guaaaguggc gcuguuucgg cgcuuuuuuu 120
guuu 124

<210> SEQ ID NO 40
<211> LENGTH: 124
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="sgRNA L2"

<400> SEQUENCE: 40
ccaugauaua gacguugugg cuguuguagu guuuuagagu cauguuaaag aacauagcaa 60
guuaaaauaa gguuuuaacc guaaucaacu guaaaguggc gcuguuucgg cgcuuuuuuu 120
guuu 124

<210> SEQ ID NO 41
<211> LENGTH: 3
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="PAM"
<220> FEATURE:
<221> NAME/KEY: modified_base
<222> LOCATION: (1)..(1)
<223> OTHER INFORMATION: a, c, t, g, unknown or other

<400> SEQUENCE: 41 ngg 3

<210> SEQ ID NO 42
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:

```
      Synthetic oligonucleotide"
<220> FEATURE:
<221> NAME/KEY: source
<223> OTHER INFORMATION: /note="Target seq and PAM region of plasmid
      library 1"
<220> FEATURE:
<221> NAME/KEY: modified_base
<222> LOCATION: (31)..(38)
<223> OTHER INFORMATION: a, c, t, g, unknown or other

<400> SEQUENCE: 42

gagcggacag cagcttccta tatctcgtac nnnnnnnn                             38


<210> SEQ ID NO 43
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Target seq and PAM region of plasmid
      library 2"
<220> FEATURE:
<221> NAME/KEY: modified_base
<222> LOCATION: (31)..(38)
<223> OTHER INFORMATION: a, c, t, g, unknown or other

<400> SEQUENCE: 43

ccatgatata gacgttgtgg ctgttgtagt nnnnnnnn                             38


<210> SEQ ID NO 44
<211> LENGTH: 119
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA with N's"
<220> FEATURE:
<221> NAME/KEY: modified_base
<222> LOCATION: (1)..(25)
<223> OTHER INFORMATION: a, c, u, g, unknown or other

<400> SEQUENCE: 44

nnnnnnnnnn nnnnnnnnnn nnnnnguuuu agagucaugu uaaagaacau agcaaguuaa     60

aauaagguuu uaaccguaau caacuguaaa guggcgcugu uucggcgcuu uuuuuguuu     119


<210> SEQ ID NO 45
<211> LENGTH: 1436
<212> TYPE: PRT
<213> ORGANISM: Enterococcus sp.
<220> FEATURE:
<221> NAME/KEY: source
<223> OTHER INFORMATION: /note="APG04583.1"

<400> SEQUENCE: 45

Met Ala Lys Asn Ile Leu Gly Leu Asp Leu Gly Thr Asn Ser Ile Gly
1               5                   10                  15

Trp Ala Leu Val Gln Gln Asp Phe Glu Asn Lys Glu Gly Asn Ile Leu
            20                  25                  30

Gly Met Gly Ser Arg Ile Ile Pro Met Ser Gln Asp Ile Leu Gly Glu
        35                  40                  45
```

-continued

```
Phe Gly Lys Gly Asn Ser Ile Ser Gln Thr Ala Glu Arg Thr Gly Tyr
    50                  55                  60

Arg Gly Val Arg Arg Leu Arg Glu Arg His Leu Leu Arg Arg Glu Arg
65                  70                  75                  80

Leu His Arg Val Leu His Leu Leu Gly Phe Leu Pro Lys His Tyr Asp
                85                  90                  95

Glu Lys Ile Asp Phe Thr Gln Arg Phe Gly Lys Phe Ile Asn Gln Ala
            100                 105                 110

Glu Pro Lys Leu Ala Phe Asp Ser Glu Phe Leu Phe Lys Asp Ser Phe
        115                 120                 125

His Glu Met Leu Ala Asp Phe Lys Gln Asn Gln Pro Glu Phe Leu Lys
    130                 135                 140

Asp Lys Asn Gly Glu Asp Cys Leu Val Pro Tyr Asp Trp Thr Ile Tyr
145                 150                 155                 160

Tyr Leu Arg Lys Lys Ala Leu Thr Gln Lys Ile Glu Lys Tyr Glu Leu
                165                 170                 175

Ala Trp Leu Ile Leu Asn Phe Asn Gln Lys Arg Gly Tyr Tyr Gln Leu
            180                 185                 190

Arg Gly Glu Glu Glu Lys Glu Asn Pro Asn Lys Leu Val Gly Phe His
        195                 200                 205

Ser Leu Lys Ile Val Asp Val Ile Pro Asp Ala Glu Thr Asn Lys Lys
    210                 215                 220

Gly Glu Thr Trp Tyr Ser Leu His Leu Glu Asn Gly Trp Val Tyr Arg
225                 230                 235                 240

Arg Ser Ser Lys Ile Ser Leu Ala Asp Trp Lys Asp Lys Val Arg Asp
                245                 250                 255

Phe Ile Val Thr Thr Asp Leu Asn Asp Asp Gly Ser Glu Lys Leu Asp
            260                 265                 270

Lys Asp Gly Ile Val Lys Arg Ser Phe Arg Ala Pro Ser Ala Asp Asp
        275                 280                 285

Trp Thr Leu Leu Lys Lys Lys Thr Glu Lys Asp Ile Asp Asn Ser Asn
    290                 295                 300

Lys Thr Val Gly Thr Tyr Ile Tyr Asp Asn Leu Leu Leu Asn Pro Lys
305                 310                 315                 320

Gln Lys Ile Lys Gly Lys Met Val Arg Thr Ile Glu Arg Lys Phe Tyr
                325                 330                 335

Lys Gln Glu Leu Glu Gln Ile Leu Lys Thr Gln Lys Glu Phe His Ser
            340                 345                 350

Glu Leu Gln Ser Glu Asn Leu Leu Gln Asp Cys Val Arg Glu Leu Tyr
        355                 360                 365

Arg Asn Asn Glu Gln His Gln Gln Met Leu Glu Ala Lys Asp Phe Val
    370                 375                 380

His Leu Phe Leu Asn Asp Ile Ile Phe Tyr Gln Arg Pro Leu Arg Ser
385                 390                 395                 400

Gln Lys Ser Ser Ile Ser Asn Cys Thr Leu Glu Phe Arg Lys Ser Lys
                405                 410                 415

Asn Glu Asn Gly Glu Glu Val Ile His Arg Leu Lys Val Ile Ala Lys
            420                 425                 430

Ser Asn Pro Tyr Tyr Gln Glu Phe Arg Leu Leu Gln Trp Val Gln Asn
        435                 440                 445

Leu Ala Ile Tyr Thr Lys Asp Asp Asp Lys Asn Val Thr Asn Glu Phe
    450                 455                 460

Leu Lys Ser Thr Gln Asp Trp Glu Asp Leu Leu Arg Trp Leu His Ser
```

```
465                 470                 475                 480

Lys Lys Glu Ile Lys Gln Asp Ala Leu Ile Lys Phe Leu Ile Glu Lys
                485                 490                 495

Lys Gly Leu Lys Gly Lys Ala Leu Thr Ile Glu Val Ala Lys Tyr Arg
            500                 505                 510

Trp Asn Tyr Val Gln Asp Lys Asp Tyr Pro Gly Asn Glu Thr Arg Tyr
        515                 520                 525

Leu Ile Gln Ser Arg Leu Asp Lys Val Glu Tyr Ala Pro Lys Asp Phe
    530                 535                 540

Leu Thr Tyr Glu Asn Glu Met Ala Leu Trp His Ile Ile Tyr Ser Ile
545                 550                 555                 560

Asn Asp Lys Ile Glu Tyr Glu Lys Ala Leu Lys Ser Phe Ala Asn Lys
                565                 570                 575

Lys Gly Leu Asp Glu Val Thr Phe Val Glu Ala Phe Lys Lys Phe Pro
            580                 585                 590

Pro Phe Lys Ser Asp Tyr Gly Ser Phe Ser Glu Lys Ala Ile Lys Lys
        595                 600                 605

Leu Leu Pro Leu Met Arg Phe Gly Thr Gln Trp Asn Trp Asp Asn Ile
    610                 615                 620

Asp Gln Asn Ser Lys Glu Arg Ile Gly Lys Ile Leu Thr Gly Glu Tyr
625                 630                 635                 640

Asp Glu Asn Ile Lys Gly Arg Val Arg Glu Lys Ala Arg His Leu Asn
                645                 650                 655

Ser Glu Thr Asp Phe Gln Ala Leu Pro Leu Trp Leu Ala Gln Tyr Val
            660                 665                 670

Val Tyr Gly Arg His Ser Glu Ala Asp Ile Ala Gly Lys Trp Asn Ser
        675                 680                 685

Val Asp Asp Leu Lys Gln Phe Leu Asp Asp Phe Lys Gln His Ser Leu
    690                 695                 700

Arg Asn Pro Ile Val Glu Gln Val Ile Thr Glu Thr Leu Arg Ala Val
705                 710                 715                 720

Lys Asp Ile Trp Asn Phe Tyr Gly Lys Gly Ala Lys Asp Phe Phe Ser
                725                 730                 735

Glu Ile His Ile Glu Leu Gly Arg Glu Met Lys Asn Thr Ala Asp Glu
            740                 745                 750

Arg Lys Arg Ile Thr Thr Met Val Thr Asp Asn Glu Asn Thr Asn Leu
        755                 760                 765

Arg Ile Lys Ala Leu Leu Ala Glu Met Ala Leu Asp Gln Asn Val Asp
    770                 775                 780

Asn Val Arg Pro Tyr Ser Pro Met Gln Gln Glu Ile Leu Lys Ile Tyr
785                 790                 795                 800

Glu Glu Gly Val Leu Asn Ala Glu Glu Asn Ile Asp Asp Asp Ile Leu
                805                 810                 815

Lys Ile Ser Lys Thr Ala Gln Pro Ser Ala Thr Asp Leu Lys Arg Tyr
            820                 825                 830

Lys Leu Trp Leu Glu Gln Lys Tyr Arg Ser Pro Tyr Thr Gly Gln Met
        835                 840                 845

Ile Pro Leu Asn Lys Leu Phe Thr Pro Glu Tyr Glu Ile Glu His Ile
    850                 855                 860

Ile Pro Gln Ser Arg Tyr Phe Asp Asp Ser Met Ser Asn Lys Val Ile
865                 870                 875                 880

Cys Glu Ala Ala Val Asn Lys Leu Lys Asp Asn Gln Ile Gly Leu Val
                885                 890                 895
```

-continued

```
Phe Ile Lys Asn His His Gly Glu Val Val Asp Phe Gly Met Gly Lys
            900                 905                 910

Gln Val Lys Ile Leu Glu Val Ser Asp Tyr Glu Asp Phe Val Lys Gln
        915                 920                 925

Asn Tyr Asn Lys Asn Arg Gly Lys Arg Asn Lys Leu Leu Leu Glu Asp
    930                 935                 940

Ile Pro Glu Lys Met Ile Glu Arg Gln Leu Asn Asp Thr Arg Tyr Ile
945                 950                 955                 960

Ser Lys Tyr Ile Thr Gln Val Leu Ser Asn Ile Val Arg Asp Asp Lys
                965                 970                 975

Glu Gly Ser Lys Asp Asp Gly Val Asn Ser Lys Asn Ile Val Pro Gly
            980                 985                 990

Asn Gly Lys Ile Thr Thr Arg Leu  Lys Gln Asp Trp Gly  Leu Asn Asp
        995                 1000                 1005

Val Trp  Asn Asp Leu Val Leu  Pro Arg Phe Glu Arg  Met Asn Thr
    1010                 1015                 1020

Leu Thr  Asn Ser Asn Asp Phe  Thr Ser Lys Asn Thr  His Gly Lys
    1025                 1030                 1035

Thr Ile  Pro Thr Val Pro Ile  Glu Leu Ser Lys Gly  Phe Ser Lys
    1040                 1045                 1050

Lys Arg  Ile Asp His Arg His  His Ala Met Asp Ala  Leu Val Ile
    1055                 1060                 1065

Ala Cys  Ala Thr Arg Asp His  Val Asn Leu Leu Asn  Asn Glu Ser
    1070                 1075                 1080

Ser Lys  Ser Asp Thr Lys Arg  Tyr Asp Leu Asn Arg  Lys Leu Arg
    1085                 1090                 1095

Lys Tyr  Glu Lys Val Ala Tyr  Asn Asp Pro Lys Thr  Gly Glu Arg
    1100                 1105                 1110

Ile Glu  Lys Glu Val Pro Lys  Asp Phe Ile Lys Pro  Trp Glu Thr
    1115                 1120                 1125

Phe Thr  Glu Asp Thr Arg Thr  Leu Leu Glu Asn Ile  Val Ile Ser
    1130                 1135                 1140

Phe Lys  Gln Asn Leu Arg Val  Ile Asn Lys Ala Thr  Asn Tyr Tyr
    1145                 1150                 1155

Glu Lys  Ile Glu Asn Gly Lys  Lys Val Lys Val Glu  Gln Lys Gly
    1160                 1165                 1170

Ile Asn  Trp Ala Val Arg Lys  Ala Leu His Lys Glu  Thr Val Ser
    1175                 1180                 1185

Gly Gln  Val His Leu Asp Arg  Ile Lys Val Ala Lys  Gly Lys Ile
    1190                 1195                 1200

Leu Thr  Ala Thr Arg Lys Thr  Leu Asp Ala Ser Phe  Asn Glu Lys
    1205                 1210                 1215

Thr Ile  Glu Ser Ile Thr Asp  Thr Gly Ile Gln Lys  Ile Leu Leu
    1220                 1225                 1230

Asn Tyr  Leu Lys Ser Lys Asp  Asn Asn Pro Glu Val  Ala Phe Ser
    1235                 1240                 1245

Pro Glu  Gly Ile Glu Glu Leu  Asn Lys Asn Ile Arg  Leu Tyr Asn
    1250                 1255                 1260

Asp Gly  Lys Ala His Gln Pro  Ile Leu Lys Val Arg  Val Phe Glu
    1265                 1270                 1275

Gln Gly  Ser Lys Phe Thr Leu  Gly Glu Thr Gly Asn  Lys Thr Thr
    1280                 1285                 1290
```

-continued

Lys Phe Val Glu Ala Ala Lys Gly Thr Asn Leu Phe Phe Gly Ile
1295 1300 1305

Tyr Glu Asp Lys Ser Gly Lys Arg Ser Tyr Glu Thr Ile Pro Leu
1310 1315 1320

Asn Ile Val Ile Glu Arg Gln Lys Gln Gly Leu Gln Ala Val Pro
1325 1330 1335

Glu Thr Asn Glu Lys Gly Lys Gln Leu Leu Phe Thr Leu Ser Pro
1340 1345 1350

Asn Asp Leu Val Tyr Val Pro Glu Glu Gly Val Phe Asp Glu Asn
1355 1360 1365

Asn Ile Lys Val Asp Arg Ile Tyr Lys Val Val Ser Phe Ser Thr
1370 1375 1380

Tyr Gln Cys Phe Phe Val Arg Asn Asp Val Ser Thr Ser Val Val
1385 1390 1395

Asn Lys Val Glu Tyr Ser Ala Leu Asn Lys Met Glu Lys Ser Ile
1400 1405 1410

Asp Asn Ile Met Ile Lys Glu Asn Cys Val Lys Leu Asn Val Asp
1415 1420 1425

Arg Leu Gly Lys Ile Ser Lys Ala
1430 1435

<210> SEQ ID NO 46
<211> LENGTH: 16
<212> TYPE: RNA
<213> ORGANISM: Enterococcus sp.
<220> FEATURE:
<221> NAME/KEY: source
<223> OTHER INFORMATION: /note="crRNA"

<400> SEQUENCE: 46
guugugaguu ccuuuc 16

<210> SEQ ID NO 47
<211> LENGTH: 78
<212> TYPE: RNA
<213> ORGANISM: Enterococcus sp.
<220> FEATURE:
<221> NAME/KEY: source
<223> OTHER INFORMATION: /note="tracrRNA"

<400> SEQUENCE: 47
gaaaggaacu cacaauaagg auuauuccgu ugugaaaaca uuuagcgccu cgacuaucuu 60
cggggcuuuu uuauuuuu 78

<210> SEQ ID NO 48
<211> LENGTH: 128
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="sgRNA L1"

<400> SEQUENCE: 48
gagcggacag cagcuuccua uaucucguac guugugaguu ccuuucacuu gaaaggaacu 60
cacaauaagg auuauuccgu ugugaaaaca uuuagcgccu cgacuaucuu cggggcuuuu 120
uuauuuuu 128

<210> SEQ ID NO 49
<211> LENGTH: 128
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="sgRNA L2"

<400> SEQUENCE: 49
ccaugauaua gacguugugg cuguuguagu guugugaguu ccuuucacuu gaaaggaacu 60
cacaauaagg auuauuccgu ugugaaaaca uuuagcgccu cgacuaucuu cggggcuuuu 120
uuauuuuu 128

<210> SEQ ID NO 50
<211> LENGTH: 7
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="PAM"
<220> FEATURE:
<221> NAME/KEY: modified_base
<222> LOCATION: (1)..(2)
<223> OTHER INFORMATION: a, c, t, g, unknown or other

<400> SEQUENCE: 50 nnraaty 7

<210> SEQ ID NO 51
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Target seq and PAM region of plasmid library 1"
<220> FEATURE:
<221> NAME/KEY: modified_base
<222> LOCATION: (31)..(38)
<223> OTHER INFORMATION: a, c, t, g, unknown or other

<400> SEQUENCE: 51
gagcggacag cagcttccta tatctcgtac nnnnnnnn 38

<210> SEQ ID NO 52
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Target seq and PAM region of plasmid library 2"
<220> FEATURE:
<221> NAME/KEY: modified_base
<222> LOCATION: (31)..(38)
<223> OTHER INFORMATION: a, c, t, g, unknown or other

<400> SEQUENCE: 52
ccatgatata gacgttgtgg ctgttgtagt nnnnnnnn 38

<210> SEQ ID NO 53
<211> LENGTH: 123
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="sgRNA with N's"
<220> FEATURE:
<221> NAME/KEY: modified_base
<222> LOCATION: (1)..(25)
<223> OTHER INFORMATION: a, c, u, g, unknown or other

<400> SEQUENCE: 53
nnnnnnnnnn nnnnnnnnnn nnnnnguugu gaguuccuuu caaaggaaag gaacucacaa 60
uaaggauuau uccguuguga aaacauuuag cgccucgacu aucuucgggg cuuuuuuauu 120
uuu 123

<210> SEQ ID NO 54
<211> LENGTH: 1456
<212> TYPE: PRT
<213> ORGANISM: Empedobacter sp.
<220> FEATURE:
<221> NAME/KEY: source
<223> OTHER INFORMATION: /note="APG01688.1"

<400> SEQUENCE: 54

Met Met Ile Lys Asn Ile Leu Gly Leu Asp Leu Gly Thr Asn Ser Ile
1 5 10 15

Gly Trp Ala Leu Ile Lys Gln Asp Phe Glu Asn Lys His Gly Glu Ile
20 25 30

Leu Gly Met Gly Ser Arg Ile Ile Pro Met Ser Gln Asp Ile Leu Gly
35 40 45

Asp Phe Gly Lys Gly Asn Ser Ile Ser Gln Thr Ala Asp Arg Thr Lys
50 55 60

Tyr Arg Ser Val Arg Arg Leu Arg Glu Arg Phe Leu Leu Arg Arg Glu
65 70 75 80

Arg Leu His Arg Val Leu His Leu Leu Asn Phe Leu Pro Gln His Tyr
85 90 95

Ala Ser Gln Ile Asp Phe Glu Lys Lys Phe Gly Lys Phe Lys Ser Glu
100 105 110

Thr Glu Pro Lys Leu Ala Trp Glu Asn Trp Gly Gly Lys Phe Ser Phe
115 120 125

Leu Phe Gln Asn Ser Phe Asn Glu Met Leu Glu Asp Phe Lys Ala Ala
130 135 140

Gly Gln Gly Leu Lys Ile Pro Tyr Asp Trp Thr Ile Tyr Tyr Leu Arg
145 150 155 160

Lys Lys Ala Leu Ser Gln Lys Ile Glu Lys Glu Glu Leu Ala Trp Ile
165 170 175

Leu Leu Asn Phe Asn Gln Lys Arg Gly Tyr Tyr Gln Leu Arg Gly Glu
180 185 190

```
Glu Glu Glu Glu Asn Pro Asn Lys Leu Val Glu Phe Tyr Ser Leu Lys
        195                 200                 205

Ile Val Asp Val Val Ala Asp Glu Pro Gln Lys Gly Lys Ser Asp Ile
    210                 215                 220

Trp Tyr Ser Leu Ile Leu Glu Asn Gly Trp Val Tyr Arg Arg Ala Ser
225                 230                 235                 240

Lys Ile Pro Leu Phe Asp Trp Lys Asp Lys Thr Arg Asp Phe Ile Val
                245                 250                 255

Thr Thr Asp Leu Asn Asp Asp Arg Ser Val Lys Thr Asp Lys Glu Gly
            260                 265                 270

Asn Glu Lys Arg Ser Phe Arg Ala Pro Ser Glu Asn Asp Trp Thr Leu
        275                 280                 285

Val Lys Lys Lys Thr Glu Gln Glu Ile Asp Gln Ser His Lys Thr Val
    290                 295                 300

Gly Thr Tyr Ile Tyr Glu Thr Leu Leu Leu Asn Pro Lys Gln Lys Ile
305                 310                 315                 320

Lys Gly Lys Leu Val Arg Thr Ile Glu Arg Lys Phe Tyr Lys Asp Glu
                325                 330                 335

Leu Lys Gln Ile Leu Glu Lys Gln Lys Glu Phe His Gln Glu Leu Lys
            340                 345                 350

Asn Asp Asp Leu Tyr Asn Asp Cys Ile Arg Glu Leu Tyr Arg Asn Asn
        355                 360                 365

Glu Ala His Gln Leu Thr Leu Ser Lys Lys Asp Phe Val His Leu Leu
    370                 375                 380

Met Asp Asp Leu Ile Phe Tyr Gln Arg Pro Leu Arg Ser Gln Lys Ser
385                 390                 395                 400

Ser Ile Ser Asn Cys Thr Leu Glu Phe Arg Lys Tyr Lys Asp Glu Asn
                405                 410                 415

Gly Ile Glu His Thr Gln Tyr Leu Lys Ala Ile Pro Lys Ser Asn Pro
            420                 425                 430

Tyr Tyr Gln Glu Phe Arg Leu Trp Gln Trp Met Tyr Asn Leu Asn Ile
        435                 440                 445

Tyr Arg Lys Asp Asp Glu Ala Asn Val Thr Lys Glu Phe Leu Asn Thr
    450                 455                 460

Asn Lys Asp Phe Glu Ser Leu Phe Glu Phe Leu Asn Asn Arg Lys Glu
465                 470                 475                 480

Ile Glu Gln Lys Pro Leu Ile Lys Phe Leu Leu Glu Gln Lys Asp Ile
                485                 490                 495

Asn Lys Lys Leu Leu Asn Ala Glu Ala Glu Lys Tyr Arg Trp Asn Tyr
            500                 505                 510

Val Glu Asp Lys Lys Tyr Pro Cys Asn Glu Thr Lys Thr Met Ile Ser
        515                 520                 525

Ser Arg Leu Asp Lys Val Glu Asn Ile Ser Asp Asp Phe Leu Thr Arg
    530                 535                 540

Asp Ile Glu Gln Lys Ile Trp His Ile Ile Tyr Ser Val Asn Asp Lys
545                 550                 555                 560

Ile Glu Tyr Glu Lys Ala Leu Lys Ser Phe Ala Thr Arg Asn Asp Leu
                565                 570                 575

Asp Glu Asn Ser Phe Ile Glu Ala Phe Lys Lys Phe Ser Pro Phe Lys
            580                 585                 590

Ser Glu Tyr Gly Ser Phe Ser Glu Lys Ala Ile Lys Lys Leu Leu Pro
        595                 600                 605

Leu Met Arg Leu Gly Lys Tyr Trp Tyr Glu Asp Glu Ile Val Lys His
```

-continued

```
    610                 615                 620

Ser Asp Ile Tyr Phe Lys Asn Ile Glu Asn Leu Leu Gly Asp Phe Ser
625                 630                 635                 640

Asn Arg Asp Lys Lys Ile Ser Glu Glu Asp Lys Glu Lys Trp Asn Lys
                645                 650                 655

Ser Ile Asn Leu Lys Leu Gln Glu Glu Leu Lys Asp Phe Gln Thr Ala
            660                 665                 670

Glu Ile Asp Leu Phe Gln Gly Leu Arg Leu His Ile Ala Gln Tyr Leu
        675                 680                 685

Val Tyr Gly Arg His Ser Glu Ala Ser Met Ile Gly Lys Trp Asn Ser
    690                 695                 700

Ala Glu Asp Leu Glu Glu Phe Leu Lys Asp Phe Lys Gln His Ser Leu
705                 710                 715                 720

Arg Asn Pro Ile Val Glu Gln Val Ile Thr Glu Thr Leu Arg Val Val
                725                 730                 735

Lys Asp Ile Trp Leu Lys Tyr Gly Asn Gly Ala Lys Asp Phe Phe Asn
            740                 745                 750

Glu Ile His Ile Glu Leu Gly Arg Glu Met Lys Leu Pro Ala Asp Asp
        755                 760                 765

Arg Lys Lys Leu Thr Asn Gln Ile Ser Glu Asn Glu Asn Thr Asn Phe
    770                 775                 780

Arg Ile Lys Ala Leu Leu Ala Glu Met Met Asn Asp Ser Ser Val Glu
785                 790                 795                 800

Asn Val Arg Pro Phe Ser Pro Met Gln Gln Glu Ile Leu Lys Ile Tyr
                805                 810                 815

Glu Asp Asp Val Leu Lys Ser Asp Ile Glu Ile Glu Asp Asp Ile Leu
            820                 825                 830

Lys Ile Ser Lys Thr Ala Gln Pro Ser Pro Ser Asp Leu Lys Arg Tyr
        835                 840                 845

Lys Leu Trp Leu Glu Gln Lys Tyr Lys Ser Pro Tyr Thr Gly Gln Ile
    850                 855                 860

Ile Pro Leu Asn Lys Leu Phe Thr Pro Glu Tyr Glu Ile Glu His Ile
865                 870                 875                 880

Ile Pro Gln Ser Arg Tyr Phe Asp Asp Ser Phe Ser Asn Lys Val Ile
                885                 890                 895

Cys Glu Ser Ala Val Asn Lys Leu Lys Asp Asn Tyr Ile Gly Leu Glu
            900                 905                 910

Phe Ile Lys Gln Phe Gly Gly Thr Ile Ile Glu Leu Gly Phe Gly Lys
        915                 920                 925

Ser Ile Lys Val Phe Glu Thr Lys Glu Tyr Glu Asp Phe Val Lys Lys
    930                 935                 940

His Tyr Ala Asn Asn Gln Gly Lys Arg Asn Lys Leu Leu Met Glu Asp
945                 950                 955                 960

Ile Pro Glu Lys Met Ile Glu Arg Gln Met Asn Asp Thr Arg Tyr Ile
                965                 970                 975

Ser Lys Tyr Ile Ser Gly Val Leu Ser Asn Ile Val Arg Val Glu Asp
            980                 985                 990

Gly Ser Asp Glu Gly Val Asn Ser  Lys Asn Ile Val Pro  Gly Asn Gly
        995                 1000                1005

Lys Ile  Thr Thr Gln Leu Lys  Gln Asp Trp Gly Leu  Asn Asp Val
    1010                1015                1020

Trp Asn  Asp Leu Ile Leu Pro  Arg Phe Glu Arg Met  Asn Gln Leu
    1025                1030                1035
```

-continued

```
Thr Asn  Ser Lys Val Phe Thr  Ala Trp Asn Glu Asn  Tyr Gln Lys
    1040                 1045                 1050

Phe Leu  Pro Thr Val Pro Ile  Glu Tyr Ser Lys Gly  Phe Ser Lys
    1055                 1060                 1065

Lys Arg  Ile Asp His Arg His  His Ala Leu Asp Ala  Leu Val Ile
    1070                 1075                 1080

Ala Cys  Ala Thr Lys Asp His  Val Asn Leu Leu Asn  Asn Gln Ser
    1085                 1090                 1095

Ala Lys  Ser Asp Thr Lys Arg  Tyr Asp Leu Lys Lys  Lys Ser Met
    1100                 1105                 1110

Lys Phe  Glu Lys Val Val Tyr  Asn Asp Ala Lys Thr  Gly Glu Lys
    1115                 1120                 1125

Ile Glu  Arg Glu Val Pro Lys  Gln Phe Leu Lys Pro  Trp Glu Asn
    1130                 1135                 1140

Phe Thr  Leu Asp Val Lys His  Asn Leu Glu Thr Ile  Ile Val Ser
    1145                 1150                 1155

Phe Lys  Gln Asn Leu Arg Val  Ile Asn Lys Ala Thr  Asn Tyr Tyr
    1160                 1165                 1170

Glu Lys  Tyr Val Glu Lys Asp  Gly Thr Lys Asn Lys  Glu Arg Val
    1175                 1180                 1185

Glu Gln  Thr Gly Thr Asn Trp  Ala Ile Arg Lys Pro  Met His Lys
    1190                 1195                 1200

Asp Thr  Val Ser Gly Lys Val  Asp Leu Pro Trp Val  Lys Val Pro
    1205                 1210                 1215

Lys Gly  Lys Ile Leu Thr Ala  Thr Arg Lys Ser Leu  Asp Ser Ser
    1220                 1225                 1230

Phe Asp  Leu Lys Ser Ile Gly  Ser Ile Thr Asp Thr  Gly Ile Gln
    1235                 1240                 1245

Lys Ile  Leu Lys Asn Tyr Leu  Ala Phe Lys Asp Gly  Asn Pro Glu
    1250                 1255                 1260

Leu Ala  Phe Ser Pro Glu Gly  Ile Asp Asp Leu Asn  Lys Asn Ile
    1265                 1270                 1275

Glu Lys  Tyr Asn Asp Gly Lys  Pro His Gln Pro Ile  Asn Lys Val
    1280                 1285                 1290

Arg Val  Phe Glu Leu Gly Ser  Lys Phe Gln Val Gly  Gln Ser Gly
    1295                 1300                 1305

Asn Lys  Lys Asp Lys Tyr Val  Glu Ala Ala Lys Gly  Thr Asn Leu
    1310                 1315                 1320

Phe Phe  Ala Val Tyr Glu Asp  Glu Lys Gly Lys Arg  Asn Tyr Glu
    1325                 1330                 1335

Thr Ile  Pro Leu Asn Glu Val  Ile Glu Arg Gln Lys  Gln Gly Leu
    1340                 1345                 1350

Ser Val  Val Asp Leu Lys Gly  Thr Asn Asp Phe Tyr  Leu Cys Pro
    1355                 1360                 1365

Asn Asp  Phe Val Tyr Ile Pro  Ser Gly Asp Glu Leu  Glu Asn Ile
    1370                 1375                 1380

Asn Asn  Val Asp Phe Lys Asp  Ile Lys Lys Glu Ile  Asn Glu Arg
    1385                 1390                 1395

Ile Tyr  Lys Val Val Ser Phe  Thr Gly Asn Arg Leu  Ser Cys Ile
    1400                 1405                 1410

Pro Tyr  Met Val Ala Thr Thr  Ile Val Asn Lys Leu  Glu Phe Thr
    1415                 1420                 1425
```

```
Gln Leu  Asn Lys Ile Glu Phe  Thr Lys Glu Lys Glu  Ile Cys Ile
    1430                1435                1440

Lys Leu  Asn Val Asp Arg Leu  Gly Asn Ile Ser Lys  Ala
    1445                1450                1455


<210> SEQ ID NO 55
<211> LENGTH: 18
<212> TYPE: RNA
<213> ORGANISM: Empedobacter sp.
<220> FEATURE:
<221> NAME/KEY: source
<223> OTHER INFORMATION: /note="crRNA"

<400> SEQUENCE: 55

guugugaauu gcuuucaa                                                   18


<210> SEQ ID NO 56
<211> LENGTH: 75
<212> TYPE: RNA
<213> ORGANISM: Empedobacter sp.
<220> FEATURE:
<221> NAME/KEY: source
<223> OTHER INFORMATION: /note="tracrRNA"

<400> SEQUENCE: 56

uugaaaagca auucacaaua aggauuauuc cguugugaaa acauucaagg cggggcaacu     60

cgucuuuuuu cuuuu                                                      75


<210> SEQ ID NO 57
<211> LENGTH: 127
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L1"

<400> SEQUENCE: 57

gagcggacag cagcuuccua uaucucguac guugugaauu gcuuucaaaa aguugaaaag     60

caauucacaa uaaggauuau uccguuguga aaacauucaa ggcggggcaa cucgucuuuu    120

uucuuuu                                                              127


<210> SEQ ID NO 58
<211> LENGTH: 127
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="sgRNA L2"

<400> SEQUENCE: 58

ccaugauaua gacguugugg cuguuguagu guugugaauu gcuuucaaaa aguugaaaag     60

caauucacaa uaaggauuau uccguuguga aaacauucaa ggcggggcaa cucgucuuuu    120

uucuuuu                                                              127


<210> SEQ ID NO 59
<211> LENGTH: 6
```

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="PAM"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(5)
<223> OTHER INFORMATION: a, c, t, g, unknown or other

<400> SEQUENCE: 59 nnrnnc 6

<210> SEQ ID NO 60
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Target seq and PAM region of plasmid
library 1"
<220> FEATURE:
<221> NAME/KEY: modified_base
<222> LOCATION: (31)..(38)
<223> OTHER INFORMATION: a, c, t, g, unknown or other

<400> SEQUENCE: 60
gagcggacag cagcttccta tatctcgtac nnnnnnnn 38

<210> SEQ ID NO 61
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Target seq and PAM region of plasmid
library 2"
<220> FEATURE:
<221> NAME/KEY: modified_base
<222> LOCATION: (31)..(38)
<223> OTHER INFORMATION: a, c, t, g, unknown or other

<400> SEQUENCE: 61
ccatgatata gacgttgtgg ctgttgtagt nnnnnnnn 38

<210> SEQ ID NO 62
<211> LENGTH: 122
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="sgRNA with N's"
<220> FEATURE:

<221> NAME/KEY: modified_base
<222> LOCATION: (1)..(25)
<223> OTHER INFORMATION: a, c, u, g, unknown or other

<400> SEQUENCE: 62
nnnnnnnnnn nnnnnnnnnn nnnnnguugu gaauugcuuu caaaaaguug aaaagcaauu 60
cacaauaagg auuauuccgu ugugaaaaca uucaaggcgg ggcaacucgu cuuuuuucuu 120
uu 122

<210> SEQ ID NO 63
<211> LENGTH: 4
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="4bp linker"

<400> SEQUENCE: 63 aaag 4

<210> SEQ ID NO 64
<211> LENGTH: 4
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="4bp linker"

<400> SEQUENCE: 64 gaaa 4

<210> SEQ ID NO 65
<211> LENGTH: 4
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="4bp linker"

<400> SEQUENCE: 65 acuu 4

<210> SEQ ID NO 66
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="6bp linker"

<400> SEQUENCE: 66 caaagg 6

<210> SEQ ID NO 67
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: source
<223> OTHER INFORMATION: /note="NLS"

<400> SEQUENCE: 67

Pro Lys Lys Lys Arg Lys Val
1 5

<210> SEQ ID NO 68
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="conserved sequence in base of hairpin stem of tracrRNA"
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (4)..(5)
<223> OTHER INFORMATION: a, c, u, g, unknown or other

<400> SEQUENCE: 68 unanng 6

<210> SEQ ID NO 69
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="APG05083.1/exemplary PAM"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 69 nnrncc 6

<210> SEQ ID NO 70
<211> LENGTH: 7
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<220> FEATURE:
<221> NAME/KEY: source
<223> OTHER INFORMATION: /note="APG07433.1/exemplary PAM"
<220> FEATURE:
<221> NAME/KEY: modified_base
<222> LOCATION: (1)..(4)
<223> OTHER INFORMATION: a, c, t, g, unknown or other

<400> SEQUENCE: 70 nnnnccr 7

<210> SEQ ID NO 71
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="APG07513.1/exemplary PAM"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(4)
<223> OTHER INFORMATION: a, c, t, g, unknown or other

<400> SEQUENCE: 71 nnrncc 6

<210> SEQ ID NO 72
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="APG01688.1/exemplary PAM"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (5)..(5)
<223> OTHER INFORMATION: a, c, t, g, unknown or other

<400> SEQUENCE: 72 nnranc 6

<210> SEQ ID NO 73
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 4"

<400> SEQUENCE: 73
gagcggacag cagcttccta tatctcgtac 30

<210> SEQ ID NO 74
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 74
gagcggacag cagcttccta tatctcgtag 30

<210> SEQ ID NO 75
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 75
gagcggacag cagcttccta tatctcgttc 30

<210> SEQ ID NO 76
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 76
gagcggacag cagcttccta tatctcgaac 30

<210> SEQ ID NO 77
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 77
gagcggacag cagcttccta tatctcctac 30

<210> SEQ ID NO 78
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 78
gagcggacag cagcttccta tatctggtac 30

<210> SEQ ID NO 79
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 79
gagcggacag cagcttccta tatcacgtac 30

<210> SEQ ID NO 80
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 80
gagcggacag cagcttccta tatgtcgtac 30

<210> SEQ ID NO 81
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 81
gagcggacag cagcttccta taactcgtac 30

<210> SEQ ID NO 82
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 82
gagcggacag cagcttccta tttctcgtac 30

<210> SEQ ID NO 83
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 83
gagcggacag cagcttccta aatctcgtac 30

<210> SEQ ID NO 84
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 84
gagcggacag cagcttcctt tatctcgtac 30

<210> SEQ ID NO 85
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 85
gagcggacag cagcttccaa tatctcgtac 30

<210> SEQ ID NO 86
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 86
gagcggacag cagcttcgta tatctcgtac 30

<210> SEQ ID NO 87
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 87
gagcggacag cagcttgcta tatctcgtac 30

<210> SEQ ID NO 88
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 4"

<400> SEQUENCE: 88
gagcggacag cagctaccta tatctcgtac 30

<210> SEQ ID NO 89
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 4"

<400> SEQUENCE: 89
gagcggacag cagcatccta tatctcgtac 30

<210> SEQ ID NO 90
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 4"

<400> SEQUENCE: 90
gagcggacag caggttccta tatctcgtac 30

<210> SEQ ID NO 91
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 4"

<400> SEQUENCE: 91
gagcggacag caccttccta tatctcgtac 30

<210> SEQ ID NO 92
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:

<221> NAME/KEY: source
<223> OTHER INFORMATION: /note="mismatch repair Table 4"

<400> SEQUENCE: 92
gagcggacag ctgcttccta tatctcgtac 30

<210> SEQ ID NO 93
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 93
gagcggacag gagcttccta tatctcgtac 30

<210> SEQ ID NO 94
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 94
gagcggacac cagcttccta tatctcgtac 30

<210> SEQ ID NO 95
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 95
gagcggactg cagcttccta tatctcgtac 30

<210> SEQ ID NO 96
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 96
gagcggagag cagcttccta tatctcgtac 30

<210> SEQ ID NO 97
<211> LENGTH: 30
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 4"

<400> SEQUENCE: 97
gagcggtcag cagcttccta tatctcgtac 30

<210> SEQ ID NO 98
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 4"

<400> SEQUENCE: 98
gagcgcacag cagcttccta tatctcgtac 30

<210> SEQ ID NO 99
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 4"

<400> SEQUENCE: 99
gagccgacag cagcttccta tatctcgtac 30

<210> SEQ ID NO 100
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 4"

<400> SEQUENCE: 100
gaggggacag cagcttccta tatctcgtac 30

<210> SEQ ID NO 101
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 4"

<400> SEQUENCE: 101

-continued gaccggacag cagcttccta tatctcgtac 30

<210> SEQ ID NO 102
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 102
gtgcggacag cagcttccta tatctcgtac 30

<210> SEQ ID NO 103
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 4"

<400> SEQUENCE: 103
cagcggacag cagcttccta tatctcgtac 30

<210> SEQ ID NO 104
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 6"

<400> SEQUENCE: 104
gagcggacag cagcttccta tatctcgtat 30

<210> SEQ ID NO 105
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 6"

<400> SEQUENCE: 105
gagcggacag cagcttccta tatctcgtgc 30

<210> SEQ ID NO 106
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<220> FEATURE:
<221> NAME/KEY: source
<223> OTHER INFORMATION: /note="mismatch repair Table 6"

<400> SEQUENCE: 106

gagcggacag cagcttccta tatctcgcac                                30


<210> SEQ ID NO 107
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 107

gagcggacag cagcttccta tatctcatac                                30


<210> SEQ ID NO 108
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 108

gagcggacag cagcttccta tatcttgtac                                30


<210> SEQ ID NO 109
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 109

gagcggacag cagcttccta tatcccgtac                                30


<210> SEQ ID NO 110
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 110

gagcggacag cagcttccta tatttcgtac                                30


<210> SEQ ID NO 111
<211> LENGTH: 30
```

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 6"

<400> SEQUENCE: 111
gagcggacag cagcttccta tacctcgtac 30

<210> SEQ ID NO 112
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 6"

<400> SEQUENCE: 112
gagcggacag cagcttccta tgtctcgtac 30

<210> SEQ ID NO 113
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 6"

<400> SEQUENCE: 113
gagcggacag cagcttccta catctcgtac 30

<210> SEQ ID NO 114
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 6"

<400> SEQUENCE: 114
gagcggacag cagcttcctg tatctcgtac 30

<210> SEQ ID NO 115
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="mismatch repair Table 6"

<400> SEQUENCE: 115
gagcggacag cagcttccca tatctcgtac 30

<210> SEQ ID NO 116
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 6"

<400> SEQUENCE: 116
gagcggacag cagcttctta tatctcgtac 30

<210> SEQ ID NO 117
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 6"

<400> SEQUENCE: 117
gagcggacag cagctttcta tatctcgtac 30

<210> SEQ ID NO 118
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 6"

<400> SEQUENCE: 118
gagcggacag cagctcccta tatctcgtac 30

<210> SEQ ID NO 119
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 6"

<400> SEQUENCE: 119
gagcggacag cagcctccta tatctcgtac 30

<210> SEQ ID NO 120
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"
<220> FEATURE:
<221> NAME/KEY: source
<223> OTHER INFORMATION: /note="mismatch repair Table 6"

<400> SEQUENCE: 120
gagcggacag cagtttccta tatctcgtac 30

<210> SEQ ID NO 121
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 6"

<400> SEQUENCE: 121
gagcggacag caacttccta tatctcgtac 30

<210> SEQ ID NO 122
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 6"

<400> SEQUENCE: 122
gagcggacag cggcttccta tatctcgtac 30

<210> SEQ ID NO 123
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 6"

<400> SEQUENCE: 123
gagcggacag tagcttccta tatctcgtac 30

<210> SEQ ID NO 124
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="mismatch repair Table 6"

<400> SEQUENCE: 124
gagcggacaa cagcttccta tatctcgtac 30

<210> SEQ ID NO 125

-continued

<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 125
gagcggacgg cagcttccta tatctcgtac 30

<210> SEQ ID NO 126
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="mismatch repair Table 6"

<400> SEQUENCE: 126
gagcggatag cagcttccta tatctcgtac 30

<210> SEQ ID NO 127
<211> LENGTH: 3210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG05083.1 mammalian codon optimized
      sequence"

<400> SEQUENCE: 127
atgagagagc tggattaccg gatcggcctg gatatcggga ccaactccat tggatggggc 60
atcatcgagc tgtcttggaa caaagacaga gaacagtacg agaaggcaag aatcgtggac 120
aagggcgtga gaatgttcga caaggccgaa atacccaaga ccggagccag cctggccgag 180
cctagaagaa ttgccagatc aagcagaaga cggctcaaca gaaagtctca gagaaaaaaa 240
gatattcgga acctgctggt ccagcacgag atcatcagcc aaaaggaact cgctagcctg 300
tatcctctga ccaagagcag catggacatt tgggacatca gactggacgg cctggacaga 360
ctgctggata gattcgagtg gaccagattg ctgatccacc tggctcagcg gagaggcttc 420
aaaagcaacc ggaagagcga gctgaaggac gtggaaaccg gcaaggtgct ctccagcatc 480
caggctaatg agaagcggct gtccctgtac agaactgtgg gcgagatgtg gatgaagaat 540
gaagatttta gcaagtacga caaaagaaga aatagtagca acgaatacgt gttctctgtg 600
tcccgggccg acctggaaaa ggaaatcgtg acactgtttg aagctcagcg gaagttccag 660
agcagctatg ccagcgccga tcttcaaaaa acctacctcc agatctgggc ccatcaactg 720
cctttcgcct ctggcaacgc catcgttaac aaggtgggct actgcagcct actgaaaggc 780
aaggagaaga gagttcctaa ggccacctac accttccaat acttcagcac cctggatcag 840
atcaacagaa ccagactggg cccaaacttc cagcccttca ccaaggaaca gagagatgtg 900
atcctggacg agatgtttaa ccggaccgat tattacaaga agaagaccat ccctgaggtg 960
acgtactacg atatcagaaa atggctggcc ctggacgaga caatccagtt caagggcctg 1020
acctacgacc ctaatgaaga actgaagaaa attgagctaa agtcttttat caatctgaag 1080
cctttctacg agataaagaa ggtggtgaca aactacgcca agaagacaaa tgaggccttt 1140
agcacactgg actatgacac ctttgcctac gccctgacag tgtacaagac cgacaaggac 1200
atccgctcct acctgaaaaa gagtaacaac ctgtccaaat gctgctacga cgaccaactg 1260
atcgaggaat tgctgacact gagctacacc aaattcggcc acctgagctt caaggctatc 1320
aaccacgttc tgcctatcat gcaggagggc agaacctacc aggaggccat tcaccagctc 1380
ggctacgatg ccacaaacct caaaaaagag aaccggtcta tgttcctgcc tctgttccct 1440
gacgagatca ccaaccccat cgtgaagagg gccctgaccc aggccaggaa ggtggtcaac 1500
gccatcatca gacgatacgg gtctccaaac agcgtgcaca tcgagctggc cagagagctg 1560
agcaagagcc acgacgagag aacaaagatc atgaaagctc atgatgaaaa ctacaaaaag 1620
aacaagggcg ctatcagcat cctgatcgag aacggtattc tgaatcctac aggttatgac 1680
atcgtccggt acaagctgtg gaaggaacag ggcgagagat gcgcctattc tctgaaacag 1740
atccccgcca acaccttctt caacgaaatg aagaaggagc ggtccggcag ccctgtgctg 1800
gaaatcgatc acatcctgcc ctacagccag agcttcatcg acagctacca caacaaagtg 1860
ctggtgtacg gggatgagaa ccagaaaaag ggcaatagaa tcccgtacac ctacttcctg 1920
gaaggcaaca aggactggga gtctttcgag agctatgtgc gcctgaactc ctttttcagc 1980
aagaaaaagc gaggatatct gctgaagaag gcttacctgc caagagagag taacatgatc 2040
aaggaacggc acctcaacga cacccggtac gccagctcct acctgaagaa cttcatcgag 2100
aagaatctga agttcaagga ggtggaaggc tctacccgga agaagcacgt gcaaaccgtg 2160
aacggcataa tcacagccca cctgagaaag agatggggcc tggaaaagga ccgccaggag 2220
acatatcttc atcacgctat ggacgccatc atcgtggcat gcaccgacca ccacatggtg 2280
acaaaggtga ccgagtacta ccagatcaaa gaaagcaata aatctattag aaagccttac 2340
ttccccctgc cttgggtggg ctttagagag gaaattctgt cccacctggc tcggcagcct 2400
atcgccagaa agatctctga agagctgaag atcggatacc agagcttcga ttacatcctc 2460
gtgtctagaa tgcctaaaag atcagtgacc ggcgccgccc acgagcagac cattatgaaa 2520
aagggaggca tcgacaaaaa aggaaaaacc atcatcatta agcgggtcta cctgaaggat 2580
atcaagttcg acgagaatgg cgatttcaag atggttggaa aggaacagga cctggctacc 2640
tacgaggcca tcaagcagag atacatcgag tacggcaagg aatccaagaa ggccttcgag 2700
acccctctgt ataagcccag caagaaaggc aaaggcaacc tgatcaagaa gatcaaagtg 2760
gaagtgcaaa ccaagagctt tgtgagagaa gtcaacggcg gagtggccca gaacggcgat 2820
ctggtgcggg ttgacctgtt cgagaaggat aatagatact acatgatccc catctacgtg 2880
atggataccg tgcacagcga acttcctaac aaggccgtga ccagcagcaa aggctatgag 2940
caatggctga ccatcgacaa cagcttcacc ttcaagttca gcctataccc ctacgacctg 3000
gtgcggctgg tcaagggtaa cgaggacaga ttcctgtact tttccaccct ggatattaac 3060
agtgatagac tcaacttcaa agacgtcaac aagcccagca agcaggccga gaacagatat 3120
agcctgaaga caatcgaaaa cctggaaaaa tacgaggtgg gcgtcctggg cgacctcaga 3180
tttgtgagac aggagatcag aaagaacttc 3210

<210> SEQ ID NO 128

-continued

<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG07433.1 mammalian codon optimized sequence"

<400> SEQUENCE: 128

```
atgagagagc tggactacag aattggcctg gacatcggca ccaacagcat cggatggggc     60
gtgatcgagc tgtcctggaa caaagaccgg gagagatacg agaaggtcag aatcgtggat    120
caaggcgtga gaatgttcga cagagccgag atgcccaaga caggcgccag cttagctgaa    180
cccagaagaa tcgccagatc cagcagacgg agactgaatc gcaagtccca gagaaagaaa    240
aacatccgga acctgctggt gcaacacggc gtgatcacac aggaggaact ggatagcctg    300
taccccctga gcaaaaagag catggacatc tggggcattc ggctcgacgg cctggacaga    360
ctcctcaatc atttcgagtg ggccagactg ctgatccacc tggctcagag acggggcttt    420
aagtccaaca gaaagagtga actgaaagat acagagacag gcaaggtgct gagcagcatc    480
caactgaacg agaaacggct gagcttgtat agaaccgtgg gcgagatgtg gatgaaggac    540
cccgacttct ctaaatacga taggaagaga aatagcccca acgaatacgt gttcagcgtg    600
tctagagccg agctggaaaa ggaaatcgtg accctgttcg ccgcccagcg gagattccag    660
agcccttacg ccagcaaaga tctgcaggag acatatctgc agatctggac ccaccaactg    720
cctttcgcca gcggcaatgc catcctgaac aaggtcggat actgctccct gttgaaaggc    780
aaagaaagaa ggattcccaa ggctacatac accttccaat acttctctgc tctggaccag    840
gtgaatcgga ccagactggg acctgatttc cagcccttca ccaaggagca acgggaaatt    900
atcttgaaca acatgttcca gaggacagat tactacaaga agaaaaccat ccccgaggtg    960
acctactatg acatacggaa gtggctggaa ttggacgaga caattcagtt caagggcctg   1020
aactacgacc ctaacgagga actgaagaag atcgagaaga agcctttat caatctgaag   1080
gccttctacg agatcaacaa ggtggtggcc aactacagcg aaagaaccaa cgagaccttc   1140
tccaccctgg actacgacgg catcggctac gccctgaccg tgtacaaaac cgacaaggat   1200
atccgcagct acctgaagag cagtcacaac ctacctaaga gatgctacga cgaccaactg   1260
atcgaggaac tgctgagcct gagctacaca aagttcggcc acctgtccct gaaagccatc   1320
aaccacgtgc tgtctatcat gcagaagggc aatacctaca aggaagccgt ggaccaactg   1380
ggctacgaca ccagcggcct taagaaggag aagaggtcca agttcctgcc acctatttct   1440
gatgaaatca cgaatccaat cgtgaaaagg gccctgaccc aggccagaaa agtggtgaac   1500
gccataatta gaagacacgg atctcctcac tccgtgcaca tcgagctggc cagagagctg   1560
agcaagaacc acgacgagcg gacaaagatc gtcagcgccc aggatgaaaa ctacaagaaa   1620
aacaagggcg ctatcagcat cctgtctgag cacggcatcc tgaaccctac aggctacgac   1680
atcgtgagat acaaactgtg gaaggagcag ggcgaacggt gcgcctacag cctgaaggaa   1740
atccctgccg atacattttt caacgagctg aagaaggaac gcaacggcgc ccctatcctt   1800
gaagtggacc acatcctgcc ctacagccag tccttcatcg actcctacca caacaaggtc   1860
ctggtgtaca gcgacgaaaa ccggaaaaag ggcaacagaa tcccttatac ctacttcctg   1920
gaaaccaaca aggattggga ggcctttgag cggtacgtgc ggagcaacaa attcttctcc   1980
```

aagaaaaagc gagagtacct tctgaagcgg gcttatctgc ctagagaatc tgagctgatc 2040
aaagaacgcc acctgaacga caccagatac gcctctacct tcctgaagaa cttcatcgag 2100
cagaacctgc agttcaagga agccgaggac aaccccagaa aaagacgggt gcaaaccgtg 2160
aacggcgtta tcaccgccca cttcagaaag cggtggggcc tggagaagga ccggcaggag 2220
acatacctcc atcacgctat ggacgccatc atcgtggctt gtacagacca ccacatggtc 2280
accagagtga ccgagtacta tcagatcaag gaaagcaaca agagcgtgaa gaagccctat 2340
tttcctatgc cttgggaagg cttccgggac gagctgctga gccacttggc ttctcagcct 2400
atcgccaaga aaatcagcga ggaactgaag gccggctacc agagcctgga ctacatcttc 2460
gtgtccagaa tgcctaagag aagcattaca ggcgctgctc ataagcagac catcatgcgg 2520
aagggaggaa ttgacaagaa gggcaaaaca atcatcatcg aacggctgca cctgaaggat 2580
atcaagttcg acgagaacgg agatttcaag atggtgggca aggaacagga catggccaca 2640
tacgaagcta ttaaacagag atacctggag cacggcaaga atagcaagaa ggccttcgag 2700
acccctctgt acaagcccag caaaaagggc acaggtaacc tgatcaagcg ggtgaaggtg 2760
gaaggacagg ccaagagctt tgtgagggaa gtgaacggcg gagtggccca aaatggcgat 2820
ctggttagag ttgatttgtt tgagaaggat gataagtact acatggtccc catctacgtg 2880
ccagacaccg tgtgtagcga gctgcccaaa aaggtggtcg ccagctctaa gggctatgag 2940
cagtggctga cactggataa cagcttcacc tttaagttca gcctgtaccc ttatgatctg 3000
gtgcggctgg tcaagggaga tgaggatcgg ttcctgtact ttggcaccct ggacatcgac 3060
agcgacagac ttaacttcaa ggacgtgaac aagccaagca agaagaacga gtaccggtac 3120
agcttgaaaa ccatcgagga cttggagaag tacgaggtgg gcgtgctggg cgatctaaga 3180
ctggtccgga aggaaactcg aagaaacttc cac 3213

<210> SEQ ID NO 129
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG07513.1 mammalian codon optimized sequence"

<400> SEQUENCE: 129
atgcgggaac tggattacag aattggactg gacatcggga ccaactcaat tggctgggga 60
gtgatcgagc tgagctggaa caaggacaga gagcagtacg agaagaccag aatcgtggac 120
aagggcgtta ggatgttcga caaggccgag atccccaaga ccggagccag cctggccgag 180
cctagacgta tcgccagatc ctccagacgt agactgaaca gaaagtccca gaggaagaag 240
gacattcgga acctgctggt gcaacacgag atcattagcc aaaaagaact gaccagcctg 300
taccctctgt ctaaatccag catggacatc tgggacatcc ggctggacgg cctggacaga 360
ctgcttgata gattcgagtg ggcccggctc ctgatccacc tggctcagcg gcggggcttt 420
aaaagcaacc ggaagtctga gcttaaagac gtggaaacag gaaaagttct gtccagcatc 480
caggtgaatg aaaagcggct gagcctgtac agaaccgtgg gcgagatgtg gatgaagaac 540
gccgattgca gcaagtacgg caaacgtaga aatagcccca acgagtacgt gttcagcgtg 600

```
tctagagccg acttggagaa agaaattgtg acacttttcg aggcccagcg aaaattccac    660
agcagctacg ccagtgtgga cctgcagaag acatacatcc aaatctgggc tcatcaactg    720
ccatttgcct ctggcaatgc cattgtgaac aaggtgggat actgctctct gctgaagggc    780
aaagaaaaga gagtgcctaa ggccacatac acctttcagt attttaacac cctggaccag    840
atcaaccgga caagactggg ccctaacttc caacctttca ccaaggagca gagagatatc    900
atcctagaca aaatgttcca gagaaccgac tactacaaga aaaaaacaat ccctgaggtg    960
acatactacg atatcagaaa gtggctggcc ctggacgaaa ccatccagtt caagggcctg   1020
acctacgatc ctaatgaaga actgaagaag atcgagatga agccattcat caacctgaaa   1080
cctttctacg agatcaagaa ggtggtgacc aactacgcca agaagacaaa cgaggtgttc   1140
tctgccctgg actatgacac cgtggcttat gccctcaccg tgtacaaaac agacaaggat   1200
atcagaagct accttaagcg gtccaacaac ctgagcaaga gatgttacga cgaccaactg   1260
atcgaggaac tgctgacact gagctacacc aagttcggcc acctgtcctt caaggccatc   1320
aatcacgtgc tgcccatcat gcaggagggc agaacctacc aagaggctat tcaccaactg   1380
ggctatgaca cgaccaacct gaagaaggaa aatagaagca tgttcctgcc catcatccct   1440
gacgagatca ccaaccctat cgtgaagcgg gccctgacgc aggcccggaa agtggtgaat   1500
gccatcatcc gcagatacgg ctctcctaat tctgtccaca tcgagctggc cagagagctg   1560
agcaaaagcc acgacgagcg gaagaagatc atgaccgccc acgacgagaa ctacaagaaa   1620
aacaagggcg ccgtgtccat cctgatcgat aacggcatcc tgaatcctac aggatacgat   1680
atcgtgcggt acaagctgtg gaaggaacag ggcgaaagat gcgcctatag cctgaaaaaa   1740
atccccgcca acaccttctt caacgagcta aaaaaggaac ggagcggccc acctgtgctg   1800
gaagtggacc acatcctgcc ctacagccag agcttcatcg acagctacca caacaaggtg   1860
ctggtgtacg gcgacgagaa ccagaagaag ggcaatagaa tcccttacac atttttcagc   1920
gaagaagata aggaatggga gagcttcgag agctacgttc ggagcaacag cttcttcagc   1980
aagaaaaagc gcggctacct gctgaagaag gcctacctgc ccagagaaag caacctgatc   2040
aaggaacggc acctcaacga cacacggtac gccagcagtt acctgaagaa tttcatcgag   2100
aagaacctga agttcaagga agccgtgggg atcacccgga agaagtacgt gcaaaccgtg   2160
aacggcgtga tcaccgccca cctgcggaag cggtggggcc ttgagaagga ccggcaggag   2220
acctacctgc accacgctat ggacgccatc atcgtggcct gcaccgatca ccacatggtg   2280
acgaaggtga ccgagtacta ccagatcaaa gaaggcaata agagcatcaa gaagccttat   2340
tttcctctgc cctggatggg cttcagagaa gaaatcctgt ctcacctgga gtctcaacct   2400
atcgccagaa aaatttctga agagctgaaa attggatacc agtcccccga ttacatcctg   2460
gtcagccgga tgcctaagag aagcgtgacc ggcagcgccc acgatcagac cgtgatgaag   2520
aagggcgata tcgataagaa gggcaagaca atcatcatca agcgggtgca cctgaaggat   2580
atcaagttcg acgaaaatgg cgacttcaaa atggtgggca aggagcagga cctggctaca   2640
tacgaagcta tcaaacagag atacctggag taccggaagg aaagcaagaa ggccttcgag   2700
acccctctgt acaagccatc taaaaaagga aaaggtaacc tgatcaaaaa gatcaaggtg   2760
gaagtgcaaa ccaaatcttt cgtgagagag attaacggcg gagtggccca gaacggcgac   2820
ctggttagag tggatctgtt cgagaaggac aacagatatt acatggtccc catctacgtg   2880
gtggacaccg tgcggtctga actccccaac aaagcagtga caagctccaa aggctatgaa   2940
cagtggctga gcatcgacaa tagtttcacc ttcaagttta gtctgtaccc ctacgacctc   3000
```

```
gtgcggctgg tcaagggcga cgaggatcgc ttcctgtact tctccaccct ggatatcaac   3060

agcgacagac tgaacttcaa ggacgtgaac aagcctagca agcaggctga ataccggtac   3120

agcctgaaga cgatcgagaa cctggaaaaa tacgagatcg gtgttctggg agatctgaga   3180

ctcgttagac aggagacaag aaaaattttc aag                               3213
```

<210> SEQ ID NO 130
<211> LENGTH: 3216
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG08290.1 mammalian codon optimized sequence"

<400> SEQUENCE: 130

```
atgagcgagc tggattatag aatcggcctg gatatcggca ccaattctat cggatgggga     60

gtgatcgagc tgttctggaa caaggatcgg gaacggtacg agaaggtccg catcgtggac    120

aaaggggtca gaatgtttga caaggccgag atccccaaca agggcgccag cctggccgag    180

cctcggagaa tcgcccggag cagcagaaga cgcctgaaca ggaagtccca aaggaagaag    240

gagatccgga acctgctggt gcaacacggc atgatcaccc aagaggaact ggacctcctg    300

taccctctga gcaaaaagtc catcgatatc tgggacatca gactagacgg cctggacaga    360

ctgctgaacc acttagagtg ggctagactg ctgattcacc tggcccagcg gcggggcttc    420

aagagcaacc gcaaaagcga gctgaaggac gctgaaacag gcaaggtgtt gtctagcatc    480

caggtgaacg agaagcggct gttcctgtac agaaccgtgg gggaaatgtg gatcaaggac    540

gcagagttca gcaagtacga caggcgtaga aactccccaa acgaatacgt gttcagcgtg    600

tcaagagccg acctggaaaa ggaaatcgtg acactgtttg aggctcagag aaagttccag    660

agcagctatg cctctaaaaa tctgcaggag acctacctgc agatctgggc ccaccaactg    720

cctttcgcca gcggcaatgc catcctgaac aaagtgggct actgcagcct gctgaaaggg    780

aaggaaaggc ggattcccaa ggccacatac accttccagt acttctccgc cctggatcag    840

gttaaccgga cccggctcgg ccctgacttc caacctttca cccaggaaca aaaggagatc    900

atcctggata agatgttcca gagaacagac tactacaaga agaagaccat ccccgaggtt    960

tcttattatg atatcagaaa gtggctggaa ctcgacgaga caatccagtt taagggactg   1020

aattacgacc ccaacgaaga gctgaagaag atcgaaaaaa aacctttcat caacctgaag   1080

gccttctacg agatcaagaa ggtggttgct aactacgccg aaagaacaaa tgaagccttt   1140

tctaccctgg actacgacgc tatcgcctat gccctgacag tctacaagac cgacaaggac   1200

atccggtcct acctgaagaa atccaacaac ctgtccaagc ggtgctacga tgatcaactg   1260

atcgaggaac tgtttaccct gagctacacc aaattcggcc acctgtcttt caaggccatt   1320

aaccacgtgc tgcctatcat gcaggagggc agaacctacc aggaggccat acaccaactg   1380

ggctacgaca ccaccaacct gaagaaagag aatagaagca tgttcctgcc tctgatccct   1440

gacgagatca caaaccccat tgtgaagcgg gccatcaccc aggccagaaa ggtggtgaac   1500

gccatcatca gaagatacgg ctctcctaac agtgtgcaca tcgaactggc cagagagctg   1560

agcaagagcc acgatgagcg gaaaaagatc atgaccgccc acgacgagaa ctacaagaaa   1620
```

aataagggcg ctatttctat cctgatcgag aacggcattc tgaaccctac cggctacgac 1680
atcgtgagat acaagctgtg gaaggaacaa ggcgagagat gcgcctacag cctgaaagaa 1740
attccacctg atactttttt caacgagctg aagaaagaaa gaaacggcag ccccattctg 1800
gaagtggacc acatcctgcc ttacagccag tccttcatcg acagctacca caacaaagtg 1860
ctggtgtact ctgacgagaa cagaaacaag ggcaacagaa tcccttacac ctacttcctg 1920
gaaacaaaca aggactggga ggcctttgaa agatacgtgc ggagtaacaa actgttttct 1980
aagaaaaaga gagaatatct gctgaagaag acttacctgc ctagagagtc tgaactaatc 2040
aaggaacggc acctgaacga cactcggtat gcttctacat tcctgaagaa tttcatcgag 2100
cagaatctgc agttcaaaga ggtcgaggtc aatctgagaa aaaagagagt gcaaaccgtg 2160
aatggcgtga tcaccgccca cctcagaaag cgttggggcc tggagaagaa ccggcaggag 2220
acgtacctgc accacgctat ggacgccatc atcgtggctt gtacagacca ccacatggtg 2280
acccggataa cagagtacta ccagatcaag gaatccaaca agagcgtgaa gaaaccttac 2340
ttccccatgc cttgggaggg ctttagagat gagctgttgt ctcacctcgc tagccagcct 2400
atcgcaaaga agatcagcga ggaactgaag gccggctacc agagcagcga ctacatcttc 2460
gtgtccagaa tgcccaagag aagcgtgacc ggcgccgccc atgatcagac catcagaaga 2520
aagggcggca tcgacaagaa gggcaagaca atcatcatta agcgggtgcg gctgaaagat 2580
atcaagttcg acgaaaacgg cgatttcaag atggtgggca aagagcagga cctggcaacc 2640
tacgaggcca tcaagcagag atacctggag cacagaaaga acagtaagaa ggccttcgag 2700
acccctctgt acaaacctag caagaaggga acaggaaacc tgattaagcg ggtgaaaatc 2760
gagggacaga ctaaggcctt cgtgcgggaa gtgaacggag gcgtggccca aaatagcgac 2820
ctggtcagag tggacctgtt cgagaaggac gacaagtact atatggtgcc tatctacgtg 2880
ccagacaccg tgtgtagcga gctgcctaag aaggtggtta agagcggaaa aggctatgag 2940
cagtggctga ccctggacaa cagcttcacc ttcaagtcta gcctgtaccc ctacgatctg 3000
gtgcggctcg tgaagggcaa cgaggacaga ttcctgtact tcggcacact ggacattgac 3060
tccgatagac tgaatttcaa ggatgtgaac aagcccagca agcagaacga gtaccggtac 3120
agcctgaaaa caatcgagaa cctggaaaaa tacgaggttg gagtgctggg agatctgcgg 3180
ctggtgaaac aggagaccag gaggatcttt aacaga 3216

<210> SEQ ID NO 131
<211> LENGTH: 4011
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG05459.1 mammalian codon optimized sequence"

<400> SEQUENCE: 131
atgaaaaaag attacgtgat cggcctggac attggcacca acagcgtcgg ctgggccgtg 60
atgacagagg actaccaact ggtgaagaag aagatgccaa tctatggcaa tactgagaag 120
aaaaagataa aaaagaattt ctggggcgtg cggctgtttg aggagggcca caccgccgag 180
gatcggcggc tgaaacggac cgctagaaga cggatctctc gccgcagaaa tagactgaga 240
tatctgcagg ccttcttcga ggaagccatg accgccctgg acgagaactt cttcgccaga 300

```
ctgcaggaga gcttcctggt gcctgaggac aagaaatggc accggcaccc tatcttcgcc    360
aagctggagg atgaggtggc ctatcacgaa acctacccta caatctacca cctgagaaag    420
aaactggctg attcctctga acaggctgac ctgagactga tctatctggc cctggcccat    480
atcgtgaagt acagaggcca cttcctgatc gaaggaaagc tgagtaccga gaacatcagc    540
gtcaaggagc agttccagca gttcatgatt atctataacc agacatttgt gaacggcgaa    600
agccggctgg tgtctgcccc tctgcctgag agcgtgctga tcgaagaaga gctgaccgaa    660
aaggccagcc ggacaaagaa atctgagaag gtgctgcaac agtttcctca ggagaaagcc    720
aatggactgt tcggccagtt cctgaaactt atggtaggca acaaagccga tttcaagaaa    780
gtctttggcc tggaagaaga ggccaaaata acatacgcca gcgagtccta cgaggaggat    840
ctggaaggca ttctggccaa ggtgggcgac gagtacagcg atgttttcct ggccgctaag    900
aacgtctacg acgccgtgga actgtctacc atcctggccg actccgacaa gaagagccac    960
gccaagttgt ctagtagcat gatcgttaga ttcaccgagc accaggagga cctgaagaag   1020
ttcaagcggt ttatcagaga gaattgcccc gacgagtacg ataacctgtt caagaacgag   1080
caaaaagacg gctacgccgg ctacatcgcc cacgccggca aggtgtccca actgaagttc   1140
taccagtacg tgaagaagat aatccaggac atcgccggcg ccgaatactt cctggagaaa   1200
atcgcccagg agaacttcct gcgaaaacag aggaccttcg acaacggcgt gatcccccac   1260
cagatccacc tggccgagct gcaggccatc atccacagac aggctgctta ctaccctttc   1320
ctgaaggaaa atcaggaaaa gattgagcaa ctggtgacat tcagaatccc ctactacgtc   1380
ggccctctga gcaaaggaga tgccagcacc ttcgcctggc tgaaaagaca aagcgaggaa   1440
cctatccggc cttggaacct gcaagagaca gtggacctgg accagtctgc taccgcattc   1500
atcgagagaa tgaccaactt cgatacctac ctgccttctg agaaggtgct gcccaagcac   1560
agcctgctct acgaaaaatt tatggtgttc aacgagctga ccaagatttc ttacactgat   1620
gacagaggca tcaaggccaa cttcagcggc aaggagaagg agaagatatt cgactacctg   1680
tttaagaccc gccggaaggt gaagaaaaag gatatcatcc agttctaccg gaacgagtac   1740
aacaccgaga tcgtcaccct gtctggcctg gaagaggacc agttcaatgc cagcttcagc   1800
acctaccaag atctgctgaa gtgcggccta actagagccg aactggacca ccctgataat   1860
gccgagaaac tggaggacat cattaagatc ctaaccatct tcgaggatag acagcggatc   1920
agaacacagc tcagcacctt caagggacag ttcagcgccg aggtgctgaa gaagctggaa   1980
cggaagcact acaccggctg gggcagactg tccaagaaac tcatcaacgg catctacgac   2040
aaggaatccg gaaagacaat cctggactac ctgatcaaag atgacggcgt ttctaagcac   2100
tacaacagaa acttcatgca gctaatcaac gacagccaac tgagcttcaa gaacgccatc   2160
cagaaggccc agagcagcga gcatgaggaa accctgtctg agaccgtgaa cgagctggcc   2220
ggcagccctg ccatcaagaa aggcatctac cagagcttaa aaatcgttga tgagctggtt   2280
gccatcatgg gctacgcccc taagagaatc gtggtggaga tggctagaga gaaccagaca   2340
acaagcaccg gaaagagaag aagcatccag aggctgaaga tcgtggaaaa agctatggcc   2400
gagattggaa gcaacctgct caaggaacag cctaccacaa acgagcaact gagagataca   2460
agactcttcc tgtattatat gcagaacggt aaggacatgt acaccggcga cgagctgagc   2520
ctgcacagac tgtctcacta cgacatcgac cacatcattc ctcagtcctt catgaaggac   2580
gattccctgg ataacctggt gctggtgggc agcaccgaga accggggcaa gtctgacgac   2640
```

gtgcccagca aggaagtggt gaaggacatg aaagcctact gggagaagct ctacgctgct 2700
ggcttgatca gccagcggaa attccagaga ctgacgaagg gcgagcaggg cggcctgacc 2760
ctggaggaca aagctcattt catccagaga caactggtgg agacaagaca gatcaccaag 2820
aacgtggctg gaattctgga tcagagatac aacgccaaca gcaaagaaaa aaaggtgcaa 2880
atcataacac tgaaagcctc tctgaccagc cagttccgga gcatcttcgg cctgtataag 2940
gtcagagaag tgaacgacta tcaccacggc caggatgcgt acctgaactg cgtggtggcc 3000
actacactcc tgaaagtgta ccccaacctg gctcctgagt tcgtgtacgg cgagtacccc 3060
aagtttcagg cctttaagga aaacaaggct acagccaaga ccatcatcta caccaatctg 3120
atgcggtttt tcaccgagga tgaacccaga ttcatgaagg acggcgagat cctgtggagc 3180
aacagctacc tgaagaacat taagaaagaa ctcaactacc atcagatgaa catagtgaaa 3240
aaggtggaag tgcaaaaggg tggcttctcc aaggaaagca tcaagcctaa gggccccagc 3300
aacaagctga tccctgtgaa gaacgggttg gacccccaga aatacggcgg atttgactct 3360
ccagtggtcg cttacacagt gctgtttacc cacgagaagg gcaaaaaacc actgatcaag 3420
caggagatcc tgggaatcac catcatggaa aagaccagat tcgagcagaa tcctatcctg 3480
ttcctggaag aaaaaggctt cctgaggcct agagtgctga tgaagctgcc taaatacacc 3540
ctgtacgagt tccctgaggg aagacggcgg ctgctggcca gcgccaaaga agcccagaaa 3600
gggaatcaga tggtgctccc cgaacacctg ctgaccctgc tgtaccacgc caaacagtgt 3660
ctgctgccta accagagcga atctctcgct tacgtggaac aacaccaacc ggagttccaa 3720
gagatcctgg agagagtggt ggacttcgct gaggtgcaca cactggccaa gagcaaggtg 3780
caacagatcg tgaaactgtt tgaggcaaac cagaccgcag atgtgaagga aatcgccgcc 3840
tccttcatcc aactgatgca gttcaacgca atgggagccc catctacctt taaattcttc 3900
cagaaggaca tcgagcgggc ccggtacact agcatcaagg aaatcttcga cgccaccatc 3960
atctaccaga gcacaaccgg cctctacgag acacggagaa aggtggtgga c 4011

<210> SEQ ID NO 132
<211> LENGTH: 4308
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG04583.1 mammalian codon optimized sequence"

<400> SEQUENCE: 132
atggccaaga atatcctggg cctggatctg ggtacaaaca gcatcggctg ggctctggtc 60
cagcaggact tcgagaacaa ggagggaaac atcctgggca tgggatctag aatcatccct 120
atgagccagg acatcctggg cgaattcggt aagggcaaca gcatcagcca gaccgccgag 180
agaacaggat accggggcgt gcgtagactg agagagagac acctcctgag aagagagaga 240
ctgcatagag tgctgcacct gctcggcttt ctgcctaagc actacgatga aaaaatcgac 300
tttacacaaa gattcggcaa gttcatcaac caggctgagc ctaagctggc ttttgatagc 360
gagttcctgt tcaaggacag cttccacgag atgctggccg acttcaagca gaatcaacct 420
gaattcctga aagacaagaa cggagaggac tgcctggttc cttacgactg gaccatctac 480
tacctgagaa agaaggctct gacccagaag atcgagaaat acgaactagc ttggctgatc 540

-continued

```
ctgaacttca accaaaagcg gggctactac cagcttagag gcgaagaaga gaaggaaaac    600
cctaacaaac tggtgggctt ccactctctg aagattgttg atgtgatccc tgatgccgag    660
accaacaaaa agggcgagac atggtacagc ctgcacctgg aaaacggctg ggtgtacagg    720
cggagcagca agatcagcct ggccgactgg aaggacaagg ttcgggactt catcgtcact    780
acagatctga acgacgatgg cagcgagaag ctggacaagg acggcatcgt gaagaggtcc    840
ttcagagccc cttctgccga cgattggaca ctcctgaaaa aaaagactga gaaggacatc    900
gacaactcca acaagactgt gggcacctac atctacgaca acttgctgct gaaccctaaa    960
cagaagatca aggggaaaat ggtcagaacc atcgaacgaa agttctacaa gcaggagctg   1020
gagcaaatcc tgaaaaccca gaaagaattt cactccgagc tgcagtctga aaacctgctg   1080
caggactgcg tgagggagct gtaccggaac aacgagcagc accagcagat gctggaagcc   1140
aaggattttg tgcacctgtt cctgaacgat atcatcttct accagagacc cctgcgcagc   1200
cagaaaagct ctattagcaa ctgcaccctg gaattccgga agagcaagaa cgagaatgga   1260
gaagaagtga tccaccggct gaaggtgatc gccaagtcca acccctacta tcaagagttt   1320
cggctgctgc agtgggtgca aaacctggct atctacacta aggacgacga caaaaacgtc   1380
acaaacgaat tcctgaagag cacccaggac tgggaggatc tgctgagatg gctgcacagc   1440
aagaaagaaa tcaagcagga tgccctgatc aaattcctga tcgaaaagaa aggcctgaag   1500
ggtaaggccc tgaccattga agtggctaag tacagatgga attacgtgca agacaaggat   1560
tatcctggca acgagacaag atacctgatt cagagccggc tggacaaggt ggaatacgcc   1620
cctaaggact tcctcacgta cgaaaatgag atggccctgt ggcacatcat ctactctatc   1680
aacgataaga tcgaatacga aaaggcccta aagagcttcg ccaacaagaa aggtctcgac   1740
gaggtgacct tcgtggaagc ctttaagaaa ttcccacctt tcaagagcga ttacggcagc   1800
ttcagcgaga aggccatcaa gaagctgctg cctctcatgc ggttcggcac acaatggaac   1860
tgggacaaca tcgaccagaa ctcgaaggaa aggattggaa aaatcctgac cggcgagtac   1920
gacgagaata tcaagggtag agtgcgggaa aaagctagac acctgaacag cgagacggac   1980
tttcaggcgc tccctctgtg gctggcccag tacgtggtgt acggcagaca tagcgaagct   2040
gacatcgccg gcaagtggaa tagtgtggac gacctgaagc agttcttgga cgacttcaag   2100
caacacagcc tgagaaatcc cattgtagaa caggtgatta ctgagacact gcgggccgtg   2160
aaggatatct ggaacttcta cggcaagggc gccaaggact ttttctctga gatccacatc   2220
gagctgggaa gagagatgaa aaacaccgcc gacgagagaa aaaggattac cacaatggtg   2280
acagataatg agaataccaa tctgagaatc aaagctctgc tggctgagat ggccctggat   2340
cagaacgtgg acaatgtgcg gccttacagc cccatgcagc aagaaatcct gaaaatctat   2400
gaggaaggcg tgctgaacgc cgaagagaac atcgacgatg acatcctgaa gatctctaaa   2460
actgctcagc ctagcgctac cgatctgaag agatacaagc tgtggctgga acagaagtac   2520
agaagcccct ataccggaca gatgatccct ctgaacaagc tgttcacccc tgagtatgaa   2580
atcgagcaca ttatccccca gagcagatac ttcgacgatt ctatgagcaa caaggtgatc   2640
tgcgaggccg ccgtgaacaa gctgaaggat aaccagatcg gcctggtgtt catcaagaac   2700
caccacggcg aagtggtgga ctttggcatg ggcaagcagg tgaaaatcct ggaggtgtct   2760
gattacgaag atttcgtgaa gcagaactac aacaaaaaca gaggcaaacg gaacaagctg   2820
ctcctcgaag atatccccga gaaaatgatt gaacggcaac tgaacgatac cagatatatc   2880
```

```
agcaagtaca tcactcaggt gctgtctaat atcgtcagag acgacaagga aggctctaag   2940

gatgacggag tgaacagcaa gaacattgtg cccggcaacg gcaagattac aaccagactc   3000

aagcaggatt ggggcctgaa cgatgtgtgg aacgacctgg tgctgcctag attcgagaga   3060

atgaacaccc tcacaaactc caatgatttt acaagcaaga acacacacgg caagaccatt   3120

cctaccgtgc ctatcgagct gagcaagggg ttcagcaaaa agcggatcga tcacagacac   3180

cacgctatgg acgccctggt gatcgcctgc gccacccggg accacgtgaa cctgctgaat   3240

aacgaatcca gcaagtctga cacaaagcgg tacgacctga atagaaaact gagaaaatac   3300

gagaaggtgg cctacaacga ccccaaaacc ggcgagagga ttgaaaaaga agtgccaaaa   3360

gacttcatca agccttggga aacttttacc gaagatacca gaacactgct ggagaatatc   3420

gtgatctcat tcaaacagaa cctgagagtg atcaacaagg ccaccaacta ctacgagaag   3480

atcgagaacg gcaaaaaggt gaaggtggaa caaaagggaa tcaactgggc cgtgagaaag   3540

gctctccata aggagaccgt gtccggccag gtccaccttg acagaatcaa ggtggccaag   3600

ggcaagatcc tgaccgccac aagaaagacc ctggacgctt cttttaacga gaaaaccata   3660

gagagcatca ccgataccgg catccagaag atcctgctga actacctgaa gtcaaaggac   3720

aacaaccctg aggtggcctt ctccccagaa ggaattgagg aactaaacaa gaatatcaga   3780

ctgtacaatg acggcaaggc ccaccagcca atcctaaaag tgcgggtgtt cgagcagggc   3840

agcaagttca cactgggcga gacaggcaac aagacaacca agttcgtgga agctgccaag   3900

ggcaccaatc ttttcttcgg aatctacgag gacaagagcg gaaaacgtag ctacgagacc   3960

atccccctga atatcgttat tgaaagacag aaacagggcc tccaggccgt gcccgagacc   4020

aacgagaagg gcaagcaact gctgttcacc ctgagcccca acgacctggt ctacgtgcca   4080

gaggaaggcg tattcgacga gaacaacatc aaggtggata gaatctacaa ggtcgtgtct   4140

ttcagcacat accaatgttt tttcgtgcgg aacgacgtat ctaccagcgt ggtcaacaag   4200

gtggagtaca gcgccctgaa caagatggaa aaatccatcg acaatatcat gatcaaggaa   4260

aactgtgtga agctgaatgt ggaccggctg ggtaagatca gcaaggcc              4308
```

<210> SEQ ID NO 133
<211> LENGTH: 4368
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG01688.1 mammalian codon optimized sequence"

<400> SEQUENCE: 133

```
atgatgatca agaacattct gggactggat ttgggcacaa acagcattgg atgggctctg     60

atcaagcagg acttcgagaa caaacacggc gagatcctgg gcatgggcag cagaatcatc    120

cctatgagcc aggatatcct gggcgatttc ggcaaaggga actcgataag ccagactgct    180

gacagaacca agtacagaag cgtgcggaga ctgagagaaa gattcttgct gcggcgggaa    240

cgcctgcacc gggtgctcca cctgctgaac ttcctccctc aacactacgc ctctcagatc    300

gacttcgaga agaagttcgg caagtttaag tctgagaccg aacctaagct ggcctgggaa    360

aactggggag gtaaattctc tttcctcttc cagaacagct tcaacgagat gctggaagac    420

ttcaaggccg ccggccaggg actcaagatt ccctatgact ggaccatcta ctacctacgg    480
```

```
aagaaagctc tgtcccagaa gatcgagaaa gaggagcttg cctggattct gctgaacttc    540
aaccagaagc gaggctacta ccagctcaga ggcgaggaag aagaagagaa cccgaacaag    600
ctggtggagt tctactccct gaagatcgtg gatgtggtcg ccgacgagcc tcagaagggg    660
aagagcgaca tctggtattc tctgatcctg gaaaacggct gggtctaccg cagagccagt    720
aagatcccac tgtttgattg gaaggataag accagagatt tcatcgtcac cacagacctt    780
aatgacgaca gaagcgtgaa gaccgacaaa gagggcaacg agaagcggtc ctttcgggcc    840
cctagcgaaa atgattggac cctggtcaag aagaagacag agcaggagat tgaccagagc    900
cacaagaccg tgggcaccta catctacgag acactgctgc tcaatccaaa gcagaaaatc    960
aagggcaagc tggtgcgaac aatcgagaga aaattttata aggacgagct gaagcaaatc   1020
ctggaaaagc agaaggaatt tcaccaggag ctgaaaaacg acgatctgta caacgactgc   1080
atcagagagc tgtaccggaa caacgaggcc caccaactga ccctgagcaa gaaagatttc   1140
gtgcacctgc tgatggacga tctgatcttc taccaaagac ccctgcgaag ccagaagtcc   1200
agcatctcta actgcaccct ggaattcaga aaatacaagg acgaaaacgg catcgaacac   1260
acccagtacc tgaaggccat cccaaagagt aatccgtact accaagagtt tagactgtgg   1320
cagtggatgt acaacctgaa catctacaga aaggacgacg aggctaatgt gaccaaggaa   1380
ttcctgaaca ccaataagga cttcgagagc ctgtttgagt tcctgaataa tagaaaggaa   1440
atcgaacaga agcctctgat caagttcctc ctggaacaga aagatattaa caagaagctg   1500
ctgaacgccg aggccgaaaa gtatcggtgg aattacgtgg aagataagaa gtatccttgc   1560
aacgaaacga agaccatgat ctccagcaga ctggacaaag tggagaatat ctctgacgac   1620
ttcctgacca gagacattga gcagaagatc tggcacatca tctacagcgt caacgacaag   1680
atagaatacg agaaggccct gaagtccttc gccaccagaa acgatctcga cgagaacagc   1740
tttatcgaag cctttaagaa gttcagccca ttcaagagcg agtacggatc tttttctgag   1800
aaagccatca agaaactgct gcccctgatg agactgggaa agtactggta cgaggacgag   1860
attgtgaagc actctgatat ttactttaag aacatcgaaa atcttctggg cgacttctcc   1920
aacagagata aaaaaatatc tgaggaagac aaagagaaat ggaacaagtc tatcaacctg   1980
aaactgcagg aggaactgaa ggactttcag accgccgaga tcgacctgtt ccagggcctt   2040
agactccata tcgcccagta cctggtgtac ggccggcaca gcgaagccag catgatcgga   2100
aagtggaaca gcgccgagga tctggaagaa ttcctgaagg acttcaagca gcacagcctg   2160
agaaacccca tcgtcgagca agtgatcacc gagaccctga gggtggttaa ggatatatgg   2220
ctgaaatacg gcaacggcgc caaggacttc ttcaacgaga ttcacatcga gctgggcaga   2280
gaaatgaagc tgcctgccga cgaccggaaa aagctgacca accagatcag cgagaacgaa   2340
aacacaaatt tcagaatcaa ggccctgctg gctgaaatga tgaacgacag cagtgtggaa   2400
aatgtgcggc ctttcagccc tatgcagcag gagatcctga agatctatga agatgacgtc   2460
ctgaagtctg acattgaaat cgaggatgac atccttaaga tctctaaaac cgcccagcct   2520
tctcctagcg atctcaagcg atacaagctc tggctggagc agaagtacaa gtctccatac   2580
accggccaga tcatacctct gaacaagctg tttacccctg aatacgagat cgagcacatt   2640
atccctcagt ctagatattt cgacgacagc ttcagcaaca aagtgatctg cgagagcgcc   2700
gtgaacaagc tgaaagacaa ctacattggc ctggaattca tcaagcaatt tggaggcacc   2760
atcatcgaac tgggctttgg caagtccatc aaagtgttcg agaccaaaga gtacgaggac   2820
```

ttcgtgaaga aacactacgc caacaatcag ggcaagagaa acaagctgct catggaagac 2880
atccccgaga aaatgatcga gagacagatg aacgacacca gatacatctc taagtacatc 2940
agcggagtgc tgagcaacat cgtcagagtg gaagatggat ctgatgaggg cgtgaacagc 3000
aagaacatcg tgcccggcaa cggcaagatt acaacacaac tgaagcagga ctggggcctg 3060
aatgacgtgt ggaacgacct tatcctgccg cggttcgaga gaatgaatca actgaccaac 3120
agcaaggtgt tcacagcctg gaacgaaaac taccagaagt tcctgcctac agtgccaatc 3180
gaatacagca aaggcttcag caagaagcgt atcgatcaca gacaccacgc cctggatgct 3240
ctggttatcg cctgcgccac caaggaccac gtgaacctgc tgaacaacca gtctgccaag 3300
agcgacacca agagatacga cttaaagaaa aaaagtatga aattcgagaa agtggtgtac 3360
aatgatgcca agaccggcga aaagatcgag cgggaagtgc ccaagcagtt cctgaagcct 3420
tgggagaact tcaccctgga tgtgaagcac aacctggaaa cgatcatcgt ctcttttaaa 3480
caaaatctgc gggtgatcaa taaagccacg aactactacg agaagtacgt cgagaaggac 3540
ggcaccaaaa acaaagagcg cgtggagcag acagggacaa actgggccat tagaaagccc 3600
atgcacaagg atacagtgtc cggcaaagtg gaccttcctt gggtgaaggt gcctaaggga 3660
aagatcctga ccgccacacg gaagagcttg gatagcagct tcgacctcaa gagcatcggc 3720
tctataacag atacaggcat tcagaagatc ctaaagaatt acctggcatt caaggacggc 3780
aaccctgagc tggctttcag ccctgagggc atcgacgatc tgaacaagaa catagagaag 3840
tacaacgatg gcaaacctca ccagcctatc aacaaggtgc gagtgtttga gctgggcagc 3900
aagttccagg tgggacaatc tggtaacaag aaggacaagt atgtggaagc tgctaagggc 3960
accaatctct tcttcgccgt gtacgaggat gaaaaaggaa agcggaacta cgagaccatc 4020
cctctcaacg aggtgatcga gagacagaag cagggcctga gcgtggtgga cctgaagggt 4080
acaaacgact tctacctgtg ccctaacgac tttgtgtaca tcccaagcgg cgacgagctg 4140
gaaaacatca acaacgtgga cttcaaggac atcaagaagg agattaacga gcgcatctac 4200
aaagtggtgt cttttacagg caatagactt tcttgtatcc cttacatggt ggccacaacg 4260
atcgtcaaca aactcgaatt cactcaactg aacaaaatcg agtttaccaa ggaaaaagaa 4320
atttgtatca agctcaacgt ggacagactg ggcaatatct ccaaggcc 4368

<210> SEQ ID NO 134
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="SV40 large T-antigen nuclear localization sequence"

<400> SEQUENCE: 134
cctaagaaga aaagaaaggt g 21

<210> SEQ ID NO 135
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<220> FEATURE:
<221> NAME/KEY: source
<223> OTHER INFORMATION: /note="Triple FLAG epitope tag"

<400> SEQUENCE: 135
gactacaagg accacgacgg cgactacaaa gatcacgata tcgactacaa ggacgacgat 60
gataag 66

<210> SEQ ID NO 136
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Nucleoplasmin nuclear localization sequence"

<400> SEQUENCE: 136
aaaagacctg ccgctacaaa gaaggccggc caggccaaga aaaagaag 48

<210> SEQ ID NO 137
<211> LENGTH: 203
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Cytomegalovirus mammalian transcription promoter"

<400> SEQUENCE: 137
tgatgcggtt ttggcagtac atcaatgggc gtggatagcg gtttgactca cggggatttc 60
caagtctcca ccccattgac gtcaatggga gtttgttttg gcaccaaaat caacgggact 120
ttccaaaatg tcgtaacaac tccgccccat tgacgcaaat gggcggtagg cgtgtacggt 180
gggaggtcta tataagcaga gct 203

<210> SEQ ID NO 138
<211> LENGTH: 304
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Cytomegalovirus transcription enhancer"

<400> SEQUENCE: 138
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catg 304

<210> SEQ ID NO 139
<211> LENGTH: 318
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="Human U6 RNA promoter"

<400> SEQUENCE: 139
tgtacaaaaa agcaggcttt aaaggaacca attcagtcga ctggatccgg taccaaggtc 60
gggcaggaag agggcctatt tcccatgatt ccttcatatt tgcatatacg atacaaggct 120
gttagagaga taattagaat taatttgact gtaaacacaa agatattagt acaaaatacg 180
tgacgtagaa agtaataatt tcttgggtag tttgcagttt taaaattatg ttttaaaatg 240
gactatcata tgcttaccgt aacttgaaag tatttcgatt tcttggcttt atatatcttg 300
tggaaaggac gaaacacc 318

<210> SEQ ID NO 140
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 189"

<400> SEQUENCE: 140
cctgaatgct gtgcggctct 20

<210> SEQ ID NO 141
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 185"

<400> SEQUENCE: 141
ggacagtgcg catctccctg 20

<210> SEQ ID NO 142
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 168"

<400> SEQUENCE: 142
cacatctcga gcaagacgtt 20

<210> SEQ ID NO 143
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 135"

<400> SEQUENCE: 143
gggccattaa aacctctcca 20

<210> SEQ ID NO 144
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 139"

<400> SEQUENCE: 144
aggttttaat ggcccagcct 20

<210> SEQ ID NO 145
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 143"

<400> SEQUENCE: 145
catggcagta cattagagca 20

<210> SEQ ID NO 146
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 190"

<400> SEQUENCE: 146
cctgaatgct gtgcggctct 20

<210> SEQ ID NO 147
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="target for Guide 194"

<400> SEQUENCE: 147
gccgcacagc attcaggtcg 20

<210> SEQ ID NO 148
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 165"

<400> SEQUENCE: 148
atggggaatg tagcaagacc 20

<210> SEQ ID NO 149
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 169"

<400> SEQUENCE: 149
cacatctcga gcaagacgtt 20

<210> SEQ ID NO 150
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 173"

<400> SEQUENCE: 150
cttctatagc ctccttcccc 20

<210> SEQ ID NO 151
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 144"

<400> SEQUENCE: 151
catggcagta cattagagca 20

<210> SEQ ID NO 152
<211> LENGTH: 20
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 136"

<400> SEQUENCE: 152
gggccattaa aacctctcca 20

<210> SEQ ID NO 153
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 145"

<400> SEQUENCE: 153
catggcagta cattagagca 20

<210> SEQ ID NO 154
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 188"

<400> SEQUENCE: 154
ggacagtgcg catctccctg 20

<210> SEQ ID NO 155
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 192"

<400> SEQUENCE: 155
cctgaatgct gtgcggctct 20

<210> SEQ ID NO 156
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 196"

<400> SEQUENCE: 156
gccgcacagc attcaggtcg 20

<210> SEQ ID NO 157
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="target for Guide 167"

<400> SEQUENCE: 157
atggggaatg tagcaagacc 20

<210> SEQ ID NO 158
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="target for Guide 171"

<400> SEQUENCE: 158
cacatctcga gcaagacgtt 20

<210> SEQ ID NO 159
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="target for Guide 175"

<400> SEQUENCE: 159
cttctatagc ctccttcccc 20

<210> SEQ ID NO 160
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="target for Guide 197"

<400> SEQUENCE: 160
cctcaccccc acgagcttgt aggaa 25

<210> SEQ ID NO 161
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source -continued
<223> OTHER INFORMATION: /note="target for Guide 199"

<400> SEQUENCE: 161
acagtgcgca tctccctggt cacca 25

<210> SEQ ID NO 162
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 146"

<400> SEQUENCE: 162
ggctgggcca ttaaaacctc tccag 25

<210> SEQ ID NO 163
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 148"

<400> SEQUENCE: 163
gaggctgggc cattaaaacc tctcc 25

<210> SEQ ID NO 164
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 176"

<400> SEQUENCE: 164
gaggctgaga caggagagtt gcttg 25

<210> SEQ ID NO 165
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 177"

<400> SEQUENCE: 165
cccacaaacc gatgtagctc aagag 25

<210> SEQ ID NO 166
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 209"

<400> SEQUENCE: 166
tagggtctta ctctgttgtc cacgc 25

<210> SEQ ID NO 167
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 151"

<400> SEQUENCE: 167
ttctcccgag ccaagtacac gtttc 25

<210> SEQ ID NO 168
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="target for Guide 152"

<400> SEQUENCE: 168
gaaaatctgc tcttagggct caagg 25

<210> SEQ ID NO 169
<211> LENGTH: 3210
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG05083.1 Soy optimized"

<400> SEQUENCE: 169
atgagagagc tagattacag gatcggactc gatatcggaa ctaattcaat cgggtgggga 60
ataattgagc tgtcctggaa taaagatcgc gagcaatatg aaaaggctag gattgtggat 120
aagggagtga ggatgttcga taaggctgaa attcctaaga ctggagcttc tcttgctgaa 180
ccaagaagaa ttgctagatc tagcaggagg agattaaaca ggaagtctca gcgcaagaag 240
gatataagga accttctcgt tcagcatgaa atcatttctc agaaggagct tgcttctctc 300
taccctctaa ccaaatcaag catggacatc tgggatataa ggcttgatgg actcgatagg 360
cttcttgata gatttgagtg gaccaggctt ctaatacacc ttgctcaaag aaggggcttc 420
aaatcaaacc gcaagtccga attaaaggat gttgagactg gaaaggtgct ttcaagcatc 480
caagctaatg aaaagaggct ttctttgtac aggactgttg gggagatgtg gatgaaaaac 540

-continued

```
gaggacttct caaaatacga taaaaggagg aactcctcca acgagtacgt gttctctgtt    600
tctagggctg atcttgagaa ggagattgtg actctttttg aggctcaacg caagttccaa    660
tcaagctacg cttctgctga tcttcaaaag acctaccttc aaatttgggc tcatcagctt    720
ccttttgctt ctggaaacgc cattgtgaat aaagtgggat actgctccct attaaaggga    780
aaggagaaga gagtgcctaa ggctacctat acattccagt acttctctac cctcgatcaa    840
atcaatagaa ctaggcttgg acctaacttc cagcctttta ctaaggagca gagggatgtg    900
atcctcgatg aaatgttcaa caggaccgac tactataaaa agaagaccat tcccgaggtg    960
acctactacg atataagaaa gtggcttgct ctcgatgaaa ccattcagtt caagggacta   1020
acttatgacc ccaacgagga gctgaagaaa atagaactca agtccttcat aaacctcaag   1080
cccttctacg aaatcaagaa ggtggtaacc aactacgcca agaagaccaa cgaagcattc   1140
tctaccctcg attacgatac attcgcttac gctcttaccg tgtataaaac cgacaaggat   1200
ataaggtcct acctcaagaa atcaaacaac ctctccaagt gctgctacga cgatcaatta   1260
attgaggagc ttctcaccct ctcctatact aagttcggac acctctcttt caaggcaatc   1320
aaccatgtgc ttccaataat gcaagaggga agaacttacc aagaggcaat acaccaactt   1380
ggatacgatg ctaccaacct taagaaggag aacaggtcta tgttccttcc tctcttccct   1440
gatgagatta ctaaccctat tgtgaagaga gctttgactc aagctaggaa ggtggtgaat   1500
gctattatta ggaggtacgg atcacctaac tctgtgcata ttgagcttgc tagggagctt   1560
tctaagtctc atgatgagag gaccaagatt atgaaggctc acgatgagaa ctacaagaag   1620
aacaaggggg ctatttccat tctcattgag aacggaattc ttaaccctac cggatacgat   1680
attgtgaggt acaagttgtg gaaggagcaa ggagagagat gcgcttactc tcttaagcaa   1740
attcctgcta acaccttctt caacgagatg aagaaggaaa gatcaggatc tcctgtgctt   1800
gagattgatc acattctccc ttactcccag tccttcattg attcttacca caacaaggtg   1860
cttgtttacg gagatgagaa ccaaaagaag gggaacagga ttccttacac ttacttcctt   1920
gagggaaaca aggattggga gtctttcgag tcttacgtga ggcttaactc cttcttctct   1980
aagaagaaga ggggatacct tcttaagaag gcttatcttc ctagggagtc caatatgatt   2040
aaggagaggc acctaaacga taccaggtac gcttcttctt acctcaagaa cttcatcgag   2100
aagaacctta agttcaagga ggttgaggga tctactagga agaagcatgt tcagaccgtg   2160
aacggaatta ttactgctca tcttagaaag aggtggggac ttgagaagga taggcaagag   2220
acttaccttc atcacgctat ggatgctatt attgtggctt gcactgatca ccatatggtg   2280
actaaggtta ccgagtacta ccagattaag gagtcaaaca agtccatcag gaagccttat   2340
tttcctcttc cttgggttgg attcagggag gagattcttt ctcatcttgc tagacaacct   2400
atcgctagaa agatttccga ggagcttaag attggatacc agtccttcga ttacattctt   2460
gtgtctagga tgcctaagag gtctgttact ggagctgctc atgagcagac tattatgaag   2520
aagggaggaa ttgataagaa ggggaagacc atcatcatta agagggtgta cctaaaggac   2580
atcaagttcg atgagaacgg ggatttcaag atggttggaa aggagcagga tcttgctact   2640
tacgaggcta ttaagcagag gtacattgag tatggaaagg agtctaagaa ggctttcgag   2700
actcctcttt acaagccttc taagaaggga aaggggaacc tcatcaagaa gattaaggtt   2760
gaggttcaga ctaagtcttt cgttagggag gttaatggag gagttgctca gaatggagat   2820
cttgtgaggg ttgatctatt cgagaaggac aacaggtact acatgatccc tatctacgtg   2880
atggatactg ttcattccga gcttcctaac aaggctgtta cttcttctaa gggatacgag   2940
```

```
cagtggctta ccattgataa ctctttcacc ttcaagttct ctctctaccc ttacgatctt   3000

gttaggcttg ttaagggaaa cgaggatagg ttcctctact tctccaccct cgatattaac   3060

tctgataggc tcaacttcaa ggatgtgaac aagccttcaa agcaagctga gaacaggtac   3120

tctcttaaga ccattgagaa ccttgagaag tacgaagtgg gagttcttgg agatcttagg   3180

ttcgttaggc aagagattag gaagaacttc                                    3210


<210> SEQ ID NO 170
<211> LENGTH: 3210
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG05083.1 Corn optimized"

<400> SEQUENCE: 170

atgcgcgagc tagattacag gatcggcctg gatatcggca ctaactcaat aggctggggc     60

atcatcgagc tgagctggaa taaagaccgc gagcagtatg aaaaggccag gatcgtggac    120

aagggcgtga ggatgttcga taaggccgag atcccaaaga caggcgcctc tctggccgaa    180

ccaaggagga tcgccaggtc ttctaggagg agattaaaca ggaagtctca gcgcaagaag    240

gatataagga acctgctggt ccagcatgaa atcatctctc agaaggagct ggccagcctg    300

tacccgctga ccaagtcaag catggacatc tgggatataa ggctggatgg cctggatagg    360

ctgctggata ggttcgagtg gacaaggctg ctgatacatc tggcccagag gaggggcttc    420

aaatcaaata ggaagagcga attaaaggac gtggagacag gcaaggtgct gtcaagcatt    480

caggccaatg aaaagcgcct gagcctgtac aggacagtgg gcgagatgtg gatgaaaaac    540

gaggacttct caaaatacga caagcgccgc aacagcagca acgagtacgt gttcagcgtg    600

agcagggccg acctggagaa ggagatcgtg acactgttcg aggcccagag gaagttccaa    660

tcaagctacg cctctgccga tctgcagaag acatacctgc agatctgggc ccaccagctg    720

ccattcgcta gcggcaatgc catcgtgaat aaagtgggct actgctctct attaaagggc    780

aaggagaaga gggtgccaaa ggccacctat acattccagt acttcagcac cctggaccaa    840

atcaatagga cacgcctggg cccaaacttc cagccattca caaaggagca gcgcgacgtg    900

atcctggatg aaatgttcaa ccgcaccgac tactataaaa agaagaccat cccggaggtg    960

acatactacg atataaggaa gtggctggcc ctggatgaaa ccatccagtt caagggccta   1020

acctacgacc cgaacgagga gctgaagaaa atagaactga agagcttcat aaacctgaag   1080

ccgttctacg aaatcaagaa ggtggtaacc aactacgcca agaaaaccaa cgaagcattc   1140

agcaccctgg actacgatac attcgcctac gccctgaccg tgtataaaac cgacaaggat   1200

ataaggagct acctgaagaa atcaaacaac ctgagcaagt gctgctacga cgaccaatta   1260

atcgaggagc tgctgaccct gagctatact aagttcggcc acctgagctt caaggcaatc   1320

aaccacgtgc tgccaataat gcaggagggc cgcacctacc aggaggcaat acaccagctg   1380

ggctacgacg caaccaacct gaagaaggag aaccgaagca tgttcctgcc gctgttcccg   1440

gacgagatca ccaacccgat cgtgaagcgc gccctgaccc aggcccgcaa ggtggtgaac   1500

gccatcatcc gccgctacgg ctcaccgaac agcgtgcaca ttgagctggc ccgcgagctg   1560

agcaagagcc acgacgagcg cacaaagatc atgaaggccc acgacgagaa ctacaagaag   1620
```

```
aacaagggcg ccatcagcat cctgatcgag aacggcatcc tgaacccaac aggctacgac   1680

atcgtgaggt acaagctgtg gaaggagcag ggcgagaggt gcgcctactc tctgaagcag   1740

atcccagcca atacattctt caacgagatg aagaaggaga ggtcaggctc tccagtgctg   1800

gagattgatc acatcctgcc atacagccag agcttcatcg acagctacca caacaaggtg   1860

ctggtgtacg gcgatgagaa ccagaagaag ggcaatcgca tcccatacac atacttcctg   1920

gagggcaaca aggattggga gagcttcgag agctacgtga ggctgaacag cttcttcagc   1980

aagaagaaga ggggctacct gctgaagaag gcctacctgc caagggagag caacatgatc   2040

aaggagaggc acctaaacga tacaaggtac gccagcagct acctgaagaa cttcatcgag   2100

aagaacctga agttcaagga ggtggagggc agcacccgta agaagcacgt ccagaccgtg   2160

aacggcatca tcacagccca cctgaggaag aggtggggcc tggagaagga taggcaggag   2220

acatacctgc atcacgccat ggatgccatc atcgtggctt gcacagatca ccacatggtg   2280

acaaaggtga cagagtacta ccagatcaag gagagcaaca agtcaatccg caagccatac   2340

ttcccactgc catgggtggg cttcagggag gagatcctgt ctcacctggc caggcagcca   2400

atcgccagga agatctctga ggagctgaag atcggctacc agtctttcga ttacatcctg   2460

gtgtctagga tgccaaagag gtctgtgaca ggcgccgccc acgagcagac aatcatgaag   2520

aagggcggca tcgataagaa gggcaagaca atcatcatca agagggtgta cctgaaggat   2580

atcaagttcg atgagaacgg cgatttcaag atggtgggca aggagcagga tctagccaca   2640

tacgaggcca tcaagcagag gtacatcgag tacggcaagg agtctaagaa ggccttcgag   2700

acaccactgt acaagccatc taagaagggc aagggcaacc tgatcaagaa gatcaaggtg   2760

gaggttcaga ccaagagctt cgtgagggag gtgaatggcg gcgtggccca gaatggcgat   2820

ctggtgaggg tggatctgtt cgagaaggat aacaggtact acatgatccc gatctacgtg   2880

atggatacag tgcacagcga gctgccaaac aaggccgtga catcttctaa gggctacgag   2940

cagtggctaa ccatcgacaa cagcttcacc ttcaagttca gcctgtaccc atacgacctg   3000

gtgaggctgg tgaagggcaa tgaggacagg ttcctgtact tcagcaccct ggacatcaac   3060

agcgacaggc tgaacttcaa ggacgtgaac aagccatcta agcaggccga gaacaggtac   3120

agcctgaaga ccatcgagaa cctggagaag tacgaggtgg gcgtgctggg cgatctgagg   3180

ttcgtgaggc aggagatcag gaagaatttc                                    3210
```

<210> SEQ ID NO 171
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG07433.1 Soy optimized"

<400> SEQUENCE: 171

```
atgagagagc tagattacag gatcggactc gatatcggaa ctaattcaat tggatggggc     60

gtgattgagc tttcctggaa taaagatagg gagcgttatg aaaaggttag gattgtggat    120

cagggagtta ggatgtttga tagagctgag atgcctaaga ctggagcttc attagctgaa    180

ccaagaagga ttgctagatc tagcaggagg agattaaaca ggaagtctca gcgcaagaag    240

aatataagga accttcttgt tcagcacgga gttattactc aggaggagct tgattctctc    300
```

-continued

```
taccctctct ccaagaaatc aatggatatc tggggaatta ggcttgatgg actcgatcgc    360
ctattaaacc attttgagtg ggctaggctt ctaatacacc ttgctcaaag aaggggcttc    420
aaatcaaacc gcaagtccga attaaaggat actgagactg gaaaggtgct ttcaagcatc    480
cagctcaatg aaaagaggct ttctttgtat aggactgttg gggagatgtg gatgaaagat    540
cccgacttct caaaatacga taggaagagg aactctccta acgagtacgt gttttctgtt    600
tctagagctg agcttgagaa ggagattgtg actttgtttg ctgctcaaag gaggttccaa    660
tctccttacg cttctaagga tcttcaagag acctaccttc agatttggac tcatcagctt    720
ccttttgctt ccgggaacgc tattctcaat aaagtgggat actgctcctt attaaaggga    780
aaggagagaa ggattcctaa ggccacctat acattccagt acttctctgc tcttgatcaa    840
gtgaatagaa ctaggcttgg acctgatttc cagcctttta ctaaggagca gcgcgagatc    900
atcctcaata atatgttcca gaggaccgac tactataaaa agaagaccat tcccgaggtg    960
acctactacg atataagaaa gtggcttgag cttgatgaaa ccattcagtt caagggatta   1020
aactacgacc ccaacgagga gctgaagaaa atagagaaga agcccttcat aaacctcaag   1080
gccttctacg aaatcaacaa ggtggtggct aactactctg agcgaaccaa tgaaaccttc   1140
tctaccctcg attacgatgg aattggatac gctcttaccg tgtataaaac cgacaaggat   1200
ataaggtcct acctcaaatc aagccataat ctccctaaga ggtgctacga cgatcaatta   1260
attgaggagc ttctctccct ctcctatact aagttcgggc acctctctct taaggcaatc   1320
aaccatgttc taagcattat gcagaagggg aacacatata aggaggctgt tgatcagctt   1380
ggatacgata cttctggact taagaaggag aagaggtcta agttcctccc tcctatttct   1440
gatgagatta ccaaccctat tgtgaagaga gctttgactc aagctaggaa ggtggtgaat   1500
gctattatta ggaggcatgg atctcctcat tctgtgcata ttgagcttgc tagggagctt   1560
tcaaagaatc acgatgagag gactaagatt gtttctgctc aggacgagaa ctacaagaag   1620
aacaaggggg ctatttctat tctctctgag cacggaattc ttaaccctac cggatacgat   1680
attgtgaggt ataagttgtg gaaggagcaa ggagagagat gcgcttactc tcttaaggaa   1740
attcctgctg ataccttctt caacgagctt aagaaggaaa ggaacggtgc tcctattcta   1800
gaggtggatc acattcttcc ttactcccag tccttcattg attcttacca taacaaggtg   1860
cttgtgtatt ccgatgagaa caggaagaag ggaaacagga ttccttacac ctacttcctt   1920
gagactaata aggattggga ggcttttgag aggtacgtga ggtctaacaa gttcttctct   1980
aagaagaaga gggagtacct tcttaagagg gcttatcttc ctagggagtc agagcttatt   2040
aaggagaggc atcttaacga taccaggtac gcttctacct tcctcaagaa cttcattgag   2100
cagaaccttc aattcaagga agctgaggat aatcctagaa agaggagggt tcagactgtg   2160
aacggagtta ttactgctca ttttagaaag aggtggggac ttgagaagga taggcaagag   2220
acttaccttc atcacgctat ggatgctatt attgtggctt gcactgatca tcatatggtg   2280
actagggtta ccgagtacta ccagatcaag gagtcaaaca agtctgtgaa gaagccttat   2340
tttcctatgc cttgggaagg attcagggat gagcttcttt ctcatcttgc ttctcagcct   2400
atcgctaaga agatttctga agagcttaag gctggatacc agtcccttga ttacattttc   2460
gtgtctagaa tgcctaagag gtctattact ggagctgctc acaagcagac tattatgagg   2520
aagggaggaa ttgataagaa ggggaagacc atcattattg agaggctcca cctcaaggat   2580
atcaagttcg atgagaacgg agatttcaag atggttggaa aggagcagga tatggctact   2640
```

-continued tacgaggcta ttaagcagag atatctagag cacggaaaga actctaagaa ggctttcgag 2700
actcctcttt acaagccttc taagaaggga accggaaacc ttattaagag agttaaggtt 2760
gagggacagg ctaagtcttt cgttagagag gttaatggag gagttgctca gaatggagat 2820
cttgtgaggg ttgatctttt cgagaaggac gataagtact acatggtgcc tatctacgtt 2880
cctgatactg tttgttccga gcttcctaag aaggttgttg cttcttctaa gggatacgag 2940
caatggctta cccttgataa ctctttcacc ttcaagttct ctctctaccc ttacgatctt 3000
gttaggctag ttaagggaga tgaggatagg ttcctttact tcgggaccct cgatattgat 3060
tctgataggc tcaacttcaa ggatgtgaac aagccttcta agaagaacga gtacaggtac 3120
tctctcaaga ccattgagga tcttgagaag tacgaagtgg gagttcttgg agatcttaga 3180
cttgttagaa aggagactag gaggaacttc cac 3213

<210> SEQ ID NO 172
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG07433.1 Corn optimized"

<400> SEQUENCE: 172
atgcgcgagc tagattacag gatcggcctg gatatcggca ctaactcaat cggctggggc 60
gtgatcgagc tgagctggaa taaagatcgc gagcgctatg aaaaggtgcg catcgtggat 120
cagggcgtta ggatgttcga tagggccgag atgccaaaga caggcgcctc actggccgaa 180
ccaaggagga tagccaggtc ttctaggagg agattaaaca ggaagtctca gcgcaagaaa 240
aatatcagga acctgctggt tcagcacggc gtgatcacac aggaggagct ggattctctg 300
tacccactga gcaagaaaag catggacatc tggggcatta ggctagatgg cctggaccgc 360
ctattaaacc acttcgagtg ggcccgccta ttaattcacc tggcccagag gaggggcttc 420
aaatcaaata ggaagagcga attaaaggac accgagacag gcaaggtgct gtcaagcatc 480
cagctgaatg aaaagcgcct gagcctgtac aggacagtgg gcgagatgtg gatgaaagac 540
ccggacttct caaaatacga ccgcaagcgc aacagcccga acgagtacgt gttctctgtg 600
tctagggccg agctggagaa ggagatcgtg acactgttcg ccgctcagag gaggttccag 660
tctccatacg cctctaagga tctgcaagag acatacctgc agatctggac acaccagctg 720
ccattcgcct ctggcaatgc catcctgaat aaagtgggct actgctctct attaaagggc 780
aaggagagga ggattccaaa ggccacctat acattccagt acttcagcgc cctggaccag 840
gtgaatagga caaggctggg cccagatttc cagccattca caaaggagca gcgcgagatc 900
atcctgaata atatgttcca gcgcaccgac tactataaaa agaagaccat cccggaggtg 960
acatactacg atataaggaa gtggctggag ctggatgaaa ccatccagtt caagggatta 1020
aactacgacc cgaacgagga gctgaagaaa atagagaaga agccgttcat aaacctgaag 1080
gccttctacg aaatcaacaa ggtggtggcc aactacagcg agcgaaccaa cgagaccttc 1140
agcaccctgg actacgacgg catcggctac gccctgaccg tgtataaaac cgacaaggat 1200
ataaggagct acctgaaatc aagccacaac ctgccgaagc gctgctacga cgaccaatta 1260
atcgaggagc tgctgagcct gagctatact aagttcggcc acctgagcct gaaggcaatc 1320

-continued

```
aaccacgtgc taagcatcat gcagaagggc aatacataca aggaggccgt ggaccagctg   1380

ggctacgaca ccagcggcct gaagaaggag aagcgcagca agttcctgcc gccgatcagc   1440

gacgagatca ccaacccgat cgtgaagcgc gccctgaccc aggccaggaa ggtggtgaac   1500

gccatcatca ggaggcacgg ctctccacat agcgtgcaca tcgagctggc cagggagctg   1560

tctaagaatc acgatgagag gacaaagatc gtgtcagccc aggacgagaa ctacaagaag   1620

aataagggcg ccatctctat cctgtctgag cacggcatcc tgaacccaac aggctacgac   1680

atcgtgaggt acaagctgtg gaaggagcag ggcgagaggt gcgcctactc tctgaaggag   1740

atcccagccg atacattctt caatgagctg aagaaggaga ggaatggcgc cccaatcctg   1800

gaggtggatc acatcctgcc atactctcag agcttcatcg attcatacca caacaaggtg   1860

ctggtgtaca gcgacgagaa caggaagaag ggcaatcgca tcccatacac atacttcctg   1920

gagaccaaca aggattggga ggccttcgag aggtacgtgc gcagcaacaa gttcttcagc   1980

aagaagaagc gcgagtacct gctgaagagg gcctacctgc ctagggagtc tgagctgatc   2040

aaggagaggc acctgaatga tacaaggtac gccagcacct tcctgaagaa cttcatcgag   2100

cagaacctac agttcaagga ggccgaggat aacccaagga agaggagggt tcagacagtg   2160

aatggcgtga tcacagccca cttcaggaag aggtggggcc tggagaagga taggcaggag   2220

acatacctgc atcacgccat ggatgccatc atcgtggctt gcacagatca ccacatggtg   2280

acaagggtga cagagtacta ccagatcaag gagagcaaca agagcgtgaa gaagccatac   2340

ttcccaatgc catgggaggg cttcagggat gagctactgt ctcacctggc ctctcagcca   2400

atcgccaaga agatctctga ggagctgaag gccggctacc agtctctgga ttacatcttc   2460

gtgtctagga tgccaaagag gtctatcaca ggcgccgccc acaagcagac aatcatgagg   2520

aagggcggca tcgataagaa gggcaagaca atcatcatcg agaggctgca tctgaaggac   2580

atcaagttcg atgagaacgg cgatttcaag atggtgggca aggagcagga tatggccaca   2640

tacgaggcca tcaagcagcg ctacctagag cacggcaaga actctaagaa ggccttcgag   2700

acaccactgt acaagccatc taagaagggc accggcaatc tgatcaagag ggtgaaggtg   2760

gagggccagg ccaagtcttt cgtgagggag gtgaatggcg gcgtggccca gaatggcgat   2820

ctggtgaggg tggatctgtt cgagaaggat gataagtact acatggtgcc aatctacgtg   2880

ccagatacag tgtgctctga gctgccaaag aaggtggtgg cctcttctaa gggctacgag   2940

cagtggctaa cactggataa cagcttcaca ttcaagttca gcctgtaccc atacgatctg   3000

gtgaggctgg tgaagggcga tgaggatagg ttcctgtact tcggcacact ggatatcgat   3060

agcgacaggc tgaacttcaa ggacgtgaac aagccgagca agaagaacga gtaccgctac   3120

agcctgaaga caatcgagga cctggagaag tacgaggtgg gcgtgctggg cgatctgagg   3180

ctggtgagga aggagacaag gaggaatttc cac                                3213
```

<210> SEQ ID NO 173
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG07513.1 Soy optimized"

<400> SEQUENCE: 173

-continued

```
atgagagagc tagattacag gatcggactc gatatcggaa ctaattcaat tggatggggc     60
gtgattgagc tttcctggaa taaagatcgc gagcaatatg aaaagaccag gattgtggat    120
aagggagtga ggatgttcga taaggctgaa attcctaaga ctggagcttc tcttgctgaa    180
ccaagaagaa ttgctagatc tagcaggagg agattaaaca ggaagtctca gcgcaagaag    240
gatataagga accttctcgt tcagcatgaa atcatttccc agaaggaatt aacctctctc    300
taccctctct ccaaatcaag catggacatc tgggatataa ggcttgatgg actcgatagg    360
cttcttgata gatttgagtg ggctaggctt ctaatacacc ttgctcaaag aaggggcttc    420
aaatcaaacc gcaagtccga attaaaggat gttgagactg gaaaggtgct ttcaagcatc    480
caggtgaatg aaaagaggct ttctttgtat aggactgttg gggagatgtg gatgaaaaac    540
gccgattgct caaaatatgg aaagaggagg aactctccta acgagtacgt gttttctgtt    600
tctagggctg atcttgagaa ggagattgtg actctttttg aggctcagag gaagttccac    660
tcttcttacg cttctgtgga tctccaaaag acatacattc agatttgggc tcatcagctt    720
ccttttgctt ctggaaacgc cattgtgaat aaagtgggat actgctccct attaaaggga    780
aaggagaaga gagtgcctaa ggctacctat acattccagt acttcaatac cctcgatcaa    840
atcaacagaa ctaggcttgg acctaacttc cagccttta ctaaggagca gagggatata    900
atcctcgata aaatgttcca gcgcaccgac tactataaaa agaagaccat ccccgaggtg    960
acctactacg atataagaaa gtggcttgct ctcgatgaaa ccattcagtt caagggacta   1020
acttatgacc ccaacgagga gctgaagaaa atagagatga aacccttcat aaacctcaag   1080
cccttctacg aaatcaagaa ggtggtaacc aactacgcca agaaaaccaa cgaggtgttc   1140
tctgctcttg attacgatac tgtggcttac gctcttaccg tgtataaaac cgacaaggat   1200
ataaggtctt acctcaagcg ctccaataat ctctctaaga ggtgctacga cgatcaatta   1260
attgaggagc ttctcaccct ctcctatact aagttcggac acctctcttt caaggcaatc   1320
aaccatgtgc ttccaataat gcaagaggga agaacttacc aagaggcaat acaccagctt   1380
ggatacgata caaccaacct caagaaggag aatagaagca tgttcctccc aatcatccct   1440
gatgaaataa ccaaccctat tgtgaagaga gctttgactc aagctaggaa ggtggtgaat   1500
gcaataatta ggaggtacgg atcacctaac tctgtgcata ttgagcttgc cagggaatta   1560
agcaagtctc atgatgagag gaagaagatt atgactgctc acgacgagaa ctacaagaag   1620
aacaagggag ctgtgtccat tctcattgat aacggaattc ttaaccctac cggatacgat   1680
attgtgaggt acaagttgtg gaaggagcaa ggagagagat gcgcttactc tcttaagaag   1740
attcctgcta acaccttctt caacgagctt aagaaggaaa gatctggacc tcctgttctt   1800
gaggtggatc acattctacc ttactcccag tccttcattg attcttacca taacaaggtg   1860
cttgtttacg gagatgagaa ccaaaagaag gggaacagga ttccttacac tttcttctct   1920
gaagaagata aggagtggga gtctttcgag tcttacgtga ggtccaactc cttcttctct   1980
aagaagaaga ggggatacct tcttaagaag gcttatcttc ctagggagtc taaccttatt   2040
aaggagaggc accttaacga taccaggtac gcttcatctt acctcaagaa cttcatcgag   2100
aagaacctta agttcaagga ggctgtggga attactagga agaagtacgt tcagactgtg   2160
aacggagtga ttactgctca tcttagaaag agatggggac ttgagaagga taggcaagag   2220
acttaccttc atcacgctat ggatgctatt attgtggctt gcactgatca ccatatggtg   2280
actaaggtta ccgagtacta ccaaattaag gaggggaaca agtccatcaa gaagccttat   2340
tttcctctac cttggatggg attcagggag gagattcttt ctcatcttga gtctcaacct   2400
```

atcgctagaa agatttccga ggagcttaag attggatacc agtcccctga ttacattctt 2460
gtgtctagaa tgcctaagag gtctgttact ggatctgctc atgatcagac tgtgatgaag 2520
aagggggata ttgataagaa ggggaagacc atcattatta agagggtgca cctcaaggac 2580
atcaagttcg atgagaacgg agatttcaag atggttggaa aggagcagga tctagctact 2640
tacgaggcta ttaagcagag gtatcttgag tataggaagg agtctaagaa ggctttcgag 2700
actcctcttt acaagccttc taagaaggga aaggggaacc tcatcaagaa gattaaggtt 2760
gaggttcaga ctaagtcttt cgtgagggag attaatggag gagttgctca gaatggagat 2820
cttgtgaggg ttgatctttt cgagaaggac aacaggtact acatggtgcc tatctacgtt 2880
gttgatactg ttaggtctga gctacctaac aaggctgtta cttcttctaa gggatacgag 2940
cagtggctct ctattgataa ctctttcacc ttcaagttct ctctctaccc ttacgatctt 3000
gttaggcttg ttaagggaga tgaggatagg ttcctctact tctccaccct cgatattaac 3060
tctgataggc tcaacttcaa ggatgtgaac aagccttcta agcaagctga gtacaggtac 3120
tctcttaaga ccattgagaa ccttgagaag tacgagattg gagttcttgg agatctaagg 3180
cttgttaggc aggagaccag gaagattttc aag 3213

<210> SEQ ID NO 174
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG07513.1 Corn optimized"

<400> SEQUENCE: 174
atgcgcgagc tagattacag gatcggcctg gatatcggca ctaactcaat cggctggggc 60
gtgatcgagc tgagctggaa taaagatcgc gagcagtatg aaaagaccag gatcgtggac 120
aagggcgtga ggatgttcga taaggccgag atcccaaaga caggcgcctc tctggccgaa 180
ccaaggagga tcgccaggtc ttctaggagg agattaaaca ggaagtctca gcgcaagaag 240
gatataagga acctgctggt ccagcatgaa atcatcagcc agaaggagct gacaagcctg 300
tacccgctga gcaagtcaag catggacatc tgggatataa ggctggatgg cctggatagg 360
ctgctggata ggttcgagtg ggccaggctg ctgatacatc tggcccagag gaggggcttc 420
aaatcaaatc gcaagagcga attaaaggac gtggagacag gcaaggtgct gtcaagcatt 480
caggtgaatg aaaagaggct gagcctgtac aggacagtgg gcgagatgtg gatgaaaaac 540
gccgactgct caaaatacgg caagcgccgc aacagcccaa acgagtacgt gttctctgtg 600
tctagggccg atctggagaa ggagatcgtg acactgttcg aggcccagag gaagttccac 660
tcttcttacg cctctgtgga cctgcagaag acatacatcc agatctgggc ccaccagctg 720
ccattcgcct ctggcaatgc catcgtgaat aaagtgggct actgctctct attaaagggc 780
aaggagaaga gggtgccaaa ggccacctat acattccagt acttcaatac cctggaccaa 840
atcaacagga cccgcctggg cccaaacttc cagccattca caaaggagca gcgcgatata 900
atcctggata aaatgttcca gcgcaccgac tactataaaa agaagaccat cccggaggtg 960
acatactacg atataaggaa gtggctggcc ctggatgaaa ccatccagtt caagggccta 1020
acctacgacc cgaacgagga gctgaagaag atcgagatga aaccgttcat aaacctgaag 1080
ccgttctacg aaatcaagaa ggtggtaacc aactacgcca agaaaaccaa cgaggtgttc 1140
agcgccctgg actacgacac cgtggcctac gccctgaccg tgtataaaac cgacaaggat 1200
ataaggagct acctgaagcg cagcaataat ctgagcaagc gctgctacga cgaccaatta 1260
atcgaggagc tgctgaccct gagctatact aagttcggcc acctgagctt caaggcaatc 1320
aaccacgtgc tgccaataat gcaggagggc cgcacctacc aggaggcaat acaccagctg 1380
ggctacgaca caaccaacct gaagaaggag aaccgaagca tgttcctgcc aataatcccg 1440
gacgagataa ccaacccgat cgtgaagcgc gccctgaccc aggcccgcaa ggtggtgaac 1500
gcaataatcc gccgctacgg ctcaccgaac agcgtgcaca ttgagctggc ccgcgaatta 1560
agcaagagcc acgacgagcg caagaagatc atgaccgccc acgatgaaaa ctacaagaaa 1620
aataagggcg ccgtgagcat cctgatcgac aacggcatcc tgaacccgac cggctacgac 1680
atcgtgcgct acaagctgtg gaaggagcag ggcgagaggt gcgcctactc tctgaagaag 1740
atcccagcca acaccttctt caacgagctg aagaaggaga ggtctggccc accagtgctg 1800
gaggtggatc acatcctgcc atactcacag agcttcatcg atagctacca caacaaggtg 1860
ctggtgtacg gcgatgagaa ccagaagaag ggcaatcgca tcccatacac attcttcagc 1920
gaggaggata aggagtggga gagcttcgag agctacgtga ggagcaacag cttcttcagc 1980
aagaagaaga ggggctacct gctgaagaag gcctacctgc caagggagtc taacctgatc 2040
aaggagaggc acctgaacga tacaaggtac gccagcagct acctaaagaa cttcatcgag 2100
aagaacctga agttcaagga ggccgtgggc atcacccgca agaagtacgt ccagacagtg 2160
aacggcgtga tcacagccca cctgaggaag aggtggggcc tggagaagga taggcaggag 2220
acatacctgc atcacgccat ggatgccatc atcgtggctt gcacagatca ccacatggtg 2280
acaaaggtga cagagtacta ccagatcaag gagggcaaca agagcatcaa gaagccatac 2340
ttcccactac catggatggg cttcagggag gagatcctgt ctcacctgga gtctcagcca 2400
atcgccagga agatctctga ggagctgaag atcggctacc agtctccaga ttacatcctg 2460
gtgtctagga tgccaaagag gtctgtgaca ggctctgccc acgatcagac agtgatgaag 2520
aagggcgata tcgacaagaa gggcaagacc atcatcatca agagggtgca cctgaaggac 2580
atcaagttcg acgagaacgg cgacttcaag atggtgggca aggagcagga tctagccaca 2640
tacgaggcca tcaagcagcg ctacctggag tacaggaagg agtctaagaa ggccttcgag 2700
acaccactgt acaagccatc taagaagggc aagggcaacc tgatcaagaa gatcaaggtg 2760
gaggtccaga ccaagagctt cgtgagggag atcaatggcg gcgtggccca gaatggcgat 2820
ctggtgaggg tggatctgtt cgagaaggat aacaggtact acatggtgcc aatctacgtg 2880
gtggatacag tgaggagcga gctaccaaac aaggccgtga catcttctaa gggctacgag 2940
cagtggctga gcatcgacaa cagcttcacc ttcaagttca gcctgtaccc atacgatctg 3000
gtgaggctgg tgaagggcga tgaggacagg ttcctgtact tcagcacact ggacatcaac 3060
agcgacaggc tgaacttcaa ggacgtgaac aagccatcta agcaggccga gtacaggtac 3120
agcctgaaga ccatcgagaa cctggagaag tacgagatcg gcgtgctggg cgatctaagg 3180
ctggtgaggc aggagacaag gaagatcttc aag 3213

<210> SEQ ID NO 175
<211> LENGTH: 3216
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG08290.1 Soy optimized"

<400> SEQUENCE: 175

atgtctgagc tagattacag gatcggactc gatatcggaa ctaattcaat tggatgggga      60

gtgattgagc ttttctggaa taaagatcgc gagcgctatg aaaaggttag gattgtggat     120

aagggagtga ggatgttcga taaggccgag attcctaata aaggagcttc acttgctgaa     180

ccaagaagga ttgctagatc tagcaggagg agattaaaca ggaagtctca gaggaagaag     240

gagattagga accttcttgt tcagcacgga atgattactc aggaggagct tgatcttctc     300

taccctctct ccaagaaatc aatcgatatc tgggatataa ggcttgatgg actcgatagg     360

ctattaaacc atcttgagtg ggctaggctt ctaatacacc ttgctcaaag aaggggcttc     420

aaatcaaacc gcaagtccga attaaaggat gctgagactg gaaaggttct ttcaagcatc     480

caggtgaatg aaaagaggct tttcttgtat aggactgtgg gcgagatgtg gataaaagat     540

gccgagttct caaaatatga taggaggagg aactctccta acgagtacgt gttttctgtt     600

tctagggctg atcttgagaa ggagattgtg actttgtttg aggctcaacg caagttccaa     660

tcaagctacg cttctaagaa ccttcaagag acctaccttc aaatttgggc tcatcagctt     720

ccttttgctt ccgggaacgc tattctcaat aaagtgggat actgctcctt attaaaggga     780

aaggagagaa ggattcctaa ggccacctat acattccagt acttctctgc tcttgatcaa     840

gtgaatagaa ctaggcttgg acctgatttc caacctttca ctcaggagca gaaggaaata     900

atcctcgata aaatgttcca gcgcaccgac tactataaaa agaagaccat ccccgaggtg     960

tcctactacg atataagaaa gtggcttgag cttgatgaaa ccattcagtt caagggatta    1020

aactacgacc ccaacgagga gctgaagaaa atagagaaga agcccttcat aaacctcaag    1080

gccttctacg aaatcaagaa ggtggttgct aactacgctg aacgaaccaa cgaagcattc    1140

tctaccctcg attacgatgc tattgcttac gctcttaccg tgtataaaac cgacaaggat    1200

ataaggtcct acctcaagaa atcaaacaac ctctccaaga ggtgctacga cgatcaatta    1260

atcgaggagc ttttcaccct ctcctatact aagttcggac acctctcttt caaggcaatc    1320

aaccatgtgc ttcctattat gcaagaggga agaacttacc aagaggctat tcatcagctt    1380

ggatacgata ccaccaacct taagaaggag aacaggtcta tgttcctccc tctcattcct    1440

gatgagatta ctaaccctat tgtgaagagg gctattactc aagctaggaa ggtggtgaat    1500

gctattatta ggaggtacgg atcacctaac tctgtgcata ttgagcttgc tagggagctt    1560

tctaagtctc atgatgagag gaagaagatt atgactgctc acgacgagaa ctacaagaag    1620

aacaaggggg ctatttccat tctcattgag aacggaattc ttaaccctac cggatacgat    1680

attgtgaggt acaagttgtg gaaggagcaa ggagagagat gcgcttactc tcttaaggaa    1740

attcctcctg ataccttctt caacgagctt aagaaggaga ggaacggatc acctattctt    1800

gaggtggatc acattcttcc ttactcccag tccttcattg attcttacca taacaaggtg    1860

cttgtgtatt ccgatgagaa caggaacaag ggaaacagga ttccttacac ctacttcctt    1920

gagactaata aggattggga ggcttttgag aggtatgtga ggtctaacaa gctcttctct    1980

aagaagaaga gggagtacct ccttaagaag acttaccttc ctagggagtc tgagcttatt    2040

aaggagaggc atctaaacga taccaggtac gcttctacct tcctcaagaa cttcattgag    2100
```

```
cagaaccttc aattcaagga ggttgaggtt aaccttagga agaagagggt tcagactgtg   2160
aacggagtta ttactgctca tcttagaaag agatggggac ttgagaagaa caggcaagag   2220
acttaccttc atcacgctat ggatgctatt attgtggctt gcactgatca tcacatggtg   2280
actaggatta ccgagtacta ccagattaag gagtcaaaca agtctgtgaa gaagccttat   2340
tttcctatgc cttgggaggg attcagggat gagcttcttt ctcatcttgc ttctcagcct   2400
atcgctaaga agatttctga agagcttaag gctggatacc agtcctctga ttacattttc   2460
gtgtctagaa tgcctaagag gtctgttact ggagctgctc atgatcaaac tattaggagg   2520
aagggaggaa ttgataagaa ggggaagacc atcattatta agagggtgag gctaaaggac   2580
atcaagttcg atgagaacgg ggatttcaag atggttggaa aggagcagga tcttgctact   2640
tacgaggcta ttaagcagag atatcttgag cacaggaaga actctaagaa ggctttcgag   2700
actcctcttt acaagccttc taagaaggga accggaaacc ttatcaagag agttaagatt   2760
gagggacaga ctaaggcttt cgttagagag gttaatggag gagttgctca gaactctgat   2820
cttgtgaggg ttgatctatt cgagaaggac gataagtact acatggtgcc tatctacgtt   2880
cctgatactg tttgttccga gcttcctaag aaggttgtta agtctggaaa gggatacgag   2940
caatggctta cccttgataa ctctttcacc ttcaagtctt ctctctaccc ttacgatctt   3000
gttaggcttg ttaagggaaa cgaggatagg ttcctttact tcgggaccct cgatattgat   3060
tctgataggc tcaacttcaa ggatgtgaac aagccttcaa agcaaaacga gtacaggtac   3120
tctctcaaga ccattgagaa ccttgagaag tacgaagtgg gagttcttgg agatcttagg   3180
cttgttaagc aagagaccag gaggattttc aatagg                             3216
```

```
<210> SEQ ID NO 176
<211> LENGTH: 3216
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG08290.1 Corn optimized"

<400> SEQUENCE: 176
```

```
atgtcagagc tggactacag gatcggcctg gacataggca ctaattcaat cggctggggc     60
gtgatcgagc tgttctggaa taaagaccgc gagcgctatg aaaaggtgcg catcgtggac    120
aagggcgtta ggatgttcga taaggccgag atcccgaata aaggcgcctc actagccgaa    180
ccaaggagga tcgccaggtc ttctaggagg agattaaaca ggaagtctca gaggaagaag    240
gagatcagga acctgctggt ccagcacggc atgatcacac aggaggagct ggatctgctg    300
tacccactga gcaagaaaag cattgacatc tgggacatca ggctagatgg cctggacagg    360
ctgctgaatc acctggagtg ggccaggctg ctgatacatc tggcccagag gaggggcttc    420
aaatcaaatc gcaagtctga attaaaggat gccgagacag gcaaggtgct gtcaagcatc    480
caggtgaatg aaaagaggct gttcctctac cgcacagtgg gcgagatgtg gataaaagac    540
gccgagttca gcaagtacga caggaggagg aacagcccaa acgagtacgt gttctctgtg    600
tcaagggccg atctggagaa ggagatcgtg acactgtttg aggctcagcg caagttccaa    660
tcaagctacg ccagcaagaa cctgcaagag acctacctgc agatctgggc ccaccagctg    720
ccattcgcta gcggcaatgc catcctgaat aaagtgggct actgctctct attaaagggc    780
```

-continued

```
aaggagagga ggattccaaa ggccacctat acattccagt acttcagcgc cctggaccag    840
gtgaatagga caaggctggg cccagatttc cagccattca cacaggagca gaaggaaata    900
atcctggata aaatgttcca gcgcaccgac tactataaaa agaagaccat cccggaggtg    960
tcatactacg atataaggaa gtggctggag ctggatgaaa ccatccagtt caagggatta   1020
aactacgacc cgaacgagga gctgaagaaa atagagaaga agccgttcat aaacctgaag   1080
gccttctacg aaatcaagaa ggtggtggcc aactacgccg agcgaaccaa cgaagcattc   1140
agcaccctgg actacgacgc catcgcctac gccctgaccg tgtataaaac cgacaaggat   1200
ataaggtcat acctgaagaa atcaaacaac ctgagcaagc gctgctacga cgaccaatta   1260
atcgaggagc tgttcaccct gagctatact aagttcggcc acctgagctt caaggcaatc   1320
aaccacgtgc tgccaataat gcaggagggc cgcacctacc aggaggcaat acaccagctg   1380
ggctacgaca ccaccaacct gaagaaggag aaccgcagca tgttcctgcc gctaatcccg   1440
gacgagatca ccaacccgat cgtgaagcgc gccatcaccc aggctaggaa ggtggtgaac   1500
gccatcatcc gccgctacgg cagcccgaac agcgtgcaca tcgagctggc ccgcgagctg   1560
agcaagagcc acgacgagcg caagaagatc atgacagccc acgacgagaa ctacaagaag   1620
aacaagggcg ccatctcaat cctgatcgag aacggcatcc tgaacccaac cggctatgac   1680
atcgtgcgct acaagctgtg gaaggagcag ggcgagaggt gcgcctactc tctgaaggag   1740
atcccaccag atacattctt caacgagctg aagaaggaga ggaatggctc tccaatcctg   1800
gaggtggatc acatcctgcc atacagccag tcattcatcg acagctacca caacaaggtg   1860
ctggtgtaca gcgatgagaa caggaacaag ggcaaccgca tcccgtacac atacttcctg   1920
gagaccaaca aggattggga ggccttcgag aggtacgtga ggagcaacaa gctgttcagc   1980
aagaagaagc gcgagtacct gctgaagaag acctacctgc caagggagtc agagctgatc   2040
aaggagaggc acctgaacga tacaaggtac gctagcacct tcctgaagaa cttcatcgag   2100
cagaacctgc agttcaagga ggtggaggtg aacctgagga agaagcgcgt tcagacagtg   2160
aacggcgtga tcacagccca cctgaggaag aggtggggcc tggagaagaa taggcaggag   2220
acatacctac accacgccat ggatgccatc atcgtggctt gcacagatca ccacatggtg   2280
acaaggatca cagagtacta ccagatcaag gagagcaaca agagcgtgaa gaagccatac   2340
ttcccaatgc catgggaggg cttcagggat gagctgctgt ctcacctggc ctctcagcca   2400
atcgccaaga agatctcaga ggagctgaag gccggctacc agtcttctga ttacatcttc   2460
gtgtctagga tgccaaagag gtctgtgaca ggcgccgccc acgatcagac aatcaggagg   2520
aagggcggca tcgataagaa gggcaagaca atcatcatca agagggtgag gctgaaggat   2580
atcaagttcg atgagaacgg cgatttcaag atggtgggca aggagcagga tctagccaca   2640
tacgaggcca tcaagcagcg ctacctggag cacaggaaga actctaagaa ggccttcgag   2700
acaccactgt acaagccatc taagaagggc accggcaatc tgatcaagag ggtgaagatc   2760
gagggccaga caaaggcctt cgtgagggag gtgaatggcg gcgtggccca gaattctgat   2820
ctggtgaggg tggatctatt cgagaaggac gataagtact acatggtgcc aatctacgtg   2880
ccagatacag tgtgctccga gctgccaaag aaggtggtga agtctggcaa gggctacgag   2940
cagtggctca cactggataa cagcttcaca ttcaagagca gcctgtaccc atacgatctg   3000
gtgaggctgg tgaagggcaa tgaggacagg ttcctgtact tcggcacact agacatcgat   3060
agcgacaggc tgaacttcaa ggacgtgaac aagccaagca agcagaacga gtaccgctac   3120
agcctgaaga ccatcgagaa cctggagaag tacgaggtgg gcgtgctggg cgatctgagg   3180
```

ctggtgaagc aggagacaag gaggatcttc aatagg 3216

<210> SEQ ID NO 177
<211> LENGTH: 4011
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="APG05459.1 Soy optimized"

<400> SEQUENCE: 177
atgaagaagg actacgtgat cggactagat attggaacta actctgtggg atgggctgtt 60
atgactgagg attaccagct agttaagaag aagatgccca tctacgggaa tacagagaag 120
aagaagatca agaagaactt ctggggagtg agactatttg aagagggtca tactgctgag 180
gataggagat taaagagaac tgctaggaga aggatttcta ggaggaggaa caggcttcgt 240
taccttcaag cattctttga agaggctatg accgctctag atgaaaattt cttcgctagg 300
cttcaggagt cttttcttgt gcctgaggat aaaaagtggc acaggcatcc tatttttgct 360
aagttagagg atgaggtggc ttaccatgaa acctacccta ctatctacca ccttaggaag 420
aagttggctg attcttcaga gcaagccgac ttgagattaa tctaccttgc tcttgcccac 480
attgtaaaat ataggggaca cttccttatc gagggaaaac tctccaccga aaatatttca 540
gtgaaggagc agtttcagca gttcatgatc atctataacc aaaccttcgt gaacggagaa 600
tcaaggcttg tgtctgctcc tcttcctgag tccgtattaa ttgaggagga acttactgag 660
aaagcatcca gaaccaagaa gtctgagaag gttcttcaac agtttcctca agagaaggct 720
aacggacttt tcggacagtt cctcaaatta atggtgggga ataaagccga cttcaagaag 780
gtttttggac ttgaggagga ggccaaaata acttacgctt ctgagtctta tgaggaggat 840
cttgagggaa tactagctaa ggtgggagat gaatacagcg atgttttcct tgctgctaag 900
aacgtttacg acgctgtgga attaagcacc atactagctg actccgataa aaagtctcac 960
gccaaactct cttcaagcat gattgttagg ttcactgagc atcaggagga tcttaagaag 1020
ttcaagaggt tcattaggga gaactgccct gatgagtacg ataacctttt caagaacgag 1080
caaaaggatg ggtacgctgg atacattgct catgctggaa aggtgtcaca attaaagttc 1140
taccagtacg tgaagaaaat aatccaggat atcgctggag ccgagtactt ccttgagaaa 1200
atagctcagg agaacttcct taggaagcag aggactttcg ataacggagt gattcctcac 1260
caaatacacc ttgctgagct acaggcaata attcataggc aagctgcata ctatcctttc 1320
ctcaaggaga atcaagagaa aatagagcag ctcgtgacct tcagaattcc atactacgtg 1380
ggacctcttt ctaagggaga tgcttctact tttgcttggc ttaagagaca gtcagaggaa 1440
ccaattaggc cttggaatct tcaagagact gtggatcttg atcaatctgc tactgctttc 1500
atagagagga tgaccaactt cgatacatac cttccttctg agaaggtgct ccctaagcat 1560
tctctcctct atgaaaagtt catggtgttc aacgagctaa ccaaaatatc ctacaccgac 1620
gataggggaa tcaaggctaa tttctctgga aaggagaagg agaaaatatt cgactacctc 1680
ttcaagacca ggaggaaggt gaagaagaag gacataatac agttctaccg caacgaatac 1740
aacaccgaga ttgtgacctt gtcaggactt gaggaggatc aattcaacgc ttctttctct 1800
acctaccagg atctattaaa gtgcggactt actagggctg agcttgatca tcctgataat 1860
gctgagaagc tggaggacat aatcaagata ctaaccatct tcgaggatag gcaaaggatt 1920
aggacccagc tttctacttt caagggacaa ttctctgctg aggttcttaa gaagttggag 1980
aggaagcatt atactggatg ggaaggctc tctaagaagc tcattaacgg aatctacgat 2040
aaggagtcag ggaagaccat cctagattac ctcattaagg atgatggagt gtctaagcac 2100
tacaacagga acttcatgca gctcattaac gattcccagc tctccttcaa gaacgctatt 2160
caaaaggctc aatcttctga gcatgaagag actctttctg agactgttaa cgaattagct 2220
gggtcccctg ctattaagaa gggaatctac cagtctctca agattgtgga tgagcttgtg 2280
gctattatgg gatatgctcc taagaggatt gttgttgaga tggctaggga gaaccaaact 2340
acttctactg gaaagaggag gtctattcag aggctaaaga ttgttgaaaa ggctatggct 2400
gagattggat ctaaccttct taaggagcag cctactacta acgagcaact tagggatacc 2460
aggctcttcc tttactacat gcagaacgga aaggatatgt acactggaga tgagctttct 2520
cttcataggc tctcacacta cgacatagat cacattatcc ctcagtcctt catgaaggat 2580
gattctctcg ataaccttgt gcttgtggga tctactgaga ataggggaaa gtctgatgat 2640
gttccttcta aggaggtggt taaggatatg aaggcttact gggagaaact atacgctgct 2700
ggacttattt ctcaaaggaa gttccagaga cttactaagg gagagcaagg aggacttact 2760
cttgaggata aggctcattt cattcaaagg cagcttgttg agaccaggca gattactaag 2820
aacgtggctg gaattctaga tcaaaggtac aacgctaact ctaaggagaa gaaggttcag 2880
atcattaccc tcaaggcttc tcttacctcc cagttcaggt ctattttcgg actttacaag 2940
gttagggagg tgaacgatta ccatcatgga caagatgctt accttaactg cgtggttgct 3000
actactctac ttaaggttta tcctaacctt gctcctgagt tcgtttacgg agagtatcct 3060
aagttccagg ctttcaagga gaataaggct accgctaaga ccattatcta caccaacctt 3120
atgaggttct ttactgagga tgagcctagg tttatgaagg atggagagat tctctggtca 3180
aactcctacc tcaagaacat caagaaggag cttaactacc accagatgaa cattgtgaag 3240
aaggtggagg ttcaaaaggg aggattctcc aaggagtcta ttaagcctaa gggaccttct 3300
aacaagctca ttcctgtgaa gaacggactt gatcctcaaa agtacggagg attcgattca 3360
cctgttgttg cttacactgt tcttttcact cacgaaaagg ggaagaagcc tctcattaag 3420
caggagattc tcggaattac cattatggag aagactaggt tcgagcagaa ccctattctt 3480
tttctagagg agaagggatt tcttaggcct agggttctta tgaagctccc taagtacact 3540
ctttatgagt ttcctgaggg aagaaggaga cttcttgctt ctgctaagga ggctcaaaag 3600
ggaaaccaaa tggttcttcc tgagcacctt cttactcttc tttaccatgc taagcaatgc 3660
ctacttccta accaatctga gtctcttgct tacgtagaac aacatcaacc tgagttccaa 3720
gagattcttg agagggttgt ggatttcgct gaggttcata cccttgctaa gtctaaggtt 3780
cagcagattg ttaagttgtt cgaggctaac cagactgctg atgttaagga gatcgctgct 3840
tcattcattc agcttatgca attcaatgct atgggtgctc cttctacctt caagttcttc 3900
cagaaggata tagagagggc taggtacacc tccatcaagg agattttcga tgctaccatt 3960
atctaccagt ctactactgg actttatgag actaggagga aggtggttga t 4011

<210> SEQ ID NO 178
<211> LENGTH: 4011
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG05459.1 Corn optimized"

<400> SEQUENCE: 178

atgaaaaagg actacgtgat cggcctggac atcggcacta attcagtggg ctgggccgtg     60

atgacagagg actaccagct ggtgaagaag aagatgccta tctacggcaa cactgagaag    120

aagaagatca agaagaactt ctggggcgtg cgcctattcg aggagggcca cacagccgag    180

gaccgcagat taaagaggac agccaggagg aggatctcta ggaggaggaa taggctgcgc    240

tacctgcaag cattcttcga ggaggccatg acagccctgg atgaaaattt cttcgccagg    300

ctgcaggagt ctttcctagt gccggaggat aaaaagtggc acaggcaccc tatcttcgcc    360

aagctggagg atgaggtggc ctaccatgaa acatacccaa caatctacca cctgaggaag    420

aagctggccg attcttctga gcaggccgac ctgagattaa tctacctggc cctggcccac    480

atcgtcaaat acaggggcca cttcctgatc gagggcaaac tgagcacaga aaatatcagc    540

gtgaaggagc agttccagca gttcatgatc atctataacc aaaccttcgt gaacggcgaa    600

tcaaggctgg tgagcgcccc actgccggag agcgtattaa tcgaggagga actgaccgag    660

aaagcatccc gaaccaagaa gagcgagaag gtgctgcagc agttcccgca agagaaggct    720

aatggcctgt tcggtcagtt cctgaaactg atggtgggca ataaagccga cttcaagaag    780

gtgttcggcc tagaggagga ggccaaaata acctacgcca gcgagagcta cgaggaggac    840

ctggagggca tactagccaa ggtgggcgat gaatacagcg atgtgttcct ggccgccaag    900

aatgtgtacg atgccgtgga gctgtctaca atactagccg acagcgataa aaagagccac    960

gccaagctct cttcaagcat gatcgtgagg ttcacagagc atcaggagga cctgaagaag   1020

ttcaagcgct tcatcaggga gaactgcccg gacgagtacg acaacctgtt caagaacgag   1080

cagaaggatg gctacgccgg atacatcgcc cacgccggta aggtgtccca attaaagttc   1140

taccagtacg tgaagaaaat aatccaggac atcgccggcg ccgagtactt cctggagaaa   1200

atagcccagg agaacttcct gcgcaagcag aggacattcg acaacggcgt catcccgcac   1260

cagatacatc tggccgagct gcaggccatc atacataggc aggccgcata ctacccattc   1320

ctaaaggaga accaagagaa aatagagcag ctggtgacct tccgcatccc atactacgtg   1380

ggcccactgt ctaagggcga tgcctctaca ttcgcctggc tgaagaggca gtctgaggaa   1440

ccaatcaggc catggaatct gcaagagaca gtggatctgg atcagtctgc cacagccttc   1500

atcgagagga tgaccaactt cgatacatac ctaccaagcg agaaggtgct gccaaagcat   1560

agcctgctgt atgaaaagtt catggtgttc aacgagctaa ccaagatcag ctacaccgac   1620

gaccgcggaa tcaaggccaa cttcagcggc aaggagaagg agaaaatatt cgactacctg   1680

ttcaagaccc gccgcaaggt gaagaagaag gacataatac agttctaccg caacgaatac   1740

aacaccgaga tcgtgaccct gagcggcctt gaggaggacc agttcaacgc cagcttctca   1800

acctaccagg acctattaaa gtgcggcctg acccgcgccg agctggacca cccggataac   1860

gccgagaagc tggaggacat aatcaagata ctaaccatct tcgaggaccg ccagcgcatc   1920

cgcacccaat taagcacctt caagggccag ttcagcgccg aggtattaaa gaagctggag   1980

cgcaagcatt acacaggctg ggcaggctg agcaagaagc taatcaacgg catctacgac   2040

aaggagagcg gcaagaccat ccttgactac ctgatcaagg acgatggcgt gagcaagcac   2100
```

-continued

```
tacaaccgca acttcatgca gctgatcaac gacagccagc tgagcttcaa gaacgccatc   2160

cagaaggccc agtcttctga gcacgaggag acactgtctg agacagtgaa tgagctggcc   2220

ggctcaccag ccatcaagaa gggcatctac cagtctctga agatcgtgga tgagctggtg   2280

gccatcatgg gctacgcccc aaagaggatc gtggtggaga tggccaggga gaatcagaca   2340

acatcaacag gcaagaggag gtctatccag aggctgaaga tcgtggagaa ggccatggcc   2400

gagatcggct ctaatctgct gaaggagcag ccaacaacaa atgagcagct gagggataca   2460

aggctgttcc tgtactacat gcagaatggc aaggatatgt acacaggcga tgagctgtct   2520

ctgcataggc tgagccacta cgacatcgat cacatcatcc cgcagtcatt catgaaggac   2580

gactctctgg ataatctggt gctggtgggc tctacagaga acaggggcaa gagcgatgat   2640

gtgccatcta aggaggtggt gaaggatatg aaggcctact gggagaagct gtacgccgcc   2700

ggcctgatct ctcagaggaa gttccagagg ctgacaaagg gcgagcaggg cggcctgaca   2760

ctggaggata aggcccactt catccagagg cagctagtgg agacaaggca gatcacaaag   2820

aatgtggccg gcatcctgga tcagaggtac aatgccaatt ctaaggagaa gaaggttcag   2880

atcatcacac tgaaggcctc tctgacatct cagttcaggt ctatcttcgg cctgtacaag   2940

gtgcgcgagg tgaatgatta ccaccacggc caggatgcct acctgaattg cgtggtggcc   3000

acaacactac tgaaggtgta cccaaatctg gccccagagt tcgtgtacgg cgagtaccca   3060

aagttccagg ccttcaagga gaataaggcc acagccaaga caatcatcta cacaaacctg   3120

atgaggttct tcacagagga cgagccaagg ttcatgaagg atggcgagat cctgtggagc   3180

aacagctacc tgaagaacat caagaaggag ctgaactacc accagatgaa catcgtgaag   3240

aaggtggagg tccagaaggg cggcttctca aaggagagca tcaagccgaa gggcccgagc   3300

aacaagctga tcccagtgaa gaatggcctg gacccacaga agtacggcgg ctttgattct   3360

ccagtggtgg cctacacagt gctgttcaca cacgagaagg gcaagaagcc actgatcaag   3420

caggagatcc tgggcatcac aatcatggag aagacaaggt tcgagcagaa cccaatcctg   3480

ttcctggagg agaagggctt cctgaggcca agggtgctga tgaagctacc aaagtacaca   3540

ctgtacgagt tcccagaggg caggaggagg ctgctggcct ctgccaagga ggcccagaag   3600

ggcaatcaga tggtgctgcc tgagcacctg ctgacactgc tgtaccacgc caagcagtgc   3660

ctgctgccaa atcagtctga gtctctggcc tacgtggagc agcaccagcc agagttccag   3720

gagatcctgg agagggtggt ggatttcgcc gaggtgcaca cactggctaa gtctaaggtt   3780

cagcagatcg tgaagctgtt cgaggccaat cagacagccg atgtgaagga gatcgccgcc   3840

tcattcatcc agctgatgca gttcaatgcc atgggcgccc catctacatt caagttcttc   3900

cagaaggata tcgagagggc caggtacaca tctatcaagg agatcttcga tgccacaatc   3960

atctaccagt ctacaacagg cctgtacgag acaaggagga aggtggtgga t            4011
```

<210> SEQ ID NO 179
<211> LENGTH: 4308
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG04583.1 Soy optimized"

<400> SEQUENCE: 179

-continued

```
atggccaaaa atattctagg actcgatctc ggaaccaact ctattggatg ggctcttgtt     60
cagcaggact ttgaaaataa ggaggggaac atactaggaa tggggtccag aataattcct    120
atgtctcagg atatactagg agagttcggg aagggtaact ctatttctca aactgctgag    180
agaactggat ataggggagt tagaaggtta agggagagac atcttcttag aagggagagg    240
cttcataggg tgcttcatct tcttggattc ctacctaagc attacgacga gaaaatagac    300
ttcactcaga ggttcgggaa gttcatcaat caagctgaac caaagttggc tttcgattca    360
gagttcctct tcaaggactc cttccatgaa atgctagctg acttcaagca gaatcaacct    420
gagttcctca aggataaaaa cggagaggat tgccttgttc cttacgactg gactatatac    480
tacctaagga agaaagcatt gacccagaag atcgaaaaat atgagctggc ctggctcatc    540
ctcaacttca atcaaaagag gggatactat caattaaggg gagaggagga gaaggagaac    600
cctaataaac tcgtggggtt ccactctctc aaaatagtgg atgttattcc tgacgctgaa    660
accaataaaa agggagagac ctggtactca cttcatcttg agaacggatg ggtttatagg    720
aggtcctcca aaatatctct cgctgattgg aaggacaaag tgagggattt cattgtgacc    780
accgatctta atgatgatgg atcagagaag ctcgataagg atggaattgt gaagaggtct    840
tttagggctc cttctgctga tgactggacc ctattaaaga agaagaccga gaaggatatc    900
gacaactcta ataaaaccgt ggggacctac atctacgaca acctcctatt aaaccccaag    960
cagaaaatca agggaaagat ggttaggacc attgagagga agttctacaa gcaagagctg   1020
gagcagatat taaagactca gaaggagttc cattctgagc ttcagtctga gaacttgctt   1080
caagattgcg ttagggagct gtacaggaat aatgagcaac atcaacagat gcttgaggct   1140
aaggatttcg tgcacctctt cctcaacgat ataattttct accagaggcc tcttaggtcc   1200
cagaaatcaa gcatttctaa ttgcaccctt gagttccgca agtccaagaa tgaaaacgga   1260
gaggaggtaa tacacagatt aaaggtgatc gccaaatcaa acccatacta ccaggagttc   1320
aggcttcttc aatgggttca gaacctcgct atctatacta aggacgacga taagaacgta   1380
accaacgagt tcctcaaatc aactcaggat tgggaggatc ttcttaggtg gcttcactct   1440
aagaaggaaa tcaagcagga tgctctaatc aagttcctca ttgagaagaa gggactcaag   1500
gggaaagcat tgactattga ggtggcaaaa tataggtgga actacgttca ggataaggat   1560
taccctggaa atgaaacccg ctacctcatt caatcaaggc ttgataaggt tgagtacgct   1620
cctaaggatt tcctcaccta tgaaaatgaa atggccctct ggcatatcat ctactcaatc   1680
aacgacaaga tcgagtatga aaaggcatta aagtccttcg ccaataaaaa ggggctcgat   1740
gaggtgacct tcgtggaagc attcaagaag ttccctcctt tcaagtccga ttacggatct   1800
ttctctgaga aggcaatcaa gaagctcctt ccattaatga ggttcggaac tcaatggaac   1860
tgggataaca tcgaccaaaa tagcaaggag aggattggaa aaatactaac cggggagtac   1920
gatgaaaata ttaaagggag ggttagggag aaggctaggc accttaactc tgagaccgat   1980
tttcaagcat tacctctttg gcttgctcag tacgttgttt atggaaggca ctctgaagct   2040
gatattgctg gaaagtggaa ctctgtggat gatctcaagc agttccttga tgatttcaag   2100
cagcattcct tgaggaaccc tattgtggag caggttatta ctgagactct tagggctgtt   2160
aaggatattt ggaacttcta cggaaagggg gctaaggatt tcttctcaga aatacacatt   2220
gagcttggga gggagatgaa aaataccgct gatgaaagga agaggattac caccatggtg   2280
accgacaatg aaaataccaa cctcagaatc aaagcattgc ttgctgagat ggctcttgat   2340
cagaacgttg ataacgttag gccttactct cctatgcagc aggagattct taagatctat   2400
```

```
gaggagggag ttctaaacgc tgaggagaac atcgatgatg atatcctcaa gatttctaag   2460
actgctcagc cttctgctac cgatcttaag aggtataagt tgtggcttga gcaaaagtac   2520
aggtctcctt acactggaca gatgattcct cttaacaagt tgttcacccc tgagtacgag   2580
atcgagcaca ttattcctca gtctaggtac ttcgacgatt caatgtccaa caaggttatt   2640
tgcgaggctg ctgtgaacaa gttgaaggat aaccagattg gactcgtgtt cattaagaac   2700
catcatggag aggtggttga tttcggaatg ggaaagcagg tgaagattct tgaggtttct   2760
gattacgagg atttcgtgaa gcagaactat aacaagaaca ggggaaagag gaacaagctc   2820
ctcttagagg atatccctga gaagatgatt gagaggcagc ttaacgatac caggtacatc   2880
tctaagtaca ttacccaggt gctttccaac attgttaggg atgataagga gggatctaag   2940
gatgatggag tgaactccaa gaacattgtt cctggaaacg gaaagattac caccaggctt   3000
aaacaggatt ggggacttaa cgatgtgtgg aacgatcttg ttcttcctag gttcgagagg   3060
atgaacactc ttaccaactc taacgatttc acctctaaga acactcacgg aaagactatt   3120
cctactgtgc ctattgagct ttcaaaggga ttctccaaga agaggattga tcacaggcat   3180
catgctatgg atgctcttgt tattgcttgc gctactaggg atcatgtgaa ccttctcaac   3240
aacgagtctt ctaagtctga taccaagagg tacgatctta acaggaagtt gaggaagtac   3300
gagaaggttg cttacaacga tcctaagact ggagagagaa ttgagaagga ggtgcctaag   3360
gattttatta agccttggga gacctttact gaggatacta ggacccttct tgagaacatc   3420
gtgatttctt tcaagcagaa cctcagggtg attaacaagg ctaccaacta ctacgagaag   3480
attgagaacg gaaagaaggt gaaggttgag cagaagggaa ttaattgggc tgttaggaag   3540
gctctacata aggagactgt ttctggacag gtgcaccttg ataggattaa agtggctaag   3600
ggaaagattc ttaccgctac taggaagact cttgatgctt ctttcaacga gaagaccatt   3660
gagtctatta ccgataccgg gattcagaag attctcctca actacctcaa gtccaaggat   3720
aacaatcctg aggttgcttt ctctcctgaa ggaattgagg agcttaacaa gaacatcagg   3780
ctctataacg atggaaaggc tcaccagcct attcttaagg ttagggtttt cgagcaggga   3840
tctaagttta ctcttggaga gactggaaac aagactacta agtttgttga ggctgctaag   3900
ggaaccaacc ttttcttcgg aatctacgag gataagtctg gaaagaggtc ttacgagacc   3960
atccctttga acattgttat tgagaggcaa aagcaaggac tacaagctgt tcctgagact   4020
aacgagaagg gaaagcagct tcttttcacc ctttctccta acgatcttgt ttatgttcct   4080
gaggagggag ttttcgatga gaacaacatc aaggtggata ggatctacaa ggtggtgtct   4140
ttctctactt accaatgctt cttcgtgagg aacgatgtgt ctacttctgt ggttaacaag   4200
gttgagtact ctgctctcaa caagatggag aagtccatcg acaacatcat gattaaggag   4260
aactgcgtga agttgaacgt tgataggctc ggaaagattt ccaaggct                4308
```

<210> SEQ ID NO 180
<211> LENGTH: 4308
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG04583.1 Corn optimized"

<400> SEQUENCE: 180

-continued

```
atggccaaga acatactagg cctggacctc ggaaccaatt ctatcggctg ggccctggtt     60
cagcaggact ttgagaacaa ggagggcaac atactaggca tgggcagccg aataatccct    120
atgtctcagg acatactggg cgagttcggt aagggcaaca gcatctcaca gacagccgag    180
aggacaggct accgcggcgt gaggaggctc agggagaggc acctgcttag gagggagagg    240
ctacacaggg tgctgcatct gctgggcttc ctgccaaagc attacgatga aaagatagat    300
ttcacacaga ggttcggcaa gttcatcaat caagccgaac caaagctagc cttcgattct    360
gagttcctgt tcaaggacag cttccatgaa atgctggccg acttcaagca gaatcaaccg    420
gagttcctga aggataaaaa cggcgaggac tgcctagtgc cgtacgactg gaccatatac    480
tacctgcgca agaaggccct cacccagaag atcgaaaaat acgagctggc ctggctgatc    540
cttaacttca accaaaagcg cggatactac cagctacgcg gcgaggagga gaaggagaac    600
ccgaataaac tggtgggctt ccacagcctg aaaatagtgg acgtgatccc ggacgccgag    660
actaataaaa agggcgagac ctggtactca cttcacctgg agaacggctg ggtgtaccgc    720
aggagcagca aaatatctct ggccgactgg aaggataaag tgagggactt catcgtgacc    780
acagacctga acgacgatgg ctcagagaag ctggacaagg atggcatcgt gaagaggtca    840
ttcagggccc catctgccga tgactggacc ctattaaaga agaagaccga gaaggacatc    900
gacaacagca ataaaaccgt gggcacctac atctacgaca acctgctatt aaacccgaag    960
cagaaaatca agggcaagat ggtgcgcacc atcgagcgca agttctacaa gcaggagctg   1020
gagcagatac taaagaccca gaaggagttc cacagcgagc tgcagagcga gaacctgctg   1080
caggactgcg tgcgcgagct gtaccgcaat aatgagcagc accagcagat gctggaggcc   1140
aaggacttcg tgcacctgtt cctgaacgat ataatcttct accagaggcc gctcaggagc   1200
cagaagtcaa gcatcagcaa ttgcaccctg gagttccgca agagcaagaa tgaaaacggc   1260
gaggaggtga tacatcgatt aaaggtgatc gccaagagca acccatacta ccaggagttc   1320
cgcctgctgc agtgggtcca gaacctggcc atctatacta aggacgacga caagaacgta   1380
accaacgagt tcctgaaatc aacccaggac tgggaggacc tgctgcgctg gctccacagc   1440
aagaaggaaa tcaagcagga cgccctaatc aagttcctga tcgagaagaa gggattaaag   1500
ggcaaagcat tgaccatcga ggtggcaaaa tacaggtgga actacgtcca ggacaaggac   1560
tacccgggca atgaaacccg ctacctaata cagagccgcc tggacaaggt ggagtacgcc   1620
ccgaaggact tcctgaccta cgagaatgaa atggccctgt ggcatatcat ctactcaatc   1680
aacgacaaga tcgagtatga aaaggcatta aagagcttcg ccaataaaaa gggcctggac   1740
gaggtgacct tcgtggaagc attcaagaag ttcccgccgt tcaagagcga ctacggcagc   1800
ttcagcgaga aggcaatcaa gaagctgctg ccattaatgc gcttcggcac ccagtggaac   1860
tgggacaaca tcgaccaaaa tagcaaggag cgcatcggca aaatactaac cggcgagtac   1920
gacgagaaca taaagggccg cgtgcgcgag aaggcccgcc acctgaacag cgagaccgac   1980
ttccaagcat tgccgctgtg gctggcccag tacgtggtct acggcaggca cagcgaggcc   2040
gatatcgccg gcaagtggaa cagcgtggat gatctcaagc agttcctgga cgatttcaag   2100
cagcacagcc tgaggaatcc aatcgtggag caggtgatca cagagacact aagggccgtg   2160
aaggacatct ggaatttcta cggcaagggc gccaaggact tcttcagcga gatacatatc   2220
gagctgggcc gcgagatgaa aaacaccgcc gatgaaagga agaggatcac aaccatggtg   2280
accgacaatg aaaacaccaa cctgcgaatc aaggccctgc tggccgagat ggccctggat   2340
```

-continued

```
cagaacgtgg ataacgtgag gccatactct ccaatgcagc aggagatcct gaaaatatac   2400
gaggagggcg tattaaacgc cgaggaaaat atcgacgacg acatcctgaa aataagcaag   2460
accgcccaac caagcgccac cgacctgaag cgatataagc tgtggctgga gcaaaaatac   2520
aggagcccgt acaccggcca gatgatcccg ctgaataaac tgttcacccc ggagtatgaa   2580
atcgagcata taatccctca gagccgctac ttcgacgaca gcatgagcaa caaggtgatc   2640
tgcgaggccg ccgtgaacaa gctaaaggac aaccagatcg gcctggtgtt catcaagaac   2700
caccacggcg aggtggtgga cttcggcatg ggcaagcagg tgaagatcct ggaggtgagc   2760
gactacgagg acttcgtgaa gcagaactac aacaagaacc gcggcaagag gaacaagctg   2820
ctgctggagg acatccctga gaagatgatc gagaggcagc tgaacgacac ccgctacatc   2880
agcaagtaca tcacacaggt gctgagcaac atcgtgaggg acgataagga gggctcaaag   2940
gatgatggcg tgaacagcaa gaacatcgtg ccaggcaacg gcaagatcac aacaaggctg   3000
aagcaggatt ggggcctgaa cgatgtgtgg aatgatctgg tgctgccaag gttcgagagg   3060
atgaacaccc tgaccaacag caacgacttc acctctaaga acacccacgg caagacaatc   3120
ccaacagtgc cgatcgagct gagcaagggc ttcagcaaga agaggatcga tcacaggcac   3180
cacgccatgg atgccctggt gatcgcctgc gccacaaggg atcacgtgaa tctactgaat   3240
aacgagtcta gcaagagcga tacaaagagg tacgatctga acaggaagct gcgcaagtac   3300
gagaaggtgg cctacaacga tccaaagaca ggcgagagga tcgagaagga ggtgccgaag   3360
gatttcatca agccatggga gacattcaca gaggacacaa ggaccctgct ggagaacatc   3420
gtgatcagct tcaagcagaa cctgcgcgtg atcaacaagg ccaccaacta ctacgagaag   3480
atcgagaacg gcaagaaggt gaaggtggag cagaagggca tcaattgggc cgtgaggaag   3540
gccctacata aggagacagt gtctggccag gtgcacctgg ataggatcaa ggtggccaag   3600
ggcaagatcc tgacagccac aaggaagaca ctggatgcct ctttcaacga gaagacaatc   3660
gagagcatca cagacaccgg catccagaag atcctgctga actacctgaa gagcaaggac   3720
aacaacccag aggtggcctt ctctccagag ggcatcgagg agctgaacaa gaacatcagg   3780
ctgtacaatg atggcaaggc ccaccagcca atcctgaagg tgcgcgtgtt cgagcagggc   3840
tcaaagttca cactgggcga gacaggcaat aagacaacaa agttcgtgga ggccgccaag   3900
ggcacaaatc tgttcttcgg catctacgag gataagtctg gcaagaggtc ttacgagaca   3960
atcccgctga atatcgtgat cgagaggcag aagcagggac tgcaggccgt gccagagaca   4020
aatgagaagg gcaagcagct gctgttcaca ctgtctccaa atgatctggt gtacgtgcca   4080
gaggagggcg tgttcgatga gaacaatatc aaggtggaca ggatctacaa ggtggtgagc   4140
ttctcaacct accagtgctt cttcgtgagg aacgacgtga gcacaagcgt ggtgaacaag   4200
gtggagtaca gcgccctgaa caagatggag aagagcatcg acaacatcat gatcaaggag   4260
aactgcgtga agctgaacgt ggaccgcctg ggcaagatct ctaaggcc                4308
```

<210> SEQ ID NO 181
<211> LENGTH: 4368
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG01688.1 Soy optimized"

-continued

<400> SEQUENCE: 181
atgatgatca agaacatact aggactcgat ctcggaacca actctatcgg atgggctcta 60
atcaagcagg atttcgagaa caagcatgga gaaatactag ggatgggctc cagaataatt 120
cctatgtccc aggatatact aggagatttc ggaaagggta actctatttc tcagaccgct 180
gatagaacca agtataggtc tgttagaagg cttagggaga gatttcttct taggagagag 240
aggcttcata gggtgctcca cctattaaac ttccttcctc aacactacgc ttctcagatc 300
gatttcgaga agaagttcgg aaagtttaag tctgagaccg aaccaaagtt agcttgggaa 360
aattggggag gaaagttctc tttcctcttc caaaatagct tcaatgaaat gctggaggat 420
ttcaaggctg ctggacaggg gctcaaaata ccttacgact ggaccatata ctatctcagg 480
aagaaagcat tgtcccagaa aatagagaag gaggagctag cttggatact cctcaacttc 540
aatcaaaaga ggggatacta tcaattaaga ggtgaggagg aggaggagaa ccctaataaa 600
ctcgtggagt tctactccct caaaatagtg gatgttgttg ctgatgagcc tcagaaggga 660
aagtccgata tctggtactc attaattctt gagaacggat gggtttatcg cagggcttcc 720
aaaatacctc tcttcgactg gaaggataaa accagggatt tcattgtgac caccgatctt 780
aacgatgata ggtctgtgaa gactgataag gagggaaatg aaaagaggtc ttttagggct 840
ccttcagaga acgattggac tcttgtgaag aagaagactg agcaggagat tgatcagtct 900
cataaaaccg tgggaaccta catctatgaa accctcctat taaaccccaa gcagaaaatc 960
aagggaaagt tggtgaggac cattgagagg aagttctaca aggacgagct taagcagata 1020
ctagagaagc aaaaggagtt ccaccaggaa ttaaagaacg acgacctata taacgactgc 1080
attagggagc tgtacaggaa taatgaggct caccaattaa ccctctccaa gaaggatttc 1140
gtgcacctat taatggacga tctcattttc taccagaggc ctcttaggtc ccagaaatca 1200
agcatttcta attgcaccct ggagttcaga aaatacaagg atgaaaacgg gattgagcac 1260
acccagtacc tcaaggctat cccaaaatca aacccatact accaagagtt taggctttgg 1320
cagtggatgt acaacttgaa catctacaga aaggatgatg aggctaacgt aaccaaggag 1380
ttcctcaaca ccaataaaga cttcgagtct ctcttcgagt tcctcaataa tcgcaaggag 1440
attgagcaga agcccctaat caagttcctt cttgagcaga aggacataaa caagaagcta 1500
ttaaacgccg aggctgagaa atacaggtgg aactacgtgg aggataaaaa gtacccctgc 1560
aatgaaacca agaccatgat ttcctctagg cttgacaagg tggaaaatat ctccgatgat 1620
ttcctcacca gggacatcga gcagaaaata tggcatataa tctactccgt gaacgacaag 1680
atcgagtatg aaaaggcatt aaagtccttc gctaccagga acgacctcga tgaaaatagc 1740
ttcatcgaag cattcaagaa gttctcccct ttcaagtccg agtacggatc tttctctgag 1800
aaggcaatca agaagctcct tccattaatg aggctcggaa aatactggta cgaggatgaa 1860
atcgtgaagc attccgacat ctacttcaaa aatattgaga acctcctcgg ggatttctcc 1920
aaccgcgaca agaaaaatatc tgaggaagac aaggagaagt ggaacaagtc aatcaacctt 1980
aagctccagg aggaattaaa ggatttccag accgctgaga ttgatttgtt ccagggactt 2040
aggcttcaca ttgctcagta ccttgtttat ggaaggcact ccgaagcatc tatgattgga 2100
aagtggaatt ctgctgagga tcttgaggag ttccttaagg atttcaagca gcattccctt 2160
aggaacccta ttgtggagca ggttattact gagactctta gggtggttaa ggatatttgg 2220
ctaaagtacg gaaacggggc taaggatttc ttcaacgaga ttcatattga gcttggaagg 2280
gaaatgaagt tgcctgctga tgataggaag aagctcacca accaaatttc tgagaacgag 2340

-continued

```
aacaccaact tcaggattaa ggctctcctt gctgagatga tgaacgattc ttctgttgag   2400
aacgttaggc ctttctctcc tatgcagcag gagattctaa agatctacga ggatgatgtg   2460
ctcaagtccg atatcgagat cgaggatgat atcctcaaga tttctaagac tgctcaacct   2520
tctccttctg atcttaagag gtacaagttg tggcttgagc agaagtacaa gtctccttac   2580
accggacaga ttattcctct taacaagttg ttcacccctg agtacgagat cgagcacatt   2640
attcctcagt caaggtactt cgatgattcc ttctccaata aggtgatttg cgagtctgct   2700
gtgaacaagc tcaaggataa ctacatcggg cttgagttca ttaagcagtt cggaggaact   2760
attattgagc ttggattcgg gaagtctatt aaggtgttcg agactaagga gtacgaggat   2820
ttcgtgaaga agcattacgc taacaaccag ggaaagagga acaagctcct tatggaagat   2880
atccctgaga agatgattga gaggcagatg aacgatacca ggtacatctc aaagtacatt   2940
tctggggtgc tttctaacat tgttagggtg gaagatggat ctgatgaggg agtgaactct   3000
aagaacattg ttcctggaaa cggaaagatt accacccaac ttaagcagga ttggggactt   3060
aacgatgtgt ggaacgatct cattcttcct aggttcgaga ggatgaatca gcttactaac   3120
tctaaggttt tcactgcttg gaacgagaac taccagaagt tccttcctac tgtgcctatt   3180
gagtactcca agggattctc aaagaagagg attgatcaca ggcatcatgc tcttgatgct   3240
cttgttattg cttgcgctac taaggatcac gtgaaccttc ttaacaacca gtctgctaag   3300
tctgatacca agaggtacga tctcaagaag aagtccatga agttcgagaa ggtggtttac   3360
aacgatgcta agactggaga aaagattgag agggaggttc ctaagcaatt tcttaagcct   3420
tgggagaact tcactcttga tgtgaagcac aaccttgaga ccatcattgt gtcattcaag   3480
cagaacctca gggtgattaa caaggctacc aactactacg agaagtacgt tgagaaggat   3540
ggaactaaga ataaggagag ggttgagcaa actggaacta actgggctat taggaagcct   3600
atgcacaagg atactgtgtc tggaaaagtt gatcttcctt gggttaaggt gcctaaggga   3660
aagattctta ctgctaccag gaagtctctc gattcttctt tcgatctcaa gtccattgga   3720
tctattaccg ataccgggat tcagaagatc ctaaagaact acctcgcttt caaggatgga   3780
aatcctgagc ttgctttctc tcctgaggga attgatgacc tcaacaagaa catcgagaag   3840
tataacgatg gaaagcctca ccagcctatt aacaaggtta gggttttcga gcttggatct   3900
aagttccaag ttggacagtc tggaaacaag aaggataagt atgttgaggc tgctaaggga   3960
accaaccttt tcttcgctgt ttatgaggat gagaagggaa agaggaacta cgagactatt   4020
cctctaaacg aggttattga gaggcaaaag cagggacttt ctgtggttga tcttaagggg   4080
accaacgatt tctatctttg ccctaacgat ttcgtgtaca ttccttctgg agatgagctg   4140
gagaacatca acaacgtgga cttcaaggat atcaagaagg agattaacga gaggatctac   4200
aaggtggtgt ctttcactgg aaacaggctt tcttgcattc cttacatggt ggctaccact   4260
attgtgaaca agttggagtt cacccagcta aacaagattg agttcaccaa ggagaaggag   4320
atctgcatta agttgaacgt ggataggctc ggaaacattt ctaaggct                4368
```

<210> SEQ ID NO 182
<211> LENGTH: 4368
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:

<221> NAME/KEY: source
<223> OTHER INFORMATION: /note="APG01688.1 Corn optimized"

<400> SEQUENCE: 182
atgatgatca agaacatcct aggcctggac ctcggaacca attctatcgg ctgggccctg 60
atcaagcagg acttcgagaa caagcatggc gagatactag gcatgggcag ccgaataatc 120
ccgatgagcc aggacatact aggcgatttc ggcaagggca atagcatctc tcagaccgcc 180
gacagaacca agtacaggtc tgttaggagg ctgagggaga ggttccttct taggagggag 240
aggctgcata gggtgctcca cctattaaac ttcctgccac agcactacgc cagccagatc 300
gacttcgaga agaagttcgg caagttcaag agcgagacag aaccaaagct ggcttgggaa 360
aactggggcg gcaagttcag cttcctgttc caaaatagct tcaatgaaat gctggaggac 420
ttcaaggccg ccggccaggg attaaagatc ccctacgact ggaccatata ctacctgcgc 480
aagaaagcat tgagccagaa aatagagaag gaggagctgg cctggatact gctgaacttc 540
aaccaaaagc gcggatacta ccagctgcgc ggtgaggagg aggaggagaa cccgaataaa 600
ctggtggagt tctactcact gaaaatagtg gacgtggtgg ccgacgagcc gcagaagggc 660
aagagcgaca tctggtacag cctgatacta gagaacggct gggtgtaccg ccgcgctagc 720
aaaataccgc tgttcgactg gaaggataaa acccgcgact tcatcgtgac caccgacctg 780
aacgacgaca ggagcgtgaa gacagataag gagggcaatg aaaagaggag cttcagggcc 840
ccaagcgaga acgattggac cctggtgaag aagaagacag agcaggagat cgatcagagc 900
cataaaaccg tgggcacata catctatgaa accctgctat taaacccgaa gcagaaaatc 960
aagggcaagc tggtgcgcac catcgagcgc aagttctaca aggacgagct gaagcagata 1020
ctagagaagc agaaggagtt ccaccaggaa ttaaagaacg acgacctata taacgactgc 1080
atccgcgagc tgtaccgcaa taatgaggcc caccaattaa ccctgagcaa gaaggacttc 1140
gtgcacctat taatggacga cctgatcttc taccagcgcc cgctgcgcag ccagaagtca 1200
agcatcagca attgcaccct ggagttccgc aaatacaagg atgaaaacgg catcgagcac 1260
acccagtacc tgaaggccat cccgaagagc aacccatact accaggagtt ccgcctgtgg 1320
cagtggatgt acaacctgaa catctaccgc aaggacgacg aggccaacgt aaccaaggag 1380
ttcctgaata caaataaaga cttcgagagc ctgttcgagt tcctgaataa tcgcaaggag 1440
atcgagcaga agccgctaat caagttcctg ctggagcaga aggacataaa caagaagcta 1500
ttaaacgccg aggccgagaa atacaggtgg aactacgtgg aggataaaaa gtacccgtgc 1560
aacgaaacca agaccatgat cagcagccgc ctggacaagg tggaaaatat cagcgacgac 1620
ttcctgaccc gcgacatcga gcagaaaata tggcatataa tctacagcgt gaacgacaag 1680
atcgagtatg aaaaggcatt aaagagcttc gccacccgca acgacctgga tgaaaacagc 1740
ttcatcgaag cattcaagaa gttcagcccg ttcaagagcg agtacggcag cttcagcgag 1800
aaggcaatca agaagctgct gccattaatg cgcctgggaa aatactggta cgaggacgag 1860
atcgtgaagc atagcgacat ctacttcaaa aatatcgaga acctgctggg cgacttcagc 1920
aaccgcgaca agaaaataag cgaggaggac aaggagaagt ggaacaaaag catcaacctg 1980
aagctgcagg aggaattaaa ggacttccag accgccgaga tcgacctgtt ccagggcctg 2040
cgcctccaca tcgcccagta cctggtgtac ggccgccaca gcgaggcaag catgatcggc 2100
aagtggaaca gcgccgagga cctggaggag ttcctgaagg acttcaagca gcatagcctg 2160
cgcaacccga tcgtggagca ggtgatcacc gagaccctgc gcgtggtgaa ggacatctgg 2220

-continued

```
ctaaaatacg gcaacggcgc caaggacttc ttcaatgaaa ttcacatcga gctgggccgc   2280
gagatgaaac tgccggccga cgaccgcaag aagctgacca accaaatcag cgagaatgaa   2340
aacaccaact tccgaatcaa ggccctgctg gccgagatga tgaacgacag cagcgtggag   2400
aacgtgcgcc cgttcagccc gatgcagcag gagatcctga aaatatacga ggacgacgtg   2460
ctgaagagcg acatcgagat cgaggacgac atcctgaaga tcagcaagac cgcccagccg   2520
agcccgagcg acctgaagcg ctacaagctg tggctggagc agaagtacaa gagcccgtac   2580
accggccaga tcatcccgct aaacaagctg ttcaccccgg agtacgagat cgagcacatc   2640
atcccgcaga gccgctactt cgacgacagc ttcagcaaca aggtgatctg cgagagcgcc   2700
gtgaacaagc tgaaggataa ctacatcggc ctggagttca tcaagcagtt cggcggcacc   2760
atcatcgagc tgggcttcgg caagagcatc aaggtgttcg agaccaagga gtacgaggac   2820
ttcgtgaaga agcactacgc caacaaccag ggcaagcgca acaagctgct gatggaggac   2880
atcccggaga agatgatcga gcgccagatg aacgacaccc gctacatcag caagtacatc   2940
agcggcgtgc tgagcaacat cgtgcgcgtg gaggatggct cagatgaggg cgtgaacagc   3000
aagaacattg tgccgggcaa cggcaagatc acaacacagc ttaagcagga ctggggcctg   3060
aacgatgtgt ggaacgatct gattctgcca aggttcgaga ggatgaacca gctgaccaac   3120
agcaaggtgt tcaccgcctg gaacgagaac taccagaagt tcctgccaac cgtgccaatc   3180
gagtacagca agggcttcag caagaagagg atcgatcaca ggcatcatgc tctggatgct   3240
ctggtgatcg cctgcgctac aaaggatcac gtgaacctgc tgaacaacca gagcgccaag   3300
agcgacacaa agaggtacga cctgaagaag aagagcatga agttcgagaa ggtggtgtac   3360
aacgacgcca agaccggcga gaagattgag agggaggtgc cgaagcagtt cctaaagcca   3420
tgggagaact tcacactgga cgtgaagcac aacctggaga ccatcatcgt gagcttcaag   3480
cagaacctga gggtgatcaa caaggccacc aactactacg agaagtacgt ggagaaggac   3540
ggcaccaaga acaaggagag ggtggagcag acaggcacaa attgggccat ccgcaagcca   3600
atgcacaagg atacagtgtc tggcaaggtg gatctgccat gggttaaggt gccaaagggc   3660
aagatcctga cagccacaag gaagagcctg gatagcagct tcgatctgaa gagcatcggc   3720
tctatcacag acaccggcat ccagaagatc ctgaagaact acctggcctt caaggatggc   3780
aatccagagc tggctttctc tccagagggc atcgacgacc tgaacaagaa catcgagaag   3840
tacaacgacg gcaagccaca ccagccaatc aataaggtgc gcgtgttcga gctaggctct   3900
aagttccagg ttggccagag cggcaacaag aaggataagt acgttgaggc cgccaagggc   3960
acaaatctgt tcttcgctgt gtacgaggat gagaagggca agcgcaacta cgagacaatc   4020
ccactgaacg aggtgatcga aaggcagaag cagggcctgt ctgttgtgga tctgaagggc   4080
accaacgatt tctacctgtg cccgaacgac ttcgtgtaca ttccatctgg cgacgagctg   4140
gagaacatca acaacgtgga cttcaaggac atcaagaagg agatcaacga gcgcatctac   4200
aaggtggtga gcttcaccgg caacaggctg agctgcatcc catacatggt ggccaccacc   4260
atcgtgaaca agctggagtt cacccagctg aacaagatcg agttcaccaa ggagaaggag   4320
atctgcatca agctgaacgt ggacaggctg ggcaacatca gcaaggcc                4368
```

<210> SEQ ID NO 183
<211> LENGTH: 3210
<212> TYPE: DNA
<213> ORGANISM: Bacillus sp.
<220> FEATURE:
<221> NAME/KEY: source
<223> OTHER INFORMATION: /note="APG05083.1 Native Seq"

<400> SEQUENCE: 183

```
atgagagagt tggattatcg cataggatta gatattggaa cgaattctat tggctggggg     60
atcattgaat tatcttggaa caaagataga gaacaatatg agaaagcaag aattgtcgac    120
aagggtgttc gtatgtttga taaggctgaa atacctaaga ctggtgcttc tcttgctgaa    180
ccgaggcgta tagcacgctc atcacgtaga agattaaatc gcaaaagcca gagaaaaaaa    240
gatatacgta atttactcgt tcaacatgaa attattagtc aaaaggaatt ggcttcgtta    300
tatcccctga caaaaagttc aatggatatt tgggatattc gcttggatgg attagatcgc    360
ttgttagacc gttttgaatg gactcgatta ttaattcatt tagcgcaaag acgcggtttt    420
aaatcaaatc gaaagtctga actgaaagat gtggagacag gaaaagtatt atcaagtatt    480
caagcaaatg aaaaacgatt atcactgtac cgtacagtgg gagagatgtg gatgaagaat    540
gaagatttta gtaaatatga caaaaggcgt aattcttcta atgagtatgt attttcggtt    600
agccgtgcag atttagaaaa agaaattgtg acactatttg aagcgcaaag aaaatttcag    660
tcatcatatg catcggctga tttacaaaaa acatacttac aaatttgggc acaccaactt    720
ccttttgctt ctgggaatgc aattgtaaat aaagtaggat attgttcatt attaaaaggg    780
aaagaaaaga gagttccgaa agcaacatat acttttcaat atttcagtac actagatcaa    840
ataaatcgaa cacgattagg tcctaatttc caaccattta cgaaggaaca gagagacgtt    900
attttagatg aaatgtttaa tcgaacagat tattataaaa aaaagacaat acccgaagtc    960
acttactatg atattcggaa atggttagca ttagatgaaa caattcaatt taaaggactt   1020
acctatgacc caaatgaaga gctgaaaaaa atagaattga aatcctttat taatttaaag   1080
ccattctatg aaattaaaaa ggtagttact aattacgcca aaaaaacaaa tgaggcattc   1140
tcaacattag actatgatac atttgcatat gctttaacag tttataaaac ggacaaagat   1200
attagatctt atttaaagaa atctaataat ttatcaaaat gttgctacga tgatcaatta   1260
atagaagagc tattaactct ctcctataca aagtttggtc atttatcatt taaagcaatt   1320
aatcatgtac tgccaattat gcaagaggga aggacttatc aggaagcaat acaccaatta   1380
ggatatgatg ccactaatct aaaaaaagaa aacagaagta tgttcttgcc cctttttccc   1440
gatgagataa caaatccaat tgttaaaaga gcactaactc aagcacgtaa agttgtaaat   1500
gctattatta gaagatatgg ttcccccaat tctgttcata ttgaactagc tcgtgagctt   1560
tctaaaagtc atgatgagag aacgaaaata atgaaagctc atgatgaaaa ttataagaaa   1620
aataaaggag ccatatcaat tttgattgag aatggaattt taaatccgac aggatatgat   1680
attgtacgtt ataagttatg gaaagagcaa ggagaacgat gtgcttattc gctaaaacag   1740
attcctgcta atacgttttt taatgaaatg aaaaaagagc gaagtggctc cccagttcta   1800
gagatagatc acattttacc gtatagtcag agttttattg atagttatca taataaagta   1860
ctagtttatg gagatgagaa tcaaaaaaag ggaaatcgaa ttccatatac ttatttttta   1920
gaaggaaata aggactggga aagctttgaa agctacgtac gattgaatag tttttttct    1980
aaaaagaagc gcggatattt attgaaaaaa gcttacttgc caagagagag taacatgatt   2040
aaggagcgtc atttaaatga tactcgatat gctagtagct atttgaaaaa cttcattgag   2100
aaaaatttga aatttaaaga agttgaaggt agtacacgaa aaaaacatgt acagacggtt   2160
aacggtataa ttacagccca tcttcgaaaa agatggggat tagaaaaaga taggcaggaa   2220
acatatttgc atcatgcaat ggacgctatt attgttgctt gtacagacca tcatatggtc   2280
```

```
actaaagtaa cggagtacta tcaaataaaa gaaagtaata agtcaataag gaaaccatac   2340
tttcctttgc catgggtggg ctttagagag gaaattttat cacatttagc aaggcagcca   2400
attgctagaa aaattagtga ggaacttaaa attggatatc aatcatttga ttatatactt   2460
gtatcgcgaa tgccaaaaag atctgtcact ggagcagctc atgaacagac aatcatgaaa   2520
aaaggtggta tcgacaaaaa aggaaaaact attatcataa agcgtgtgta cttaaaggat   2580
attaagtttg atgagaatgg cgattttaaa atggttggaa aagaacagga tttagcaact   2640
tatgaagcga taaagcaaag atatatagag tatggaaaag aatcgaaaaa agcatttgaa   2700
acacctttat acaagcctag taaaaaagga aaaggaaacc tcattaaaaa gatcaaagta   2760
gaagtgcaaa ccaaatcttt tgttcgagaa gttaatgggg gcgtagctca aaatggtgat   2820
ttagtaagag tagatttgtt tgaaaaggat aatagatatt atatgatacc tatttatgta   2880
atggatactg ttcattccga actaccaaat aaagctgtaa caagcagtaa aggctatgag   2940
caatggttaa caatagataa cagctttacg ttcaaattca gtttatatcc ttatgattta   3000
gtacgacttg taaaaggtaa tgaagatcgt ttcctatatt ttagtaccct tgatattaat   3060
tcggatcgtc ttaatttcaa agatgtaaac aagccatcaa agcaggctga aaatcgttat   3120
agccttaaaa caattgagaa tttagaaaaa tatgaggttg gtgttttagg tgatttaagg   3180
tttgtgagac aagaaatacg taaaaatttt                                     3210
```

<210> SEQ ID NO 184
<211> LENGTH: 3210
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG05083.1 E. coli optimized"

<400> SEQUENCE: 184

```
atgcgcgagc tagattatcg catcggcctg gatattggca ctaactcaat aggctggggc     60
atcatcgaac tgagctggaa taaagaccgc gagcagtatg aaaaggcgcg catcgtggat    120
aaaggcgtgc gcatgttcga caaagcggaa attccgaaaa ccggtgcaag tctggcggaa    180
ccaagacgta ttgcacgtag tagtcgccgc cgattaaacc gcaaaagtca gcgcaagaag    240
gatataagga acctgctggt ccagcatgaa atcatcagcc agaaggaact ggcgagcctg    300
tacccgctga ccaaatcaag tatggacatc tgggatataa ggctggacgg cctggatcgt    360
ctgctggatc gctttgaatg gacccgccta ttaatccatc tggcacagcg ccgtggcttc    420
aaatcaaacc gcaagagcga attaaaggac gtggagaccg gtaaagtgct gtcaagcatt    480
caggcgaatg aaaagcgcct gagcctgtat cgtaccgtgg gcgagatgtg gatgaaaaac    540
gaggacttct caaaatacga taaaaggcgc aacagcagca acgagtacgt gttcagcgtg    600
agccgcgcgg acctggagaa agaaatcgtg accctgtttg aggcgcagcg caaattccaa    660
tcaagctatg cgagcgcgga tctgcagaaa acctacctgc agatttgggc acatcagctg    720
ccgtttgcaa gcggtaacgc gatcgtgaat aaagtgggct attgcagcct attaaaaggc    780
aaagaaaaac gcgtgccgaa agcgacctat acattccagt acttcagcac cctggaccaa    840
atcaaccgca cccgcctggg cccgaacttc cagccgttca ccaaagaaca gcgcgacgtg    900
atcctggatg aaatgttcaa ccgcaccgac tactataaaa agaaaaccat cccggaggtg    960
```

acatactacg atataaggaa atggctggcg ctggatgaaa ccatccagtt caaaggctta 1020
acctacgatc cgaacgagga attaaagaag atcgaattaa aatcgttcat taatctgaaa 1080
ccgttctatg aaattaaaaa ggtggtaacc aactacgcga agaaaaccaa cgaagcattc 1140
agcaccctgg actacgatac attcgcgtac gcgctgaccg tgtataaaac cgacaaggat 1200
ataaggagct acctgaagaa atcaaacaac ctgagcaaat gctgctacga cgaccaatta 1260
atcgaagaac tgctgaccct gagctacacc aaattcggcc acctgagctt caaagcgatc 1320
aaccacgtgc tgccgatcat gcaggaaggc cgcacctacc aggaagcgat ccaccagctg 1380
ggctacgatg cgaccaacct gaaaaaggaa aaccgcagca tgttcctgcc gctgttccct 1440
gatgaaatca ccaacccgat cgtgaaacgc gcgctgaccc aggcgcgcaa ggtggtgaac 1500
gcgatcatcc gccgctacgg ctcaccgaac agcgtgcaca tcgaactggc gcgcgaactg 1560
agcaaaagcc acgatgaacg caccaaaatc atgaaagcgc acgatgaaaa ctacaaaaag 1620
aacaaaggcg cgatcagcat cctgatcgaa aacggcatcc tgaacccgac cggctacgat 1680
atcgtgcgct acaaactgtg gaaagaacag ggcgaacgct gcgcgtacag cctgaaacag 1740
atcccggcga acaccttctt caacgaaatg aaaaaggaac gctcaggcag cccggtgctg 1800
gaaatcgatc acatcctgcc gtacagccag agcttcatcg atagctacca caacaaagtg 1860
ctggtgtacg gcgatgaaaa ccagaaaaag ggcaaccgca tcccgtacac ctacttcctg 1920
gaaggcaaca aagattggga gagcttcgaa agctacgtgc gcctgaacag cttcttcagc 1980
aaaaagaaac gcggctacct gctgaaaaag gcgtacctgc cgcgcgaaag caacatgatc 2040
aaagaacgcc acttaaacga tacccgctac gcgagcagct acctgaaaaa cttcatcgag 2100
aaaaacctga aattcaaaga agtggaaggc agcacccgta aaaagcatgt ccagaccgtg 2160
aacggcatca tcaccgcgca tctgcgcaaa cgctggggcc tggaaaaaga tcgccaggaa 2220
acctatctgc atcatgcgat ggatgcgatc atcgtggcgt gcaccgatca tcatatggtg 2280
accaaagtga ccgaatatta tcagatcaaa gaaagcaaca aatcaatccg caaaccgtat 2340
tttccgctgc cgtgggtggg ctttcgcgaa gaaatcctga gccatctggc gcgtcagccg 2400
atcgcgcgta aaatcagcga agaactgaaa atcggctatc agagctttga ttatatcctg 2460
gtgagccgca tgccgaaacg cagcgtgacc ggcgcggcgc atgaacagac catcatgaaa 2520
aagggcggca tcgataaaaa gggcaaaacc atcatcatca aacgcgtgta tctgaaagat 2580
atcaaatttg atgaaaacgg cgattttaaa atggtgggca aggaacagga cttagcgacc 2640
tacgaagcga tcaaacagcg ctacatcgag tacggcaaag agagcaaaaa ggcgtttgaa 2700
accccgctgt acaaaccgag caaaaagggc aagggcaacc tgatcaaaaa gatcaaagtg 2760
gaagtccaga ccaaatcgtt tgtgcgcgaa gtgaacggcg gcgtggcgca gaacggcgat 2820
ctggtgcgcg tggatctgtt tgaaaaagat aaccgctact atatgatccc gatctacgtg 2880
atggataccg tgcatagcga gctgccgaac aaagcggtga ccagcagcaa aggctatgaa 2940
cagtggttaa ccatcgataa cagctttacc ttcaaattca gcctgtatcc gtacgacctg 3000
gtgcgcctgg tgaaaggcaa cgaagatcgc ttcctgtatt tcagcaccct ggacatcaac 3060
agcgatcgcc tgaacttcaa ggacgtgaac aaaccgagca aacaggcgga aaaccgctat 3120
agcctgaaga ccatcgagaa cctggagaaa tatgaagtgg gcgtgctggg cgatctgcgc 3180
tttgtgcgcc aggaaattcg caaaaacttc 3210

<210> SEQ ID NO 185

-continued

<211> LENGTH: 3213
<212> TYPE: DNA
<213> ORGANISM: Bacillus sp.
<220> FEATURE:
<221> NAME/KEY: source
<223> OTHER INFORMATION: /note="APG07433.1 Native Seq"

<400> SEQUENCE: 185

```
atgagggagt tggactatcg catagggtta gatattggga cgaattctat tggatggggt     60
gttattgaat tatcctggaa caaggacaga gaacgatatg aaaaagtaag gattgtcgac    120
cagggtgttc gtatgtttga tagggctgaa atgccaaaaa caggtgcttc tcttgctgaa    180
ccgaggcgta tagcacgttc atcacgtaga aggttaaatc gtaaaagtca gaggaagaaa    240
aatatacgta atttacttgt tcaacatggg gtgattactc aagaagagct ggattcgtta    300
tatcctcttt caaaaaaatc aatggatatt tggggtattc gattggatgg attagatcgt    360
ctgctaaatc attttgaatg ggctcgatta ttaattcatt tagctcaaag acgtggtttt    420
aaatcgaatc gtaagtctga actgaaagat acggagacgg ggaaggtatt atcgagtatt    480
caattaaatg aaaaacgatt atcactgtac cgtacagtgg gagaaatgtg gatgaaagat    540
cctgatttta gtaagtatga tagaaaacgg aattctccta atgagtatgt attttcggtt    600
agtcgtgcgg aactagaaaa ggaaatagtt actttatttg cagcacaaag aaggtttcag    660
tcaccatacg catcgaagga tttacaagaa acatatttac aaatttggac acaccaactt    720
ccctttgctt ctgggaatgc aattttaaat aaagtgggat attgttcatt attgaaaggg    780
aaagaaagaa gaattccgaa agcaacatat acttttcagt attttagtgc actagatcaa    840
gtgaatcgaa cacgattagg acctgatttt cagccattta cgaaggaaca aagagaaatt    900
attttaaata acatgtttca acgtacagat tattataaaa aaaagactat acctgaagtt    960
acatactatg atatccggaa atggctagaa ctagatgaaa ctattcaatt taaaggactt   1020
aattatgatc caaacgaaga attgaaaaaa atagaaaaga aaccatttat taatttaaag   1080
gcattctatg aaattaataa ggtagtcgca aattattctg agagaacaaa tgagacattt   1140
tcaacgttag actatgatgg gattggatat gctttaacag tttataaaac ggacaaagat   1200
attaggtctt atttgaagag ctctcataat ttacctaaac gttgttacga tgatcaatta   1260
atagaggaac tattaagtct ttcttataca aagtttggtc acttatcact gaaagcaatc   1320
aatcacgtac tatcgattat gcaaaaaggc aatacttata aagaagcagt agaccagtta   1380
gggtatgata caagcggttt aaagaaagaa aaaagaagta agttcttgcc tcctatttca   1440
gatgagataa cgaatccaat tgttaaaaga gcgttaacac aagcgcgtaa agttgtgaat   1500
gctataatta gaagacatgg ttctccacat tcagttcata ttgaactggc tcgtgaactt   1560
tctaaaaatc atgacgagag aacaaaaata gtgtcagctc aagatgaaaa ttataagaag   1620
aataaagggg ctatatcaat tttaagtgag catggaattt tgaatccaac aggctatgat   1680
attgttcgtt ataagttatg gaaagaacaa ggagaacgat gtgcttattc gttaaaggag   1740
attcctgcgg atacgttttt taatgaatta aaaaaagaac gaaatggtgc tccaattcta   1800
gaggtagatc acattttacc gtacagtcaa agttttattg atagttatca taataaagta   1860
ttagtttaca gtgatgaaaa tcgaaaaaag gggaatcgaa ttccatatac ctatttttta   1920
gagacaaata aggattggga agcttttgaa agatatgtaa gatcaaataa atttttttct   1980
aaaaagaagc gtgagtattt attgaaaaga gcatatttgc caagagaaag tgaactgata   2040
aaggagcgac atttaaatga tacgcgatat gctagtacct tttgaaaaa cttcattgag   2100
```

cagaatttgc aatttaaaga agctgaagat aatccgcgta aaagacgtgt acaaacagtt 2160
aacggtgtaa ttacagcaca ttttcgaaaa agatggggat tagaaaaaga tagacaagaa 2220
acatacttac atcatgcaat ggacgctatc attgttgctt gtacagacca tcatatggtt 2280
actagagtaa cagagtatta tcaaataaaa gaaagtaata aatcagtaaa gaaaccgtat 2340
tttcctatgc catgggaggg ctttagagat gaactcttat cacatttagc gagtcagcca 2400
atagctaaaa aaattagtga ggagcttaaa gctggatatc aatcattaga ttatatattt 2460
gtgtctcgaa tgccaaaaag atctatcact ggagcagcac ataaacaaac gatcatgaga 2520
aaaggcggta ttgataaaaa aggaaaaact attattatag agcgtttgca tttaaaggat 2580
attaagtttg atgagaatgg tgattttaaa atggttggca aagaacaaga tatggcaact 2640
tacgaggcga taaagcaaag atatttggag catggaaaaa actcgaaaaa agcatttgaa 2700
acacctctat acaaacctag taaaaaagga acaggaaatc ttattaaaag agttaaagtt 2760
gaaggacaag ctaaatcttt tgttcgagaa gtaaatgggg gcgtagccca aaatggtgat 2820
ttagtgagag ttgatttatt tgaaaaagat gataaatatt acatggtgcc tatttatgta 2880
ccagataccg tttgttcaga attacccaaa aaagttgtgg caagtagtaa gggttatgag 2940
caatggttaa cactagataa cagctttacg tttaaattta gtttataccc ttatgattta 3000
gtacggcttg taaaagggga cgaagatcgt ttcttatact ttggtactct cgatatcgat 3060
tcagatcgtc ttaattttaa agatgtaaat aagccatcaa aaaagaatga atatcgttat 3120
agccttaaaa caattgagga tttagaaaaa tatgaggtgg gtgttttagg agatttaagg 3180
ttagtaagaa aagaaacacg tagaaatttt cac 3213

<210> SEQ ID NO 186
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG07433.1 E. coli optimized"

<400> SEQUENCE: 186
atgcgcgagc tagattatcg catcggcctg gatattggca ctaactcaat aggctggggc 60
gtgatcgaac tgagctggaa taaagaccgc gagcgctatg aaaaggtgcg cattgtggat 120
cagggcgtca gaatgtttga tcgtgcggaa atgccgaaaa ccggtgcatc actggcagaa 180
ccaagacgta tagcacgtag tagtcgccgc cgattaaacc gtaaaagcca gcgcaagaaa 240
aatatccgca acctgctggt tcagcatggc gtcatcaccc aggaagaact ggatagcctg 300
tacccgctga gcaagaaatc aatggacatc tggggcattc gtctggatgg tctggaccgc 360
ctattaaacc actttgaatg ggcccgccta ttaattcatc tggcgcagcg ccgcggcttc 420
aaatcaaacc gcaagagcga attaaaggac accgagaccg gtaaagtgct gtcatcgatc 480
cagctgaatg aaaaacgcct gagcctgtat cgcaccgtgg gcgagatgtg gatgaaagac 540
ccggacttct caaaatacga ccgcaaacgc aacagcccga acgaatacgt gtttagcgtt 600
agccgtgcgg aactggagaa agaaatcgtg accctgtttg cagctcagcg ccgttttcag 660
agcccgtatg cgagcaaaga tctgcaagaa acctacctgc agatctggac ccatcagctg 720
ccgtttgcaa gcggtaacgc gatattaaac aaagtgggct attgcagcct attaaaaggc 780

-continued

```
aaagaacgcc gcatcccgaa agcgacctat acattccagt acttcagcgc gctggaccag    840
gtgaaccgta cccgtctggg tccggatttt cagccgttca ccaaagaaca gcgcgagatc    900
atattaaaca acatgttcca gcgcaccgac tactataaaa agaaaaccat cccggaggtg    960
acatattacg atataaggaa atggctggaa ctggatgaaa ccatccagtt caaaggcctg   1020
aactacgatc cgaacgagga gctgaaaaaa atcgagaaaa aaccgttcat taatctgaaa   1080
gcgttctatg aaatcaacaa agtggtggcg aactacagcg aacgcaccaa tgaaaccttc   1140
tcaaccctgg attacgatgg catcggctac gcgctgaccg tgtataaaac cgacaaggat   1200
ataaggagct acctgaaatc aagccacaac ctgccgaaac gctgctacga cgaccaatta   1260
atcgaagaac tgctgagcct gagctatact aagttcggcc acctgtcatt aaaagcgatt   1320
aatcacgtgt taagcatcat gcagaaaggc aacacatata aagaagcggt ggatcagctg   1380
ggctacgata ccagcggatt aaaaaaagaa aaacgcagca aattcctgcc gccgatcagc   1440
gatgaaatca ccaacccgat cgtgaaacgc gcgctgaccc aggcgcgcaa agtggtgaac   1500
gcgatcatcc gccgccacgg cagcccgcac agcgtgcaca tcgaactggc gcgcgaactg   1560
agcaaaaacc acgatgaacg caccaaaatc gtgagcgcgc aggatgaaaa ctacaaaaag   1620
aacaaaggcg cgatcagcat cctgtcagaa cacggcatcc tgaacccgac cggctacgat   1680
atcgtgcgct acaaactgtg gaaagagcag ggcgaacgct gcgcgtacag cctgaaagaa   1740
atcccggcgg ataccttctt caacgagctg aaaaaagaac gcaacggcgc cccgatcctg   1800
gaagtggatc acatcctgcc gtacagccag agcttcatcg atagctacca caacaaagtg   1860
ctggtgtaca gcgatgaaaa ccgcaaaaaa ggcaaccgca tcccgtacac ctacttctta   1920
gagaccaaca aagattggga agcgttcgaa cgctacgtgc gcagcaacaa gttcttcagc   1980
aaaaagaagc gcgagtacct gctgaaacgc gcgtacctgc cgcgcgaaag cgaactgatc   2040
aaagaacgcc atctgaacga tacccgctac gcgagcacct tcctgaaaaa cttcatcgaa   2100
cagaacctgc agttcaaaga agcggaagat aacccgcgca aacgccgcgt ccagaccgtg   2160
aacggcgtga tcaccgcgca ttttcgcaaa cgctggggct tagaaaaaga tcgccaggaa   2220
acctatctgc atcatgcgat ggatgcgatc atcgtggcgt gcaccgatca tcatatggtg   2280
acccgcgtga ccgaatatta tcagatcaaa gaaagcaaca aaagcgtgaa aaaaccgtat   2340
tttccgatgc cgtgggaagg ctttcgcgat gaactgctga gccatctggc gagccagccg   2400
atcgcgaaaa aaatcagcga agaactgaaa gcgggctatc agagcctgga ttatatcttt   2460
gtgagccgca tgccgaaacg ctcaatcacc ggcgcggcgc ataaacagac catcatgcgc   2520
aaaggcggca tcgataaaaa aggcaaaacc atcatcatcg aacgcctgca tctgaaagat   2580
atcaaatttg atgaaaacgg cgattttaaa atggtgggca aagaacagga catggcgacc   2640
tacgaagcga tcaaacagcg ctatctggag catggcaaga acagcaaaaa agcgtttgag   2700
accccgctgt acaaaccgag caaaaaaggc accggcaacc tgatcaaacg cgtgaaagtg   2760
gaaggccagg cgaaatcatt tgtgcgcgaa gtgaacggcg gcgtggcgca gaacggcgat   2820
ctggtgcgcg tggatctgtt tgaaaaagat gacaaatatt atatggtgcc gatctatgtg   2880
ccggataccg tgtgtagcga actgccgaaa aaagtggtgg cgagcagcaa aggctatgaa   2940
cagtggctga ccctggataa cagctttacc ttcaaattca gcctgtatcc gtatgatctg   3000
gtgcgcctgg tgaaaggcga tgaagatcgc tttctgtatt ttggcaccct ggacatcgat   3060
tcagatcgcc tgaacttcaa ggacgtgaac aaaccgagca aaaagaacga atatcgctat   3120
agcctgaaaa ccattgaaga tctggaaaaa tatgaagtgg gcgtgctggg cgatctgcgc   3180
```

ctggtgcgca aagagacccg ccgcaacttt cat 3213

<210> SEQ ID NO 187
<211> LENGTH: 3213
<212> TYPE: DNA
<213> ORGANISM: Bacillus sp.
<220> FEATURE:
<221> NAME/KEY: source
<223> OTHER INFORMATION: /note="APG07513.1 Native Seq"

<400> SEQUENCE: 187
atgagagagt tggattatcg cataggatta gatattggaa cgaattctat tggctggggt 60
gttattgaat tatcttggaa caaagataga gaacaatatg agaaaacgag aattgtcgac 120
aagggtgttc gtatgtttga taaggctgaa atacctaaga ctggtgcttc tcttgctgaa 180
ccgagacgta tagcgcgctc atcacgtaga aggttaaatc gtaaaagcca gagaaaaaaa 240
gatatacgta atttacttgt tcaacatgaa attattagcc aaaaggaatt gacttcgtta 300
tatcccctgt caaaaagttc aatggatatt tgggatattc gcttagatgg attagatcgc 360
ttgttagacc gttttgaatg ggctcgatta ttaattcatt tagcacaaag acgcggtttt 420
aaatcaaatc gaaagtctga actgaaagat gtggagacag gaaaagtatt atcaagtatt 480
caagtaaatg aaaaacgatt atctctgtac cgtacagtgg gagagatgtg gatgaagaat 540
gcggattgta gtaaatatgg caaaaggcgt aattctccta atgagtatgt attttcggtt 600
agccgtgcag atttagaaaa ggaaattgtg actctatttg aggcgcaaag aaaattccat 660
tcatcatatg catcggttga tttacaaaaa acatatatac aaatttgggc acaccaactt 720
ccttttgctt ctgggaatgc aattgtaaat aaagtaggat attgttcatt attaaaaggt 780
aaagaaaaga gagttccaaa agcaacatat acttttcaat atttcaatac actagatcaa 840
ataaaccgaa cacgattagg gcccaatttc caaccattta cgaaggaaca gagagacata 900
attttagata aaatgtttca acggacagat tattataaaa aaaagacaat acccgaagtt 960
acttactatg atattcggaa atggttagca ctagatgaaa caattcaatt taaaggactt 1020
acctatgacc caaacgaaga gctgaaaaaa atagaaatga aaccctttat taatttaaag 1080
ccattctatg aaattaaaaa ggtagttact aattacgcaa aaaaaacaaa tgaggtattc 1140
tcagcattag attatgatac agttgcatac gctttaacag tttataaaac ggacaaagat 1200
attagatctt atttgaagag atctaataat ttatcaaaac gttgctacga tgatcaatta 1260
atagaagagc tattaactct ctcctataca aagtttggtc atttatcatt taaagcaatt 1320
aatcatgtac tgccaattat gcaagaggga aggacttatc aggaagcaat acaccaatta 1380
gggtatgata ccactaatct taaaaaagaa aacagaagta tgttcttgcc tattattcca 1440
gatgagataa caaatccaat tgttaaaaga gcgttaactc aagcacgtaa agttgtaaat 1500
gctattatta gaagatatgg ttctccaaat tctgttcata ttgaactagc tcgtgagctt 1560
tcgaaaagtc atgacgagag aaaaaaaata atgacagctc atgatgaaaa ttataagaaa 1620
aataaaggag ctgtatcaat tttgatcgat aatggaattt taaatccgac aggatatgat 1680
attgtacgtt ataagttatg gaaagagcaa ggagaacgat gtgcttattc gttaaaaaag 1740
attcctgcta atacgttttt taatgaattg aaaaaagagc gaagtggccc tccggttcta 1800
gaggtagatc acattttacc gtatagtcag agttttattg atagttacca taataaagta 1860
ttagtttatg gggatgaaaa tcaaaaaaag ggaaatcgaa ttccatatac tttttttca 1920 gaagaagata aggagtggga aagctttgaa agctacgtaa gatcgaatag ttttttttct 1980

```
aaaaagaagc gcggatattt attgaaaaaa gcttacttgc caagagagag taacttgatt   2040

aaggagcgtc atttaaatga tacccgatat gctagtagct atttgaaaaa cttcattgag   2100

aaaaatttaa aatttaaaga agctgtaggt attacacgaa aaaaatatgt acagacggtt   2160

aacggtgtaa ttacagccca tctgcgaaaa aggtggggtt tagaaaaaga taggcaggaa   2220

acatatttgc atcatgcaat ggacgctatt attgttgctt gtacagatca tcatatggtc   2280

actaaagtaa cggagtacta tcaaataaaa gaaggtaata agtcaataaa gaaaccgtat   2340

tttcctttgc catggatggg atttagagag gaaattttat cacatttaga aagtcagcca   2400

attgctagaa aaattagtga ggaacttaaa attggatatc aatcacctga ttatatactt   2460

gtatcgcgaa tgccaaaaag atctgtcact ggatcagctc atgatcagac agtcatgaaa   2520

aaaggcgata tcgataaaaa aggaaagact attatcataa agcgtgtgca cttaaaggat   2580

attaagtttg atgagaatgg cgattttaaa atggttggca aagaacaaga tttagcaact   2640

tacgaagcga taaagcaaag atatttagag tatagaaaag aatcgaaaaa agcatttgaa   2700

acacctttat acaagcctag taaaaaagga aaaggaaacc tcattaaaaa aattaaagta   2760

gaagtgcaaa ccaaatcttt tgttcgagaa attaatgggg gcgtagctca aaatggtgat   2820

ttagtaagag tagatttgtt tgaaaaggat aataggtatt atatggtgcc tatttacgta   2880

gtagatactg ttcgttccga actaccaaat aaagctgtaa caagcagtaa aggctatgag   2940

caatggttat caatagataa cagctttacg ttcaaattca gtttatatcc ttatgattta   3000

gtacgacttg taaaaggcga tgaagatcgt tttctatact ttagtactct tgatattaat   3060

tcggaccgtc ttaattttaa agatgtaaat aagccatcaa agcaagctga atatcgttat   3120

agtcttaaaa caattgagaa tttagaaaaa tatgagattg gtgttttagg tgatttaagg   3180

ttagtgagac aagaaacacg taaaattttt aaa                                3213
```

<210> SEQ ID NO 188
<211> LENGTH: 3213
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG07513.1 E. coli optimized"

<400> SEQUENCE: 188

```
atgcgcgagc tagattatcg catcggcctg gatattggca ctaactcaat aggctggggc     60

gtgatcgaac tgagctggaa taaagaccgc gagcagtatg aaaagacccg catcgtggat    120

aaaggcgtgc gcatgttcga caaagcggaa attccgaaaa ccggtgcaag tctggcggaa    180

ccaagacgta ttgcacgtag tagtcgccgc cgattaaacc gcaaaagtca gcgcaagaag    240

gatatcagga acctgctggt ccagcatgaa atcatcagcc agaaggaatt aaccagcctg    300

tacccgctga gcaaatcaag tatggacatc tgggatataa ggctggacgg cctggaccgc    360

ctgctggatc gttttgaatg ggcccgccta ttaatccatc tggcacagcg ccgtggcttc    420

aaatcaaacc gcaagagcga attaaaggac gtggagaccg gtaaagtgct gtcaagcatt    480

caggtgaatg aaaagcgcct gagcctgtat cgcaccgtgg gcgagatgtg gatgaaaaac    540

gcggactgct caaaatatgg caaacgccgc aacagcccga acgaatacgt gtttagcgtt    600

agccgtgcgg acctggaaaa agaaatcgtg accctgtttg aggcgcagcg caaattccat    660
```

-continued

```
agcagctatg cgagcgtgga tctgcagaaa acatacatcc agatctgggc acatcagctg    720
ccgtttgcga gcggtaacgc gatcgtgaat aaagtgggct attgcagcct attaaaaggc    780
aaagaaaaac gcgtgccgaa agcgacctat acattccagt acttcaatac actggaccaa    840
atcaaccgca cccgcctggg cccgaacttc cagccgttca ccaaagaaca gcgcgatata    900
atcctggata aaatgttcca gcgcaccgac tactataaaa agaaaaccat cccggaggtg    960
acatactacg atataaggaa atggctggcg ctggatgaaa ccatccagtt caagggctta   1020
acctacgatc cgaacgagga gctgaaaaag atcgagatga aaccgttcat taatctgaaa   1080
ccgttctatg aaattaaaaa ggtggtaacc aactacgcga agaaaaccaa cgaagtgttc   1140
agcgcgctgg attacgatac cgtggcgtac gcgctgaccg tgtataaaac cgacaaggat   1200
ataaggagct acctgaaacg cagcaataat ctgagcaaac gctgctacga cgaccaatta   1260
atcgaagaac tgctgaccct gagctatact aagttcggcc acctgagctt caaagcgatt   1320
aatcacgtgc tgccaataat gcaggaaggc cgcacctacc aggaagcaat acaccagctg   1380
ggctacgata caaccaacct gaaaaaggaa aataggagca tgttcctgcc aataatcccg   1440
gatgaaatca ccaacccgat cgtgaaacgc gcgctgaccc aggcgcgcaa agtggtgaac   1500
gcaataatcc gccgctacgg ctcaccgaac agcgtgcaca tcgaactggc gcgcgaactg   1560
agcaaaagcc acgatgaacg caaaaagatc atgaccgcgc acgatgaaaa ctacaaaaag   1620
aacaaaggcg cggtgagcat cctgatcgat aacggcatcc tgaacccgac cggctacgat   1680
atcgtgcgct acaaactgtg gaaagaacag ggcgaacgct gcgcgtacag cctgaaaaag   1740
atcccggcga acaccttctt caacgaactg aaaaaggaac gctcaggccc gccggtgctg   1800
gaagtggatc acatcctgcc gtacagccag agcttcatcg atagctacca caacaaagtg   1860
ctggtgtacg gcgacgaaaa ccagaaaaag ggcaaccgca tcccgtacac cttcttcagc   1920
gaagaagaca aagaatggga gagcttcgaa agctacgtgc gcagcaacag cttcttcagc   1980
aaaaagaaac gcggctacct gctgaaaaag gcgtacctgc cgcgcgaaag caacttaatc   2040
aaagaacgcc atctgaacga tacccgctac gcgagcagct acctgaaaaa cttcattgag   2100
aaaaacctga aattcaagga agcggtgggc atcacccgca agaagtacgt ccagaccgtg   2160
aacggcgtga tcaccgcgca tctgcgcaaa cgctggggcc tggaaaaaga tcgccaggaa   2220
acctatctgc atcatgcgat ggatgcgatc atcgtggcgt gcaccgatca tcatatggtg   2280
accaaagtga ccgaatatta tcagatcaaa gaaggcaaca aatcaatcaa aaagccgtat   2340
tttccgctgc cgtggatggg cttccgcgaa gaaatcctta gccatctgga aagccagccg   2400
atcgcgcgca aaatcagcga agaactgaaa atcggctatc agagcccgga ttatatcctg   2460
gtgagccgca tgccgaaacg cagcgtgacc ggcagcgcgc atgatcagac cgtgatgaaa   2520
aagggcgata tcgataaaaa gggcaaaacc atcatcatca aacgcgtgca tctgaaagac   2580
atcaaattcg acgaaaacgg cgacttcaaa atggtgggca aggaacagga cttagcgacc   2640
tacgaagcga tcaaacagcg ctacctggaa taccgcaaag agagcaaaaa ggcgtttgaa   2700
accccgctgt acaaaccgag caaaaagggc aagggcaacc tgatcaaaaa gatcaaagtg   2760
gaagtccaga ccaaatcgtt tgtgcgcgag atcaacggcg gcgtggcgca gaacggcgat   2820
ctggtgcgcg tggatctgtt tgaaaaagat aaccgctatt atatggtgcc gatctacgtg   2880
gtggataccg tgcgcagcga actgccgaac aaagcggtga ccagcagcaa aggctatgaa   2940
cagtggttaa gcatcgataa cagcttcacc ttcaaattca gcctgtaccc gtatgatctg   3000
```

-continued

```
gtgcgcctgg tgaaaggcga tgaagatcgc ttcctgtatt ttagcaccct ggacatcaac   3060

agcgatcgcc tgaacttcaa agacgtgaac aaaccgagca aacaggcgga atatcgctac   3120

agcctgaaga ccatcgagaa cctggagaaa tacgaaattg gcgtgctggg cgatctgcgc   3180

ctggtgcgcc aggaaacccg caaaatcttc aaa                                3213
```

<210> SEQ ID NO 189
<211> LENGTH: 3216
<212> TYPE: DNA
<213> ORGANISM: Bacillus sp.
<220> FEATURE:
<221> NAME/KEY: source
<223> OTHER INFORMATION: /note="APG08290.1 Native Seq"

<400> SEQUENCE: 189

```
atgagtgagt tggattaccg catagggttg gatattggta cgaattccat tggctggggt     60

gttattgaat tattttggaa caaggacaga gaacgatatg aaaaagtaag gattgtcgac    120

aagggcgttc gtatgtttga taaggctgaa atacctaata agggtgcttc tcttgctgaa    180

ccgagacgta tagcgcgttc atcacgtaga aggttaaatc gcaaaagtca gaggaagaaa    240

gagatacgta atttacttgt tcaacacgga atgattaccc aagaggaatt ggatttgtta    300

tatcctcttt caaaaaaatc aatagatatt tgggatattc gtttggatgg attagatcgt    360

ctgttgaatc atcttgaatg ggctcgatta ttaattcatt tagcacaaag acgtggtttt    420

aagtcgaatc gaaagtctga attgaaagat gctgagacgg ggaaggtatt atcgagtatt    480

caagtaaatg aaaaacgact atttctgtac cgtacagtgg gggaaatgtg gataaaagat    540

gctgagttta gtaagtatga tagaagacgt aattctccta atgagtatgt attttcggtt    600

agtcgtgcgg acttagaaaa ggaaattgtt actctatttg aagcacaaag aaagtttcag    660

tcatcatacg catcgaagaa cttacaagaa acatatttac aaatttgggc acaccaactt    720

ccttttgctt ctgggaatgc aattttaaac aaagtaggct attgttcatt attgaaaggg    780

aaagaaagga gaattccgaa agcaacatat acttttcaat atttcagtgc actagatcag    840

gtgaatcgaa cacgattagg acctgatttt caaccattta cgcaggaaca gaaagagatt    900

attttagata aaatgtttca acgtacagat tattataaaa aaaagactat acctgaagtt    960

agctactatg atatacggaa atggctagag ttagatgaaa ctattcaatt taaaggactt   1020

aattatgatc caaacgaaga actgaaaaaa atagaaaaaa aaccatttat taatttaaag   1080

gcattctatg aaattaaaaa ggtagttgca aattatgctg agagaacaaa tgaggcattt   1140

tcaacgttag actatgatgc gattgcatat gctttaacag tttataaaac ggacaaagat   1200

attagatctt atttgaagaa atctaataat ttatcaaaac gttgctacga cgatcaatta   1260

atagaagagc tatttactct ctcctataca aagtttggtc atttatcatt taaagcaatt   1320

aatcatgtac ttccaattat gcaagaggga aggacttatc aagaagcgat acaccaatta   1380

ggatatgata ccactaatct taaaaaagaa aacagaagta tgttcttgcc tcttattcca   1440

gatgaaataa caaatccaat tgttaaaaga gcgataactc aagcacgtaa agttgtaaac   1500

gctattatta gaagatatgg ttctccaaat tctgttcata ttgaactagc tcgtgagctt   1560

tctaaaagtc atgacgagag aaagaaaata atgacggctc atgatgaaaa ttataagaaa   1620

aataaaggag ctatatccat tttgatcgag aatggaattt taaatccgac aggatatgat   1680

attgtacgtt ataagttatg gaaagagcaa ggagaacgat gtgcttattc gttaaaggag   1740

attcctccgg atacgttttt taatgaatta aaaaaagaac gaaatggttc tccaattcta   1800
```

```
gaggtagatc acattttacc gtatagccaa agttttattg atagttatca taataaagta   1860

ttagtttaca gtgatgaaaa tcgaaacaag ggaaatcgaa ttccatatac ctatttttta   1920

gagacaaata aggattggga agcttttgaa aggtatgtaa gatcaaataa gctttttttct  1980

aaaaagaagc gtgagtattt attgaaaaaa acatatttgc caagagagag tgaactaata   2040

aaggagcgac atttaaatga tacgcgatat gctagtacct tttgaaaaa cttcattgag   2100

cagaacttgc aatttaaaga agttgaagtt aatctgcgta aaaaacgtgt gcaaacagtt   2160

aatggtgtaa ttacagcgca ccttcgaaaa agatggggat tagaaaaaaa tagacaggaa   2220

acatatctgc atcatgcaat ggacgctatc attgttgctt gtacagacca tcatatggtt   2280

actagaataa cagagtatta tcaaataaaa gaaagtaata aatcagtaaa gaaaccatat   2340

tttccgatgc catgggaggg ttttagagat gaactcttat cacatttagc gagccagcca   2400

attgctaaaa aaattagtga ggagcttaaa gctggatatc aatcatctga ttatatattt   2460

gtgtctcgaa tgccaaaaag atctgtcact ggagcagctc atgatcaaac gattaggaga   2520

aaaggtggta ttgataaaaa aggaaaaact attattataa agcgtgtgcg cttaaaggat   2580

attaagtttg atgagaatgg cgattttaaa atggttggaa aagaacaaga tttagcaact   2640

tatgaggcga taaagcaaag atatttggag catagaaaaa actcgaaaaa agcatttgaa   2700

acacctctat acaagcctag taaaaaaggg acaggaaatc tcatcaaaag agttaaaatt   2760

gaaggacaaa ctaaagcttt tgttcgagaa gtaaatgggg gagtagccca aaatagtgat   2820

ttagtaagag ttgatttatt tgaaaaagat gataaatatt acatggtgcc tatttatgta   2880

ccagataccg tttgttcaga attacccaaa aaagttgtga aaagtggtaa gggttatgag   2940

caatggctaa cactagataa cagctttacg tttaaatcta gtttataccc ttatgattta   3000

gtacgtcttg taaaaggtaa tgaagatcgt tttttatact ttggtactct cgatatcgat   3060

tctgaccgtc ttaattttaa agatgtaaat aagccatcaa aacagaatga atatcgttat   3120

agtcttaaaa caattgagaa tttagaaaaa tatgaggttg gtgttttagg tgatttaagg   3180

ttagtgaaac aagaaacacg tagaattttt aataga                            3216
```

<210> SEQ ID NO 190
<211> LENGTH: 3216
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: source
<223> OTHER INFORMATION: /note="APG08290.1 E. coli optimized"

<400> SEQUENCE: 190

```
atgagcgagc tagattatcg catcggcctg gatatcggca ctaactcaat aggctggggc     60

gtgatcgaac tgttctggaa taaagaccgc gagcgctatg aaaaggtgcg catcgtggac    120

aaaggcgtca ggatgttcga caaagcggag atcccgaata aaggtgcatc actggcggaa    180

ccaagacgta tagcacgtag tagtcgccgc cgattaaacc gcaaaagtca gcgcaagaaa    240

gagatccgta acctgctggt tcagcatggc atgatcaccc aggaagaact ggatctgctg    300

tacccgctga gcaagaaatc aatcgacatc tgggatataa ggctggacgg cctggaccgc    360

ctattaaacc atctggaatg ggcccgccta ttaatccatc tggcgcagcg tagaggcttc    420

aaatcaaacc gcaagagcga attaaaggac gcggagaccg gtaaagtgct gtcaagcatt    480
```

```
caggtgaatg aaaagcgcct gttcctgtat cgcaccgtgg gcgagatgtg gattaaagac    540
gcggagttct caaaatacga ccgccgtcgc aacagcccga acgaatacgt gtttagcgtt    600
agccgtgcgg acctggagaa agaaatcgtg accctgtttg aagcgcagcg caaattccaa    660
tcaagctacg cgagcaagaa cctgcaagag acctacctgc agatttgggc acatcagctg    720
ccgtttgcaa gcggcaacgc gatattaaac aaagtgggct attgcagcct attaaaaggc    780
aaagaacgcc gcatcccgaa agcgacctat acattccagt acttcagcgc gctggaccag    840
gtgaaccgta cccgtctggg ccctgatttt cagccgttta cccaggaaca gaaagaaata    900
atcctggata aaatgttcca gcgcaccgac tactataaaa agaaaaccat cccggaagtg    960
tcatattacg atataaggaa atggctggag ctggatgaga ccatccagtt caagggcctg   1020
aactacgatc cgaacgagga gctgaaaaaa atcgagaaaa aaccgttcat taatctgaaa   1080
gcgttctatg aaattaaaaa agtggtggcg aactacgcgg aacgaaccaa cgaagcattc   1140
agcaccctgg attacgatgc gatcgcgtac gcgttaaccg tgtataaaac cgacaaggat   1200
ataaggagct acctgaaaaa atcaaacaac ctgagcaaac gctgctacga cgaccaatta   1260
atcgaagaac tgttcaccct gagctatact aagttcggcc acctgagctt caaagcgatt   1320
aatcacgtgc tgccaataat gcaggaaggc cgcacctacc aggaagcgat ccaccagctg   1380
ggctacgata ccaccaacct gaaaaaagaa aaccgcagca tgttcctgcc gctgatcccg   1440
gatgaaatca ccaacccgat cgtgaaacgc gcgatcaccc aggcgcgcaa agtggtgaac   1500
gcgatcatcc gccgctacgg ctcaccgaac agcgtgcaca tcgagctggc gcgcgagctg   1560
agcaaaagcc acgacgagcg caaaaaaatc atgaccgcgc acgacgagaa ctacaagaaa   1620
aacaaaggcg cgatcagcat cctgatcgag aacggcatcc tgaacccgac cggctacgat   1680
atcgtgcgct acaaactgtg gaaagaacag ggtgaacgct gcgcgtacag cctgaaagaa   1740
atcccgccgg ataccttctt caacgaactg aaaaaagaac gcaacggctc accgatcctg   1800
gaagtggatc acatcctgcc gtacagccag agcttcatcg atagctacca caacaaagtg   1860
ctggtgtaca gcgatgaaaa ccgcaacaaa ggcaaccgca tcccgtacac ctacttcctg   1920
gaaaccaaca aagattggga agcgttcgaa cgctacgtgc gcagcaacaa actgttcagc   1980
aaaaagaaac gcgaatacct gctgaaaaaa acctacctgc cgcgcgaaag cgaactgatc   2040
aaagaacgcc acttaaacga tacccgctac gcgagcacct tcctgaaaaa cttcatcgaa   2100
cagaacctgc agttcaaaga agtggaggtg aacctgcgta aaaagcgcgt ccagaccgtg   2160
aacggcgtga tcaccgcgca tctgcgcaaa cgctggggcc tggaaaaaaa ccgccaggaa   2220
acctatctgc atcatgcgat ggatgcgatc atcgtggcgt gcaccgatca tcatatggtg   2280
acccgcatca ccgaatatta tcagatcaaa gaaagcaaca aatcagtgaa aaaaccgtat   2340
tttccgatgc cgtgggaagg ctttcgcgat gaactgctga gccatctggc gagccagccg   2400
atcgcgaaaa aaatcagcga agaactgaaa gcgggctatc agagcagcga ttatatcttt   2460
gtgagccgca tgccgaaacg cagcgtgacc ggcgcggcgc atgatcagac catccgccgc   2520
aaaggcggca tcgataaaaa aggcaaaacc atcatcatca aacgcgtgcg cctgaaagat   2580
atcaaatttg atgaaaacgg cgattttaaa atggtgggca aagaacagga cttagcgacc   2640
tacgaagcga tcaaacagcg ctatctggag catcgcaaga acagcaaaaa agcgtttgag   2700
accccgctgt acaaaccgag caaaaaaggc accggcaacc tgatcaaacg cgtgaaaatc   2760
gagggccaga ccaaagcgtt tgtgcgcgaa gtgaacggcg gcgtggcgca gaacagcgat   2820
ctggtgcgcg tggatctgtt tgaaaaagat gacaaatatt atatggtgcc gatctatgtg   2880
```

ccggataccg tgtgtagcga actgccgaaa aaagtggtga aaagcggcaa aggctatgaa 2940
cagtggttaa ccctggataa cagcttcacc ttcaagagca gcctgtaccc gtatgatctg 3000
gtgcgcctgg tgaaaggcaa cgaagatcgc tttctgtatt ttggcaccct ggacatcgat 3060
agcgatcgcc tgaacttcaa agacgtgaac aaaccgagca agcagaacga ataccgctac 3120
agcctgaaga ccatcgagaa cctggagaaa tatgaagtgg gcgtgctggg cgatctgcgc 3180
ctggtgaaac aggaaacccg ccgcattttt aaccgc 3216

<210> SEQ ID NO 191
<211> LENGTH: 4011
<212> TYPE: DNA
<213> ORGANISM: Enterococcus sp.
<220> FEATURE:
<221> NAME/KEY: source
<223> OTHER INFORMATION: /note="APG05459.1 Native Seq"

<400> SEQUENCE: 191
atgaagaaag actacgttat tggtctggat atagggacta attctgtcgg ctgggcagtt 60
atgacagaag actatcagtt ggtgaagaaa aaaatgccta tttatggaaa cactgaaaaa 120
aagaaaatca agaaaaattt ttggggtgtg cgtttatttg aagaagggca tacagccgaa 180
gatcgccgat taaaaagaac agcacgacga agaattagtc gtcgacggaa tcgtttacgc 240
tacttacaag cttttttga agaagcgatg acagctttgg atgaaaactt ttttgctcgt 300
ttacaagaga gtttttagt gcctgaagat aagaagtggc acagacatcc gatttttgct 360
aagttggaag atgaagtagc ttaccatgaa acgtatccga caatctacca tttacgcaaa 420
aaattagcag attcatctga gcaagcagat ttacgactaa tttatttggc gttggcacat 480
attgtcaaat atcgtggaca tttttaatt gaaggaaaat taagtacaga aaatatttct 540
gttaaagaac aatttcaaca atttatgatc atttataacc aaacctttgt gaatggagag 600
agtcgcttag ttagtgcgcc attacctgaa tctgtcttga ttgaggaaga gttgactgaa 660
aaagcttctc gtactaaaaa atctgaaaaa gtcttacaac aatttcctca agaaaaagct 720
aatggcttat ttggtcagtt cttaaagcta atggtaggga ataaagctga ctttaaaaaa 780
gtttttggtt tggaagaaga agccaaaata acctacgcta gtgaaagcta tgaagaagat 840
ttagaaggca ttttagcaaa ggttggggat gaatatagtg acgtgttttt agctgctaaa 900
aatgtgtacg atgcagttga attatcaacg attttagcag attcggataa aaaaagtcac 960
gcgaaattat cttctagcat gattgtccgt tttacagaac atcaagaaga tttaaaaaaa 1020
ttcaaacgat ttattcgtga aaattgtcca gacgaatatg ataatctctt taaaaatgaa 1080
cagaaagacg gctatgcagg ctacattgca cacgcaggta aggtttcaca gcttaaattt 1140
taccagtatg ttaagaaaat cattcaagat attgctggag cagaatattt tttagaaaaa 1200
attgctcaag aaaacttttt aagaaagcaa cggacctttg ataatggggt gattcctcat 1260
caaattcatt tggctgagtt acaagcaatc attcatcgtc aagcggccta ttatccattt 1320
ttaaaagaaa atcaagaaaa aattgaacaa ctggttacat ttcgaattcc ttattatgtc 1380
ggaccattat caaaaggaga tgcaagtacc ttcgcttggc taaaacgtca aagtgaggaa 1440
ccaattcgac cttggaacct tcaagaaacc gttgatttgg accaatcagc gacagccttt 1500
attgaacgaa tgaccaattt tgatacgtat ttaccttctg aaaaagtttt accgaaacat 1560
agtttgttat atgaaaagtt tatggtattt aatgaattga ccaagatttc ttatacggat 1620
gatcgaggaa tcaaagccaa tttttcaggt aaagaaaaag aaaaaatctt tgattatctg 1680

```
tttaagacgc gtcgaaaagt taagaaaaag gatatcattc aattctatcg aaacgaatat   1740
aatacggaga ttgtcacgct tagtggactt gaagaagacc aatttaatgc tagttttagc   1800
acgtatcagg atttactgaa atgtggttta acaagagctg aattagacca ccctgataat   1860
gccgaaaaat tggaagatat cataaaaatt ttaactattt ttgaagatcg gcaacgaatt   1920
cggacgcaac tttccacatt caaagggcag ttctcagcag aagtactaaa aaaattagaa   1980
cgcaagcact acactggctg gggaagattg tcgaaaaaat taatcaatgg tatctacgat   2040
aaagaatcgg gtaaaacaat tttggactat ttaattaaag atgatggggt ctcaaaacac   2100
tataatcgca attttatgca actgattaat gattcacaat tatcttttaa aaatgctatt   2160
caaaaagcac agtccagtga acatgaagaa acattaagtg aaactgtcaa tgaattagct   2220
ggtagtccag caataaaaaa aggaatttat caaagtttaa aaattgtcga tgaactagtc   2280
gcgattatgg gttatgcgcc caagcggatt gttgtcgaaa tggcacgtga aaatcaaacg   2340
actagcactg gcaagagaag atccatccaa cgcttgaaaa tagttgaaaa agcaatggcc   2400
gaaatcggca gcaatttatt aaaagaacaa ccaacgacta atgaacagtt acgagatacc   2460
cgtcttttcc tttactatat gcaaaatggt aaagatatgt acacgggaga tgaattatcg   2520
cttcatcgtt tatctcacta tgatattgat catattatcc cacaaagctt tatgaaagac   2580
gattcattgg ataacctagt tttagtgggc tctactgaaa atcgagggaa atccgatgat   2640
gtacctagca aggaagttgt taaggatatg aaagcttatt gggagaaatt atatgctgct   2700
ggcttaatta gtcaacggaa attccaacgt ctgaccaagg gggagcaagg tggcttgact   2760
ctcgaagaca aagcgcattt tatccaacga caattagtag aaactcgtca aattaccaaa   2820
aatgttgcag ggatcttaga tcaacgctac aatgctaatt caaaagagaa aaaagtccaa   2880
atcatcacct tgaaagctag tttaacgagc caatttcgtt cgatttttgg cttgtataaa   2940
gttcgtgaag tgaatgatta tcaccatgga caagatgctt atttaaactg tgtggtcgca   3000
accacgttat taaaagttta tcctaattta gcaccagaat ttgtttacgg agaatatcct   3060
aaattccagg cctttaaaga aaataaagcc acggcgaaga ctataattta tacaaatttg   3120
atgcgctttt tcacggaaga tgaaccacgg ttcatgaagg atggcgaaat tctttggagt   3180
aacagttatt taaaaaatat caaaaaagaa ttaaattacc atcaaatgaa tattgtcaaa   3240
aaagtagaag tgcaaaaagg cggtttttca aaagagtcga ttaaacccaa aggaccatcg   3300
aataaattga ttcctgtcaa aaatggtttg gatccccaaa aatatggcgg ttttgatagt   3360
cctgtagttg cttatacagt gttattcacg catgaaaaag gtaaaaaacc tcttattaaa   3420
caggagatac tgggcattac gattatggaa aaaacaaggt ttgaacaaaa tcctattctt   3480
tttttagagg agaaaggctt cctacggcct cgtgtattaa tgaaattgcc taagtataca   3540
ctgtatgaat ttccagaggg gcgcaggcgc ttattagcca gcgctaaaga agcgcaaaaa   3600
gggaaccaga tggttttacc tgaacattta cttacgttac tgtaccatgc gaaacaatgt   3660
ttgttaccaa atcaatcaga aagtttggct tatgtagaac aacatcaacc agaatttcaa   3720
gagattttag agagagtggt tgactttgct gaagtgcata cattagccaa gtcaaaagtc   3780
cagcaaattg tgaaactttt tgaagcaaat caaacagcag atgtgaaaga gattgcggca   3840
tcctttatcc aacttatgca gtttaatgcg atgggcgcac caagtacgtt taaatttttc   3900
caaaaagaca ttgagcgagc acgctacacg tcaatcaaag aaatttttga tgccactatc   3960
atttaccaat cgactacggg actgtatgaa acacgcagaa aggttgtcga c            4011
```

<210> SEQ ID NO 192
<211> LENGTH: 4011
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG05459.1 E. coli optimized"

<400> SEQUENCE: 192
atgaaaaagg actacgtgat cggcctagac atcggcacta acagcgttgg ttgggcggtg 60
atgaccgaag attaccagct agtgaagaag aagatgccta tctacggtaa tacagagaag 120
aagaagatta aaaagaactt ctggggcgtg aggctattcg aggagggtca caccgcggag 180
gaccgccgcc tgaagcgcac cgctagacgc cgtatttcac gtcgtcgtaa ccgtctgcgt 240
tacctgcaag cattcttcga agaagcaatg accgcgctgg atgaaaactt cttcgctagg 300
ctgcaggagt catttctggt gccggaggat aaaaagtggc accgtcatcc gatcttcgcg 360
aaactagaag acgaggtggc gtaccatgaa acctacccga ctatctacca cctgcgcaaa 420
aagctggcgg atagcagcga acaagcagac ctgcgattaa tctatctggc gctggcgcac 480
atcgtaaaat acagaggcca cttcctcatc gagggcaaat tatcgaccga aaatattagc 540
gtgaaggagc agttccagca gttcatgatc atctacaacc aaaccttcgt gaacggcgaa 600
tcaaggctgg tgagcgcgcc gctgccggag agcgtattaa ttgaggagga attaaccgag 660
aaagcgagcc gcactaagaa aagcgagaaa gtgcttcagc agttcccgca agaaaaagcg 720
aacggcctgt tcggccagtt cctgaaatta atggtgggca ataaagcgga cttcaaaaag 780
gtgttcggcc tggaagagga ggcgaaaata acctacgcga gcgaaagcta cgaggaagac 840
ctggagggca tactagcgaa agtgggcgac gaatacagtg acgtgttcct ggcggctaaa 900
aacgtgtacg acgcggtgga attaagcacc atactagcgg acagcgataa aaagagtcac 960
gcgaaattaa gctcaagcat gatcgtgcgc ttcaccgaac accaggaaga cctgaaaaag 1020
ttcaaacgct tcatccgcga aaactgcccg gacgaatacg ataacctgtt caaaaacgaa 1080
cagaaagatg gctacgcggg atacatcgcg cacgcgggca aagtgtcaca attaaagttc 1140
taccagtacg tgaagaaaat aatccaggat atcgcgggcg cggaatactt cctggagaaa 1200
atagcgcagg agaacttcct taggaaacag cgcaccttcg acaacggcgt gatcccgcac 1260
caaatacacc tggcggaact acaggcaata attcaccgcc aggcggcata ctacccgttc 1320
ctgaaagaga accaggagaa aatagaacag ctggtgacct tccgcatccc atactacgtg 1380
ggcccgctta gcaaaggcga tgcgagcacc ttcgcgtggc tgaaacgcca gagcgaagaa 1440
ccaatccgcc cgtggaactt acaagaaacc gtggatctgg atcagagcgc gaccgcgttc 1500
atcgaacgca tgaccaactt cgatacatac ctgccgagcg aaaaagtgct gccgaagcat 1560
agcctgctgt atgaaaaatt catggtgttc aacgaactga ccaaaataag ctacaccgat 1620
gatcgcggca ttaaagcgaa cttcagcggc aaagaaaaag agaaaatatt cgattaccta 1680
ttcaaaaccc gccgcaaagt gaaaaagaaa gacataatac agttctaccg caacgaatac 1740
aacaccgaaa tcgtgaccct gagcggcctg gaagaagatc agttcaacgc gagcttcagc 1800
acctaccagg acttattaaa atgcggcctg acccgcgcgg agcttgacca cccggacaac 1860
gcggaaaaac tggaagatat cattaaaata ctgaccatct tcgaagatcg ccagcgcatc 1920
cgcacccagc tgagcacctt caagggccag ttcagcgcgg aagtgctgaa aaagctggaa 1980
cgcaaacatt acaccggctg gggccgcctg agcaaaaagc tgatcaacgg catctacgat 2040
aaagaatcag gcaaaaccat cctggactac ctgatcaaag atgacggcgt gagcaaacac 2100
tacaaccgca acttcatgca gctgatcaac gatagccagc tgagcttcaa gaacgcgatc 2160
cagaaagcgc agagcagcga acatgaagaa accctgagcg aaaccgtgaa cgaactggcg 2220
ggcagcccgg cgatcaaaaa gggcatctat cagagcctga aatcgtgga tgaattagtg 2280 gcgatcatgg gctatgcgcc gaaacgcatc gtggtggaaa tggcgcgcga aaaccagacc 2340
accagcaccg gcaaacgccg cagcatccag cgcctgaaaa tcgtggaaaa agcgatggcg 2400
gaaatcggca gcaacctgct gaaagaacag ccgaccacca acgaacagct gcgcgatacc 2460
cgcctgtttc tgtattatat gcagaacggc aaagatatgt ataccggcga tgaactgtca 2520
ctgcatcgcc tcagccatta tgatatcgat catatcatcc cgcagagctt tatgaaagat 2580
gatagcctgg ataacctggt gctggtgggc agcaccgaaa accgcggcaa aagcgatgat 2640
gtgccgagca aagaagtggt gaaagatatg aaagcgtatt gggaaaaact gtatgcggcg 2700
ggcctgatca gccagcgcaa atttcagcgc ctgaccaaag gcgaacaggg cggcctgacc 2760
ttagaagata aagcgcattt tatccagcgc cagctggtgg aaacccgcca gatcaccaaa 2820
aacgtggcgg gcatcctgga tcagcgctat aacgcgaaca gcaaagaaaa gaaagtccag 2880
atcatcaccc tgaaagcgag cctgaccagc cagtttcgca gcatctttgg cctgtataaa 2940
gtgcgcgaag tgaacgatta tcatcatggc caggatgcgt atctgaactg cgtggtggcg 3000
accaccttac tgaaagtgta tccgaacctg gcgccggaat ttgtgtatgg cgaatatccg 3060
aaatttcagg cgtttaaaga aaacaaagcg accgcgaaaa ccatcatcta taccaacctg 3120
atgcgcttct ttaccgaaga tgaaccgcgc tttatgaaag atggcgaaat tctgtggagc 3180
aacagctatc tgaaaaacat caaaaaggaa ctgaactacc accagatgaa catcgtgaaa 3240
aaggtggagg tccagaaagg cggcttctca aaggaaagca tcaaaccgaa aggcccgagc 3300
aacaaactga tcccggtgaa aaacggcctg gacccgcaga aatatggcgg ctttgatagc 3360
ccggtggtgg cgtataccgt gctgtttacc catgaaaaag gcaaaaagcc gctgatcaaa 3420
caggaaattc tgggcatcac catcatggag aaaacccgct ttgaacagaa cccgatcctg 3480
ttcctggaag aaaaaggctt tctgcgcccg cgcgtgctga tgaaactgcc gaaatatacc 3540
ctctatgaat ttccggaagg ccgccgccgc ctgctggcga gcgcgaaaga agcgcagaaa 3600
ggcaaccaga tggtgttacc ggaacatctg ctgaccctgc tgtatcatgc gaaacagtgc 3660
ctgctgccga accagagcga aagcctggcg tatgtggaac agcatcagcc ggaatttcag 3720
gaaattctgg aacgcgtggt ggattttgcg gaagtgcata ccctggcgaa aagcaaagtt 3780
cagcagattg ttaaactgtt tgaagcgaac cagaccgcgg atgtgaaaga aattgcggcg 3840
agctttattc agctgatgca gtttaacgcg atgggcgccc cgagcacctt caaattcttt 3900
cagaaagata ttgaacgcgc gcgctatacc agcattaaag aaatttttga tgcgaccatt 3960
atctatcagt caaccaccgg cctgtatgaa acccgccgca aagtggtgga t 4011

<210> SEQ ID NO 193
<211> LENGTH: 4308
<212> TYPE: DNA
<213> ORGANISM: Enterococcus sp.
<220> FEATURE:
<221> NAME/KEY: source
<223> OTHER INFORMATION: /note="APG04583.1 Native Seq"

<400> SEQUENCE: 193
atggctaaaa atatacttgg attagatttg ggaaccaata gtattggttg ggcgttggta 60
cagcaagact ttgaaaacaa agaaggaaat attcttggaa tgggaagtag gattattccg 120
atgtcgcaag atattttagg agaattcggt aaggggaatt ctatttctca aactgctgaa 180
cgtactggtt atcgtggtgt ccgtcggtta agagaacgac atttattacg tcgtgagcgt 240
ttgcaccgag ttttgcattt gttgggtttc ttgccaaaac attatgatga aaaaatagat 300
tttacacaac gttttgggaa attcattaac caagccgaac ctaaattggc ttttgatagt 360
gaatttcttt ttaaagattc tttccatgaa atgttagctg attttaaaca aaatcaacca 420
gagtttttga aagataaaaa tggagaagat tgtttagttc cttatgattg gacgatttat 480
tatttacgta aaaaagcatt aacgcaaaaa attgagaaat atgaattagc ttggttgatt 540
cttaatttta atcaaaaacg tggttattat caattaagag gtgaagaaga gaaagaaaat 600
ccaaataaat tggtgggatt tcattctttg aaaatcgttg atgttattcc cgatgctgaa 660
acaaataaaa aaggagagac ttggtattct ttgcatttag aaaatggttg ggtatatcgc 720
cgttcttcta aatttcatt agcggattgg aaagataaag ttcgagattt tattgttacg 780
actgatttaa acgatgatgg ttctgaaaaa ttggataaag atggaattgt gaaacgtagc 840
tttcgtgcac caagtgcgga tgattggact ttgttgaaaa agaaaacaga aaaagatatt 900
gataactcta acaaaactgt tggaacttat atttacgaca atcttttatt gaacccaaaa 960
caaaaaataa aaggaaaaat ggttcgtacc atcgaacgta agttttacaa gcaagaatta 1020
gaacaaattt taaaaactca aaaagaattt cattcagaat tacaaagtga aaatttgcta 1080
caagattgtg ttcgagaatt gtatcgaaat aatgaacaac atcaacaaat gttagaagct 1140
aaagattttg tgcatttgtt cctaaatgat attattttct atcaacgtcc tttgagaagt 1200
caaaaatcca gtatatcgaa ttgtactttg gaatttagaa aatcgaaaaa tgaaaatggt 1260
gaagaagtta ttcatcgttt aaaagtaatt gcaaaatcga atccatatta tcaggaattt 1320
agattgttac aatgggtgca aaatttagca atttatacaa aagatgatga taaaaatgta 1380
acaaacgaat ttctaaagtc tactcaagat tgggaggatt tattgagatg gctacattct 1440
aaaaaagaaa ttaaacagga tgctttaatt aagtttttga ttgaaaagaa aggtttaaaa 1500
ggcaaagctt taactattga agtagcaaaa tatcgttgga attatgttca ggacaaagat 1560
taccctggta atgaaacccg atatttaatt caatctcgtt tggataaagt tgaatatgca 1620
cctaaggatt ttttaactta tgaaaatgaa atggctttgt ggcacatcat ttattcgata 1680
aacgataaaa ttgagtacga aaaagcctta aaatcttttg ccaacaaaaa aggtttggac 1740
gaagtaactt ttgttgaagc gtttaagaaa ttcccgcctt ttaaaagtga ttacggaagt 1800
ttttctgaaa aagcaatcaa gaaattattg cctttgatgc gttttggaac tcaatggaat 1860
tgggataata tcgatcaaaa ttctaaagaa agaattggaa aaatattgac aggcgaatat 1920
gatgaaaaca tcaaaggtcg tgttcgcgaa aaagcaagac atctcaattc tgaaaccgat 1980
tttcaagctt tacctttgtg gttggcgcaa tacgtagttt acggaagaca ttctgaagct 2040
gatattgcag gtaaatggaa ttcggtggat gatttaaagc aatttttaga tgactttaaa 2100
caacattcgc ttcgtaatcc tattgtagag caagtgatta ctgaaacgtt gcgtgcggta 2160
aaagatattt ggaattttta tggaaaaggt gctaaagatt tcttctctga aattcatatc 2220
gagctggggc gtgaaatgaa aaatacggct gatgaacgca agcgtattac tacaatggtt 2280
acggataacg aaaacaccaa tttgcgtatc aaagctttgt tggctgaaat ggctttggat 2340

```
caaaatgtag ataatgttcg tccatattct ccaatgcaac aagaaatttt gaaaatctat   2400
gaagaaggtg ttttgaatgc tgaagaaaat atcgatgatg atattctgaa aattagtaaa   2460
acggctcaac cttctgctac agatttaaag cgttacaaat tgtggttaga acaaaaatat   2520
cgttcgcctt atacaggtca aatgattcct ttgaataagc tgtttacacc tgaatatgag   2580
attgaacaca taattccgca aagtcgctat tttgatgata gtatgagcaa taaagtgatt   2640
tgcgaagcag cggtgaataa acttaaagac aatcaaattg gtttggtttt cattaagaat   2700
catcacggag aagttgtgga tttcggaatg ggaaaacaag tgaagatttt ggaagtttcc   2760
gattatgagg attttgtaaa acaaaattac aataaaaaca gaggaaaacg taataagttg   2820
ttattggaag atattcctga gaaaatgatt gaacgtcaac taaatgatac acgttacatc   2880
agcaaatata ttacgcaagt gttatcgaat attgttcgtg atgataaaga aggtagtaaa   2940
gatgatggtg taaattctaa aaatattgtt cctggaaacg gaaaaattac cacaagactt   3000
aaacaagatt ggggattgaa tgacgtttgg aatgatttgg ttttacctcg ttttgaacga   3060
atgaatacat tgactaattc aaatgatttt acatcaaaaa atacacatgg aaaaacaatt   3120
ccaacagttc caattgagtt atccaaaggt tttctaaaa aacgtatcga tcatcgtcat   3180
cacgcaatgg atgcgttggt aattgcctgt gcaacgagag atcacgtgaa tttgttgaat   3240
aacgaaagtt caaaatcgga tacaaaacgt tatgatttga ataggaaatt aagaaaatac   3300
gagaaagtag cttacaatga tcccaaaaca ggcgaacgaa ttgagaaaga agttccaaaa   3360
gacttcatta aaccttggga gacctttacc gaagatacgc gaactttgtt agaaaatatt   3420
gtaattagtt tcaagcaaaa tctacgagtt atcaataaag caaccaatta ttatgaaaaa   3480
attgagaatg ggaaaaaagt aaaagttgaa caaaagggaa taaattgggc tgtaagaaaa   3540
gctttgcata aagaaaccgt ttctggacaa gtgcatttgg atagaataaa agttgcaaaa   3600
ggtaaaatat taacggctac tcgtaaaact ttggatgcct cttttaatga aaaaacaatt   3660
gagtcaatta cggatacagg gattcaaaag attttattga attatttaaa atcaaaagat   3720
aacaatccag aggttgcatt ttcaccagaa ggaatagaag aattaaataa aaatattagg   3780
ctatataatg atggaaaagc acatcaacca attttgaaag ttcgtgtttt tgagcaagga   3840
agcaaattta ctttaggtga gacgggaaat aaaaccacta agtttgtaga agcagcaaag   3900
ggtactaatc tatttttcgg aatttatgaa gacaaatcag gtaagagaag ctacgaaacc   3960
attccattaa atattgtcat cgaaagacaa aaacaaggtc tgcaagctgt tcccgaaacc   4020
aatgagaaag ggaaacaatt gttgtttacg ttatctccaa atgatttggt ttacgttcct   4080
gaagaaggag tttttgatga gaataatatc aaggtagata ggatttataa ggtagtgagt   4140
ttttctacct atcaatgttt ttttgtaaga aatgatgttt ctacttctgt agttaataag   4200
gttgaatatt ccgctttaaa taaaatggaa aaatctattg acaacataat gataaaagaa   4260
aactgcgtca aactgaatgt agaccgttta ggaaagattt caaaagct                4308
```

<210> SEQ ID NO 194
<211> LENGTH: 4308
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"
<220> FEATURE:
<221> NAME/KEY: source
<223> OTHER INFORMATION: /note="APG04583.1 E. coli optimized"

<400> SEQUENCE: 194

```
atggcgaaga acatactagg cctggatctc ggaaccaaca gcattggttg ggcactggtc     60
cagcaggact tcgagaataa agagggcaac atactaggca tgggcagccg aataatccct    120
atgagtcagg acatactagg cgagttcggc aagggcaaca gcattagcca gaccgcagaa    180
cgtactggtt atcgtggtgt gcgccgttta cgtgaacgtc atctgttacg tcgtgaacgt    240
ctgcatcgtg ttctgcatct gttaggcttc ctgccgaagc attacgatga aaagatcgac    300
ttcacccagc gcttcggcaa gttcattaat caagcggaac caaagctggc gttcgacagc    360
gagttcctgt tcaaggacag cttccatgaa atgctagcgg acttcaagca gaatcaaccg    420
gagttcctga aggataaaaa cggcgaggac tgcctggtgc cgtacgactg gaccatatac    480
tacctgcgca agaaagcact gacccagaag atcgaaaaat acgagctagc gtggctcatc    540
ctgaacttca atcaaaagcg cggatactac cagcttaggg gcgaggagga gaaagagaac    600
ccgaataaac tggtgggctt ccacagcctg aaaatagtgg acgtgatccc ggacgcggaa    660
accaataaaa agggcgagac ctggtactca ctgcatctgg aaaacggctg ggtgtaccgc    720
cgcagcagca aaataagcct ggcggactgg aaagacaaag tgcgcgactt catcgtgacc    780
accgacctga acgatgacgg cagcgaaaaa ctggacaaag acggcatcgt gaaacgcagc    840
tttcgtgcac cgagcgcaga tgattggacc ctattaaaga aaaagaccga aaaagacatc    900
gacaacagca ataaaaccgt gggcacctac atctacgaca acctgttatt aaaccccgaag   960
cagaaaatca aaggcaaaat ggtgcgcacc atcgaacgca aattctacaa acaggagctg   1020
gagcagatcc tgaaaaccca gaaggaattc cacagcgaac tgcagagcga aaacctgctg   1080
caggattgcg tgcgcgaact gtaccgcaat aatgaacagc accagcagat gctggaagcg   1140
aaagatttcg tgcacctgtt cctgaacgat ataatcttct accagcgccc gctgcgcagc   1200
cagaaatcaa gcatcagcaa ttgcaccctg gaattccgca aaagcaagaa tgaaaacggc   1260
gaagaagtga tccaccgcct gaaagtgatc gcgaaaagca acccatacta ccaggaattc   1320
cgcctgctgc agtgggtcca gaacctggcg atctatacta aagacgacga caagaacgta   1380
accaacgagt tcctgaaatc aacccaggac tgggaagatc tgctgcgctg gctgcatagc   1440
aagaaggaga ttaaacagga cgcgctgatc aagttcctga tcgagaaaaa gggcctgaag   1500
ggcaaagcat tgaccatcga ggtggcaaaa taccgctgga actacgtcca ggacaaagat   1560
tacccgggca atgaaacccg ctacctgatc caatcaaggc tggacaaagt ggaatacgcg   1620
ccgaaagatt tcctgaccta cgagaatgaa atggcgctgt ggcacatcat ctacagcatt   1680
aatgataaaa tcgaatatga aaaagcatta aaatcgttcg cgaataaaaa gggcctggat   1740
gaagtgacct tcgtggaagc attcaaaaag ttcccgccgt tcaaaagcga ttacggcagc   1800
ttcagcgaaa aagcgattaa aaagctgctg ccattaatgc gcttcggcac ccagtggaac   1860
tgggataaca tcgatcaaaa tagcaaagaa cgcatcggca aaatactaac cggcgaatac   1920
gatgaaaata ttaaaggccg cgtgcgcgaa aaagcgcgcc atctgaacag cgaaaccgat   1980
ttccaagcat tgccgctgtg gctggcgcag tacgtggtgt acggccgcca tagcgaagcg   2040
gatatcgcgg gcaaatggaa cagcgtggat gatctgaaac agttcctgga tgatttcaaa   2100
cagcatagcc tgcgcaaccc gatcgtggaa caggtgatca ccgaaaccct gcgcgcggtg   2160
aaagatatct ggaacttcta tggcaaaggc gcgaaagatt tcttcagcga aatacacatc   2220
gaactgggcc gcgaaatgaa aaataccgcg gatgaaagaa aacgcatcac caccatggtg   2280
```

-continued accgataatg aaaataccaa cttacgcatt aaagcattgc tggcggaaat ggcgctggat 2340
cagaacgtgg ataacgtgcg cccgtatagc ccgatgcagc aggaaatcct gaaaatatat 2400
gaagaaggcg tattaaacgc ggaagaaaat atcgacgatg atatcctgaa aataagcaaa 2460
accgcgcaac caagcgcgac cgatctgaaa cgctataaac tgtggctgga acagaaatat 2520
cgcagcccgt ataccggcca gatgatcccg ctgaacaaac tgtttacccc ggaatatgaa 2580
atcgaacata tcatcccgca gagccgctat tttgatgata gcatgagcaa caaagtgatc 2640
tgcgaagcgg cggtgaacaa actgaaagat aaccagatcg gcctggtgtt tatcaaaaac 2700
catcatggcg aagtggtgga ttttggcatg ggcaaacagg tgaaaatcct ggaagtgagc 2760
gattatgaag attttgtgaa acagaactat aacaaaaacc gcggcaaacg caacaaatta 2820
ctgctggaag atatcccgga gaaaatgatc gaacgccagc tgaacgatac ccgctatatc 2880
agcaaatata tcacccaggt gctgagcaac atcgtgcgcg atgataaaga aggcagcaaa 2940
gatgatggcg tgaacagcaa aaacatcgtg ccgggcaacg gcaaaatcac cacccgcctg 3000
aaacaggatt ggggcctgaa cgatgtgtgg aacgatctgg tgctgccgcg ctttgaacgc 3060
atgaacaccc tgaccaacag caacgatttt accagcaaaa acacccatgg caaaaccatt 3120
ccgaccgtgc cgattgaact gagcaaaggc tttagcaaaa agcgcattga tcatcgccat 3180
catgcgatgg atgcgctggt gattgcgtgc gcgacccgcg atcatgtgaa cttactgaac 3240
aacgaaagca gcaaaagcga taccaaacgc tatgatctga accgcaaact gcgcaaatat 3300
gaaaaagtgg cgtataacga tccgaaaacc ggcgaacgca ttgaaaaaga agtgccgaaa 3360
gattttatta aaccgtggga aacctttacc gaagataccc gcaccctgct ggaaaacatt 3420
gtgattagct ttaaacagaa cctgcgcgtg attaacaaag cgaccaacta ttatgagaaa 3480
attgaaaacg gcaaaaaggt gaaagtggaa cagaaaggca ttaactgggc ggtgcgcaaa 3540
gcgctgcata aagaaaccgt gagcggccag gtgcatctgg atcgcattaa agtggcgaaa 3600
ggcaaaattc tgaccgcgac ccgcaaaacc ctggatgcgt cattcaacga gaaaaccatt 3660
gaaagcatta ccgataccgg cattcagaaa attctgctga actatctgaa aagcaaagat 3720
aacaacccgg aagtggcgtt tagcccggaa ggcattgaag aactgaacaa aaacattcgc 3780
ctgtataacg atggcaaagc gcatcagccg attctgaaag tgcgcgtgtt tgaacagggc 3840
agcaaattca ccctgggcga aaccggcaac aaaaccacca aatttgtgga agcggcgaaa 3900
ggcaccaacc tgttctttgg catctatgaa gataaaagcg gcaaacgcag ctatgaaacc 3960
attccgctga acattgtgat tgaacgccag aaacagggcc tgcaagcggt gccggaaacc 4020
aacgaaaaag gcaaacagct gctgtttacc ctgtcaccga acgatctggt gtatgtgccg 4080
gaagaaggcg tgtttgatga aaacaacatt aaagtggatc gcatctataa agtggtgagc 4140
tttagcacct atcagtgctt ctttgtgcgc aacgatgtga gcaccagcgt ggtgaacaaa 4200
gtggaatata gcgcgctgaa caaaatggaa aaatcgattg ataacattat gattaaagaa 4260
aactgcgtga aactgaacgt ggatcgcctg ggcaaaatta gcaaagcg 4308

<210> SEQ ID NO 195
<211> LENGTH: 4368
<212> TYPE: DNA
<213> ORGANISM: Empedobacter sp.
<220> FEATURE:
<221> NAME/KEY: source
<223> OTHER INFORMATION: /note="APG01688.1 Native Seq"

<400> SEQUENCE: 195

-continued

```
atgatgatta aaaatatact tggattagat ttggggacta actctattgg gtgggcattg     60
ataaaacaag attttgaaaa taagcatggc gaaattcttg gaatgggtag ccggattatt    120
ccgatgtcac aggatattct gggcgatttt gggaaaggaa attctatttc gcaaaccgct    180
gatcgtacca aatacagaag cgtgagaaga ttacgtgaac gatttttatt gaggagagaa    240
cgactacaca gagttttaca tcttttaaat tttcttccac agcattatgc ttcacaaatt    300
gattttgaaa aaaaattcgg gaagtttaaa tctgaaactg aacccaaatt ggcatgggaa    360
aattggggtg gaaagttttc attccttttc caaaactctt tcaatgaaat gcttgaagat    420
tttaaagcag ctggacaggg tttaaaaatt ccttacgact ggacaattta ttatctccgt    480
aaaaaagcac tttcacaaaa aattgaaaag gaggaactgg cctggattct tttaaacttt    540
aatcagaaac gaggatatta tcaattgcgt ggtgaggaag aagaagagaa tcctaataag    600
ctggttgaat tttattcttt aaaaattgta gatgttgtag cagatgaacc tcaaaaagga    660
aaatctgata tttggtattc tttgatttta gagaatggat gggtttacag acgagcaagc    720
aaaatacccc tatttgactg gaaagataaa acaagagatt ttattgtaac aactgatttg    780
aatgatgaca gaagtgttaa aacagacaaa gaaggaaatg aaaaaagaag tttcagagca    840
ccaagcgaaa acgattggac attggtaaaa aagaaaaccg aacaggaaat cgaccaatct    900
cacaaaaccg ttggaaccta tatctacgaa acacttcttc taaatccgaa acaaaaaatt    960
aaaggaaaat tggttcggac gattgaaaga aaattctata aagatgagct aaaacaaatt   1020
ttagaaaaac aaaaggaatt tcatcaggaa cttaaaaatg atgatttgta taatgattgc   1080
attcgtgagt tgtacagaaa caacgaagca catcagctga ctttgagcaa gaaagatttt   1140
gttcatcttt tgatggatga tcttattttc taccaaagac ctttgagaag ccagaaatca   1200
tctatttcca actgtacgtt agagtttaga aaatataaag atgaaaatgg aatagagcat   1260
acacaatatt taaaagccat tccaaaatcc aatccgtatt atcaggaatt tcgtctttgg   1320
caatggatgt ataatctgaa tatttacaga aaggacgatg aagcgaatgt taccaaagaa   1380
tttttaaata cgaacaaaga ttttgaaagt ctgtttgaat ttttaaataa tagaaaagaa   1440
attgagcaaa agccattgat taaatttctt ttggaacaaa aagatatcaa taaaaaattg   1500
cttaacgctg aagcagaaaa atatcgctgg aactatgtag aagacaagaa atatccttgc   1560
aatgaaacca aaacgatgat ttcttctcgt ttggataaag tcgaaaacat ttctgatgat   1620
ttcctgacaa gggacattga gcagaaaatt tggcacatca tctattccgt caatgataaa   1680
atagaatatg aaaaagcttt gaaatctttt gcaactagaa acgatttgga tgaaaactct   1740
tttatcgaag cgtttaagaa attctcgcct tttaaaagtg aatatggttc tttttcggaa   1800
aaagcaatta aaaagttact gcctttaatg cgattgggta aatattggta tgaagatgaa   1860
attgtaaagc atagtgatat ttatttcaaa aatattgaga atcttttggg tgattttttca   1920
aatagagaca aaaaaatttc tgaagaagac aaagagaaat ggaataaatc tataaatcta   1980
aagttacagg aagagttaaa agattttcaa acagctgaaa tagatttatt tcaaggatta   2040
cgattgcata ttgctcaata ccttgtttat ggaagacatt cagaagcttc aatgattgga   2100
aaatggaatt ccgccgaaga tttagaagaa tttttaaagg attttaaaca gcattcgctt   2160
cgcaacccga ttgtagaaca agtgattaca gaaactttgc gtgttgtaaa agatatttgg   2220
ttgaaatacg gaaatggagc aaaggatttc ttcaatgaaa ttcatattga gttaggaaga   2280
gaaatgaaac ttcccgcaga tgatcgaaaa aaactaacga accagatttc tgaaaacgaa   2340
aataccaatt tccgcatcaa agctctattg gctgaaatga tgaatgacag ttcggtagaa   2400
```

```
aatgtccgtc cgttttcgcc gatgcagcaa gaaattttaa aaatttatga agacgatgtt   2460

ttaaaatcag atatagaaat tgaagatgat attctgaaaa tcagcaaaac cgctcaacct   2520

tctccttccg atttgaaacg atataaactt tggttggaac agaaatacaa atcgccttac   2580

acggggcaaa ttattccttt gaataaattg tttacaccag aatacgaaat tgagcacatt   2640

attccgcaga gccgatattt tgatgacagt tttagcaata aagtaatttg tgagtctgcg   2700

gttaataaat tgaaagataa ctacatcgga cttgaattta ttaagcagtt cggaggaacg   2760

attattgaac ttggttttgg taaaagcata aaagtttttg aaacaaaaga atacgaagat   2820

ttcgtcaaaa aacattacgc caacaatcaa ggtaaaagaa acaaactttt gatggaagat   2880

attccagaga aaatgattga acgtcaaatg aacgatacac gatatatcag caaatatatt   2940

tcgggcgttt tgtctaatat tgttcgggta gaagatggtt cagatgaagg ggtaaattct   3000

aaaaatattg ttcccggaaa cggaaaaatc accacacagc tgaaacaaga ttggggattg   3060

aatgatgttt ggaatgattt gattttacca cgctttgaaa gaatgaacca actcaccaat   3120

tcaaaagttt ttactgcctg gaatgagaat tatcaaaagt tttaccaac tgttcctatt    3180

gaatattcca aagggttttc aaagaaaaga atagaccacc gccatcacgc tttagatgct   3240

ttggtgattg cctgtgctac aaaagatcac gtgaatttat taaataatca atcggcaaaa   3300

tcggatacca aacgatacga tttgaaaaag aaatcgatga agtttgaaaa agtagtttac   3360

aatgatgcca aaacaggaga gaaaatcgaa agggaagtgc caaaacaatt tttaaaacct   3420

tgggaaaatt ttacgctaga tgttaaacat aatttggaaa ctattattgt aagttttaag   3480

caaaatcttc gtgttattaa taaagcgact aattattacg aaaagtatgt tgagaaagac   3540

ggtacaaaaa ataaggaaag agtagagcag accggaacaa actgggcgat taggaaacca   3600

atgcataaag acacggtttc cggtaaagta gatttacctt gggtaaaagt cccaaaaggg   3660

aaaattttaa cagcaacaag gaaaagcctt gatagttcgt ttgacttaaa gtcaataggc   3720

tctattacgg atacaggaat tcagaaaata ctcaaaaatt atttagcatt taaagacgga   3780

aatcctgaac tggctttttc accagaagga attgacgatt tgaataaaaa tattgaaaaa   3840

tacaatgatg gaaaaccgca tcaacccatc aataaagtaa gggtttttga attgggaagt   3900

aaatttcagg taggacaaag tggaaataaa aaagataaat atgtagaagc tgcaaaagga   3960

actaatctat tctttgctgt ttatgaagat gaaaaaggaa agagaaatta tgaaaccatt   4020

cctttgaatg aagtgattga aaggcaaaag caaggtttat ctgtggttga tttaaaaggt   4080

acaaatgatt tctacttatg tccgaatgat tttgtatata ttccatcagg cgacgaactt   4140

gaaaatataa ataatgttga ttttaaagac attaaaaaag agataaacga aagaatttac   4200

aaagtagtaa gttttacagg taatagactt tcctgtattc catatatggt tgcaacaacg   4260

attgttaata aattagagtt tacgcaactt aataaaattg aattcacaaa agaaaaagaa   4320

atttgtataa aactaaatgt cgatcgttta ggtaacattt caaaagcg                4368
```

<210> SEQ ID NO 196
<211> LENGTH: 4368
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="APG01688.1 E. coli optimized"

<400> SEQUENCE: 196
atgatgatta aaaatatcct aggcctggac ctgggaacca acagcatcgg ctgggcgctg 60
attaaacagg acttcgaaaa taagcatggc gagatactag gcatgggcag ccgaataatc 120
ccgatgagtc aggacatact aggcgacttc ggcaagggca acagcatcag ccagaccgcg 180
gaccgcacaa aatatcgcag cgtgcgtaga ctgcgcgaac gctttctgtt acgtcgtgaa 240
cgtctgcatc gtgttcttca cctattaaac ttcctgccgc agcattacgc tagccagatc 300
gacttcgaga agaagttcgg caagttcaag agcgagaccg aaccaaaact ggcgtgggaa 360
aactggggcg gcaaattcag cttcctattc caaaatagct tcaacgagat gctagaggac 420
ttcaaggcgg cgggtcaggg attaaaaata ccgtacgact ggaccatata ctacctgcgc 480
aagaaagcgc tgagccagaa gatcgagaag gaggagctgg cgtggatact actgaacttt 540
aatcaaaagc gcggatacta ccagctgcgc ggcgaggagg aggaggagaa cccgaataaa 600
ctggtggagt tctacagcct gaaaatagtg gacgtggtgg cggacgagcc gcagaaaggc 660
aaaagcgaca tctggtactc actcatacta gaaaacggct gggtgtatcg ccgcgcgagc 720
aaaataccgc tgttcgactg gaaagataaa acccgcgact tcatcgtgac caccgacctg 780
aacgacgacc gcagcgtgaa aaccgacaaa gaaggcaatg aaaaacgcag ctttcgcgcg 840
ccgagcgaaa acgattggac cctggtgaaa aagaaaaccg aacaggaaat cgatcagagc 900
cataaaaccg tgggcacata tatctatgaa accctgttat taaacccgaa gcagaagatt 960
aaaggcaaac tggtgcgcac catcgaacgc aaattctaca aagacgaatt aaaacagata 1020
ctagaaaaac agaaagaatt ccaccaggaa ttaaagaacg acgacttata taacgattgc 1080
atccgcgaac tgtaccgcaa taatgaagcg caccaattaa ccctgagcaa aaaggatttc 1140
gtgcacttat taatggatga tctgatcttc taccagcgcc cgctgcgcag ccagaaatca 1200
agcatcagca attgcaccct ggaattccgc aaatacaaag atgaaaacgg catcgaacac 1260
acccagtacc tgaaagcgat cccgaaatca aacccatact accaggaatt ccgcctgtgg 1320
cagtggatgt acaacctgaa catctaccgc aaagatgatg aagcgaacgt aaccaaagaa 1380
ttcctgaaca ccaataaaga tttcgaaagc ctgttcgaat tcctgaataa tcgcaaagaa 1440
atcgaacaga aaccattaat caaattcctg ctggaacaga aagatattaa taaaaagtta 1500
ttaaacgcgg aagcggaaaa atacagatgg aactacgtgg aagataaaaa gtacccgtgc 1560
aatgaaacca aaaccatgat cagcagccgc ctggataaag tggaaaatat cagcgatgat 1620
ttcctgaccc gcgatatcga acagaaaata tggcatataa tctacagcgt gaacgataaa 1680
atcgaatatg aaaaagcatt aaaatcgttc gcgacccgca acgatctgga tgaaaatagc 1740
ttcatcgaag cattcaaaaa gttcagcccg ttcaaaagcg aatacggcag cttcagcgaa 1800
aaagcgatta aaaagctgct gccattaatg cgcctgggaa aatactggta cgaagatgaa 1860
atcgtgaaac acagcgatat ctacttcaaa aacatcgaaa acctgctggg cgatttcagc 1920
aaccgcgata aaaagatcag cgaagaagat aaagaaaaat ggaacaaaag catcaacctg 1980
aaactgcagg aagaactgaa agatttccag accgcggaaa tcgatctgtt ccagggcctg 2040
cgcctgcata tcgcgcagta cctggtgtac ggccgccata gcgaagcgag catgatcggc 2100
aaatggaact cagcggaaga tctggaagaa ttcctgaaag atttcaaaca gcatagcctg 2160
cgcaacccga tcgtggaaca ggtgatcacc gaaaccctgc gcgtggtgaa agatatctgg 2220
ctgaaatatg gcaacggcgc gaaagatttc tttaacgaaa ttcatatcga actgggccgc 2280

-continued

```
gaaatgaaac tgccggcgga tgatcgcaaa aagctgacca accagatcag cgaaaacgaa   2340
aacaccaact ttcgcatcaa agcgctgctg gcggaaatga tgaacgatag cagcgtggaa   2400
aacgtgcgcc cgtttagccc gatgcagcag gaaatcctga aaatctatga agatgatgtg   2460
ctgaaaagcg atatcgaaat cgaagatgat atcttaaaaa tcagcaaaac cgcgcagccg   2520
agcccgagcg atctgaaacg ctataaactg tggctggaac agaaatataa aagcccgtat   2580
accggccaga tcatcccgct gaacaaactg tttaccccgg aatatgaaat cgaacatatc   2640
atcccgcaga gccgctattt tgatgatagc tttagcaaca aagtgatctg cgaaagcgcg   2700
gtgaacaaac tgaaagataa ctatatcggc ctggaattca tcaaacagtt tggcggcacc   2760
atcatcgaac tgggctttgg caaaagcatc aaagtgtttg aaaccaaaga atatgaagat   2820
tttgtgaaaa agcattatgc gaacaaccag ggcaaacgca acaaactgtt aatggaagat   2880
atcccggaga aaatgatcga acgccagatg aacgataccc gctatatcag caaatatatc   2940
agcggcgtgc tgagcaacat cgtgcgcgtg gaagatggca gcgatgaagg cgtgaacagc   3000
aaaaacatcg tgccgggcaa cggcaaaatc accacccagc tgaaacagga ttggggcctg   3060
aacgatgtgt ggaacgatct gatcctgccg cgctttgaac gcatgaacca gctgaccaac   3120
agcaaagtgt ttaccgcgtg gaacgaaaac tatcagaaat ttctgccgac cgtgccgatt   3180
gaatatagca aaggctttag caaaaagcgc attgatcatc gccatcatgc gctggatgcg   3240
ttagtgattg cgtgcgcgac caaagatcat gtgaacctgc tgaacaacca gagcgcgaaa   3300
agcgatacca aacgctatga tctgaaaaag aaaagcatga aatttgaaaa agtggtgtat   3360
aacgatgcga aaaccggcga gaaaattgaa cgcgaagtgc cgaaacagtt tctgaaaccg   3420
tgggaaaact ttaccctgga tgtgaaacat aacctggaaa ccattattgt gagctttaaa   3480
cagaacctgc gcgtgattaa caaagcgacc aactattatg aaaaatatgt ggaaaaagat   3540
ggcaccaaaa acaaagaacg cgtggaacag accggcacca actgggcgat tcgcaaaccg   3600
atgcataaag ataccgtgtc aggcaaagtg gatctgccgt gggtgaaagt gccgaaaggc   3660
aaaattctga ccgcgacccg caaaagcctg gatagcagct ttgatctgaa aagcattggc   3720
agcattaccg ataccggcat tcagaaaatt ctgaaaaact atctggcgtt taaagatggc   3780
aacccggaac tggcgtttag cccggaaggc attgatgatc tgaacaaaaa cattgaaaaa   3840
tataacgatg gcaaaccgca tcagccgatt aacaaagtgc gcgtgtttga actgggcagc   3900
aaatttcagg tgggccagag cggcaacaaa aaggacaaat atgtggaagc ggcgaaaggc   3960
accaacctgt tctttgcggt gtatgaagat gaaaaaggca aacgcaacta tgaaaccatc   4020
ccgttaaacg aagtgattga acgccagaaa cagggcctga gcgtggtgga tctgaaaggc   4080
accaacgatt tttatctgtg cccgaacgat tttgtgtata ttccgagcgg cgatgaactg   4140
gaaaacatta acaacgtgga ttttaaagat attaaaaagg aaattaacga acgcatctat   4200
aaagtggtga gctttaccgg caaccgcctg agctgcattc cgtatatggt ggcgaccacc   4260
attgtgaaca aactggaatt cacccagctg aacaaaattg aattcaccaa agaaaaagaa   4320
atttgcatta aactgaacgt ggatcgcctg ggcaacatta gcaaagcg                4368
```

<210> SEQ ID NO 197
<211> LENGTH: 25
<212> TYPE: DNA
<213> ORGANISM: Homo sapiens
<220> FEATURE:
<221> NAME/KEY: source
<223> OTHER INFORMATION: /note="target seq for Ataxia-telangiectasia
syndrome"

<400> SEQUENCE: 197
gaattattcc agaaagccaa agtag 25

<210> SEQ ID NO 198
<211> LENGTH: 20
<212> TYPE: DNA
<213> ORGANISM: Homo sapiens
<220> FEATURE:
<221> NAME/KEY: source
<223> OTHER INFORMATION: /note="target seq for Very long chain acyl-CoA dehydrogenase deficiency"

<400> SEQUENCE: 198
ggcttcatga aggtacagga 20

<210> SEQ ID NO 199
<211> LENGTH: 25
<212> TYPE: DNA
<213> ORGANISM: Homo sapiens
<220> FEATURE:
<221> NAME/KEY: source
<223> OTHER INFORMATION: /note="target seq for Abnormality of T cell physiology"

<400> SEQUENCE: 199
ggtgtgctca ccagaatgga gtaca 25

<210> SEQ ID NO 200
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 200
gcagatcatt ggggtggatc ccgaa 25

<210> SEQ ID NO 201
<211> LENGTH: 25
<212> TYPE: DNA
<213> ORGANISM: Homo sapiens
<220> FEATURE:
<221> NAME/KEY: source
<223> OTHER INFORMATION: /note="target seq for 3-Oxo-5 alpha-steroid delta 4-dehydrogenase deficiency"

<400> SEQUENCE: 201
ggctgcaagc ttttcaccac cayag 25

<210> SEQ ID NO 202
<211> LENGTH: 25
<212> TYPE: DNA
<213> ORGANISM: Homo sapiens
<220> FEATURE:
<221> NAME/KEY: source
<223> OTHER INFORMATION: /note="target seq for Acute myeloid leukemia"

<400> SEQUENCE: 202
gggcggcatg aaccggaggc ccatc 25

<210> SEQ ID NO 203
<211> LENGTH: 20
<212> TYPE: DNA
<213> ORGANISM: Homo sapiens
<220> FEATURE:

<221> NAME/KEY: source
<223> OTHER INFORMATION: /note="target seq for Acute myeloid leukemia"

<400> SEQUENCE: 203
gcatgggcgg catgaaccgg 20

<210> SEQ ID NO 204
<211> LENGTH: 20
<212> TYPE: DNA
<213> ORGANISM: Homo sapiens
<220> FEATURE:
<221> NAME/KEY: source
<223> OTHER INFORMATION: /note="target seq for Cutaneous malignant melanoma 3"

<400> SEQUENCE: 204
gtggccactg tggggatcac 20

<210> SEQ ID NO 205
<211> LENGTH: 20
<212> TYPE: DNA
<213> ORGANISM: Homo sapiens
<220> FEATURE:
<221> NAME/KEY: source
<223> OTHER INFORMATION: /note="target seq for Alpha-1-antitrypsin deficiency"

<400> SEQUENCE: 205
gtgctgacca tcgacgagaa 20

<210> SEQ ID NO 206
<211> LENGTH: 20
<212> TYPE: DNA
<213> ORGANISM: Homo sapiens
<220> FEATURE:
<221> NAME/KEY: source
<223> OTHER INFORMATION: /note="target seq for Charcot-Marie-Tooth disease, type 2"

<400> SEQUENCE: 206
ggcgagctgc atgatctgcg 20

<210> SEQ ID NO 207
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-predisposing syndrome"

<400> SEQUENCE: 207
gcacatgacg gaggttgtga ggcgc 25

<210> SEQ ID NO 208
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-predisposing syndrome"

<400> SEQUENCE: 208
gaggttgtga ggcactgccc ccacc 25

<210> SEQ ID NO 209

<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 209
gcagcatccg gctgcaggta 20

<210> SEQ ID NO 210
<211> LENGTH: 25
<212> TYPE: DNA
<213> ORGANISM: Homo sapiens
<220> FEATURE:
<221> NAME/KEY: source
<223> OTHER INFORMATION: /note="target seq for Brugada syndrome"

<400> SEQUENCE: 210
ggccaagggg atccgcacgc tgctc 25

<210> SEQ ID NO 211
<211> LENGTH: 20
<212> TYPE: DNA
<213> ORGANISM: Homo sapiens
<220> FEATURE:
<221> NAME/KEY: source
<223> OTHER INFORMATION: /note="target seq for Brugada syndrome"

<400> SEQUENCE: 211
gcctgatgac gcaggactgc 20

<210> SEQ ID NO 212
<211> LENGTH: 20
<212> TYPE: DNA
<213> ORGANISM: Homo sapiens
<220> FEATURE:
<221> NAME/KEY: source
<223> OTHER INFORMATION: /note="target seq for GRACILE syndrome"

<400> SEQUENCE: 212
ggtacgaagt ctcgacactg 20

<210> SEQ ID NO 213
<211> LENGTH: 20
<212> TYPE: DNA
<213> ORGANISM: Homo sapiens
<220> FEATURE:
<221> NAME/KEY: source
<223> OTHER INFORMATION: /note="target seq for Enhanced s-cone syndrome"

<400> SEQUENCE: 213
ggcattggcg gtggacccca 20

<210> SEQ ID NO 214
<211> LENGTH: 25
<212> TYPE: DNA
<213> ORGANISM: Homo sapiens
<220> FEATURE:
<221> NAME/KEY: source
<223> OTHER INFORMATION: /note="target seq for Charcot-Marie-Tooth
      disease, type 2"

<400> SEQUENCE: 214
gaagaacagg ttctggacgt caaag 25

<210> SEQ ID NO 215
<211> LENGTH: 20
<212> TYPE: DNA
<213> ORGANISM: Homo sapiens
<220> FEATURE:
<221> NAME/KEY: source
<223> OTHER INFORMATION: /note="target seq for Charcot-Marie-Tooth disease, type 2"

<400> SEQUENCE: 215
gaacaggttc tggacgtcaa 20

<210> SEQ ID NO 216
<211> LENGTH: 20
<212> TYPE: DNA
<213> ORGANISM: Homo sapiens
<220> FEATURE:
<221> NAME/KEY: source
<223> OTHER INFORMATION: /note="target seq for Arylsulfatase a, allele a"

<400> SEQUENCE: 216
gacaggtcat agagcagcgg 20

<210> SEQ ID NO 217
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 217
gaacgtggtc gctctggaca 20

<210> SEQ ID NO 218
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 218
gaacgtggtc gctctggaca 20

<210> SEQ ID NO 219
<211> LENGTH: 25
<212> TYPE: DNA
<213> ORGANISM: Homo sapiens
<220> FEATURE:
<221> NAME/KEY: source
<223> OTHER INFORMATION: /note="target seq for HEMOGLOBIN ARLINGTON PARK"

<400> SEQUENCE: 219
ggtgcatctg actcctgagg agaag 25

<210> SEQ ID NO 220
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial hypertrophic cardiomyopathy 1"

<400> SEQUENCE: 220
gaagtccgag gctcgccgca 20

<210> SEQ ID NO 221
<211> LENGTH: 20
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 221
gtcaaggtca tcggtgaggc 20

<210> SEQ ID NO 222
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 222
ggtcatcagt gaggccggcc ggggt 25

<210> SEQ ID NO 223
<211> LENGTH: 25
<212> TYPE: DNA
<213> ORGANISM: Homo sapiens
<220> FEATURE:
<221> NAME/KEY: source
<223> OTHER INFORMATION: /note="target seq for Brugada syndrome"

<400> SEQUENCE: 223
gtctcagcct tacgcacctt ccgag 25

<210> SEQ ID NO 224
<211> LENGTH: 25
<212> TYPE: DNA
<213> ORGANISM: Homo sapiens
<220> FEATURE:
<221> NAME/KEY: source
<223> OTHER INFORMATION: /note="target seq for Brugada syndrome"

<400> SEQUENCE: 224
gcaccttcca agtcctccgg gccct 25

<210> SEQ ID NO 225
<211> LENGTH: 26
<212> TYPE: DNA
<213> ORGANISM: Homo sapiens
<220> FEATURE:
<221> NAME/KEY: source
<223> OTHER INFORMATION: /note="target seq for Hereditary cancer-
predisposing syndrome"

<400> SEQUENCE: 225
gaagccagcc cctcagggca actgac 26

<210> SEQ ID NO 226
<211> LENGTH: 20
<212> TYPE: DNA
<213> ORGANISM: Homo sapiens
<220> FEATURE:
<221> NAME/KEY: source
<223> OTHER INFORMATION: /note="target seq for Deficiency of butyryl-CoA
dehydrogenase"

<400> SEQUENCE: 226
ggcgactcat gggttctgaa 20

<210> SEQ ID NO 227
<211> LENGTH: 25
<212> TYPE: DNA
<213> ORGANISM: Homo sapiens
<220> FEATURE:
<221> NAME/KEY: source
<223> OTHER INFORMATION: /note="target seq for Deficiency of butyryl-CoA dehydrogenase"

<400> SEQUENCE: 227
gcgactcacg ggttctgaat ggaac 25

<210> SEQ ID NO 228
<211> LENGTH: 20
<212> TYPE: DNA
<213> ORGANISM: Homo sapiens
<220> FEATURE:
<221> NAME/KEY: source
<223> OTHER INFORMATION: /note="target seq for Benign scapuloperoneal muscular dystrophy with cardiomyopathy"

<400> SEQUENCE: 228
ggaactgcgg gcccagcatg 20

<210> SEQ ID NO 229
<211> LENGTH: 20
<212> TYPE: DNA
<213> ORGANISM: Homo sapiens
<220> FEATURE:
<221> NAME/KEY: source
<223> OTHER INFORMATION: /note="target seq for Benign scapuloperoneal muscular dystrophy with cardiomyopathy"

<400> SEQUENCE: 229
ggacgagtac caggagcttc 20

<210> SEQ ID NO 230
<211> LENGTH: 20
<212> TYPE: DNA
<213> ORGANISM: Homo sapiens
<220> FEATURE:
<221> NAME/KEY: source
<223> OTHER INFORMATION: /note="target seq for Cone-rod dystrophy 6"

<400> SEQUENCE: 230
ggatctgatc cgggagcgca 20

<210> SEQ ID NO 231
<211> LENGTH: 25
<212> TYPE: DNA
<213> ORGANISM: Homo sapiens
<220> FEATURE:
<221> NAME/KEY: source
<223> OTHER INFORMATION: /note="target seq for Cone-rod dystrophy 6"

<400> SEQUENCE: 231
gaatgcacta tgttctattc catcc 25

<210> SEQ ID NO 232
<211> LENGTH: 25
<212> TYPE: DNA
<213> ORGANISM: Homo sapiens
<220> FEATURE:

<221> NAME/KEY: source
<223> OTHER INFORMATION: /note="target seq for Stargardt disease 1"

<400> SEQUENCE: 232
gagctgctca caggacgaga acatc 25

<210> SEQ ID NO 233
<211> LENGTH: 20
<212> TYPE: DNA
<213> ORGANISM: Homo sapiens
<220> FEATURE:
<221> NAME/KEY: source
<223> OTHER INFORMATION: /note="target seq for Leber congenital amaurosis 2"

<400> SEQUENCE: 233
gtctatccag taagtatctc 20

<210> SEQ ID NO 234
<211> LENGTH: 20
<212> TYPE: DNA
<213> ORGANISM: Homo sapiens
<220> FEATURE:
<221> NAME/KEY: source
<223> OTHER INFORMATION: /note="target seq for Cone-rod dystrophy 3"

<400> SEQUENCE: 234
ggtacgtcca tgccacaccc 20

<210> SEQ ID NO 235
<211> LENGTH: 20
<212> TYPE: DNA
<213> ORGANISM: Homo sapiens
<220> FEATURE:
<221> NAME/KEY: source
<223> OTHER INFORMATION: /note="target seq for Nonsyndromic Oculocutaneous Albinism"

<400> SEQUENCE: 235
ggacctttac ggcgtaatcc 20

<210> SEQ ID NO 236
<211> LENGTH: 20
<212> TYPE: DNA
<213> ORGANISM: Homo sapiens
<220> FEATURE:
<221> NAME/KEY: source
<223> OTHER INFORMATION: /note="target seq for Phenylketonuria"

<400> SEQUENCE: 236
gtcatccttt ggtgaattac 20

<210> SEQ ID NO 237
<211> LENGTH: 25
<212> TYPE: DNA
<213> ORGANISM: Homo sapiens
<220> FEATURE:
<221> NAME/KEY: source
<223> OTHER INFORMATION: /note="target seq for Phenylketonuria"

<400> SEQUENCE: 237
gtattacgtg gcagagagtt ttaat 25

<210> SEQ ID NO 238
<211> LENGTH: 20
<212> TYPE: DNA
<213> ORGANISM: Homo sapiens

```
<220> FEATURE:
<221> NAME/KEY: source
<223> OTHER INFORMATION: /note="target seq for Breast-ovarian cancer,
      familial 1"

<400> SEQUENCE: 238

ggacgctctt gtattatctg                                               20


<210> SEQ ID NO 239
<211> LENGTH: 25
<212> TYPE: DNA
<213> ORGANISM: Homo sapiens
<220> FEATURE:
<221> NAME/KEY: source
<223> OTHER INFORMATION: /note="target seq for Hyperphenylalaninemia,
      non-pku"

<400> SEQUENCE: 239

gcccttctca gttcgctacg accca                                         25


<210> SEQ ID NO 240
<211> LENGTH: 20
<212> TYPE: DNA
<213> ORGANISM: Homo sapiens
<220> FEATURE:
<221> NAME/KEY: source
<223> OTHER INFORMATION: /note="target seq for Hyperphenylalaninemia,
      non-pku"

<400> SEQUENCE: 240

gctacgaccc atacacccaa                                               20


<210> SEQ ID NO 241
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 241

gcgctatgtt ctattccatc                                               20


<210> SEQ ID NO 242
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 242

ggggctggta ttcatgaaag gcaac                                         25


<210> SEQ ID NO 243
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 243

gcgctatgtt ctattccatc                                               20
```

<210> SEQ ID NO 244
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-
predisposing syndrome"

<400> SEQUENCE: 244
gtgttctcag gttatcggta agttt 25

<210> SEQ ID NO 245
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-
predisposing syndrome"

<400> SEQUENCE: 245
ggaaatgctg ttagtcggta tgtcg 25

<210> SEQ ID NO 246
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-
predisposing syndrome"

<400> SEQUENCE: 246
ggaaatgctg ttagtcagta tgtcg 25

<210> SEQ ID NO 247
<211> LENGTH: 20
<212> TYPE: DNA
<213> ORGANISM: Homo sapiens
<220> FEATURE:
<221> NAME/KEY: source
<223> OTHER INFORMATION: /note="target seq for Anterior segment
dysgenesis 6"

<400> SEQUENCE: 247
gtggccactg atcggaaacg 20

<210> SEQ ID NO 248
<211> LENGTH: 25
<212> TYPE: DNA
<213> ORGANISM: Homo sapiens
<220> FEATURE:
<221> NAME/KEY: source
<223> OTHER INFORMATION: /note="target seq for Brugada syndrome"

<400> SEQUENCE: 248
gaacctgatc ctggccgtgg tcgca 25

<210> SEQ ID NO 249
<211> LENGTH: 20
<212> TYPE: DNA
<213> ORGANISM: Homo sapiens
<220> FEATURE:
<221> NAME/KEY: source
<223> OTHER INFORMATION: /note="target seq for Brugada syndrome"

<400> SEQUENCE: 249
gatcctggcc gtggtcgcaa 20

<210> SEQ ID NO 250
<211> LENGTH: 25
<212> TYPE: DNA
<213> ORGANISM: Homo sapiens
<220> FEATURE:
<221> NAME/KEY: source
<223> OTHER INFORMATION: /note="target seq for Ornithine carbamoyltransferase deficiency"

<400> SEQUENCE: 250
gaagggccat gaccttctca ctcta 25

<210> SEQ ID NO 251
<211> LENGTH: 25
<212> TYPE: DNA
<213> ORGANISM: Homo sapiens
<220> FEATURE:
<221> NAME/KEY: source
<223> OTHER INFORMATION: /note="target seq for Osteogenesis imperfecta type I"

<400> SEQUENCE: 251
ggtgctcgag gattgcccgg aacag 25

<210> SEQ ID NO 252
<211> LENGTH: 25
<212> TYPE: DNA
<213> ORGANISM: Homo sapiens
<220> FEATURE:
<221> NAME/KEY: source
<223> OTHER INFORMATION: /note="target seq for Osteogenesis imperfecta type I"

<400> SEQUENCE: 252
gctcgaggat tgcccggaac agctg 25

<210> SEQ ID NO 253
<211> LENGTH: 25
<212> TYPE: DNA
<213> ORGANISM: Homo sapiens
<220> FEATURE:
<221> NAME/KEY: source
<223> OTHER INFORMATION: /note="target seq for Constipation"

<400> SEQUENCE: 253
gattccagtt aaatggatgg caatt 25

<210> SEQ ID NO 254
<211> LENGTH: 25
<212> TYPE: DNA
<213> ORGANISM: Homo sapiens
<220> FEATURE:
<221> NAME/KEY: source
<223> OTHER INFORMATION: /note="target seq for Dopamine beta hydroxylase deficiency"

<400> SEQUENCE: 254
ggacactgcc tattttgcgg tgagt 25

<210> SEQ ID NO 255
<211> LENGTH: 25
<212> TYPE: DNA
<213> ORGANISM: Homo sapiens
<220> FEATURE:
<221> NAME/KEY: source
<223> OTHER INFORMATION: /note="target seq for Cystic fibrosis"

<400> SEQUENCE: 255
gacttcatcc aggtatgtaa aaata 25

<210> SEQ ID NO 256
<211> LENGTH: 25
<212> TYPE: DNA
<213> ORGANISM: Homo sapiens
<220> FEATURE:
<221> NAME/KEY: source
<223> OTHER INFORMATION: /note="target seq for Phenylketonuria"

<400> SEQUENCE: 256
gatgtaaacc tgacccacac tgaat 25

<210> SEQ ID NO 257
<211> LENGTH: 20
<212> TYPE: DNA
<213> ORGANISM: Homo sapiens
<220> FEATURE:
<221> NAME/KEY: source
<223> OTHER INFORMATION: /note="target seq for Deficiency of UDPglucose-hexose-1-phosphate uridylyltransferase"

<400> SEQUENCE: 257
gagcccctga cacccttacc 20

<210> SEQ ID NO 258
<211> LENGTH: 20
<212> TYPE: DNA
<213> ORGANISM: Homo sapiens
<220> FEATURE:
<221> NAME/KEY: source
<223> OTHER INFORMATION: /note="target seq for Amyloid Cardiomyopathy, Transthyretin-related"

<400> SEQUENCE: 258
gtcaccaatc ccaaggaatg 20

<210> SEQ ID NO 259
<211> LENGTH: 25
<212> TYPE: DNA
<213> ORGANISM: Homo sapiens
<220> FEATURE:
<221> NAME/KEY: source
<223> OTHER INFORMATION: /note="target seq for Carbohydrate-deficient glycoprotein syndrome type I"

<400> SEQUENCE: 259
ggctactcca tgacagcgcc tgagg 25

<210> SEQ ID NO 260
<211> LENGTH: 25
<212> TYPE: DNA
<213> ORGANISM: Homo sapiens
<220> FEATURE:
<221> NAME/KEY: source
<223> OTHER INFORMATION: /note="target seq for Metachromatic leukodystrophy"

<400> SEQUENCE: 260
gcatcccgta ctcccacgac cagat 25

<210> SEQ ID NO 261
<211> LENGTH: 25
<212> TYPE: DNA

<213> ORGANISM: Homo sapiens
<220> FEATURE:
<221> NAME/KEY: source
<223> OTHER INFORMATION: /note="target seq for Smith-Lemli-Opitz syndrome"

<400> SEQUENCE: 261
gttcttcaat gggcgccccg ggatc 25

<210> SEQ ID NO 262
<211> LENGTH: 20
<212> TYPE: DNA
<213> ORGANISM: Homo sapiens
<220> FEATURE:
<221> NAME/KEY: source
<223> OTHER INFORMATION: /note="target seq for Deafness, autosomal recessive 1A"

<400> SEQUENCE: 262
gcaggtgagc ccgccggccc 20

<210> SEQ ID NO 263
<211> LENGTH: 25
<212> TYPE: DNA
<213> ORGANISM: Homo sapiens
<220> FEATURE:
<221> NAME/KEY: source
<223> OTHER INFORMATION: /note="target seq for Congenital omphalocele"

<400> SEQUENCE: 263
gccagcgctc ctagtggcca tgcac 25

<210> SEQ ID NO 264
<211> LENGTH: 25
<212> TYPE: DNA
<213> ORGANISM: Homo sapiens
<220> FEATURE:
<221> NAME/KEY: source
<223> OTHER INFORMATION: /note="target seq for Congenital omphalocele"

<400> SEQUENCE: 264
gcgctcctag tggccatgca cgtgg 25

<210> SEQ ID NO 265
<211> LENGTH: 20
<212> TYPE: DNA
<213> ORGANISM: Homo sapiens
<220> FEATURE:
<221> NAME/KEY: source
<223> OTHER INFORMATION: /note="target seq for Congenital omphalocele"

<400> SEQUENCE: 265
gtccacgcca gcgctcctag 20

<210> SEQ ID NO 266
<211> LENGTH: 20
<212> TYPE: DNA
<213> ORGANISM: Homo sapiens
<220> FEATURE:
<221> NAME/KEY: source
<223> OTHER INFORMATION: /note="target seq for Congenital omphalocele"

<400> SEQUENCE: 266
gctcctagtg gccatgcacg 20

<210> SEQ ID NO 267
<211> LENGTH: 25

<212> TYPE: DNA
<213> ORGANISM: Homo sapiens
<220> FEATURE:
<221> NAME/KEY: source
<223> OTHER INFORMATION: /note="target seq for Congenital myotonia, autosomal dominant form"

<400> SEQUENCE: 267
gagaggattc tttgcagcca cgttc 25

<210> SEQ ID NO 268
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 1"

<400> SEQUENCE: 268
ggtgacccga gagtgggtgt 20

<210> SEQ ID NO 269
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast and/or ovarian cancer"

<400> SEQUENCE: 269
gatgcctgga cagaggacaa 20

<210> SEQ ID NO 270
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 1"

<400> SEQUENCE: 270
ggacaatggc ttccatggta 20

<210> SEQ ID NO 271
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 1"

<400> SEQUENCE: 271
gggctagaaa tctgttgcta 20

<210> SEQ ID NO 272
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 1"

<400> SEQUENCE: 272
ggtgacccga gagtgggtgt 20

<210> SEQ ID NO 273
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 1"

<400> SEQUENCE: 273
gattctgcaa ctttcaattg 20

<210> SEQ ID NO 274
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 1"

<400> SEQUENCE: 274
ggacaatggc ttccatggta 20

<210> SEQ ID NO 275
<211> LENGTH: 25
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 275
gaaagcccga cttatagcca gtaat 25

<210> SEQ ID NO 276
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 2"

<400> SEQUENCE: 276
gattacatga acaaatgggc 20

<210> SEQ ID NO 277
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 2"

<400> SEQUENCE: 277
gattacatga acaaatgggc 20

<210> SEQ ID NO 278
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 2"

<400> SEQUENCE: 278
gactggaaaa ggaatacagt 20

<210> SEQ ID NO 279
<211> LENGTH: 25
<212> TYPE: DNA
<213> ORGANISM: Homo sapiens
<220> FEATURE:
<221> NAME/KEY: source
<223> OTHER INFORMATION: /note="target seq for Breast and/or ovarian cancer"

<400> SEQUENCE: 279
gttggctgat ggtggatggc tcata 25

<210> SEQ ID NO 280
<211> LENGTH: 25
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 2"

<400> SEQUENCE: 280
gttggctgat ggtggatggc tcata 25

<210> SEQ ID NO 281
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 2"

<400> SEQUENCE: 281
ggtcagaaga ttattcttca 20

<210> SEQ ID NO 282
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 2"

<400> SEQUENCE: 282
ggcttctagt ctcttttgtt 20

<210> SEQ ID NO 283
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 2"

<400> SEQUENCE: 283
ggcttctagt ctcttttgtt 20

<210> SEQ ID NO 284
<211> LENGTH: 20

<212> TYPE: DNA
<213> ORGANISM: Homo sapiens
<220> FEATURE:
<221> NAME/KEY: source
<223> OTHER INFORMATION: /note="target seq for Smith-Lemli-Opitz syndrome"

<400> SEQUENCE: 284
gttgcgattt tgcagccatt 20

<210> SEQ ID NO 285
<211> LENGTH: 25
<212> TYPE: DNA
<213> ORGANISM: Homo sapiens
<220> FEATURE:
<221> NAME/KEY: source
<223> OTHER INFORMATION: /note="target seq for Alport syndrome 1, X-linked recessive"

<400> SEQUENCE: 285
ggcctatggg tccccctggt ttcgg 25

<210> SEQ ID NO 286
<211> LENGTH: 20
<212> TYPE: DNA
<213> ORGANISM: Homo sapiens
<220> FEATURE:
<221> NAME/KEY: source
<223> OTHER INFORMATION: /note="target seq for Acute neuronopathic Gaucher's disease"

<400> SEQUENCE: 286
ggcatcaggt gagtgagtca 20

<210> SEQ ID NO 287
<211> LENGTH: 20
<212> TYPE: DNA
<213> ORGANISM: Homo sapiens
<220> FEATURE:
<221> NAME/KEY: source
<223> OTHER INFORMATION: /note="target seq for Gonadotropin deficiency"

<400> SEQUENCE: 287
gtaactctcc agcataccat 20

<210> SEQ ID NO 288
<211> LENGTH: 20
<212> TYPE: DNA
<213> ORGANISM: Homo sapiens
<220> FEATURE:
<221> NAME/KEY: source
<223> OTHER INFORMATION: /note="target seq for Distal arthrogryposis type 1A"

<400> SEQUENCE: 288
gaagctggag gaggccgaga 20

<210> SEQ ID NO 289
<211> LENGTH: 20
<212> TYPE: DNA
<213> ORGANISM: Homo sapiens
<220> FEATURE:
<221> NAME/KEY: source
<223> OTHER INFORMATION: /note="target seq for Distal arthrogryposis type 1A"

<400> SEQUENCE: 289
gctggaggag gccgagaagg 20

<210> SEQ ID NO 290
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-
predisposing syndrome"

<400> SEQUENCE: 290
gctgccacct tcagggcctc 20

<210> SEQ ID NO 291
<211> LENGTH: 20
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 291
gataaacttc ttgaagagga 20

<210> SEQ ID NO 292
<211> LENGTH: 25
<212> TYPE: DNA
<213> ORGANISM: Homo sapiens
<220> FEATURE:
<221> NAME/KEY: source
<223> OTHER INFORMATION: /note="target seq for Death in early adulthood"

<400> SEQUENCE: 292
gtgttctcca tgttcgaaca gaccc 25

<210> SEQ ID NO 293
<211> LENGTH: 20
<212> TYPE: DNA
<213> ORGANISM: Homo sapiens
<220> FEATURE:
<221> NAME/KEY: source
<223> OTHER INFORMATION: /note="target seq for Death in early adulthood"

<400> SEQUENCE: 293
gttcgaacag acccaaatcc 20

<210> SEQ ID NO 294
<211> LENGTH: 20
<212> TYPE: DNA
<213> ORGANISM: Homo sapiens
<220> FEATURE:
<221> NAME/KEY: source
<223> OTHER INFORMATION: /note="target seq for Severe autosomal
recessive muscular dystrophy of childhood - North African type"

<400> SEQUENCE: 294
gaaatctgtg tgtgtccaga 20

<210> SEQ ID NO 295
<211> LENGTH: 20
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 295
ggtcatcatt gagagcgacc 20

<210> SEQ ID NO 296
<211> LENGTH: 20
<212> TYPE: DNA
<213> ORGANISM: Homo sapiens
<220> FEATURE:
<221> NAME/KEY: source
<223> OTHER INFORMATION: /note="target seq for Carbohydrate-deficient glycoprotein syndrome type I"

<400> SEQUENCE: 296
gaatgctgaa gatgatcgac 20

<210> SEQ ID NO 297
<211> LENGTH: 20
<212> TYPE: DNA
<213> ORGANISM: Homo sapiens
<220> FEATURE:
<221> NAME/KEY: source
<223> OTHER INFORMATION: /note="target seq for Charcot-Marie-Tooth disease, type I"

<400> SEQUENCE: 297
gaatgctgaa gatgatcgac 20

<210> SEQ ID NO 298
<211> LENGTH: 25
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 298
gctcagtaca ccaccgtcgg ccgca 25

<210> SEQ ID NO 299
<211> LENGTH: 20
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 299
gtacaccacc gtcggccgca 20

<210> SEQ ID NO 300
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial Mediterranean fever"

<400> SEQUENCE: 300
ggacacgtga tggagggaag aacac 25

<210> SEQ ID NO 301
<211> LENGTH: 25
<212> TYPE: DNA
<213> ORGANISM: Homo sapiens
<220> FEATURE:
<221> NAME/KEY: source
<223> OTHER INFORMATION: /note="target seq for Deafness, autosomal recessive 2"

<400> SEQUENCE: 301
ggacctttgt caatgggaca cggac 25

<210> SEQ ID NO 302
<211> LENGTH: 25
<212> TYPE: DNA
<213> ORGANISM: Homo sapiens
<220> FEATURE:
<221> NAME/KEY: source
<223> OTHER INFORMATION: /note="target seq for Deafness, autosomal recessive 2"

<400> SEQUENCE: 302
ggacctttgt caatgggaca cagac 25

<210> SEQ ID NO 303
<211> LENGTH: 25
<212> TYPE: DNA
<213> ORGANISM: Homo sapiens
<220> FEATURE:
<221> NAME/KEY: source
<223> OTHER INFORMATION: /note="target seq for Deafness, X-linked 2"

<400> SEQUENCE: 303
gcgctcctag tggccatgca cgtgg 25

<210> SEQ ID NO 304
<211> LENGTH: 25
<212> TYPE: DNA
<213> ORGANISM: Homo sapiens
<220> FEATURE:
<221> NAME/KEY: source
<223> OTHER INFORMATION: /note="target seq for Enlarged vestibular aqueduct"

<400> SEQUENCE: 304
gccaccactg ctctttcccg cacgg 25

<210> SEQ ID NO 305
<211> LENGTH: 20
<212> TYPE: DNA
<213> ORGANISM: Homo sapiens
<220> FEATURE:
<221> NAME/KEY: source
<223> OTHER INFORMATION: /note="target seq for Congenital sensorineural hearing impairment"

<400> SEQUENCE: 305
gtggtcatta acacaaactc 20

<210> SEQ ID NO 306
<211> LENGTH: 20
<212> TYPE: DNA
<213> ORGANISM: Homo sapiens
<220> FEATURE:
<221> NAME/KEY: source
<223> OTHER INFORMATION: /note="target seq for Deficiency of UDPglucose-hexose-1-phosphate uridylyltransferase"

<400> SEQUENCE: 306
gccagatatt gcccagcgtg 20

<210> SEQ ID NO 307
<211> LENGTH: 20
<212> TYPE: DNA
<213> ORGANISM: Homo sapiens
<220> FEATURE:
<221> NAME/KEY: source
<223> OTHER INFORMATION: /note="target seq for Very long chain acyl-CoA dehydrogenase deficiency"

<400> SEQUENCE: 307
gccactaatc gtacccagtt 20

<210> SEQ ID NO 308
<211> LENGTH: 20
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 308
gatattccac tggtggtcga 20

<210> SEQ ID NO 309
<211> LENGTH: 20
<212> TYPE: DNA
<213> ORGANISM: Homo sapiens
<220> FEATURE:
<221> NAME/KEY: source
<223> OTHER INFORMATION: /note="target seq for Pyruvate kinase deficiency of red cells"

<400> SEQUENCE: 309
ggaagactcc tgggcataag 20

<210> SEQ ID NO 310
<211> LENGTH: 25
<212> TYPE: DNA
<213> ORGANISM: Homo sapiens
<220> FEATURE:
<221> NAME/KEY: source
<223> OTHER INFORMATION: /note="target seq for Autosomal dominant progressive external ophthalmoplegia with mitochondrial DNA deletions 1"

<400> SEQUENCE: 310
gaagtcgttg atggatctgg ccaat 25

<210> SEQ ID NO 311
<211> LENGTH: 20
<212> TYPE: DNA
<213> ORGANISM: Homo sapiens
<220> FEATURE:
<221> NAME/KEY: source
<223> OTHER INFORMATION: /note="target seq for Very long chain acyl-CoA dehydrogenase deficiency"

<400> SEQUENCE: 311
gaagatcaca gcttttgtgg 20

<210> SEQ ID NO 312
<211> LENGTH: 20
<212> TYPE: DNA
<213> ORGANISM: Homo sapiens
<220> FEATURE:
<221> NAME/KEY: source
<223> OTHER INFORMATION: /note="target seq for Cystinosis, ocular nonnephropathic"

<400> SEQUENCE: 312
gtccatctcc ttctaccctc 20

<210> SEQ ID NO 313
<211> LENGTH: 20
<212> TYPE: DNA
<213> ORGANISM: Homo sapiens
<220> FEATURE:
<221> NAME/KEY: source
<223> OTHER INFORMATION: /note="target seq for Pyruvate kinase deficiency of red cells"

<400> SEQUENCE: 313
gctcagccca gcttctgtct 20

<210> SEQ ID NO 314
<211> LENGTH: 25
<212> TYPE: DNA
<213> ORGANISM: Homo sapiens
<220> FEATURE:
<221> NAME/KEY: source
<223> OTHER INFORMATION: /note="target seq for Distal myopathy, Tateyama type"

<400> SEQUENCE: 314
gattgacctg gtgaaccaag acccc 25

<210> SEQ ID NO 315
<211> LENGTH: 25
<212> TYPE: DNA
<213> ORGANISM: Homo sapiens
<220> FEATURE:
<221> NAME/KEY: source
<223> OTHER INFORMATION: /note="target seq for Malignant hyperthermia, susceptibility to, 1"

<400> SEQUENCE: 315
ggccctgcgg atccgcgcca tcctc 25

<210> SEQ ID NO 316
<211> LENGTH: 25
<212> TYPE: DNA
<213> ORGANISM: Homo sapiens
<220> FEATURE:
<221> NAME/KEY: source
<223> OTHER INFORMATION: /note="target seq for Malignant hyperthermia, susceptibility to, 1"

<400> SEQUENCE: 316
ggatccgcgc catcctccgc tccct 25

<210> SEQ ID NO 317
<211> LENGTH: 25
<212> TYPE: DNA
<213> ORGANISM: Homo sapiens
<220> FEATURE:
<221> NAME/KEY: source
<223> OTHER INFORMATION: /note="target seq for Myopathy, Central Core"

<400> SEQUENCE: 317
ggtctgatca tcgacgcttt tggtg 25

<210> SEQ ID NO 318
<211> LENGTH: 20
<212> TYPE: DNA
<213> ORGANISM: Homo sapiens
<220> FEATURE:
<221> NAME/KEY: source
<223> OTHER INFORMATION: /note="target seq for Myopathy, Central Core"

<400> SEQUENCE: 318
ggtctgatca tcgacgcttt 20

<210> SEQ ID NO 319
<211> LENGTH: 25
<212> TYPE: DNA
<213> ORGANISM: Homo sapiens
<220> FEATURE:
<221> NAME/KEY: source
<223> OTHER INFORMATION: /note="target seq for Myopathy, Central Core"

<400> SEQUENCE: 319
gatcatcgac acttttggtg agctc 25

<210> SEQ ID NO 320
<211> LENGTH: 25
<212> TYPE: DNA
<213> ORGANISM: Homo sapiens
<220> FEATURE:
<221> NAME/KEY: source
<223> OTHER INFORMATION: /note="target seq for Malignant hyperthermia, susceptibility to, 1"

<400> SEQUENCE: 320
ggcggaggca ttggggacga gatcg 25

<210> SEQ ID NO 321
<211> LENGTH: 20
<212> TYPE: DNA
<213> ORGANISM: Homo sapiens
<220> FEATURE:
<221> NAME/KEY: source
<223> OTHER INFORMATION: /note="target seq for Ceroid lipofuscinosis neuronal 2"

<400> SEQUENCE: 321
gtgacagtgg ggccgggtgt 20

<210> SEQ ID NO 322
<211> LENGTH: 25
<212> TYPE: DNA
<213> ORGANISM: Homo sapiens
<220> FEATURE:
<221> NAME/KEY: source
<223> OTHER INFORMATION: /note="target seq for Ceroid lipofuscinosis neuronal 2"

<400> SEQUENCE: 322
ggggccgggt attggtctgt ctctg 25

<210> SEQ ID NO 323
<211> LENGTH: 25
<212> TYPE: DNA
<213> ORGANISM: Homo sapiens
<220> FEATURE:
<221> NAME/KEY: source
<223> OTHER INFORMATION: /note="target seq for Niemann-Pick disease type C1"

<400> SEQUENCE: 323
ggatcgacga ttatttcgac tgggt 25

<210> SEQ ID NO 324
<211> LENGTH: 25
<212> TYPE: DNA
<213> ORGANISM: Homo sapiens
<220> FEATURE:
<221> NAME/KEY: source
<223> OTHER INFORMATION: /note="target seq for Glutaric aciduria, type 1"

<400> SEQUENCE: 324
gagtatcacg tgatccggca cgcca 25

<210> SEQ ID NO 325
<211> LENGTH: 25
<212> TYPE: DNA
<213> ORGANISM: Homo sapiens
<220> FEATURE:
<221> NAME/KEY: source
<223> OTHER INFORMATION: /note="target seq for CAPN3-Related Disorders"

<400> SEQUENCE: 325
gccctgatgc agaagaaccg gcgga 25

<210> SEQ ID NO 326
<211> LENGTH: 20
<212> TYPE: DNA
<213> ORGANISM: Homo sapiens
<220> FEATURE:
<221> NAME/KEY: source
<223> OTHER INFORMATION: /note="target seq for CAPN3-Related Disorders"

<400> SEQUENCE: 326
gatgcagaag aaccggcgga 20

<210> SEQ ID NO 327
<211> LENGTH: 20
<212> TYPE: DNA
<213> ORGANISM: Homo sapiens
<220> FEATURE:
<221> NAME/KEY: source
<223> OTHER INFORMATION: /note="target seq for Glycogen storage disease, type II"

<400> SEQUENCE: 327
gtcccagaac agctcccctc 20

<210> SEQ ID NO 328
<211> LENGTH: 25
<212> TYPE: DNA
<213> ORGANISM: Homo sapiens
<220> FEATURE:
<221> NAME/KEY: source
<223> OTHER INFORMATION: /note="target seq for Nonsyndromic Oculocutaneous Albinism"

<400> SEQUENCE: 328
gtacagggat ctgccaacga tccta 25

<210> SEQ ID NO 329
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 329
gcgaagatgg ctcggatgag 20

<210> SEQ ID NO 330
<211> LENGTH: 20
<212> TYPE: DNA

<213> ORGANISM: Homo sapiens
<220> FEATURE:
<221> NAME/KEY: source
<223> OTHER INFORMATION: /note="target seq for Familial
hypercholesterolemia"

<400> SEQUENCE: 330
gagtggccgc agcgctgtag 20

<210> SEQ ID NO 331
<211> LENGTH: 20
<212> TYPE: DNA
<213> ORGANISM: Homo sapiens
<220> FEATURE:
<221> NAME/KEY: source
<223> OTHER INFORMATION: /note="target seq for Deafness, autosomal
recessive 7"

<400> SEQUENCE: 331
ggtctcaagc tctctcttcg 20

<210> SEQ ID NO 332
<211> LENGTH: 20
<212> TYPE: DNA
<213> ORGANISM: Homo sapiens
<220> FEATURE:
<221> NAME/KEY: source
<223> OTHER INFORMATION: /note="target seq for Chronic infantile
neurological, cutaneous and articular syndrome"

<400> SEQUENCE: 332
gacggcttcg atgagctgca 20

<210> SEQ ID NO 333
<211> LENGTH: 20
<212> TYPE: DNA
<213> ORGANISM: Homo sapiens
<220> FEATURE:
<221> NAME/KEY: source
<223> OTHER INFORMATION: /note="target seq for Eichsfeld type congenital
muscular dystrophy"

<400> SEQUENCE: 333
gactctccgg gagactgtcc 20

<210> SEQ ID NO 334
<211> LENGTH: 20
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 334
gctcaaaagt ggatgagcgc 20

<210> SEQ ID NO 335
<211> LENGTH: 20
<212> TYPE: DNA
<213> ORGANISM: Homo sapiens
<220> FEATURE:
<221> NAME/KEY: source
<223> OTHER INFORMATION: /note="target seq for Hyperkalemic Periodic
Paralysis Type 1"

<400> SEQUENCE: 335
gcagctgcgg gtcttcaagc 20

<210> SEQ ID NO 336
<211> LENGTH: 20
<212> TYPE: DNA
<213> ORGANISM: Homo sapiens
<220> FEATURE:
<221> NAME/KEY: source
<223> OTHER INFORMATION: /note="target seq for Inclusion body myopathy 2"

<400> SEQUENCE: 336
ggacgtggat gtggtggttt 20

<210> SEQ ID NO 337
<211> LENGTH: 25
<212> TYPE: DNA
<213> ORGANISM: Homo sapiens
<220> FEATURE:
<221> NAME/KEY: source
<223> OTHER INFORMATION: /note="target seq for Severe APG05083.1, APG07433.1, APG07513.1, APG08290.1 immunodeficiency due to ADA Deficiency"

<400> SEQUENCE: 337
gaagagcggc attcaccgta ctgtc 25

<210> SEQ ID NO 338
<211> LENGTH: 25
<212> TYPE: DNA
<213> ORGANISM: Homo sapiens
<220> FEATURE:
<221> NAME/KEY: source
<223> OTHER INFORMATION: /note="target seq for Severe APG05083.1, APG07433.1, APG07513.1, APG08290.1 immunodeficiency due to ADA Deficiency"

<400> SEQUENCE: 338
gcggtacagt ccgcacctgc tggcc 25

<210> SEQ ID NO 339
<211> LENGTH: 20
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 339
gtgtccgagc agcgccactg 20

<210> SEQ ID NO 340
<211> LENGTH: 20
<212> TYPE: DNA
<213> ORGANISM: Homo sapiens
<220> FEATURE:
<221> NAME/KEY: source
<223> OTHER INFORMATION: /note="target seq for Cystic fibrosis"

<400> SEQUENCE: 340
ggacacttcg tgccttcgga 20

<210> SEQ ID NO 341
<211> LENGTH: 20
<212> TYPE: DNA
<213> ORGANISM: Homo sapiens
<220> FEATURE:
<221> NAME/KEY: source
<223> OTHER INFORMATION: /note="target seq for Cystic fibrosis"

<400> SEQUENCE: 341
ggacacttcg tgccttcgga 20

<210> SEQ ID NO 342
<211> LENGTH: 25
<212> TYPE: DNA
<213> ORGANISM: Homo sapiens
<220> FEATURE:
<221> NAME/KEY: source
<223> OTHER INFORMATION: /note="target seq for Adrenocortical carcinoma, pediatric"

<400> SEQUENCE: 342
gggcgtgagc acttcgagat gttcc 25

<210> SEQ ID NO 343
<211> LENGTH: 20
<212> TYPE: DNA
<213> ORGANISM: Homo sapiens
<220> FEATURE:
<221> NAME/KEY: source
<223> OTHER INFORMATION: /note="target seq for Fumarase deficiency"

<400> SEQUENCE: 343
gattggacgt actcatactc 20

<210> SEQ ID NO 344
<211> LENGTH: 20
<212> TYPE: DNA
<213> ORGANISM: Homo sapiens
<220> FEATURE:
<221> NAME/KEY: source
<223> OTHER INFORMATION: /note="target seq for Adenocarcinoma of prostate"

<400> SEQUENCE: 344
gaacactgtc cattggcatg 20

<210> SEQ ID NO 345
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial hypertrophic cardiomyopathy 1"

<400> SEQUENCE: 345
gcatcctcta cggggacttc 20

<210> SEQ ID NO 346
<211> LENGTH: 25
<212> TYPE: DNA
<213> ORGANISM: Homo sapiens
<220> FEATURE:
<221> NAME/KEY: source
<223> OTHER INFORMATION: /note="target seq for Adult hypophosphatasia"

<400> SEQUENCE: 346
gacaacgaga tgccccctga ggcct 25

<210> SEQ ID NO 347
<211> LENGTH: 25
<212> TYPE: DNA
<213> ORGANISM: Homo sapiens
<220> FEATURE:
<221> NAME/KEY: source
<223> OTHER INFORMATION: /note="target seq for Adult hypophosphatasia"

<400> SEQUENCE: 347
ggtactcaga caacaagatg ccccc 25

<210> SEQ ID NO 348
<211> LENGTH: 25
<212> TYPE: DNA
<213> ORGANISM: Homo sapiens
<220> FEATURE:
<221> NAME/KEY: source
<223> OTHER INFORMATION: /note="target seq for Adult hypophosphatasia"

<400> SEQUENCE: 348
gacaacaaga tgccccctga ggcct 25

<210> SEQ ID NO 349
<211> LENGTH: 25
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 349
gccttcttgg acaacgtcac cacca 25

<210> SEQ ID NO 350
<211> LENGTH: 25
<212> TYPE: DNA
<213> ORGANISM: Homo sapiens
<220> FEATURE:
<221> NAME/KEY: source
<223> OTHER INFORMATION: /note="target seq for Inborn genetic diseases"

<400> SEQUENCE: 350
ggtttgccat ccgaggggta gtgct 25

<210> SEQ ID NO 351
<211> LENGTH: 20
<212> TYPE: DNA
<213> ORGANISM: Homo sapiens
<220> FEATURE:
<221> NAME/KEY: source
<223> OTHER INFORMATION: /note="target seq for Crouzon syndrome"

<400> SEQUENCE: 351
gcaaatgcct ccacagtggt 20

<210> SEQ ID NO 352
<211> LENGTH: 20
<212> TYPE: DNA
<213> ORGANISM: Homo sapiens
<220> FEATURE:
<221> NAME/KEY: source
<223> OTHER INFORMATION: /note="target seq for Propionyl-CoA carboxylase deficiency"

<400> SEQUENCE: 352
gacatcatag gcacctccat 20

<210> SEQ ID NO 353
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 353
ggtggaaggg atcggctacg acttc 25

<210> SEQ ID NO 354
<211> LENGTH: 25
<212> TYPE: DNA
<213> ORGANISM: Homo sapiens
<220> FEATURE:
<221> NAME/KEY: source
<223> OTHER INFORMATION: /note="target seq for Dysostosis multiplex"

<400> SEQUENCE: 354
ggagcagctc tgggccgaag tgtcg 25

<210> SEQ ID NO 355
<211> LENGTH: 20
<212> TYPE: DNA
<213> ORGANISM: Homo sapiens
<220> FEATURE:
<221> NAME/KEY: source
<223> OTHER INFORMATION: /note="target seq for Multiple sulfatase deficiency"

<400> SEQUENCE: 355
ggcgactcct ttgtctttga 20

<210> SEQ ID NO 356
<211> LENGTH: 20
<212> TYPE: DNA
<213> ORGANISM: Homo sapiens
<220> FEATURE:
<221> NAME/KEY: source
<223> OTHER INFORMATION: /note="target seq for Bifunctional peroxisomal enzyme deficiency"

<400> SEQUENCE: 356
ggtggtactg gtcaccggcg 20

<210> SEQ ID NO 357
<211> LENGTH: 25
<212> TYPE: DNA
<213> ORGANISM: Homo sapiens
<220> FEATURE:
<221> NAME/KEY: source
<223> OTHER INFORMATION: /note="target seq for Bifunctional peroxisomal enzyme deficiency"

<400> SEQUENCE: 357
gtactggtca ccagcgcggg ggcag 25

<210> SEQ ID NO 358
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-predisposing syndrome"

<400> SEQUENCE: 358
ggaaacttgt aagggcttcg 20

<210> SEQ ID NO 359
<211> LENGTH: 25
<212> TYPE: DNA

<213> ORGANISM: Homo sapiens
<220> FEATURE:
<221> NAME/KEY: source
<223> OTHER INFORMATION: /note="target seq for Cardiovascular phenotype"

<400> SEQUENCE: 359
gtgcagacat tgacgaatgc cgcat 25

<210> SEQ ID NO 360
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 360
gacattgacg aatgccgcat atctc 25

<210> SEQ ID NO 361
<211> LENGTH: 20
<212> TYPE: DNA
<213> ORGANISM: Homo sapiens
<220> FEATURE:
<221> NAME/KEY: source
<223> OTHER INFORMATION: /note="target seq for Limb-girdle muscular dystrophy, type 2L"

<400> SEQUENCE: 361
gcatagtagt aaactagacg 20

<210> SEQ ID NO 362
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 362
gcatcgatgt caacgagggc aaccg 25

<210> SEQ ID NO 363
<211> LENGTH: 20
<212> TYPE: DNA
<213> ORGANISM: Homo sapiens
<220> FEATURE:
<221> NAME/KEY: source
<223> OTHER INFORMATION: /note="target seq for Spastic Paraplegia, Recessive"

<400> SEQUENCE: 363
gcactgctgc tcggcccccc 20

<210> SEQ ID NO 364
<211> LENGTH: 20
<212> TYPE: DNA
<213> ORGANISM: Homo sapiens
<220> FEATURE:
<221> NAME/KEY: source
<223> OTHER INFORMATION: /note="target seq for Isovaleryl-CoA dehydrogenase deficiency"

<400> SEQUENCE: 364
ggagcagtgg ggctcagtta 20

<210> SEQ ID NO 365
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 365
gaggagctgc ctcacaggtg 20

<210> SEQ ID NO 366
<211> LENGTH: 20
<212> TYPE: DNA
<213> ORGANISM: Homo sapiens
<220> FEATURE:
<221> NAME/KEY: source
<223> OTHER INFORMATION: /note="target seq for Biotinidase deficiency"

<400> SEQUENCE: 366
gctccagcgc ctgagttgta 20

<210> SEQ ID NO 367
<211> LENGTH: 20
<212> TYPE: DNA
<213> ORGANISM: Homo sapiens
<220> FEATURE:
<221> NAME/KEY: source
<223> OTHER INFORMATION: /note="target seq for Biotinidase deficiency"

<400> SEQUENCE: 367
gcctgagttg tatggccatc 20

<210> SEQ ID NO 368
<211> LENGTH: 25
<212> TYPE: DNA
<213> ORGANISM: Homo sapiens
<220> FEATURE:
<221> NAME/KEY: source
<223> OTHER INFORMATION: /note="target seq for Leber congenital amaurosis"

<400> SEQUENCE: 368
gcataatttg tacagctcta agagt 25

<210> SEQ ID NO 369
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hyperinsulinism"

<400> SEQUENCE: 369
ggtggctgag cccagcccgg ccccc 25

<210> SEQ ID NO 370
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial cancer of breast"

<400> SEQUENCE: 370
ggatgcttgg cagtgggaaa aactt 25

<210> SEQ ID NO 371
<211> LENGTH: 20
<212> TYPE: DNA
<213> ORGANISM: Homo sapiens
<220> FEATURE:
<221> NAME/KEY: source
<223> OTHER INFORMATION: /note="target seq for Cohen syndrome"

<400> SEQUENCE: 371
ggaggtctac tacaggtctg 20

<210> SEQ ID NO 372
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 372
gctccctctg tactgtgcag gagtc 25

<210> SEQ ID NO 373
<211> LENGTH: 20
<212> TYPE: DNA
<213> ORGANISM: Homo sapiens
<220> FEATURE:
<221> NAME/KEY: source
<223> OTHER INFORMATION: /note="target seq for Wilson disease"

<400> SEQUENCE: 373
ggcaatgaac acaaagagca 20

<210> SEQ ID NO 374
<211> LENGTH: 25
<212> TYPE: DNA
<213> ORGANISM: Homo sapiens
<220> FEATURE:
<221> NAME/KEY: source
<223> OTHER INFORMATION: /note="target seq for Wilson disease"

<400> SEQUENCE: 374
gccctggatg ggctcagcgg ccatg 25

<210> SEQ ID NO 375
<211> LENGTH: 20
<212> TYPE: DNA
<213> ORGANISM: Homo sapiens
<220> FEATURE:
<221> NAME/KEY: source
<223> OTHER INFORMATION: /note="target seq for Wilson disease"

<400> SEQUENCE: 375
gcagccctgg atgggctcag 20

<210> SEQ ID NO 376
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial
hypercholesterolemia"

<400> SEQUENCE: 376
gtggcccagc gaagatgcga 20

<210> SEQ ID NO 377
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial
hypercholesterolemia"

<400> SEQUENCE: 377
gaagatgcga aggtgatttc 20

<210> SEQ ID NO 378
<211> LENGTH: 20
<212> TYPE: DNA
<213> ORGANISM: Homo sapiens
<220> FEATURE:
<221> NAME/KEY: source
<223> OTHER INFORMATION: /note="target seq for Floating-Harbor syndrome"

<400> SEQUENCE: 378
gctgaagctg gagtgggtcg 20

<210> SEQ ID NO 379
<211> LENGTH: 25
<212> TYPE: DNA
<213> ORGANISM: Homo sapiens
<220> FEATURE:
<221> NAME/KEY: source
<223> OTHER INFORMATION: /note="target seq for Congenital long QT
syndrome"

<400> SEQUENCE: 379
gatgctacac gtcgaccgcc aggga 25

<210> SEQ ID NO 380
<211> LENGTH: 20
<212> TYPE: DNA
<213> ORGANISM: Homo sapiens
<220> FEATURE:
<221> NAME/KEY: source
<223> OTHER INFORMATION: /note="target seq for Congenital long QT
syndrome"

<400> SEQUENCE: 380
gatgctacac gtcgaccgcc 20

<210> SEQ ID NO 381
<211> LENGTH: 25
<212> TYPE: DNA
<213> ORGANISM: Homo sapiens
<220> FEATURE:
<221> NAME/KEY: source
<223> OTHER INFORMATION: /note="target seq for Andersen Tawil syndrome"

<400> SEQUENCE: 381
gaggaagaga tcaaggtcct ttcca 25

<210> SEQ ID NO 382
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 382
gagctgataa ccaccctgta catcg 25

<210> SEQ ID NO 383
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 383
ggaaaactgc ggtatgggcg 20

<210> SEQ ID NO 384
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 384
gtatttgaag gtctcctccg gggtc 25

<210> SEQ ID NO 385
<211> LENGTH: 20
<212> TYPE: DNA
<213> ORGANISM: Homo sapiens
<220> FEATURE:
<221> NAME/KEY: source
<223> OTHER INFORMATION: /note="target seq for Gastrointestinal stroma tumor"

<400> SEQUENCE: 385
gagggctaaa gtgggctcgg 20

<210> SEQ ID NO 386
<211> LENGTH: 20
<212> TYPE: DNA
<213> ORGANISM: Homo sapiens
<220> FEATURE:
<221> NAME/KEY: source
<223> OTHER INFORMATION: /note="target seq for Dyskeratosis congenita"

<400> SEQUENCE: 386
gctgccaagc ctgctggcaa 20

<210> SEQ ID NO 387
<211> LENGTH: 25
<212> TYPE: DNA
<213> ORGANISM: Homo sapiens
<220> FEATURE:
<221> NAME/KEY: source
<223> OTHER INFORMATION: /note="target seq for Dyskeratosis congenita"

<400> SEQUENCE: 387
gccctgcctg tgacttccag cactg 25

<210> SEQ ID NO 388
<211> LENGTH: 25
<212> TYPE: DNA
<213> ORGANISM: Homo sapiens
<220> FEATURE:
<221> NAME/KEY: source
<223> OTHER INFORMATION: /note="target seq for Glycogen storage disease IIIa"

<400> SEQUENCE: 388
gatgagtaga acagaaaaat acaag 25

<210> SEQ ID NO 389
<211> LENGTH: 25
<212> TYPE: DNA
<213> ORGANISM: Homo sapiens
<220> FEATURE:
<221> NAME/KEY: source
<223> OTHER INFORMATION: /note="target seq for Dilated cardiomyopathy 1DD"

<400> SEQUENCE: 389
gtctcgtagt ccggtgagcc ggtca 25

<210> SEQ ID NO 390
<211> LENGTH: 20
<212> TYPE: DNA
<213> ORGANISM: Homo sapiens
<220> FEATURE:
<221> NAME/KEY: source
<223> OTHER INFORMATION: /note="target seq for Renal carnitine transport defect"

<400> SEQUENCE: 390
gtggccatgg aatagcgccg 20

<210> SEQ ID NO 391
<211> LENGTH: 25
<212> TYPE: DNA
<213> ORGANISM: Homo sapiens
<220> FEATURE:
<221> NAME/KEY: source
<223> OTHER INFORMATION: /note="target seq for Baraitser-Winter syndrome 1"

<400> SEQUENCE: 391
gatcctcacc gagcgcggct acagc 25

<210> SEQ ID NO 392
<211> LENGTH: 25
<212> TYPE: DNA
<213> ORGANISM: Homo sapiens
<220> FEATURE:
<221> NAME/KEY: source
<223> OTHER INFORMATION: /note="target seq for Very long chain acyl-CoA dehydrogenase deficiency"

<400> SEQUENCE: 392
gggcatgcat gaccttggcg tgggc 25

<210> SEQ ID NO 393
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 393
gtcagatttg tccttgcagt 20

<210> SEQ ID NO 394
<211> LENGTH: 20
<212> TYPE: DNA

<213> ORGANISM: Homo sapiens
<220> FEATURE:
<221> NAME/KEY: source
<223> OTHER INFORMATION: /note="target seq for Limb-girdle muscular
dystrophy, type 2A"

<400> SEQUENCE: 394
gtacggggtt gctctgccgg 20

<210> SEQ ID NO 395
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial
hypercholesterolemia"

<400> SEQUENCE: 395
gacagtagcc cctgctcggc cttcg 25

<210> SEQ ID NO 396
<211> LENGTH: 20
<212> TYPE: DNA
<213> ORGANISM: Homo sapiens
<220> FEATURE:
<221> NAME/KEY: source
<223> OTHER INFORMATION: /note="target seq for Aortic aneurysm, familial
thoracic 6"

<400> SEQUENCE: 396
gccccatgcc atcatgcgtc 20

<210> SEQ ID NO 397
<211> LENGTH: 25
<212> TYPE: DNA
<213> ORGANISM: Homo sapiens
<220> FEATURE:
<221> NAME/KEY: source
<223> OTHER INFORMATION: /note="target seq for Acromicric dysplasia"

<400> SEQUENCE: 397
gctttgtcat cgacatttat accgg 25

<210> SEQ ID NO 398
<211> LENGTH: 25
<212> TYPE: DNA
<213> ORGANISM: Homo sapiens
<220> FEATURE:
<221> NAME/KEY: source
<223> OTHER INFORMATION: /note="target seq for Charcot-Marie-Tooth
disease type 2C"

<400> SEQUENCE: 398
ggcggacatg cggcaccagg actcg 25

<210> SEQ ID NO 399
<211> LENGTH: 25
<212> TYPE: DNA
<213> ORGANISM: Homo sapiens
<220> FEATURE:
<221> NAME/KEY: source
<223> OTHER INFORMATION: /note="target seq for Breast-ovarian cancer,
familial 2"

<400> SEQUENCE: 399
gtgtaactgt atacgtatgg cgttt 25

<210> SEQ ID NO 400
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 1"

<400> SEQUENCE: 400
gatgcctgga cagaggacaa 20

<210> SEQ ID NO 401
<211> LENGTH: 25
<212> TYPE: DNA
<213> ORGANISM: Homo sapiens
<220> FEATURE:
<221> NAME/KEY: source
<223> OTHER INFORMATION: /note="target seq for Charcot-Marie-Tooth disease type 2C"

<400> SEQUENCE: 401
gcctaactga tgaggagttt cgagg 25

<210> SEQ ID NO 402
<211> LENGTH: 25
<212> TYPE: DNA
<213> ORGANISM: Homo sapiens
<220> FEATURE:
<221> NAME/KEY: source
<223> OTHER INFORMATION: /note="target seq for Charcot-Marie-Tooth disease type 2C"

<400> SEQUENCE: 402
gcctaactga tgaggagttt caagg 25

<210> SEQ ID NO 403
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-predisposing syndrome"

<400> SEQUENCE: 403
gagcgctgct cagatagcga 20

<210> SEQ ID NO 404
<211> LENGTH: 25
<212> TYPE: DNA
<213> ORGANISM: Homo sapiens
<220> FEATURE:
<221> NAME/KEY: source
<223> OTHER INFORMATION: /note="target seq for Early infantile epileptic encephalopathy"

<400> SEQUENCE: 404
gatgatccgc atggaccggc gggga 25

<210> SEQ ID NO 405
<211> LENGTH: 20
<212> TYPE: DNA
<213> ORGANISM: Homo sapiens
<220> FEATURE:
<221> NAME/KEY: source
<223> OTHER INFORMATION: /note="target seq for Early infantile epileptic encephalopathy"

<400> SEQUENCE: 405
ggatgatccg catggaccgg 20

<210> SEQ ID NO 406
<211> LENGTH: 25
<212> TYPE: DNA
<213> ORGANISM: Homo sapiens
<220> FEATURE:
<221> NAME/KEY: source
<223> OTHER INFORMATION: /note="target seq for Early infantile epileptic encephalopathy"

<400> SEQUENCE: 406
gcggatgatc cgcatggacc agcgg 25

<210> SEQ ID NO 407
<211> LENGTH: 20
<212> TYPE: DNA
<213> ORGANISM: Homo sapiens
<220> FEATURE:
<221> NAME/KEY: source
<223> OTHER INFORMATION: /note="target seq for Acromicric dysplasia"

<400> SEQUENCE: 407
gtacgtgatc catcctaggt 20

<210> SEQ ID NO 408
<211> LENGTH: 25
<212> TYPE: DNA
<213> ORGANISM: Homo sapiens
<220> FEATURE:
<221> NAME/KEY: source
<223> OTHER INFORMATION: /note="target seq for Hypertrophic cardiomyopathy"

<400> SEQUENCE: 408
gacaccacgg tctccctcaa gtggc 25

<210> SEQ ID NO 409
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 409
gctgtccggg gtagccccaa gatag 25

<210> SEQ ID NO 410
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 410
gtccacggtg agggggccct ggtgt 25

<210> SEQ ID NO 411
<211> LENGTH: 25
<212> TYPE: DNA
<213> ORGANISM: Homo sapiens
<220> FEATURE:
<221> NAME/KEY: source
<223> OTHER INFORMATION: /note="target seq for Cardiovascular phenotype"

<400> SEQUENCE: 411
gcctagactg caggacacag ggact 25

<210> SEQ ID NO 412
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hypertrophic cardiomyopathy 1"

<400> SEQUENCE: 412
gcatctgcag acatagagac ctgtg 25

<210> SEQ ID NO 413
<211> LENGTH: 20
<212> TYPE: DNA
<213> ORGANISM: Homo sapiens
<220> FEATURE:
<221> NAME/KEY: source
<223> OTHER INFORMATION: /note="target seq for Benign scapuloperoneal muscular dystrophy with cardiomyopathy"

<400> SEQUENCE: 413
gccctccaag agcttgcggt 20

<210> SEQ ID NO 414
<211> LENGTH: 25
<212> TYPE: DNA
<213> ORGANISM: Homo sapiens
<220> FEATURE:
<221> NAME/KEY: source
<223> OTHER INFORMATION: /note="target seq for Glycogen storage disease, type II"

<400> SEQUENCE: 414
ggccctcacc ctgcgctacg cactc 25

<210> SEQ ID NO 415
<211> LENGTH: 25
<212> TYPE: DNA
<213> ORGANISM: Homo sapiens
<220> FEATURE:
<221> NAME/KEY: source
<223> OTHER INFORMATION: /note="target seq for Diffuse mesangial sclerosis"

<400> SEQUENCE: 415
gtttaggcac ttgttttacc tgtat 25

<210> SEQ ID NO 416
<211> LENGTH: 20
<212> TYPE: DNA
<213> ORGANISM: Homo sapiens
<220> FEATURE:
<221> NAME/KEY: source
<223> OTHER INFORMATION: /note="target seq for Colobomatous microphthalmia"

<400> SEQUENCE: 416
gggtcgaggc ggacgccata 20

<210> SEQ ID NO 417
<211> LENGTH: 20

```
<212> TYPE: DNA
<213> ORGANISM: Homo sapiens
<220> FEATURE:
<221> NAME/KEY: source
<223> OTHER INFORMATION: /note="target seq for Ataxia-telangiectasia
      syndrome"

<400> SEQUENCE: 417

gtaaatacat atttactact                                                 20


<210> SEQ ID NO 418
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial cancer of
      breast"

<400> SEQUENCE: 418

ggctacagca cacagctcgt                                                 20


<210> SEQ ID NO 419
<211> LENGTH: 25
<212> TYPE: DNA
<213> ORGANISM: Homo sapiens
<220> FEATURE:
<221> NAME/KEY: source
<223> OTHER INFORMATION: /note="target seq for Limb-girdle muscular
      dystrophy, type 2A"

<400> SEQUENCE: 419

gctacgagat gcaaaatgca gtcaa                                           25


<210> SEQ ID NO 420
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 420

gccgcttacc aaaaggagta                                                 20


<210> SEQ ID NO 421
<211> LENGTH: 25
<212> TYPE: DNA
<213> ORGANISM: Homo sapiens
<220> FEATURE:
<221> NAME/KEY: source
<223> OTHER INFORMATION: /note="target seq for Asymmetric septal
      hypertrophy"

<400> SEQUENCE: 421

gtgctgcagg ttgttggtgc atggc                                           25


<210> SEQ ID NO 422
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary cancer-
      predisposing syndrome"

<400> SEQUENCE: 422
```

gtaattctat aactccttag 20

<210> SEQ ID NO 423
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hypertrophic cardiomyopathy 2"

<400> SEQUENCE: 423
gctaaagtca ccgggcgctg gaaat 25

<210> SEQ ID NO 424
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hypertrophic cardiomyopathy 2"

<400> SEQUENCE: 424
ggctaaagtc accgggcgct agaaa 25

<210> SEQ ID NO 425
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hypertrophic cardiomyopathy 2"

<400> SEQUENCE: 425
gctaaagtca ccgggcgcta gaaat 25

<210> SEQ ID NO 426
<211> LENGTH: 25
<212> TYPE: DNA
<213> ORGANISM: Homo sapiens
<220> FEATURE:
<221> NAME/KEY: source
<223> OTHER INFORMATION: /note="target seq for Erythrocytosis, familial, 2"

<400> SEQUENCE: 426
gaaagagcaa tgcctccagg ttgtc 25

<210> SEQ ID NO 427
<211> LENGTH: 25
<212> TYPE: DNA
<213> ORGANISM: Homo sapiens
<220> FEATURE:
<221> NAME/KEY: source
<223> OTHER INFORMATION: /note="target seq for Death in infancy"

<400> SEQUENCE: 427
gtattggaat ccggagcatc cacgt 25

<210> SEQ ID NO 428
<211> LENGTH: 20
<212> TYPE: DNA
<213> ORGANISM: Homo sapiens
<220> FEATURE:
<221> NAME/KEY: source
<223> OTHER INFORMATION: /note="target seq for Muscular Diseases"

<400> SEQUENCE: 428
gcatcttccg gatctttgag 20

<210> SEQ ID NO 429
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 429
gctgcgagca tggggccctg aggct 25

<210> SEQ ID NO 430
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial cancer of breast"

<400> SEQUENCE: 430
ggcagcgtta cccagtccga 20

<210> SEQ ID NO 431
<211> LENGTH: 25
<212> TYPE: DNA
<213> ORGANISM: Homo sapiens
<220> FEATURE:
<221> NAME/KEY: source
<223> OTHER INFORMATION: /note="target seq for Hereditary cancer-predisposing syndrome"

<400> SEQUENCE: 431
gtgtaggcaa cttctatagc cacag 25

<210> SEQ ID NO 432
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 432
ggaactcccg ccaagatcaa gaaag 25

<210> SEQ ID NO 433
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 433
gcggctgcca gtatctgtgc ctccc 25

<210> SEQ ID NO 434
<211> LENGTH: 25
<212> TYPE: DNA

<213> ORGANISM: Homo sapiens
<220> FEATURE:
<221> NAME/KEY: source
<223> OTHER INFORMATION: /note="target seq for Familial
hypercholesterolemia"

<400> SEQUENCE: 434
gaatgatctg caggtgagcg tcgcc 25

<210> SEQ ID NO 435
<211> LENGTH: 25
<212> TYPE: DNA
<213> ORGANISM: Homo sapiens
<220> FEATURE:
<221> NAME/KEY: source
<223> OTHER INFORMATION: /note="target seq for Inclusion body myopathy
2"

<400> SEQUENCE: 435
gtgctgtagt gcaccaatgt aatct 25

<210> SEQ ID NO 436
<211> LENGTH: 20
<212> TYPE: DNA
<213> ORGANISM: Homo sapiens
<220> FEATURE:
<221> NAME/KEY: source
<223> OTHER INFORMATION: /note="target seq for Ataxia-telangiectasia
syndrome"

<400> SEQUENCE: 436
gctttgatgt taacaatcgc 20

<210> SEQ ID NO 437
<211> LENGTH: 25
<212> TYPE: DNA
<213> ORGANISM: Homo sapiens
<220> FEATURE:
<221> NAME/KEY: source
<223> OTHER INFORMATION: /note="target seq for Benign familial
neonatal-infantile seizures"

<400> SEQUENCE: 437
gtcagttctc cgatcattcc agctg 25

<210> SEQ ID NO 438
<211> LENGTH: 20
<212> TYPE: DNA
<213> ORGANISM: Homo sapiens
<220> FEATURE:
<221> NAME/KEY: source
<223> OTHER INFORMATION: /note="target seq for Marfan Syndrome/Loeys-
Dietz Syndrome/Familial Thoracic Aortic Aneurysms and
Dissections"

<400> SEQUENCE: 438
gtatctccat tgtctcctcg 20

<210> SEQ ID NO 439
<211> LENGTH: 25
<212> TYPE: DNA
<213> ORGANISM: Homo sapiens
<220> FEATURE:
<221> NAME/KEY: source
<223> OTHER INFORMATION: /note="target seq for Dilated cardiomyopathy
1G"

<400> SEQUENCE: 439
gtttcagatt cccctggccc acgtg 25

<210> SEQ ID NO 440
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 440
gcggtgagtc tcggtgcagg 20

<210> SEQ ID NO 441
<211> LENGTH: 20
<212> TYPE: DNA
<213> ORGANISM: Homo sapiens
<220> FEATURE:
<221> NAME/KEY: source
<223> OTHER INFORMATION: /note="target seq for Breast-ovarian cancer, familial 2"

<400> SEQUENCE: 441
gatacagtat taattgactg 20

<210> SEQ ID NO 442
<211> LENGTH: 20
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 442
gcgagtgcat ccactccagc 20

<210> SEQ ID NO 443
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 443
ggctacaagt gccagtgtga ggaag 25

<210> SEQ ID NO 444
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial hypercholesterolemia"

<400> SEQUENCE: 444
gggtggctac aagtgccagc gtgag 25

<210> SEQ ID NO 445
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial
hypercholesterolemia"

<400> SEQUENCE: 445
gtacaccagc ctcaccccca acctg 25

<210> SEQ ID NO 446
<211> LENGTH: 25
<212> TYPE: DNA
<213> ORGANISM: Homo sapiens
<220> FEATURE:
<221> NAME/KEY: source
<223> OTHER INFORMATION: /note="target seq for Familial cancer of
breast"

<400> SEQUENCE: 446
gcctgcccga tagacgagcc tcccg 25

<210> SEQ ID NO 447
<211> LENGTH: 20
<212> TYPE: DNA
<213> ORGANISM: Homo sapiens
<220> FEATURE:
<221> NAME/KEY: source
<223> OTHER INFORMATION: /note="target seq for Hereditary hemorrhagic
telangiectasia type 2"

<400> SEQUENCE: 447
gatccgcagc gcggtgagtc 20

<210> SEQ ID NO 448
<211> LENGTH: 3
<212> TYPE: DNA
<213> ORGANISM: Streptococcus pyogenes
<220> FEATURE:
<221> NAME/KEY: source
<223> OTHER INFORMATION: /note="SpyCas9 PAM"
<220> FEATURE:
<221> NAME/KEY: modified_base
<222> LOCATION: (1)..(1)
<223> OTHER INFORMATION: a, c, t, g, unknown or other

<400> SEQUENCE: 448 ngg 3

<210> SEQ ID NO 449
<211> LENGTH: 5
<212> TYPE: DNA
<213> ORGANISM: Staphylococcus aureus
<220> FEATURE:
<221> NAME/KEY: source
<223> OTHER INFORMATION: /note="SauCas9"
<220> FEATURE:
<221> NAME/KEY: modified_base
<222> LOCATION: (1)..(1)
<223> OTHER INFORMATION: a, c, t, g, unknown or other

<400> SEQUENCE: 449 ngrrt 5

<210> SEQ ID NO 450
<211> LENGTH: 415
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"
<220> FEATURE:

<221> NAME/KEY: source
<223> OTHER INFORMATION: /note="ADAT"

<400> SEQUENCE: 450

Met Ala Lys Arg Pro Ala Ala Thr Lys Lys Ala Gly Gln Ala Lys Lys
1 5 10 15

Lys Lys Ser Glu Val Glu Phe Ser His Glu Tyr Trp Met Arg His Ala
20 25 30

Leu Thr Leu Ala Lys Arg Ala Trp Asp Glu Arg Glu Val Pro Val Gly
35 40 45

Ala Val Leu Val His Asn Asn Arg Val Ile Gly Glu Gly Trp Asn Arg
50 55 60

Pro Ile Gly Arg His Asp Pro Thr Ala His Ala Glu Ile Met Ala Leu
65 70 75 80

Arg Gln Gly Gly Leu Val Met Gln Asn Tyr Arg Leu Ile Asp Ala Thr
85 90 95

Leu Tyr Val Thr Leu Glu Pro Cys Val Met Cys Ala Gly Ala Met Ile
100 105 110

His Ser Arg Ile Gly Arg Val Val Phe Gly Ala Arg Asp Ala Lys Thr
115 120 125

Gly Ala Ala Gly Ser Leu Met Asp Val Leu His His Pro Gly Met Asn
130 135 140

His Arg Val Glu Ile Thr Glu Gly Ile Leu Ala Asp Glu Cys Ala Ala
145 150 155 160

Leu Leu Ser Asp Phe Phe Arg Met Arg Arg Gln Glu Ile Lys Ala Gln
165 170 175

Lys Lys Ala Gln Ser Ser Thr Asp Ser Gly Gly Ser Ser Gly Gly Ser
180 185 190

Ser Gly Ser Glu Thr Pro Gly Thr Ser Glu Ser Ala Thr Pro Glu Ser
195 200 205

Ser Gly Gly Ser Ser Gly Gly Ser Ser Glu Val Glu Phe Ser His Glu
210 215 220

Tyr Trp Met Arg His Ala Leu Thr Leu Ala Lys Arg Ala Arg Asp Glu
225 230 235 240

Arg Glu Val Pro Val Gly Ala Val Leu Val Leu Asn Asn Arg Val Ile
245 250 255

Gly Glu Gly Trp Asn Arg Ala Ile Gly Leu His Asp Pro Thr Ala His
260 265 270

Ala Glu Ile Met Ala Leu Arg Gln Gly Gly Leu Val Met Gln Asn Tyr
275 280 285

Arg Leu Ile Asp Ala Thr Leu Tyr Val Thr Phe Glu Pro Cys Val Met
290 295 300

Cys Ala Gly Ala Met Ile His Ser Arg Ile Gly Arg Val Val Phe Gly
305 310 315 320

Val Arg Asn Ala Lys Thr Gly Ala Ala Gly Ser Leu Met Asp Val Leu
325 330 335

His Tyr Pro Gly Met Asn His Arg Val Glu Ile Thr Glu Gly Ile Leu
340 345 350

Ala Asp Glu Cys Ala Ala Leu Leu Cys Tyr Phe Phe Arg Met Pro Arg
355 360 365

Gln Val Phe Asn Ala Gln Lys Lys Ala Gln Ser Ser Thr Asp Ser Gly
370 375 380

Gly Ser Ser Gly Gly Ser Ser Gly Ser Glu Thr Pro Gly Thr Ser Glu
385 390 395 400

```
Ser Ala Thr Pro Glu Ser Ser Gly Gly Ser Ser Gly Gly Ser Ser
                405                 410                 415


<210> SEQ ID NO 451
<211> LENGTH: 1494
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: source
<223> OTHER INFORMATION: /note="Nuc-ADAT-Linker-dAPG08290.1-Linker-SV40"

<400> SEQUENCE: 451

Met Ala Lys Arg Pro Ala Ala Thr Lys Lys Ala Gly Gln Ala Lys Lys
1               5                   10                  15

Lys Lys Ser Glu Val Glu Phe Ser His Glu Tyr Trp Met Arg His Ala
            20                  25                  30

Leu Thr Leu Ala Lys Arg Ala Trp Asp Glu Arg Glu Val Pro Val Gly
        35                  40                  45

Ala Val Leu Val His Asn Asn Arg Val Ile Gly Glu Gly Trp Asn Arg
    50                  55                  60

Pro Ile Gly Arg His Asp Pro Thr Ala His Ala Glu Ile Met Ala Leu
65                  70                  75                  80

Arg Gln Gly Gly Leu Val Met Gln Asn Tyr Arg Leu Ile Asp Ala Thr
                85                  90                  95

Leu Tyr Val Thr Leu Glu Pro Cys Val Met Cys Ala Gly Ala Met Ile
            100                 105                 110

His Ser Arg Ile Gly Arg Val Val Phe Gly Ala Arg Asp Ala Lys Thr
        115                 120                 125

Gly Ala Ala Gly Ser Leu Met Asp Val Leu His His Pro Gly Met Asn
    130                 135                 140

His Arg Val Glu Ile Thr Glu Gly Ile Leu Ala Asp Glu Cys Ala Ala
145                 150                 155                 160

Leu Leu Ser Asp Phe Phe Arg Met Arg Arg Gln Glu Ile Lys Ala Gln
                165                 170                 175

Lys Lys Ala Gln Ser Ser Thr Asp Ser Gly Gly Ser Ser Gly Gly Ser
            180                 185                 190

Ser Gly Ser Glu Thr Pro Gly Thr Ser Glu Ser Ala Thr Pro Glu Ser
        195                 200                 205

Ser Gly Gly Ser Ser Gly Gly Ser Ser Glu Val Glu Phe Ser His Glu
    210                 215                 220

Tyr Trp Met Arg His Ala Leu Thr Leu Ala Lys Arg Ala Arg Asp Glu
225                 230                 235                 240

Arg Glu Val Pro Val Gly Ala Val Leu Val Leu Asn Asn Arg Val Ile
                245                 250                 255

Gly Glu Gly Trp Asn Arg Ala Ile Gly Leu His Asp Pro Thr Ala His
            260                 265                 270

Ala Glu Ile Met Ala Leu Arg Gln Gly Gly Leu Val Met Gln Asn Tyr
        275                 280                 285

Arg Leu Ile Asp Ala Thr Leu Tyr Val Thr Phe Glu Pro Cys Val Met
    290                 295                 300

Cys Ala Gly Ala Met Ile His Ser Arg Ile Gly Arg Val Val Phe Gly
305                 310                 315                 320
```

```
Val Arg Asn Ala Lys Thr Gly Ala Ala Gly Ser Leu Met Asp Val Leu
                325                 330                 335

His Tyr Pro Gly Met Asn His Arg Val Glu Ile Thr Glu Gly Ile Leu
            340                 345                 350

Ala Asp Glu Cys Ala Ala Leu Leu Cys Tyr Phe Phe Arg Met Pro Arg
        355                 360                 365

Gln Val Phe Asn Ala Gln Lys Lys Ala Gln Ser Ser Thr Asp Ser Gly
    370                 375                 380

Gly Ser Ser Gly Gly Ser Ser Gly Ser Glu Thr Pro Gly Thr Ser Glu
385                 390                 395                 400

Ser Ala Thr Pro Glu Ser Ser Gly Gly Ser Ser Gly Gly Ser Ser Met
                405                 410                 415

Ser Glu Leu Asp Tyr Arg Ile Gly Leu Ala Ile Gly Thr Asn Ser Ile
            420                 425                 430

Gly Trp Gly Val Ile Glu Leu Phe Trp Asn Lys Asp Arg Glu Arg Tyr
        435                 440                 445

Glu Lys Val Arg Ile Val Asp Lys Gly Val Arg Met Phe Asp Lys Ala
    450                 455                 460

Glu Ile Pro Asn Lys Gly Ala Ser Leu Ala Glu Pro Arg Arg Ile Ala
465                 470                 475                 480

Arg Ser Ser Arg Arg Arg Leu Asn Arg Lys Ser Gln Arg Lys Lys Glu
                485                 490                 495

Ile Arg Asn Leu Leu Val Gln His Gly Met Ile Thr Gln Glu Glu Leu
            500                 505                 510

Asp Leu Leu Tyr Pro Leu Ser Lys Lys Ser Ile Asp Ile Trp Asp Ile
        515                 520                 525

Arg Leu Asp Gly Leu Asp Arg Leu Leu Asn His Leu Glu Trp Ala Arg
    530                 535                 540

Leu Leu Ile His Leu Ala Gln Arg Arg Gly Phe Lys Ser Asn Arg Lys
545                 550                 555                 560

Ser Glu Leu Lys Asp Ala Glu Thr Gly Lys Val Leu Ser Ser Ile Gln
                565                 570                 575

Val Asn Glu Lys Arg Leu Phe Leu Tyr Arg Thr Val Gly Glu Met Trp
            580                 585                 590

Ile Lys Asp Ala Glu Phe Ser Lys Tyr Asp Arg Arg Arg Asn Ser Pro
        595                 600                 605

Asn Glu Tyr Val Phe Ser Val Ser Arg Ala Asp Leu Glu Lys Glu Ile
    610                 615                 620

Val Thr Leu Phe Glu Ala Gln Arg Lys Phe Gln Ser Ser Tyr Ala Ser
625                 630                 635                 640

Lys Asn Leu Gln Glu Thr Tyr Leu Gln Ile Trp Ala His Gln Leu Pro
                645                 650                 655

Phe Ala Ser Gly Asn Ala Ile Leu Asn Lys Val Gly Tyr Cys Ser Leu
            660                 665                 670

Leu Lys Gly Lys Glu Arg Arg Ile Pro Lys Ala Thr Tyr Thr Phe Gln
        675                 680                 685

Tyr Phe Ser Ala Leu Asp Gln Val Asn Arg Thr Arg Leu Gly Pro Asp
    690                 695                 700

Phe Gln Pro Phe Thr Gln Glu Gln Lys Glu Ile Ile Leu Asp Lys Met
705                 710                 715                 720

Phe Gln Arg Thr Asp Tyr Tyr Lys Lys Lys Thr Ile Pro Glu Val Ser
                725                 730                 735

Tyr Tyr Asp Ile Arg Lys Trp Leu Glu Leu Asp Glu Thr Ile Gln Phe
```

-continued

```
            740                 745                 750

Lys Gly Leu Asn Tyr Asp Pro Asn Glu Glu Leu Lys Lys Ile Glu Lys
        755                 760                 765

Lys Pro Phe Ile Asn Leu Lys Ala Phe Tyr Glu Ile Lys Lys Val Val
    770                 775                 780

Ala Asn Tyr Ala Glu Arg Thr Asn Glu Ala Phe Ser Thr Leu Asp Tyr
785                 790                 795                 800

Asp Ala Ile Ala Tyr Ala Leu Thr Val Tyr Lys Thr Asp Lys Asp Ile
                805                 810                 815

Arg Ser Tyr Leu Lys Lys Ser Asn Asn Leu Ser Lys Arg Cys Tyr Asp
            820                 825                 830

Asp Gln Leu Ile Glu Glu Leu Phe Thr Leu Ser Tyr Thr Lys Phe Gly
        835                 840                 845

His Leu Ser Phe Lys Ala Ile Asn His Val Leu Pro Ile Met Gln Glu
    850                 855                 860

Gly Arg Thr Tyr Gln Glu Ala Ile His Gln Leu Gly Tyr Asp Thr Thr
865                 870                 875                 880

Asn Leu Lys Lys Glu Asn Arg Ser Met Phe Leu Pro Leu Ile Pro Asp
                885                 890                 895

Glu Ile Thr Asn Pro Ile Val Lys Arg Ala Ile Thr Gln Ala Arg Lys
            900                 905                 910

Val Val Asn Ala Ile Ile Arg Arg Tyr Gly Ser Pro Asn Ser Val His
        915                 920                 925

Ile Ala Leu Ala Arg Glu Leu Ser Lys Ser His Asp Glu Arg Lys Lys
    930                 935                 940

Ile Met Thr Ala His Asp Glu Asn Tyr Lys Lys Asn Lys Gly Ala Ile
945                 950                 955                 960

Ser Ile Leu Ile Glu Asn Gly Ile Leu Asn Pro Thr Gly Tyr Asp Ile
                965                 970                 975

Val Arg Tyr Lys Leu Trp Lys Glu Gln Gly Glu Arg Cys Ala Tyr Ser
            980                 985                 990

Leu Lys Glu Ile Pro Pro Asp Thr  Phe Phe Asn Glu Leu  Lys Lys Glu
        995                 1000                1005

Arg Asn  Gly Ser Pro Ile Leu  Glu Val Asp His Ile  Leu Pro Tyr
    1010                1015                1020

Ser Gln  Ser Phe Ile Asp Ser  Tyr His Asn Lys Val  Leu Val Tyr
    1025                1030                1035

Ser Asp  Glu Asn Arg Asn Lys  Gly Asn Arg Ile Pro  Tyr Thr Tyr
    1040                1045                1050

Phe Leu  Glu Thr Asn Lys Asp  Trp Glu Ala Phe Glu  Arg Tyr Val
    1055                1060                1065

Arg Ser  Asn Lys Leu Phe Ser  Lys Lys Lys Arg Glu  Tyr Leu Leu
    1070                1075                1080

Lys Lys  Thr Tyr Leu Pro Arg  Glu Ser Glu Leu Ile  Lys Glu Arg
    1085                1090                1095

His Leu  Asn Asp Thr Arg Tyr  Ala Ser Thr Phe Leu  Lys Asn Phe
    1100                1105                1110

Ile Glu  Gln Asn Leu Gln Phe  Lys Glu Val Glu Val  Asn Leu Arg
    1115                1120                1125

Lys Lys  Arg Val Gln Thr Val  Asn Gly Val Ile Thr  Ala His Leu
    1130                1135                1140

Arg Lys  Arg Trp Gly Leu Glu  Lys Asn Arg Gln Glu  Thr Tyr Leu
    1145                1150                1155
```

His His Ala Met Asp Ala Ile Ile Val Ala Cys Thr Asp His His
1160 1165 1170

Met Val Thr Arg Ile Thr Glu Tyr Tyr Gln Ile Lys Glu Ser Asn
1175 1180 1185

Lys Ser Val Lys Lys Pro Tyr Phe Pro Met Pro Trp Glu Gly Phe
1190 1195 1200

Arg Asp Glu Leu Leu Ser His Leu Ala Ser Gln Pro Ile Ala Lys
1205 1210 1215

Lys Ile Ser Glu Glu Leu Lys Ala Gly Tyr Gln Ser Ser Asp Tyr
1220 1225 1230

Ile Phe Val Ser Arg Met Pro Lys Arg Ser Val Thr Gly Ala Ala
1235 1240 1245

His Asp Gln Thr Ile Arg Arg Lys Gly Gly Ile Asp Lys Lys Gly
1250 1255 1260

Lys Thr Ile Ile Ile Lys Arg Val Arg Leu Lys Asp Ile Lys Phe
1265 1270 1275

Asp Glu Asn Gly Asp Phe Lys Met Val Gly Lys Glu Gln Asp Leu
1280 1285 1290

Ala Thr Tyr Glu Ala Ile Lys Gln Arg Tyr Leu Glu His Arg Lys
1295 1300 1305

Asn Ser Lys Lys Ala Phe Glu Thr Pro Leu Tyr Lys Pro Ser Lys
1310 1315 1320

Lys Gly Thr Gly Asn Leu Ile Lys Arg Val Lys Ile Glu Gly Gln
1325 1330 1335

Thr Lys Ala Phe Val Arg Glu Val Asn Gly Gly Val Ala Gln Asn
1340 1345 1350

Ser Asp Leu Val Arg Val Asp Leu Phe Glu Lys Asp Asp Lys Tyr
1355 1360 1365

Tyr Met Val Pro Ile Tyr Val Pro Asp Thr Val Cys Ser Glu Leu
1370 1375 1380

Pro Lys Lys Val Val Lys Ser Gly Lys Gly Tyr Glu Gln Trp Leu
1385 1390 1395

Thr Leu Asp Asn Ser Phe Thr Phe Lys Ser Ser Leu Tyr Pro Tyr
1400 1405 1410

Asp Leu Val Arg Leu Val Lys Gly Asn Glu Asp Arg Phe Leu Tyr
1415 1420 1425

Phe Gly Thr Leu Asp Ile Asp Ser Asp Arg Leu Asn Phe Lys Asp
1430 1435 1440

Val Asn Lys Pro Ser Lys Gln Asn Glu Tyr Arg Tyr Ser Leu Lys
1445 1450 1455

Thr Ile Glu Asn Leu Glu Lys Tyr Glu Val Gly Val Leu Gly Asp
1460 1465 1470

Leu Arg Leu Val Lys Gln Glu Thr Arg Arg Ile Phe Asn Arg Pro
1475 1480 1485

Lys Lys Lys Arg Lys Val
1490

<210> SEQ ID NO 452
<211> LENGTH: 1494
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

```
<220> FEATURE:
<221> NAME/KEY: source
<223> OTHER INFORMATION: /note="Nuc-ADAT-Linker-nAPG08290.1-Linker-SV40"

<400> SEQUENCE: 452

Met Ala Lys Arg Pro Ala Ala Thr Lys Lys Ala Gly Gln Ala Lys Lys
1               5                   10                  15

Lys Lys Ser Glu Val Glu Phe Ser His Glu Tyr Trp Met Arg His Ala
            20                  25                  30

Leu Thr Leu Ala Lys Arg Ala Trp Asp Glu Arg Glu Val Pro Val Gly
        35                  40                  45

Ala Val Leu Val His Asn Asn Arg Val Ile Gly Glu Gly Trp Asn Arg
    50                  55                  60

Pro Ile Gly Arg His Asp Pro Thr Ala His Ala Glu Ile Met Ala Leu
65                  70                  75                  80

Arg Gln Gly Gly Leu Val Met Gln Asn Tyr Arg Leu Ile Asp Ala Thr
                85                  90                  95

Leu Tyr Val Thr Leu Glu Pro Cys Val Met Cys Ala Gly Ala Met Ile
            100                 105                 110

His Ser Arg Ile Gly Arg Val Val Phe Gly Ala Arg Asp Ala Lys Thr
        115                 120                 125

Gly Ala Ala Gly Ser Leu Met Asp Val Leu His His Pro Gly Met Asn
    130                 135                 140

His Arg Val Glu Ile Thr Glu Gly Ile Leu Ala Asp Glu Cys Ala Ala
145                 150                 155                 160

Leu Leu Ser Asp Phe Phe Arg Met Arg Arg Gln Glu Ile Lys Ala Gln
                165                 170                 175

Lys Lys Ala Gln Ser Ser Thr Asp Ser Gly Gly Ser Ser Gly Gly Ser
            180                 185                 190

Ser Gly Ser Glu Thr Pro Gly Thr Ser Glu Ser Ala Thr Pro Glu Ser
        195                 200                 205

Ser Gly Gly Ser Ser Gly Gly Ser Ser Glu Val Glu Phe Ser His Glu
    210                 215                 220

Tyr Trp Met Arg His Ala Leu Thr Leu Ala Lys Arg Ala Arg Asp Glu
225                 230                 235                 240

Arg Glu Val Pro Val Gly Ala Val Leu Val Leu Asn Asn Arg Val Ile
                245                 250                 255

Gly Glu Gly Trp Asn Arg Ala Ile Gly Leu His Asp Pro Thr Ala His
            260                 265                 270

Ala Glu Ile Met Ala Leu Arg Gln Gly Gly Leu Val Met Gln Asn Tyr
        275                 280                 285

Arg Leu Ile Asp Ala Thr Leu Tyr Val Thr Phe Glu Pro Cys Val Met
    290                 295                 300

Cys Ala Gly Ala Met Ile His Ser Arg Ile Gly Arg Val Val Phe Gly
305                 310                 315                 320

Val Arg Asn Ala Lys Thr Gly Ala Ala Gly Ser Leu Met Asp Val Leu
                325                 330                 335

His Tyr Pro Gly Met Asn His Arg Val Glu Ile Thr Glu Gly Ile Leu
            340                 345                 350

Ala Asp Glu Cys Ala Ala Leu Leu Cys Tyr Phe Phe Arg Met Pro Arg
        355                 360                 365

Gln Val Phe Asn Ala Gln Lys Lys Ala Gln Ser Ser Thr Asp Ser Gly
    370                 375                 380

Gly Ser Ser Gly Gly Ser Ser Gly Ser Glu Thr Pro Gly Thr Ser Glu
```

-continued 385 390 395 400

Ser Ala Thr Pro Glu Ser Ser Gly Gly Ser Ser Gly Gly Ser Ser Met
405 410 415

Ser Glu Leu Asp Tyr Arg Ile Gly Leu Ala Ile Gly Thr Asn Ser Ile
420 425 430

Gly Trp Gly Val Ile Glu Leu Phe Trp Asn Lys Asp Arg Glu Arg Tyr
435 440 445

Glu Lys Val Arg Ile Val Asp Lys Gly Val Arg Met Phe Asp Lys Ala
450 455 460

Glu Ile Pro Asn Lys Gly Ala Ser Leu Ala Glu Pro Arg Arg Ile Ala
465 470 475 480

Arg Ser Ser Arg Arg Arg Leu Asn Arg Lys Ser Gln Arg Lys Lys Glu
485 490 495

Ile Arg Asn Leu Leu Val Gln His Gly Met Ile Thr Gln Glu Glu Leu
500 505 510

Asp Leu Leu Tyr Pro Leu Ser Lys Lys Ser Ile Asp Ile Trp Asp Ile
515 520 525

Arg Leu Asp Gly Leu Asp Arg Leu Leu Asn His Leu Glu Trp Ala Arg
530 535 540

Leu Leu Ile His Leu Ala Gln Arg Arg Gly Phe Lys Ser Asn Arg Lys
545 550 555 560

Ser Glu Leu Lys Asp Ala Glu Thr Gly Lys Val Leu Ser Ser Ile Gln
565 570 575

Val Asn Glu Lys Arg Leu Phe Leu Tyr Arg Thr Val Gly Glu Met Trp
580 585 590

Ile Lys Asp Ala Glu Phe Ser Lys Tyr Asp Arg Arg Arg Asn Ser Pro
595 600 605

Asn Glu Tyr Val Phe Ser Val Ser Arg Ala Asp Leu Glu Lys Glu Ile
610 615 620

Val Thr Leu Phe Glu Ala Gln Arg Lys Phe Gln Ser Ser Tyr Ala Ser
625 630 635 640

Lys Asn Leu Gln Glu Thr Tyr Leu Gln Ile Trp Ala His Gln Leu Pro
645 650 655

Phe Ala Ser Gly Asn Ala Ile Leu Asn Lys Val Gly Tyr Cys Ser Leu
660 665 670

Leu Lys Gly Lys Glu Arg Arg Ile Pro Lys Ala Thr Tyr Thr Phe Gln
675 680 685

Tyr Phe Ser Ala Leu Asp Gln Val Asn Arg Thr Arg Leu Gly Pro Asp
690 695 700

Phe Gln Pro Phe Thr Gln Glu Gln Lys Glu Ile Ile Leu Asp Lys Met
705 710 715 720

Phe Gln Arg Thr Asp Tyr Tyr Lys Lys Lys Thr Ile Pro Glu Val Ser
725 730 735

Tyr Tyr Asp Ile Arg Lys Trp Leu Glu Leu Asp Glu Thr Ile Gln Phe
740 745 750

Lys Gly Leu Asn Tyr Asp Pro Asn Glu Glu Leu Lys Lys Ile Glu Lys
755 760 765

Lys Pro Phe Ile Asn Leu Lys Ala Phe Tyr Glu Ile Lys Lys Val Val
770 775 780

Ala Asn Tyr Ala Glu Arg Thr Asn Glu Ala Phe Ser Thr Leu Asp Tyr
785 790 795 800

Asp Ala Ile Ala Tyr Ala Leu Thr Val Tyr Lys Thr Asp Lys Asp Ile
805 810 815

```
Arg Ser Tyr Leu Lys Lys Ser Asn Asn Leu Ser Lys Arg Cys Tyr Asp
            820                 825                 830

Asp Gln Leu Ile Glu Glu Leu Phe Thr Leu Ser Tyr Thr Lys Phe Gly
        835                 840                 845

His Leu Ser Phe Lys Ala Ile Asn His Val Leu Pro Ile Met Gln Glu
    850                 855                 860

Gly Arg Thr Tyr Gln Glu Ala Ile His Gln Leu Gly Tyr Asp Thr Thr
865                 870                 875                 880

Asn Leu Lys Lys Glu Asn Arg Ser Met Phe Leu Pro Leu Ile Pro Asp
                885                 890                 895

Glu Ile Thr Asn Pro Ile Val Lys Arg Ala Ile Thr Gln Ala Arg Lys
            900                 905                 910

Val Val Asn Ala Ile Ile Arg Arg Tyr Gly Ser Pro Asn Ser Val His
        915                 920                 925

Ile Glu Leu Ala Arg Glu Leu Ser Lys Ser His Asp Glu Arg Lys Lys
    930                 935                 940

Ile Met Thr Ala His Asp Glu Asn Tyr Lys Lys Asn Lys Gly Ala Ile
945                 950                 955                 960

Ser Ile Leu Ile Glu Asn Gly Ile Leu Asn Pro Thr Gly Tyr Asp Ile
                965                 970                 975

Val Arg Tyr Lys Leu Trp Lys Glu Gln Gly Glu Arg Cys Ala Tyr Ser
            980                 985                 990

Leu Lys Glu Ile Pro Pro Asp Thr  Phe Phe Asn Glu Leu  Lys Lys Glu
        995                 1000                1005

Arg Asn  Gly Ser Pro Ile Leu  Glu Val Asp His Ile  Leu Pro Tyr
    1010                1015                1020

Ser Gln  Ser Phe Ile Asp Ser  Tyr His Asn Lys Val  Leu Val Tyr
    1025                1030                1035

Ser Asp  Glu Asn Arg Asn Lys  Gly Asn Arg Ile Pro  Tyr Thr Tyr
    1040                1045                1050

Phe Leu  Glu Thr Asn Lys Asp  Trp Glu Ala Phe Glu  Arg Tyr Val
    1055                1060                1065

Arg Ser  Asn Lys Leu Phe Ser  Lys Lys Lys Arg Glu  Tyr Leu Leu
    1070                1075                1080

Lys Lys  Thr Tyr Leu Pro Arg  Glu Ser Glu Leu Ile  Lys Glu Arg
    1085                1090                1095

His Leu  Asn Asp Thr Arg Tyr  Ala Ser Thr Phe Leu  Lys Asn Phe
    1100                1105                1110

Ile Glu  Gln Asn Leu Gln Phe  Lys Glu Val Glu Val  Asn Leu Arg
    1115                1120                1125

Lys Lys  Arg Val Gln Thr Val  Asn Gly Val Ile Thr  Ala His Leu
    1130                1135                1140

Arg Lys  Arg Trp Gly Leu Glu  Lys Asn Arg Gln Glu  Thr Tyr Leu
    1145                1150                1155

His His  Ala Met Asp Ala Ile  Ile Val Ala Cys Thr  Asp His His
    1160                1165                1170

Met Val  Thr Arg Ile Thr Glu  Tyr Tyr Gln Ile Lys  Glu Ser Asn
    1175                1180                1185

Lys Ser  Val Lys Lys Pro Tyr  Phe Pro Met Pro Trp  Glu Gly Phe
    1190                1195                1200

Arg Asp  Glu Leu Leu Ser His  Leu Ala Ser Gln Pro  Ile Ala Lys
    1205                1210                1215
```

```
Lys Ile  Ser Glu Glu Leu Lys  Ala Gly Tyr Gln Ser  Ser Asp Tyr
    1220                 1225                 1230

Ile Phe  Val Ser Arg Met Pro  Lys Arg Ser Val Thr  Gly Ala Ala
    1235                 1240                 1245

His Asp  Gln Thr Ile Arg Arg  Lys Gly Gly Ile Asp  Lys Lys Gly
    1250                 1255                 1260

Lys Thr  Ile Ile Ile Lys Arg  Val Arg Leu Lys Asp  Ile Lys Phe
    1265                 1270                 1275

Asp Glu  Asn Gly Asp Phe Lys  Met Val Gly Lys Glu  Gln Asp Leu
    1280                 1285                 1290

Ala Thr  Tyr Glu Ala Ile Lys  Gln Arg Tyr Leu Glu  His Arg Lys
    1295                 1300                 1305

Asn Ser  Lys Lys Ala Phe Glu  Thr Pro Leu Tyr Lys  Pro Ser Lys
    1310                 1315                 1320

Lys Gly  Thr Gly Asn Leu Ile  Lys Arg Val Lys Ile  Glu Gly Gln
    1325                 1330                 1335

Thr Lys  Ala Phe Val Arg Glu  Val Asn Gly Gly Val  Ala Gln Asn
    1340                 1345                 1350

Ser Asp  Leu Val Arg Val Asp  Leu Phe Glu Lys Asp  Asp Lys Tyr
    1355                 1360                 1365

Tyr Met  Val Pro Ile Tyr Val  Pro Asp Thr Val Cys  Ser Glu Leu
    1370                 1375                 1380

Pro Lys  Lys Val Val Lys Ser  Gly Lys Gly Tyr Glu  Gln Trp Leu
    1385                 1390                 1395

Thr Leu  Asp Asn Ser Phe Thr  Phe Lys Ser Ser Leu  Tyr Pro Tyr
    1400                 1405                 1410

Asp Leu  Val Arg Leu Val Lys  Gly Asn Glu Asp Arg  Phe Leu Tyr
    1415                 1420                 1425

Phe Gly  Thr Leu Asp Ile Asp  Ser Asp Arg Leu Asn  Phe Lys Asp
    1430                 1435                 1440

Val Asn  Lys Pro Ser Lys Gln  Asn Glu Tyr Arg Tyr  Ser Leu Lys
    1445                 1450                 1455

Thr Ile  Glu Asn Leu Glu Lys  Tyr Glu Val Gly Val  Leu Gly Asp
    1460                 1465                 1470

Leu Arg  Leu Val Lys Gln Glu  Thr Arg Arg Ile Phe  Asn Arg Pro
    1475                 1480                 1485

Lys Lys  Lys Arg Lys Val
    1490
```

<210> SEQ ID NO 453
<211> LENGTH: 25
<212> TYPE: DNA
<213> ORGANISM: Homo sapiens
<220> FEATURE:
<221> NAME/KEY: source
<223> OTHER INFORMATION: /note="Hurler target 1"

<400> SEQUENCE: 453
ggagcagctc taggccgaag tgtcg 25

<210> SEQ ID NO 454
<211> LENGTH: 25
<212> TYPE: DNA
<213> ORGANISM: Homo sapiens
<220> FEATURE:
<221> NAME/KEY: source
<223> OTHER INFORMATION: /note="Hurler target 2"

<400> SEQUENCE: 454
taggccgaag tgtcgcaggc cggga 25

<210> SEQ ID NO 455
<211> LENGTH: 25
<212> TYPE: DNA
<213> ORGANISM: Homo sapiens
<220> FEATURE:
<221> NAME/KEY: source
<223> OTHER INFORMATION: /note="Hurler target 3"

<400> SEQUENCE: 455
gctctaggcc gaagtgtcgc aggcc 25

<210> SEQ ID NO 456
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="sgRNA Hurler target 1"

<400> SEQUENCE: 456
ggagcagctc taggccgaag tgtcggtcat agttccatga aagccaaaag tggctttgat 60
gtttctatga taagggtttc ggcccgtggc gtcggggatc gcctgcccat tccgatgggc 120
ttctccccat ttatt 135

<210> SEQ ID NO 457
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="sgRNA Hurler target 2"

<400> SEQUENCE: 457
taggccgaag tgtcgcaggc cgggagtcat agttccatga aagccaaaag tggctttgat 60
gtttctatga taagggtttc ggcccgtggc gtcggggatc gcctgcccat tccgatgggc 120
ttctccccat ttatt 135

<210> SEQ ID NO 458
<211> LENGTH: 135
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="sgRNA Hurler target 3"

<400> SEQUENCE: 458
ggcctgcgac acttcggcct agagcgtcat agttccatga aagccaaaag tggctttgat 60
gtttctatga taagggtttc ggcccgtggc gtcggggatc gcctgcccat tccgatgggc 120
ttctccccat ttatt 135

```
<210> SEQ ID NO 459
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Hurler Forward Amplification Primer"

<400> SEQUENCE: 459

gactccttca ccaag                                                   15


<210> SEQ ID NO 460
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Hurler Reverse Amplification Primer"

<400> SEQUENCE: 460

gtagatcagc accg                                                    14


<210> SEQ ID NO 461
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Hurler Wild Type Probe"

<400> SEQUENCE: 461

ctctgggccg aagt                                                    14


<210> SEQ ID NO 462
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Hurler W402X Probe-beta"

<400> SEQUENCE: 462

ctctaggccg aagt                                                    14


<210> SEQ ID NO 463
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Hurler NGS forward"

<400> SEQUENCE: 463

acttcctcca gcc                                                          13

<210> SEQ ID NO 464
<211> LENGTH: 13
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Hurler NGS Reverse"

<400> SEQUENCE: 464

gaaccccggc tta                                                          13

<210> SEQ ID NO 465
<211> LENGTH: 31
<212> TYPE: DNA
<213> ORGANISM: Homo sapiens
<220> FEATURE:
<221> NAME/KEY: source
<223> OTHER INFORMATION: /note="Human W402X"

<400> SEQUENCE: 465

ggagcagctc taggccgaag tgtcgcaggc c                                      31

<210> SEQ ID NO 466
<211> LENGTH: 31
<212> TYPE: DNA
<213> ORGANISM: Mus musculus
<220> FEATURE:
<221> NAME/KEY: source
<223> OTHER INFORMATION: /note="Mouse W392X"

<400> SEQUENCE: 466

agaacaactc taggcagagg tctcaaaggc t                                      31

<210> SEQ ID NO 467
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="humanized mouse"

<400> SEQUENCE: 467

ggagcagctc taggccgaag tgtcgcaggc c                                      31

<210> SEQ ID NO 468
<211> LENGTH: 25
<212> TYPE: DNA
<213> ORGANISM: Homo sapiens
<220> FEATURE:
<221> NAME/KEY: source
<223> OTHER INFORMATION: /note="FRDA target 1"

<400> SEQUENCE: 468

atcacctgag gtccggagtt caaga                                             25
```

<210> SEQ ID NO 469
<211> LENGTH: 25
<212> TYPE: DNA
<213> ORGANISM: Homo sapiens
<220> FEATURE:
<221> NAME/KEY: source
<223> OTHER INFORMATION: /note="FRDA target 2"

<400> SEQUENCE: 469
gtcttgaact ccggacctca ggtga 25

<210> SEQ ID NO 470
<211> LENGTH: 25
<212> TYPE: DNA
<213> ORGANISM: Homo sapiens
<220> FEATURE:
<221> NAME/KEY: source
<223> OTHER INFORMATION: /note="FRDA target 3"

<400> SEQUENCE: 470
tgaactccgg acctcaggtg atcca 25

<210> SEQ ID NO 471
<211> LENGTH: 25
<212> TYPE: DNA
<213> ORGANISM: Homo sapiens
<220> FEATURE:
<221> NAME/KEY: source
<223> OTHER INFORMATION: /note="FRDA target 4"

<400> SEQUENCE: 471
gaaaagttag ccgggcgtgg tgtcg 25

<210> SEQ ID NO 472
<211> LENGTH: 500
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: source
<223> OTHER INFORMATION: /note="BCL11A enhancer region"

<400> SEQUENCE: 472
aaaaatggac aattatgagg aggggagagt gcagacaggg gaagcttcac ctcctttaca 60
attttgggag tccacacggc atggcataca aattatttca ttcccattga gaaataaaat 120
ccaattctcc atcaccaaga gagccttccg aaagaggccc ccctgggcaa acggccaccg 180
atggagaggt ctgccagtcc tcttctaccc cacccacgcc cccaccctaa tcagaggcca 240
aacccttcct ggagcctgtg ataaaagcaa ctgttagctt gcactagact agcttcaaag 300
ttgtattgac cctggtgtgt tatgtctaag agtagatgcc atatctcttt tctggcctat 360
gttattacct gtatggactt tgcactggaa tcagctatct gctcttactt atgcacacct 420
ggggcataga gccagccctg tatcgctttt cagccatctc actacagata actcccaagt 480
cctgtctagc tgccttcctt 500

<210> SEQ ID NO 473
<211> LENGTH: 26
<212> TYPE: DNA
<213> ORGANISM: Homo sapiens
<220> FEATURE:

<221> NAME/KEY: source
<223> OTHER INFORMATION: /note="SCD target seq 1"

<400> SEQUENCE: 473
gcactagact agcttcaaag ttgtag 26

<210> SEQ ID NO 474
<211> LENGTH: 26
<212> TYPE: DNA
<213> ORGANISM: Homo sapiens
<220> FEATURE:
<221> NAME/KEY: source
<223> OTHER INFORMATION: /note="SCD target seq 2"

<400> SEQUENCE: 474
cctaatcaga ggccaaaccc ttcctg 26

<210> SEQ ID NO 475
<211> LENGTH: 26
<212> TYPE: DNA
<213> ORGANISM: Homo sapiens
<220> FEATURE:
<221> NAME/KEY: source
<223> OTHER INFORMATION: /note="SCD target seq 3"

<400> SEQUENCE: 475
caagctaaca gttgctttta tcacag 26

<210> SEQ ID NO 476
<211> LENGTH: 26
<212> TYPE: DNA
<213> ORGANISM: Homo sapiens
<220> FEATURE:
<221> NAME/KEY: source
<223> OTHER INFORMATION: /note="SCD target seq 4"

<400> SEQUENCE: 476
gcactagact agcttcaaag ttgtag 26

<210> SEQ ID NO 477
<211> LENGTH: 26
<212> TYPE: DNA
<213> ORGANISM: Homo sapiens
<220> FEATURE:
<221> NAME/KEY: source
<223> OTHER INFORMATION: /note="SCD target seq 5"

<400> SEQUENCE: 477
cctaatcaga ggccaaaccc ttcctg 26

<210> SEQ ID NO 478
<211> LENGTH: 26
<212> TYPE: DNA
<213> ORGANISM: Homo sapiens
<220> FEATURE:
<221> NAME/KEY: source
<223> OTHER INFORMATION: /note="SCD target seq 6"

<400> SEQUENCE: 478
caagctaaca gttgctttta tcacag 26

<210> SEQ ID NO 479
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="RelA FWD"

<400> SEQUENCE: 479
cttagtttca ccgcaggttc ta 22

<210> SEQ ID NO 480
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="RelA REV"

<400> SEQUENCE: 480
ctgtgcactc aacactgatc ta 22

<210> SEQ ID NO 481
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="AurkB FWD"

<400> SEQUENCE: 481
cccagcccta ggttgtttat t 21

<210> SEQ ID NO 482
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="AurkB REV"

<400> SEQUENCE: 482
ctggctacat cttccttgac tac 23

<210> SEQ ID NO 483
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="HPRT1 FWD"

<400> SEQUENCE: 483
gtggcagaag cagtgagtaa 20

<210> SEQ ID NO 484
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="HPRT1 REV"

<400> SEQUENCE: 484
tcccatctag gcactaggta aa 22

<210> SEQ ID NO 485
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 134, Guide 135, Guide 136, Guide 137"

<400> SEQUENCE: 485
gtctcgtggg ctcggagatg tgtataagag acagacaatt ctcctgcctc agcc 54

<210> SEQ ID NO 486
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 134, Guide 135, Guide 136, Guide 137"

<400> SEQUENCE: 486
tcgtcggcag cgtcagatgt gtataagaga cagactgcca tgggaagaag gtg 53

<210> SEQ ID NO 487
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 138, Guide 139, Guide 140, Guide 141"

<400> SEQUENCE: 487
gtctcgtggg ctcggagatg tgtataagag acagacaatt ctcctgcctc agcc 54

<210> SEQ ID NO 488
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<220> FEATURE:
<221> NAME/KEY: source
<223> OTHER INFORMATION: /note="REV_Guide 138, Guide 139, Guide 140, Guide 141"

<400> SEQUENCE: 488
tcgtcggcag cgtcagatgt gtataagaga cagactgcca tgggaagaag gtg 53

<210> SEQ ID NO 489
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 142, Guide 143, Guide 144, Guide 145"

<400> SEQUENCE: 489
tcgtcggcag cgtcagatgt gtataagaga caggagctgc acatttgacg agc 53

<210> SEQ ID NO 490
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 142, Guide 143, Guide 144, Guide 145"

<400> SEQUENCE: 490
gtctcgtggg ctcggagatg tgtataagag acagattaca ggtgtgagcc acgg 54

<210> SEQ ID NO 491
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 164, Guide 165, Guide 166, Guide 167"

<400> SEQUENCE: 491
tcgtcggcag cgtcagatgt gtataagaga cagctgacct caggtgatac gcc 53

<210> SEQ ID NO 492
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 164, Guide 165, Guide 166, Guide 167"

<400> SEQUENCE: 492
gtctcgtggg ctcggagatg tgtataagag acagctttgg gaggctgaga cagg 54

<210> SEQ ID NO 493
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 168, Guide 169, Guide 170, Guide 171"

<400> SEQUENCE: 493
tcgtcggcag cgtcagatgt gtataagaga cagtgctcta ttgtccaggc tgg 53

<210> SEQ ID NO 494
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 168, Guide 169, Guide 170, Guide 171"

<400> SEQUENCE: 494
gtctcgtggg ctcggagatg tgtataagag acagtccagc aggtcagcaa agaa 54

<210> SEQ ID NO 495
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 172, Guide 173, Guide 174, Guide 175"

<400> SEQUENCE: 495
tcgtcggcag cgtcagatgt gtataagaga caggcagtat aactggccag cct 53

<210> SEQ ID NO 496
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 172, Guide 173, Guide 174, Guide 175"

<400> SEQUENCE: 496
gtctcgtggg ctcggagatg tgtataagag acagtcagtt gaggagttca gcttaa 56

<210> SEQ ID NO 497
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 185, Guide 186, Guide 187, Guide 188"

<400> SEQUENCE: 497
tcgtcggcag cgtcagatgt gtataagaga cagtggcccc tatgtggaga tca 53

<210> SEQ ID NO 498
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 185, Guide 186, Guide 187, Guide 188"

<400> SEQUENCE: 498
gtctcgtggg ctcggagatg tgtataagag acagggcaga gctcagcctc atag 54

<210> SEQ ID NO 499
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 189, Guide 190, Guide 191, Guide 192"

<400> SEQUENCE: 499
tcgtcggcag cgtcagatgt gtataagaga cagatatccc cacttcccct gct 53

<210> SEQ ID NO 500
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 189, Guide 190, Guide 191, Guide 192"

<400> SEQUENCE: 500
gtctcgtggg ctcggagatg tgtataagag acagcacctc aaggacagct ctgg 54

<210> SEQ ID NO 501
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 193, Guide 194, Guide 195, Guide 196"

<400> SEQUENCE: 501
tcgtcggcag cgtcagatgt gtataagaga cagatatccc cacttcccct gct 53

<210> SEQ ID NO 502
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 193, Guide 194, Guide 195, Guide 196"

<400> SEQUENCE: 502
gtctcgtggg ctcggagatg tgtataagag acagcacctc aaggacagct ctgg 54

<210> SEQ ID NO 503
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 146"

<400> SEQUENCE: 503
gtctcgtggg ctcggagatg tgtataagag acagacaatt ctcctgcctc agcc 54

<210> SEQ ID NO 504
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 146"

<400> SEQUENCE: 504
tcgtcggcag cgtcagatgt gtataagaga cagactgcca tgggaagaag gtg 53

<210> SEQ ID NO 505
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 147"

<400> SEQUENCE: 505
gtctcgtggg ctcggagatg tgtataagag acagacaatt ctcctgcctc agcc 54

<210> SEQ ID NO 506
<211> LENGTH: 53
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 147"

<400> SEQUENCE: 506
tcgtcggcag cgtcagatgt gtataagaga cagactgcca tgggaagaag gtg 53

<210> SEQ ID NO 507
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 148"

<400> SEQUENCE: 507
tcgtcggcag cgtcagatgt gtataagaga cagactgcca tgggaagaag gtg 53

<210> SEQ ID NO 508
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 148"

<400> SEQUENCE: 508
gtctcgtggg ctcggagatg tgtataagag acagacaatt ctcctgcctc agcc 54

<210> SEQ ID NO 509
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 176"

<400> SEQUENCE: 509
tcgtcggcag cgtcagatgt gtataagaga caggtagctc actgcagcct caa 53

<210> SEQ ID NO 510
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 176"

<400> SEQUENCE: 510
gtctcgtggg ctcggagatg tgtataagag acagtgggtg atgaacatac gggt 54

<210> SEQ ID NO 511
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 177"

<400> SEQUENCE: 511
tcgtcggcag cgtcagatgt gtataagaga cagtcagact gaagagctat tgtgtga 57

<210> SEQ ID NO 512
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 177"

<400> SEQUENCE: 512
gtctcgtggg ctcggagatg tgtataagag acagccccac aaaccgatgt agct 54

<210> SEQ ID NO 513
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 209"

<400> SEQUENCE: 513
tcgtcggcag cgtcagatgt gtataagaga cagtggagtg cagtggtgtg atc 53

<210> SEQ ID NO 514
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 209"

<400> SEQUENCE: 514
gtctcgtggg ctcggagatg tgtataagag acagttgagg ctgcagtgag ctac 54

<210> SEQ ID NO 515
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<220> FEATURE:
<221> NAME/KEY: source
<223> OTHER INFORMATION: /note="REV_Guide 197"

<400> SEQUENCE: 515
tcgtcggcag cgtcagatgt gtataagaga cagtggcccc tatgtggaga tca 53

<210> SEQ ID NO 516
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 197"

<400> SEQUENCE: 516
gtctcgtggg ctcggagatg tgtataagag acagggcaga gctcagcctc atag 54

<210> SEQ ID NO 517
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 198"

<400> SEQUENCE: 517
tcgtcggcag cgtcagatgt gtataagaga cagccaagcc gaccaaacaa gtg 53

<210> SEQ ID NO 518
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 198"

<400> SEQUENCE: 518
gtctcgtggg ctcggagatg tgtataagag acaggatgcg ctgactgata gcct 54

<210> SEQ ID NO 519
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 199"

<400> SEQUENCE: 519
tcgtcggcag cgtcagatgt gtataagaga cagtggcccc tatgtggaga tca 53

<210> SEQ ID NO 520
<211> LENGTH: 54

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 199"

<400> SEQUENCE: 520
gtctcgtggg ctcggagatg tgtataagag acagggcaga gctcagcctc atag 54

<210> SEQ ID NO 521
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 149"

<400> SEQUENCE: 521
gtctcgtggg ctcggagatg tgtataagag acagggtaag gggaaactgg aggc 54

<210> SEQ ID NO 522
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 149"

<400> SEQUENCE: 522
tcgtcggcag cgtcagatgt gtataagaga cagtccactt tctaagcagg cgg 53

<210> SEQ ID NO 523
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 150"

<400> SEQUENCE: 523
gtctcgtggg ctcggagatg tgtataagag acaggtgggc ctggatttcg atct 54

<210> SEQ ID NO 524
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 150"

<400> SEQUENCE: 524
tcgtcggcag cgtcagatgt gtataagaga cagatgaaca ggcaggaagt cgg 53

<210> SEQ ID NO 525
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 151"

<400> SEQUENCE: 525
tcgtcggcag cgtcagatgt gtataagaga cagcggttct gagttgcctt cct 53

<210> SEQ ID NO 526
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 151"

<400> SEQUENCE: 526
gtctcgtggg ctcggagatg tgtataagag acagggtaag gggaaactgg aggc 54

<210> SEQ ID NO 527
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 179"

<400> SEQUENCE: 527
tcgtcggcag cgtcagatgt gtataagaga cagtcagtgg tccacatgca agt 53

<210> SEQ ID NO 528
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 179"

<400> SEQUENCE: 528
gtctcgtggg ctcggagatg tgtataagag acagaaggca agttgatcgc tcga 54

<210> SEQ ID NO 529
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"
<220> FEATURE:
<221> NAME/KEY: source
<223> OTHER INFORMATION: /note="REV_Guide 180"

<400> SEQUENCE: 529
tcgtcggcag cgtcagatgt gtataagaga cagagtggtt ctgttgcaca cgt 53

<210> SEQ ID NO 530
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 180"

<400> SEQUENCE: 530
gtctcgtggg ctcggagatg tgtataagag acagtcgctt aagcccagga gttc 54

<210> SEQ ID NO 531
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 181"

<400> SEQUENCE: 531
tcgtcggcag cgtcagatgt gtataagaga cagtctggct gatccgtact aatcc 55

<210> SEQ ID NO 532
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 181"

<400> SEQUENCE: 532
gtctcgtggg ctcggagatg tgtataagag acagtaggct caagggatgc tcct 54

<210> SEQ ID NO 533
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 200"

<400> SEQUENCE: 533
tcgtcggcag cgtcagatgt gtataagaga cagccagagc tgtccttgag gtg 53

<210> SEQ ID NO 534

<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 200"

<400> SEQUENCE: 534
gtctcgtggg ctcggagatg tgtataagag acaggtccat acccaccttg gcaa 54

<210> SEQ ID NO 535
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 201"

<400> SEQUENCE: 535
tcgtcggcag cgtcagatgt gtataagaga cagccaagcc gaccaaacaa gtg 53

<210> SEQ ID NO 536
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 201"

<400> SEQUENCE: 536
gtctcgtggg ctcggagatg tgtataagag acaggatgcg ctgactgata gcct 54

<210> SEQ ID NO 537
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 202"

<400> SEQUENCE: 537
tcgtcggcag cgtcagatgt gtataagaga cagaggctat cagtcagcgc atc 53

<210> SEQ ID NO 538
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 202"

<400> SEQUENCE: 538
gtctcgtggg ctcggagatg tgtataagag acagagcagg ggaagtgggg atat 54

<210> SEQ ID NO 539
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 152"

<400> SEQUENCE: 539
gtctcgtggg ctcggagatg tgtataagag acagattaca ggtgtgagcc acgg 54

<210> SEQ ID NO 540
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 152"

<400> SEQUENCE: 540
tcgtcggcag cgtcagatgt gtataagaga caggagctgc acatttgacg agc 53

<210> SEQ ID NO 541
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 153"

<400> SEQUENCE: 541
gtctcgtggg ctcggagatg tgtataagag acagacaatt ctcctgcctc agcc 54

<210> SEQ ID NO 542
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 153"

<400> SEQUENCE: 542
tcgtcggcag cgtcagatgt gtataagaga cagactgcca tgggaagaag gtg 53

<210> SEQ ID NO 543
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 154"

<400> SEQUENCE: 543
gtctcgtggg ctcggagatg tgtataagag acagattaca ggtgtgagcc acgg 54

<210> SEQ ID NO 544
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 154"

<400> SEQUENCE: 544
tcgtcggcag cgtcagatgt gtataagaga caggagctgc acatttgacg agc 53

<210> SEQ ID NO 545
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 182"

<400> SEQUENCE: 545
gtctcgtggg ctcggagatg tgtataagag acagtgggtg atgaacatac gggt 54

<210> SEQ ID NO 546
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="REV_Guide 182"

<400> SEQUENCE: 546
tcgtcggcag cgtcagatgt gtataagaga caggtagctc actgcagcct caa 53

<210> SEQ ID NO 547
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="FWD_Guide 183"

<400> SEQUENCE: 547
gtctcgtggg ctcggagatg tgtataagag acagtgcctg tagtcccagc tact 54

<210> SEQ ID NO 548
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 183"

<400> SEQUENCE: 548
tcgtcggcag cgtcagatgt gtataagaga cagtcagctc agtgcaacct ctg 53

<210> SEQ ID NO 549
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 184"

<400> SEQUENCE: 549
gtctcgtggg ctcggagatg tgtataagag acagctttgg gaggctgaga cagg 54

<210> SEQ ID NO 550
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 184"

<400> SEQUENCE: 550
tcgtcggcag cgtcagatgt gtataagaga cagctgacct caggtgatac gcc 53

<210> SEQ ID NO 551
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 203"

<400> SEQUENCE: 551
gtctcgtggg ctcggagatg tgtataagag acaggatgcg ctgactgata gcct 54

<210> SEQ ID NO 552
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 203"

<400> SEQUENCE: 552
tcgtcggcag cgtcagatgt gtataagaga cagccaagcc gaccaaacaa gtg 53

<210> SEQ ID NO 553
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 204"

<400> SEQUENCE: 553
gtctcgtggg ctcggagatg tgtataagag acagcacctc aaggacagct ctgg 54

<210> SEQ ID NO 554
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 204"

<400> SEQUENCE: 554
tcgtcggcag cgtcagatgt gtataagaga cagatatccc cacttcccct gct 53

<210> SEQ ID NO 555
<211> LENGTH: 54
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="FWD_Guide 205"

<400> SEQUENCE: 555
gtctcgtggg ctcggagatg tgtataagag acagggcaga gctcagcctc atag 54

<210> SEQ ID NO 556
<211> LENGTH: 53
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="REV_Guide 205"

<400> SEQUENCE: 556
tcgtcggcag cgtcagatgt gtataagaga cagtggcccc tatgtggaga tca 53

<210> SEQ ID NO 557
<211> LENGTH: 6
<212> TYPE: RNA
<213> ORGANISM: Artificial Sequence
<220> FEATURE:

<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="seq in base of hairpin stem of tracrRNA"
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (4)..(5)
<223> OTHER INFORMATION: a, c, u, g, unknown or other

<400> SEQUENCE: 557 unannu 6

<210> SEQ ID NO 558
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="seq in base of hairpin stem of tracrRNA"
<220> FEATURE:
<221> NAME/KEY: modified_base
<222> LOCATION: (2)..(2)
<223> OTHER INFORMATION: a, c, u, g, unknown or other
<220> FEATURE:
<221> NAME/KEY: modified_base
<222> LOCATION: (4)..(5)
<223> OTHER INFORMATION: a, c, u, g, unknown or other

<400> SEQUENCE: 558 unanna 6

<210> SEQ ID NO 559
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="sequence 2 for cleavage site assay"

<400> SEQUENCE: 559
ccatgatata gacgttgtgg ctgttgtagt 30

<210> SEQ ID NO 560
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 6xHis tag"

<400> SEQUENCE: 560

His His His His His His
1 5

<210> SEQ ID NO 561
<211> LENGTH: 10

<212> TYPE: PRT
<213> ORGANISM: Artificial Sequence
<220> FEATURE:
<221> NAME/KEY: source
<223> OTHER INFORMATION: /note="Description of Artificial Sequence:
Synthetic 10xHis tag"

<400> SEQUENCE: 561

His His His His His His His His His His
1 5 10

<210> SEQ ID NO 562
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 562
cctgggtgtg aggctgggcc attaaaacct ctcc 34

<210> SEQ ID NO 563
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 563
cctgaaaacc tctcc 15

<210> SEQ ID NO 564
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 564
cctgggtgtg agctgggcca ttaaaacctc tcc 33

<210> SEQ ID NO 565
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 565
cctgggccat taaaacctct cc 22

<210> SEQ ID NO 566
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 566
cctggctctc c 11

<210> SEQ ID NO 567
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 567
cgggccatta aaacctctcc 20

<210> SEQ ID NO 568
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 568
cctgggtgtg aggccagacc tgggccatta aaacctctcc 40

<210> SEQ ID NO 569
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 569
cctgggtgtg aggggaagct gacgtccttt ccatggctgc tcgcctgtgt tgccaccgct 60
gggccattaa aacctctcc 79

<210> SEQ ID NO 570
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 570
cctgggtgtg acctgggcca ttaaaacctc tcc 33

<210> SEQ ID NO 571
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 571
cctgggtgtg aggactgggc cattaaaacc tctcc 35

<210> SEQ ID NO 572
<211> LENGTH: 34
<212> TYPE: DNA

<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 572
agttggcaga tgctctaatg tactgccatg ggaa 34

<210> SEQ ID NO 573
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 573
agttggcaga tgcaatgtac tgccatggga a 31

<210> SEQ ID NO 574
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 574
agttggcaga tgcatgtact gccatgggaa 30

<210> SEQ ID NO 575
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 575
agttggcaga tgctatgtac tgccatggga a 31

<210> SEQ ID NO 576
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 576
agttggcaga tgctaatgta ctgccatggg aa 32

<210> SEQ ID NO 577
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 577
agttggcaga tgctatgtaa tgccatggga a 31

<210> SEQ ID NO 578
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 578
agttggcaga tgctctatgt actgccatgg gaa 33

<210> SEQ ID NO 579
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 579
cgacctgaat gctgtgcggc gctctggctt cattcaatc 39

<210> SEQ ID NO 580
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 580
cgacctgaat gctgtgcggc tctgcttcca ggtga 35

<210> SEQ ID NO 581
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 581
cgacctgaat gctgtgcggc atctgcttcc aggtga 36

<210> SEQ ID NO 582
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 582
cgacctgaat gctgcttcca ggtga 25

<210> SEQ ID NO 583
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 583
cgacctgaat gcttctgctt ccaggtga 28

<210> SEQ ID NO 584
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 584
cgacctgaat gcttccaggt ga 22

<210> SEQ ID NO 585
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 585
gcgtggggac tacgacctga atgctgtgcg gctct 35

<210> SEQ ID NO 586
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 586
gcgacctgaa tgctgtgcgg ctct 24

<210> SEQ ID NO 587
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 587
gcgtggggac tacgagctgt gcggctct 28

<210> SEQ ID NO 588
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 588
gcgtggggac tgaatgctgt gcggctct 28

<210> SEQ ID NO 589
<211> LENGTH: 31

<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 589
gcgtggggac tcctgaatgc tgtgcggctc t 31

<210> SEQ ID NO 590
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 590
gcgtggggac tacgaacctg aatgctgtgc ggctct 36

<210> SEQ ID NO 591
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 591
gcgtggggac tacgaatgct gtgcggctct 30

<210> SEQ ID NO 592
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 592
gcgtggggac tacctgaatg ctgtgcggct ct 32

<210> SEQ ID NO 593
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 593
gcgtgaatgc tgtgcggctc t 21

<210> SEQ ID NO 594
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 594
gcgacctgac tgctgtgcgg ctct 24

<210> SEQ ID NO 595
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 595
gcgtggggac tacgcctgaa tgctgtgcgg ctct 34

<210> SEQ ID NO 596
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 596
atggaggagt tggcagatgc tctaatgtac tgccatggga ag 42

<210> SEQ ID NO 597
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 597
atggaggagt tggcagatgc taatgtactg ccatgggaag 40

<210> SEQ ID NO 598
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 598
atggaggagt tggcagatgt actgccatgg gaag 34

<210> SEQ ID NO 599
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 599
atgtactgcc atgggaag 18

<210> SEQ ID NO 600
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 600
atggaggagt tggtgtactg ccatgggaag 30

<210> SEQ ID NO 601
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 601
atggaggagt tggcagatgc tctaaatgta ctgccatggg aag 43

<210> SEQ ID NO 602
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 602
atggaggagt tggcagatgc tcttctaatg tactgccatg ggaag 45

<210> SEQ ID NO 603
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 603
atggaggagt tggcagatgc cctctaatgt actgccatgg gaag 44

<210> SEQ ID NO 604
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 604
atggaggagt tggcagataa tgtactgcca tgggaagaag 40

<210> SEQ ID NO 605
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 605
atggcgtact gccatgggaa gaag 24

<210> SEQ ID NO 606

-continued

<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 606
atggaggagt tggcagatgc ttctaatgta ctgccatggg aagaag 46

<210> SEQ ID NO 607
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 607
atggaggagt tggcatctgc catgggaaga ag 32

<210> SEQ ID NO 608
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 608
atggaggagt tggcagatgc aatgtactgc catgggaaga ag 42

<210> SEQ ID NO 609
<211> LENGTH: 124
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 609
atggaggagt tggcagatgc caaactgaaa aacaaatcaa agcactctta ttgagtgctg 60
gcgatccccg acgccacggg ccgaaaccct tatcatagaa actctaatgt actgccatgg 120
gaag 124

<210> SEQ ID NO 610
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 610
atggaggagt tggcagatgc tgcttatata gacctcccac cgtacacgcc taccgcccat 60
tttctaatgt actgccatgg gaag 84

<210> SEQ ID NO 611
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
atggaggagt tgtctaatgt actgccatgg gaag 34

<210> SEQ ID NO 612
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612
ctgccatggg aagaag 16

<210> SEQ ID NO 613
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
atggaggagt tggcagatgc gcggctgttc ctgtacagaa ccgtgggcga gatgtggatc 60
aaggatgctc taatgtactg ccatgggaag 90

<210> SEQ ID NO 614
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
atggaggagt tggcagatgc ctaatgtact gccatgggaa g 41

<210> SEQ ID NO 615
<211> LENGTH: 97
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
atggaggagt tggcagatgc tgtcatgatc tttttccgct cgtcgtggga cttgctcagt 60
tctctggcca gctcgtctaa tgtactgcca tgggaag 97

<210> SEQ ID NO 616
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
atggaggagt tggcagatgc tctatgtact gccatgggaa g 41

<210> SEQ ID NO 617
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 617
cagggacagt gcgcatctcc ctggtcacca ag 32

<210> SEQ ID NO 618
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 618
cagggacagt caccaag 17

<210> SEQ ID NO 619
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 619
cagggacagt gcgcatctcc tggtcaccaa g 31

<210> SEQ ID NO 620
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 620
cagggacagt gcgcatctct ggtcaccaag 30

<210> SEQ ID NO 621
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 621
cagggacagt gcgcatctcc tctggtcacc aag 33

<210> SEQ ID NO 622
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 622
cagggacagt gcgcatcctg gtcaccaag 29

<210> SEQ ID NO 623
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 623
cagggacggt caccaag 17

<210> SEQ ID NO 624
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 624
cggggacagg gcgcatctcc tggtcaccaa g 31

<210> SEQ ID NO 625
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 625
cgacctgaat gctgtgcggc tctgcttcca gg 32

<210> SEQ ID NO 626
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 626
cgacctgaat gctgtgcggc atctgcttcc agg 33

<210> SEQ ID NO 627
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 627
cgacctgaat gctgtgcggc ttctgcttcc agg 33

<210> SEQ ID NO 628
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 628
cgacctgaat gctgtgtctg cttccagg 28

<210> SEQ ID NO 629
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 629
cgacctgcat gctgtgcggc atctgcttcc agg 33

<210> SEQ ID NO 630
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 630
cgacctgcat gctgtgcggc ttctgcttcc agg 33

<210> SEQ ID NO 631
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 631
cgacctgcat gctgtgtctg cttccagg 28

<210> SEQ ID NO 632
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 632
cgacctgaat gctgtgcgac atctgcttcc agg 33

<210> SEQ ID NO 633
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 633
tggggactac gacctgaatg ctgtgcggct ct 32

<210> SEQ ID NO 634
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 634
tggggactac gaatgctgtg cggctct 27

<210> SEQ ID NO 635
<211> LENGTH: 66
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 635
tggggactac gagcaggcag aagtatgcaa agcatgcatc tcaattcctg aatgctgtgc 60
ggctct 66

<210> SEQ ID NO 636
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 636
tggggactac gaagaaggcg atagaaggcc atgcgctgcg aatcgggagc ggcctgaatg 60
ctgtgcggct ct 72

<210> SEQ ID NO 637
<211> LENGTH: 99
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 637
tggggactac gatgactcgc tgcgctcggt cgttcggctg cggcgagcgg tatcagctca 60
ctcaaaggcg gtaatacggc ctgaatgctg tgcggctct 99

<210> SEQ ID NO 638
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 638
tggggtgcgg ctct 14

<210> SEQ ID NO 639
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 639
tggggactac gactgctgtg cggctct 27

<210> SEQ ID NO 640
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 640
cgacctgaat gctgtgcggc gctctggctt cattcaatc 39

<210> SEQ ID NO 641
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 641
cgacctgaat gctgtgcggc tctgcttcca ggtga 35

<210> SEQ ID NO 642
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 642
cgacctgaat gctgtgcggc atctgcttcc aggtga 36

<210> SEQ ID NO 643
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 643
cgacctgaat gctgcttcca ggtga 25

<210> SEQ ID NO 644
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
cgacctgaat gcttctgctt ccaggtga 28

<210> SEQ ID NO 645
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
cgacctgaat gcttccaggt ga 22

<210> SEQ ID NO 646
<211> LENGTH: 4
<212> TYPE: PRT
<213> ORGANISM: Homo sapiens

<400> SEQUENCE: 646

Glu Glu Gln Leu
1

<210> SEQ ID NO 647
<211> LENGTH: 6
<212> TYPE: PRT
<213> ORGANISM: Homo sapiens

<400> SEQUENCE: 647

Ala Glu Val Ser Gln Ala
1               5

<210> SEQ ID NO 648
<211> LENGTH: 4
<212> TYPE: PRT
<213> ORGANISM: Mus musculus

<400> SEQUENCE: 648

Gly Glu Gln Leu
1

<210> SEQ ID NO 649
<211> LENGTH: 6
<212> TYPE: PRT
<213> ORGANISM: Mus musculus

<400> SEQUENCE: 649

Ala Glu Val Ser Lys Ala
1               5

<210> SEQ ID NO 650
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 650

Gly Glu Gln Leu
1

-continued

```
<210> SEQ ID NO 651
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 651

Ala Glu Val Ser Gln Ala
1               5
```